United States Patent
Hattori et al.

(10) Patent No.: US 9,944,629 B2
(45) Date of Patent: Apr. 17, 2018

(54) MATERIAL FOR ORGANIC ELECTROLUMINESCENT ELEMENT, ORGANIC ELECTROLUMINESCENT ELEMENT, ILLUMINATION DEVICE, AND DISPLAY DEVICE

(71) Applicant: Konica Minolta, Inc., Tokyo (JP)

(72) Inventors: Takamune Hattori, Hachioji (JP); Norio Miura, Sagamihara (JP); Kaori Ono, Ichihara (JP)

(73) Assignee: KONICA MINOLTA, INC., Tokyo (JP)

(*) Notice: Subject to any disclaimer, the term of this patent is extended or adjusted under 35 U.S.C. 154(b) by 269 days.

(21) Appl. No.: 14/650,753

(22) PCT Filed: Dec. 2, 2013

(86) PCT No.: PCT/JP2013/082333
§ 371 (c)(1),
(2) Date: Jun. 9, 2015

(87) PCT Pub. No.: WO2014/091958
PCT Pub. Date: Jun. 19, 2014

(65) Prior Publication Data
US 2015/0322337 A1    Nov. 12, 2015

(30) Foreign Application Priority Data

Dec. 10, 2012  (JP) .................................. 2012-269292
Jan. 18, 2013  (JP) .................................. 2013-007631

(51) Int. Cl.
*H01L 51/00* (2006.01)
*C07D 405/04* (2006.01)
(Continued)

(52) U.S. Cl.
CPC ......... *C07D 405/04* (2013.01); *C07D 405/14* (2013.01); *C07D 409/04* (2013.01);
(Continued)

(58) Field of Classification Search
CPC .. C07D 405/04; C07D 405/14; C07D 409/04; C07D 409/14; C07D 493/04;
(Continued)

(56) References Cited

U.S. PATENT DOCUMENTS

| 8,114,530 B2 | 2/2012 | Iwakuma et al. |
| 2013/0341602 A1* | 12/2013 | Hikime .................. C09K 11/06 257/40 |
| 2014/0159023 A1* | 6/2014 | Matsumoto ......... H01L 51/0061 257/40 |

FOREIGN PATENT DOCUMENTS

| EP | 2902391 A1 | 8/2015 |
| JP | 2007-311460 A | 11/2007 |

(Continued)

OTHER PUBLICATIONS

Extended European Search Report dated Sep. 29, 2016 from corresponding European Application; Application No./Patent No. 13861633.9-1454 / 2930762 PCT/JP2013082333; Applicant: Konica Minolta, Inc.; Total of 16 pages.

(Continued)

*Primary Examiner* — Ruiyun Zhang
(74) *Attorney, Agent, or Firm* — Lucas & Mercanti, LLP

(57) ABSTRACT

A material for an organic electroluminescent element contains a compound represented by Formula (1):

(Continued)

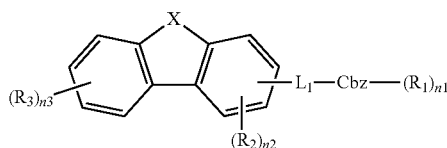

where $R_1$ to $R_3$ independently represent a group such as a deuterium atom and a halogen atom; at least one of $R_1$ to $R_3$ is a group represented by Formula (2); if pluralities of $R_1$ to $R_3$ are present, these substituents may be the same or different or may be bonded to each other to form a ring; n1 represents an integer of 0 to 8; n2 represents an integer of 0 to 3; n3 represents an integer of 0 to 4; n1+n2+n3 is 1 or more; Cbz represents a carbazolyl group; X represents an oxygen atom or a sulfur atom; and $L_1$ represents a single bond or a divalent linking group.

11 Claims, 5 Drawing Sheets

(51) Int. Cl.
| | |
|---|---|
| C07D 405/14 | (2006.01) |
| C07F 9/6558 | (2006.01) |
| C07F 15/00 | (2006.01) |
| C07D 409/04 | (2006.01) |
| C07D 409/14 | (2006.01) |
| C07D 487/04 | (2006.01) |
| C07D 493/04 | (2006.01) |
| C07F 7/08 | (2006.01) |
| C09K 11/06 | (2006.01) |
| H05B 33/14 | (2006.01) |
| H01L 51/52 | (2006.01) |
| H01L 51/50 | (2006.01) |

(52) U.S. Cl.
CPC ......... *C07D 409/14* (2013.01); *C07D 487/04* (2013.01); *C07D 493/04* (2013.01); *C07F 7/0814* (2013.01); *C07F 9/65586* (2013.01); *C07F 15/002* (2013.01); *C07F 15/0033* (2013.01); *C09K 11/06* (2013.01); *H01L 51/0061* (2013.01); *H01L 51/0067* (2013.01); *H01L 51/0072* (2013.01); *H01L 51/0073* (2013.01); *H01L 51/0074* (2013.01); *H01L 51/0085* (2013.01); *H01L 51/0087* (2013.01); *H01L 51/0094* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/1096* (2013.01); *C09K 2211/185* (2013.01); *H01L 51/5016* (2013.01); *H01L 51/5206* (2013.01); *H01L 51/5221* (2013.01)

(58) Field of Classification Search
CPC ................ C07F 9/65586; C09K 11/06; C09K 2211/1011; C09K 2211/1014; C09K 2211/1029; C09K 2211/1088; C09K 2211/1092; H01L 51/0061; H01L 51/0067; H01L 51/0072–51/0074

USPC ............. 428/690, 917; 257/40, E51.028, 257/E51.029; 544/333; 548/439; 546/80, 84, 89
See application file for complete search history.

(56) References Cited

FOREIGN PATENT DOCUMENTS

| | | |
|---|---|---|
| JP | 2012049518 A | 3/2012 |
| KR | 10-2011-0117168 A | 10/2011 |
| KR | 10-2012-0030009 A | 3/2012 |
| KR | 10-2012-0038374 A | 4/2012 |
| KR | 10-2012-0109744 A | 10/2012 |
| KR | 10-2013-0055198 A | 5/2013 |
| KR | 10-2013-0139535 A | 12/2013 |
| KR | 10-2015-0058173 A | 5/2015 |
| WO | 2007132886 A1 | 11/2007 |
| WO | 2009008099 A1 | 1/2009 |
| WO | 2009008100 A1 | 1/2009 |
| WO | 2010095621 A1 | 8/2010 |
| WO | 2011152596 A1 | 12/2011 |
| WO | 2012036482 A1 | 3/2012 |
| WO | 2012050371 A1 | 4/2012 |
| WO | 2012134124 A1 | 10/2012 |
| WO | 2012141499 A1 | 10/2012 |
| WO | 2012150826 A1 | 11/2012 |
| WO | 2012157211 A1 | 11/2012 |
| WO | 2013039073 A1 | 3/2013 |
| WO | 2013073874 A1 | 5/2013 |
| WO | 2013137001 A1 | 9/2013 |
| WO | 2013187689 A1 | 12/2013 |

OTHER PUBLICATIONS

Office Action dated Feb. 6, 2017 from the corresponding Korean Patent Application No. KR 10-2015-7014994; Applicant: Konica Minolta,Inc.; English translation of Office Action; Total of 14 pages.
The International Preliminary Report on Patentability dated Jun. 16, 2015 from the corresponding International Patent Application No. PCT/JP2013/082333.
The Written Opinion of the International Search Authority dated Mar. 4, 2014 from the corresponding International Patent Application No. PCT/JP2013/082333.
English translation of The Written Opinion of the International Search Authority dated Mar. 4, 2014 from the corresponding International Patent Application No. PCT/JP2013/082333.
International Search Report dated Mar. 4, 2014 for Application No. PCT/JP2013/082333 and English translation.
Daisuke Yokoyama, et al; Enhancement of electron transport by horizontal molecular . . . ; Appl. Phys. Letters; 95, 243303 (2009); 4 pages—243303-1 to 243303-3.
Partial Supplementary European Search Report dated Jun. 20, 2016; Application No./Patent No. 13861633.9-1454 / 2930762 PCT/JP2013082333; Applicant: Konica Minolta, Inc.; Total of 7 pages.
Office Action dated Jun. 23, 2017 from the corresponding Korean Patent Application No. KR 10-2015-7014994 and English translation; Applicant: Konica Minolta,Inc.
Notification of Reasons of Rejection dated Jul. 11, 2017 from the corresponding Japanese Patent Application No. JP 2014-551985 and English translation.
Office Action dated Nov. 27, 2017 from the corresponding Korean Patent Application No. KR 10-2017-7032476 and English translation.

\* cited by examiner

LIGHT

LIGHT

LIGHT

MATERIAL FOR ORGANIC ELECTROLUMINESCENT ELEMENT, ORGANIC ELECTROLUMINESCENT ELEMENT, ILLUMINATION DEVICE, AND DISPLAY DEVICE

CROSS REFERENCE TO RELATED APPLICATION

This Application is a 371 of PCT/JP2013/082333 filed on Dec. 2, 2013 which, in turn, claimed the priority of Japanese Patent Application No. JP2012-269292 filed on Dec. 10, 2012, and Japanese Patent Application No. JP2013-007631 filed on Jan. 18, 2013, all applications are incorporated herein by reference.

TECHNICAL FIELD

The present invention relates to materials for organic electroluminescent elements, organic electroluminescent elements, illumination devices, and display devices including the organic electroluminescent elements. In particular, the present invention relates to materials for organic electroluminescent elements represented by Formulae (1) to (7) to enhance the performance of organic electroluminescent elements including organic layers containing such materials.

BACKGROUND ART

A typical organic electroluminescent element (hereinafter also referred to as an organic EL element) is composed of a cathode, an anode, and a luminous layer containing a luminous compound and disposed therebetween. An electric field applied to such a light-emitting element recombines holes injected from the anode with electrons injected from the cathode in the luminous layer to generate excitons, which are deactivated with luminescence (fluorescence and/or phosphorescence). The organic EL element can emit light by such a mechanism. The organic EL elements are completely solid elements each including submicron films composed of organic materials, the films being disposed between electrodes and being capable of emitting light at an applied voltage of about several volts to several tens of volts. Such organic EL elements have great potential in applications to next-generation flat panel displays and illumination devices.

Since Princeton University reported an organic EL element by phosphorescence from the excited triplet state, phosphorescent materials at room temperature have been extensively investigated for practical use.

The luminescence efficiency of organic electrophosphorescent elements, in principle, can be about four times higher than that of traditional organic electrofluorescent elements, and world-wide studies and developments have been conducted on phosphorescent materials, layer configurations, and electrodes included in light-emitting elements. Especially, tremendous expectations have been placed on the development of novel materials for enhancing the performance of the organic EL elements.

As described above, the phosphorescent mechanisms have significantly high potential. Unlike organic EL devices utilizing emission of fluorescence, however, the organic phosphorescent devices should satisfy the following technical requirements for the efficiency and the service life of organic EL devices through control of the central position of light emission, particularly control of recombination of holes with electrons inside the luminous layer to attain stable light emission.

One of known solutions to such problems is multi-layered elements each including a laminate of a luminous layer, a hole transporting layer adjacent to an anode, and an electron transporting layer adjacent to a cathode. The luminous layer is composed of a mixed layer of a luminous host and a phosphorescent compound as a luminous dopant in many cases.

As for the materials, development of novel materials has been tremendously expected for enhancing the performance of organic EL elements.

A variety of materials for organic EL elements have been reported. For example, it is already known that dibenzofuran or dibenzothiophene compounds having specific substituents are useful as materials for organic EL elements in view of heat resistance and reduced defects of pixels (for example, see Patent Literature 1, 2, 3, and 4).

Unfortunately, high luminescence efficiency in organic EL elements requires homogeneous dispersion of a dopant as a luminous material for a reduction in concentration quenching caused by agglomeration of the dopant or quenching caused by interaction between excitons. It has been found that organic EL elements containing the compounds described in these documents as luminous hosts have insufficient luminescence efficiency and emission lifetimes, in regions containing particularly high concentration of dopants, and additional techniques are required to attain sufficient luminescence efficiency and prolonged emission lifetimes.

The performance of organic EL elements highly depends on the morphology of thin films. Typically, the organic EL elements suitably include amorphous thin films. Microcrystals present in a thin film function as nuclei to grow into crystals in the film during a driving mode and storage over time of the organic EL elements. These crystals increase grain boundaries into which an electric field is concentrated, resulting in unsatisfactory electrical characteristics and short service lives of the organic EL elements.

It has been reported that the control of molecular orientation even in amorphous films is important to control the electrical and optical characteristics of organic EL elements. For example, the results of detailed analysis of the molecular orientation (for example, see Non-Patent Literature 1) suggest that charge transportation is significantly influenced by the molecular orientation in amorphous films. Molecules in amorphous films are normally oriented in different directions. Such different directions of orientation reduce interaction between the molecules and preclude movement of carriers, leading to an increased driving voltage.

Requirements for an increase in area of organic EL elements, a reduction in cost, and higher productivity lead to expectations on wet processes. In addition, the wet processes can form films at lower temperature compared to vacuum processes to reduce damage of an underlying organic layer and increase the luminescence efficiency and the service life of the organic EL elements.

Bottlenecks in preparation of organic EL elements by wet processes are the film forming characteristics of the luminous host included in a luminous layer and an electron transporting material deposited on the luminous layer, and the solubilities of these materials in solvents for preparing coating solutions. The present inventors have found that traditional luminous hosts and electron transporting materials have low solubilities in solvents and solution stability at a practical level, and should be further technically improved.

In conclusion, such traditional materials cannot produce high-performance organic EL elements, and novel materials have been demanded for enhancing the performance of organic EL elements. Such materials should preferably be suitable for preparation of organic EL elements by wet processes.

PRIOR ART DOCUMENT

Patent Literature

Patent Literature 1: WO2009/008099
Patent Literature 2: U.S. Pat. No. 8,114,530
Patent Literature 3: WO2009/008100
Patent Literature 4: Japanese Patent Application Laid-Open No. 2012-049518

Non-Patent Literature

Non-Patent Literature 1: Appl. Phys. Lett. 95, 243303(2009)

SUMMARY OF INVENTION

Problems to be Solved by the Invention

The present invention has been achieved in consideration of the problems and circumstances described above. An object of the present invention is to provide a material for an organic electroluminescent element having high luminescence efficiency, low driving voltage, a long service life, a small increase in driving voltage, and high long-term stability, and an organic electroluminescent element, an illumination device, and a display device that contain the material.

Another object of the present invention is to provide a material for an organic electroluminescent element suitable for preparation of organic electroluminescent elements by wet processes, and an organic electroluminescent element, an illumination device, and a display device that contain the material.

Means for Solving the Problem

The present inventors, who have investigated to address the problems, have found that compounds represented by Formulae (1) to (7) can be used as materials for organic electroluminescent elements, and have achieved the present invention.

Namely, in the present invention, the problems are solved by the following methods:

1. A material for an organic electroluminescent element, comprising a compound represented by Formula (1):

[Formula 1]

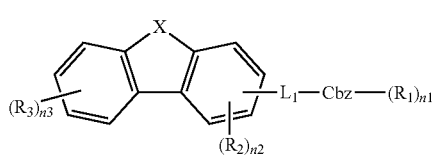

Formula (1)

where $R_1$ to $R_3$ each independently represent a deuterium atom, a halogen atom, a cyano group, an alkyl group, an alkenyl group, an alkynyl group, an alkoxy group, a carbonyl group, an amino group, a silyl group, a hydroxy group, a thiol group, a phosphine oxide group, an aromatic hydrocarbon ring group, an aromatic heterocyclic group, a non-aromatic hydrocarbon ring group, or a non-aromatic heterocyclic group, and may further have an optional substituent; at least one of $R_1$ to $R_3$ is a group represented by Formula (2); if pluralities of $R_1$'s to $R_3$'s are present, these substituents may be the same or different or may be bonded to each other to form a ring; n1 represents an integer of 0 to 8; n2 represents an integer of 0 to 3; n3 represents an integer of 0 to 4; n1+n2+n3 is 1 or more; Cbz represents a carbazolyl group; X represents an oxygen atom or a sulfur atom; $L_1$ represents a single bond or a divalent linking group;

[Formula 2]

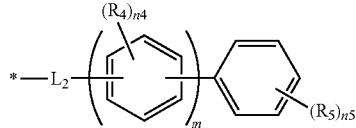

Formula (2)

where * represents a binding site to the structure represented by Formula (1); $L_2$ represents a single bond or a divalent linking group; $R_4$ represents a substituent; $R_5$ represents a deuterium atom, a halogen atom, a cyano group, an alkyl group, an alkenyl group, an alkynyl group, an alkoxy group, a carbonyl group, a silyl group, a phosphine oxide group, an aromatic hydrocarbon ring group, an aromatic heterocyclic group bonded to a phenyl group via a carbon atom, a non-aromatic hydrocarbon ring group, or a non-aromatic heterocyclic group; $R_5$ may further have optional substituents, and the optional substituents may be bonded to each other to form a ring; if pluralities of $R_4$'s and $R_5$'s are present, these substituents may be the same or different; n4 represents an integer of 0 to 4; n5 represents an integer of 0 to 5; m represents an integer of 2 to 10.

2. The material for an organic electroluminescent element according to Aspect 1,
wherein the compound represented by Formula (1) is a compound represented by Formula (3):

[Formula 3]

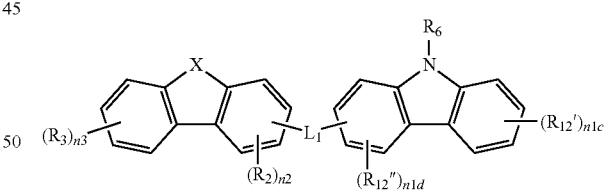

Formula (3)

where $R_2$, $R_3$, $R_6$, $R_{12}'$, and $R_{12}''$ each independently represent a deuterium atom, a halogen atom, a cyano group, an alkyl group, an alkenyl group, an alkynyl group, an alkoxy group, a carbonyl group, an amino group, a silyl group, a hydroxy group, a thiol group, a phosphine oxide group, an aromatic hydrocarbon ring group, an aromatic heterocyclic group, a non-aromatic hydrocarbon ring group, or a non-aromatic heterocyclic group, and may further have an optional substituent; at least one of $R_2$'s, $R_3$'s, $R_6$'s, $R_{12}''$s, and $R_{12}'''$s is a group represented by Formula (2); if pluralities of $R_2$'s, $R_3$'s, $R_{12}''$s, and $R_{12}'''$s are present, these $R_2$'s, $R_3$'s, $R_{12}''$s, and $R_{12}'''$s may be the same or different or may be bonded to each other to form a ring; n2 and n1d each represent an integer of 0 to 3; n3 and n1c each represent an integer of 0 to 4; n2+n3+n1c+n1d is 1 or more; X represents an oxygen atom or a sulfur atom; $L_1$ represents a single bond or a divalent linking group.

3. The material for an organic electroluminescent element according to Aspect 2, wherein the compound represented by Formula (3) is a compound represented by Formula (6):

[Formula 4]

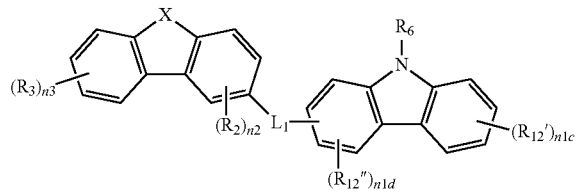

Formula (6)

where $R_2$, $R_3$, $R_6$, $R_{12}'$, $R_{12}''$, n2, n3, n1c, n1d, X, and $L_1$ are the same as $R_2$, $R_3$, $R_6$, $R_{12}'$, $R_{12}''$, n2, n3, n1c, n1d, X, and $L_1$ defined in Formula (3).

4. The material for an organic electroluminescent element according to Aspect 1, wherein the compound represented by Formula (1) is a compound represented by Formula (4):

[Formula 5]

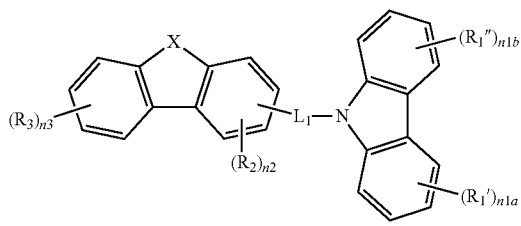

Formula (4)

where $R_2$, $R_3$, $R_1'$, and $R_1''$ each independently represent a deuterium atom, a halogen atom, a cyano group, an alkyl group, an alkenyl group, an alkynyl group, an alkoxy group, a carbonyl group, an amino group, a silyl group, a hydroxy group, a thiol group, a phosphine oxide group, an aromatic hydrocarbon ring group, an aromatic heterocyclic group, a non-aromatic hydrocarbon ring group, or a non-aromatic heterocyclic group, and may further have an optional substituent; at least one of $R_2$, $R_3$, $R_1'$, and $R_1''$ is a group represented by Formula (2); if pluralities of $R_2$'s, $R_3$'s, $R_1'$'s, and $R_1'''$'s are present, these $R_2$'s, $R_3$'s, $R_1'$'s, and $R_1'''$'s may be the same or different or may be bonded to each other to form a ring; n2 represents an integer of 0 to 3; n3, n1a, and n1b each independently represent an integer of 0 to 4; n2+n3+n1a+n1b is 1 or more; X represents an oxygen atom or a sulfur atom; $L_1$ represents a single bond or a divalent linking group.

5. The material for an organic electroluminescent element according to Aspect 4, wherein the compound represented by Formula (4) is a compound represented by Formula (7):

[Formula 6]

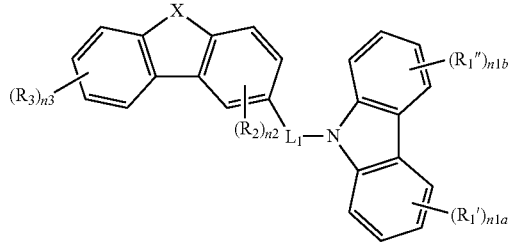

Formula (7)

where $R_2$, $R_3$, $R_1'$, $R_1''$, n2, n3, n1a, n1b, X, and $L_1$ are the same as $R_2$, $R_3$, $R_1'$, $R_1''$, n2, n3, n1a, n1b, X, and $L_1$ defined in Formula (4).

6. The material for an organic electroluminescent element according to any one of Aspects 1 to 5, wherein the group represented by Formula (2) is a group represented by Formula (5):

[Formula 7]

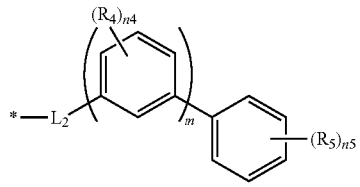

Formula (5)

where * represents a binding site to a structure represented by Formula (1), (3), (4), (6), or (7); $L_2$ represents a single bond or a divalent linking group; $R_4$ represents a substituent; $R_5$ represents a deuterium atom, a halogen atom, a cyano group, an alkyl group, an alkenyl group, an alkynyl group, an alkoxy group, a carbonyl group, a silyl group, a phosphine oxide group, an aromatic hydrocarbon ring group, a non-aromatic hydrocarbon ring group, or a non-aromatic heterocyclic group; $R_5$ may further have optional substituents, and the optional substituents may be bonded to each other to form a ring; if pluralities of $R_4$'s and $R_5$'s are present, these $R_4$'s and $R_5$'s may be the same or different; n4 represents an integer of 0 to 4; n5 represents an integer of 0 to 5; m represents an integer of 2 to 10.

7. The material for an organic electroluminescent element according to any one of Aspects 1 to 6, wherein $L_2$ in Formula (2) or (5) represents a single bond.

8. The material for an organic electroluminescent element according to any one of Aspects 1 to 7, wherein m in Formula (2) or (5) represents an integer of 2 to 5.

9. The material for an organic electroluminescent element according to any one of Aspects 1 to 8, wherein $L_1$ in Formula (1), (3), (4), (6), or (7) represents a single bond.

10. The material for an organic electroluminescent element according to any one of Aspects 1 to 9, wherein X in Formula (1), (3), (4), (6), or (7) represents an oxygen atom.

11. An organic electroluminescent element, comprising:
an anode,
a cathode, and
an organic layer composed of at least one organic layer including a luminous layer, the organic layer being disposed between the anode and the cathode, wherein the at least one organic layer contains the material for an organic electroluminescent element according to any one of Aspects 1 to 10.

12. The organic electroluminescent element according to Aspect 11, wherein the at least one organic layer further contains a phosphorescent compound represented by Formula (DP):

[Formula 8]

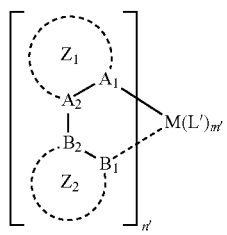

Formula (DP)

where M represents Ir, Pt, Rh, Ru, Ag, Cu, or Os; $A_1$, $A_2$, $B_1$, and $B_2$ each independently represent a carbon atom or a nitrogen atom; ring $Z_1$ represents a 6-membered aromatic hydrocarbon ring or 5- or 6-membered aromatic heterocyclic ring including $A_1$ and $A_2$; ring $Z_2$ represents a 5- or 6-membered aromatic heterocyclic ring including $B_1$ and $B_2$; ring $Z_1$ and ring $Z_2$ may have optional substituents, and the optional substituents may be bonded to form a fused ring structure; substituents of ligands may be bonded to each other to link the ligands; L' represents a monoanionic bidentate ligand coordinated with M; m' represents an integer of 0 to 2; n' represents an integer of 1 to 3; m'+n' is 2 or 3; if m' and n' both are 1 or more, ligands represented by ring $Z_1$ and ring $Z_2$ may be the same as or different from L'.

13. The organic electroluminescent element according to Aspect 11 or 12, wherein a color of light emitted is white.

14. An illumination device, comprising the organic electroluminescent element according to any one of Aspects 11 to 13.

15. A display device, comprising the organic electroluminescent element according to any one of Aspects 11 to 13.

Advantageous Effects of Invention

The present invention can provide a material for an organic electroluminescent element having high luminescence efficiency, low driving voltage, a long service life, a small increase in driving voltage, and high long-term stability, and an organic electroluminescent element, an illumination device, and a display device which contain the material. The present invention also can provide a material for an organic electroluminescent element suitable for preparation of organic electroluminescent elements by wet processes, and an organic electroluminescent element, an illumination device, and a display device that contain the material.

Although the mechanism or the action has not been clarified, the present inventors infer the reason for the advantageous effects of the present invention as follows:

In the material for an organic EL element according to the present invention, any one of $R_1$ to $R_3$ includes a flexible substructure represented by Formula (2), which attains high interaction between molecules in the same material or different materials. In detail, the material for an organic EL element according to the present invention used as a luminous host has enhanced compatibility with a luminous dopant to suppress agglomeration of the dopant, and thus suppress concentration quenching or quenching caused by interaction between excitons. The uniformly dispersed dopant promotes the movement of carriers in the luminous layer. It is believed that such a mechanism can attain high luminescence efficiency, low driving voltage, and prolonged light emission at the same time.

If $R_5$ in Formula (2) in the present invention is an aromatic heterocyclic group, a compound represented by Formula (1) should have aromatic heterocyclic groups at its two terminals, which may readily cause undesirable association of the compound. The associated compound will impair interaction between molecules in the same material or different materials, readily resulting in low luminescence efficiency and a short emission lifetime of the organic EL element. The present inventors, who have further investigated, have found that such association does not occur in a compound having an aromatic heterocyclic ring represented by $R_5$ bonded to a benzene ring via a carbon atom in Formula (2).

In general, heteroatom-carbon atom bond has lower energy than that of carbon atom-carbon atom bond and is readily broken. If charges are concentrated on the aromatic heterocyclic site represented by $R_5$ in a compound represented by Formula (1) particularly in an excited or charged state, load is readily applied to the binding portion between the aromatic heterocyclic ring and the benzene ring in Formula (2). An aromatic heterocyclic ring bonded via a heteroatom is more readily broken compared to that bonded via a carbon atom. Accordingly, the aromatic heterocyclic ring represented by $R_5$ is preferably bonded via a carbon atom to the benzene ring also in view of the durability of the compound.

The material for an organic EL element according to the present invention also has a substituent having high affinity with a phosphorescent compound represented by Formula (DP) described later in the molecule. In a luminous host composed of such a material, molecules can be densely contained in the luminous layer to enhance interaction between π electrons while the luminous layer is kept amorphous. The present inventors infer that such densely contained molecules enhance electrical characteristics (driving at low voltage), and thus extend the service lives of organic EL elements.

The material for an organic EL element according to the present invention has a flexible substructure represented by Formula (2) in the molecule. Such a structure can keep the amorphous state of a layer prepared with the material even during storage of organic EL elements under high temperature and high humidity. Since the material for an organic EL element according to the present invention has high film forming ability, the material can be formed into a uniform thin film having small change in the morphology, keeping high performance of organic EL elements after storage.

EMBODIMENT FOR CARRYING OUT THE INVENTION

Figure 1:
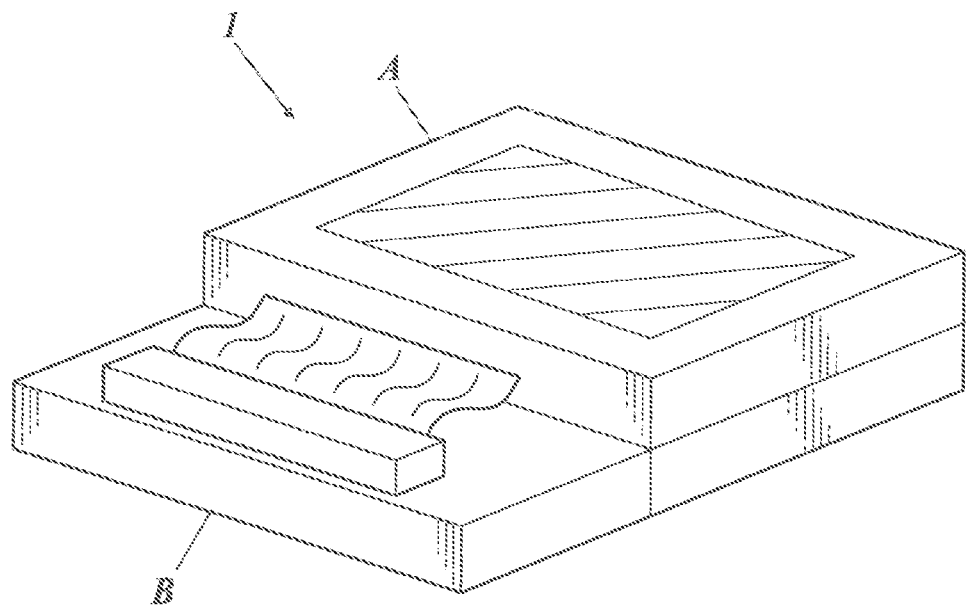
FIG. 1 is a schematic view illustrating an example of a display device including an organic EL element.

The material for an organic EL element according to the present invention comprises a compound represented by Formula (1), wherein at least one of $R_1$ to $R_3$ in Formula (1) represents a substituent represented by Formula (2). These technical features are common to aspects 1 to 15 in the invention.

In the present invention, the substituent represented by Formula (2) is preferably represented by Formula (5). The substituent attains an organic EL element to enhance luminescence efficiency, driving voltage, emission lifetime, increase in driving voltage, and long-term stability.

In the present invention, a compound represented by Formula (3) is preferably represented by Formula (6). Such a compound attains an organic EL element to enhance luminescence efficiency, driving voltage, emission lifetime, increase in driving voltage, and long-term stability.

In the present invention, a compound represented by Formula (4) is preferably represented by Formula (7). Such a compound attains an organic EL element to enhance luminescence efficiency, driving voltage, emission lifetime, increase in driving voltage, and long-term stability.

In the present invention, in Formulae (1) to (7), $L_1$ or $L_2$ preferably represents a single bond. The single bond increases the proportion of the substituent represented by Formula (2) or (5) in the compound represented by each of Formulae (1) to (7) to enhance interaction with a dopant and thus attain a preferred dispersion state of the dopant. The present inventors infer that the single bond as the linking group also enhances electrical stability, which also improves the functions of the organic EL element.

The present invention, components, and embodiments and aspects of the present invention will now be described in detail. Throughout the specification, the term "to" between numeric values indicates that the numeric values before and after the term are inclusive as the lower limit and the upper limit, respectively.

The material for an organic EL element according to the present invention will now be described.

<<Compound represented by Formula (1)>>

The material for an organic EL element according to the present invention comprises a compound represented by Formula (1). The organic EL element according to the present invention comprises an organic layer including at least one organic layer containing the compound represented by Formula (1). Preferably, the compound is contained in at least one of a luminous layer and an electron transporting layer.

[Formula 9]

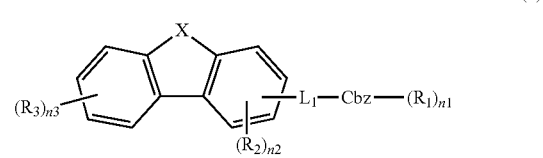

Formula (1)

In Formula (1), X represents an oxygen atom or a sulfur atom. Preferably, X represents an oxygen atom.

In Formula (1), $L_1$ represents a single bond or a divalent linking group.

Examples of the divalent linking group represented by $L_1$ include an alkylene group, an alkenylene group, an ether group, a thioether group, an ester group, a carbonyl group, an amino group, an amide group, a silyl group, a phosphine oxide group, divalent linking groups derived from aromatic hydrocarbon rings, divalent linking groups derived from aromatic heterocyclic rings, divalent linking groups derived from non-aromatic hydrocarbon rings, divalent linking groups derived from non-aromatic heterocyclic rings, or divalent linking groups derived from combinations thereof.

Preferred examples of aromatic hydrocarbon rings include a benzene ring, a naphthalene ring, a triphenylene ring, an indene ring, and a fluorene ring. More preferred is a benzene ring. Preferred examples of aromatic heterocyclic rings include rings of pyridine, pyrazine, pyrimidine, pyridazine, triazine, imidazole, indole, benzofuran, benzothiophene, carbazole, dibenzofuran, dibenzothiophene, benzofuranoindole, and indoloindole. More preferred are rings of pyridine, pyrazine, imidazole, indole, benzofuran, benzothiophene, carbazole, dibenzofuran, dibenzothiophene, benzofuranoindole, and indoloindole. Examples of non-aromatic hydrocarbon rings include rings of cyclopropane, cyclopentane, cyclohexane, cyclohexadiene, tetrahydronaphthalene, and dihydroindene. Examples of non-aromatic heterocyclic rings include a piperidine ring and a morpholine ring.

Specific examples of the divalent linking group represented by $L_1$ in Formula (1) are listed. The linking groups exemplified below may further have an optional substituent. The present invention will not be limited to these examples. Examples of an optional substituent in the linking group include the same optional substituents as those included in $R_1$ to $R_3$ described later.

[Formula 10]

L-1

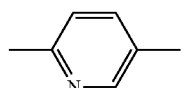

L-2

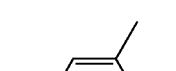

L-3

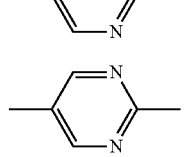

L-4

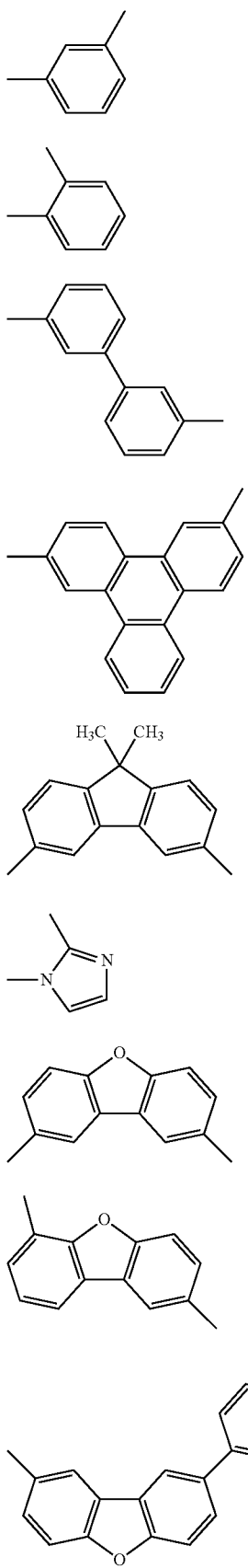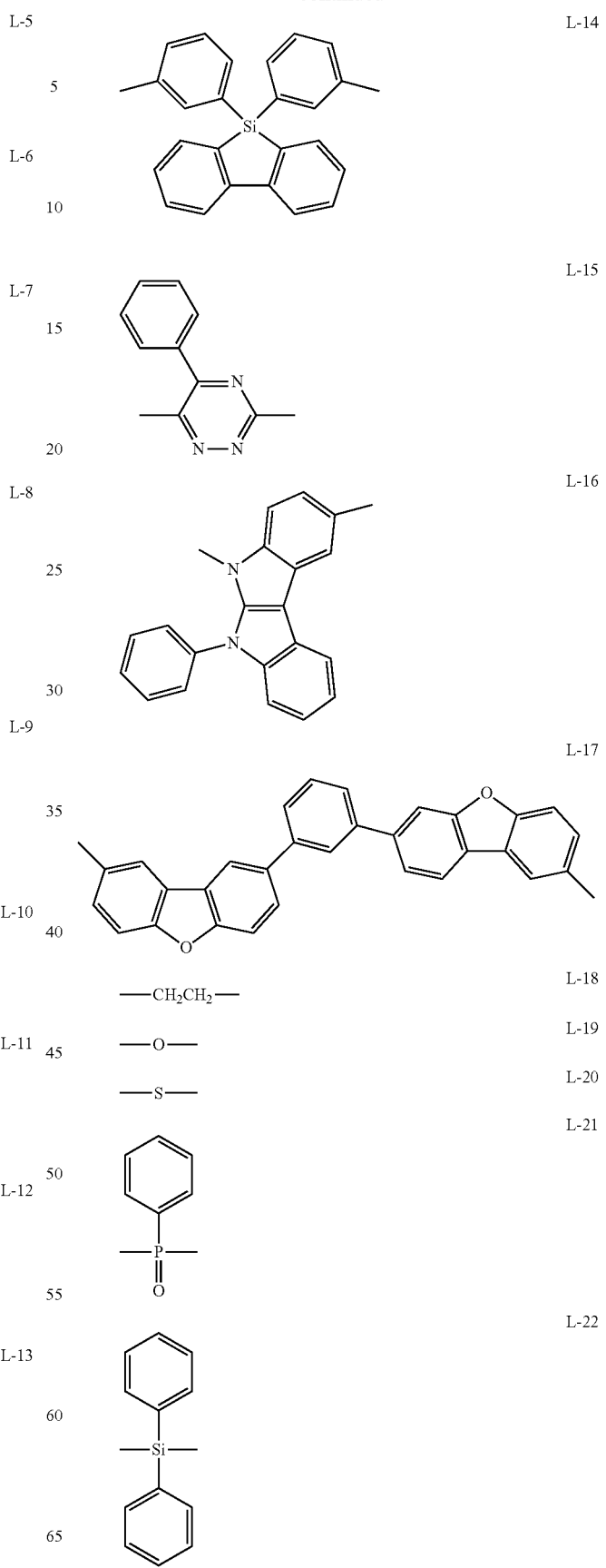

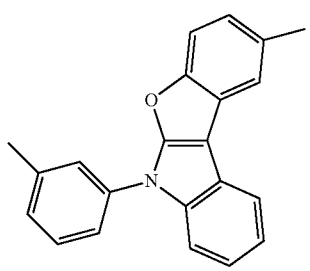
L-23
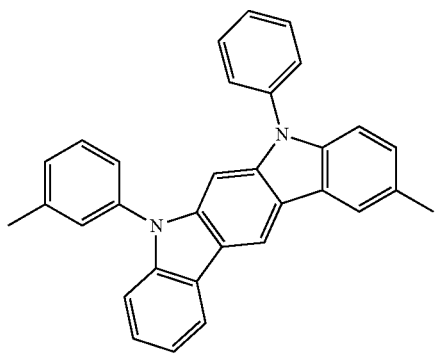
L-24
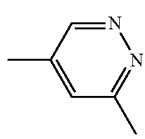
L-25
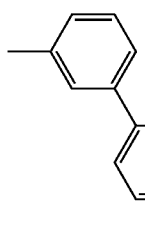
L-26
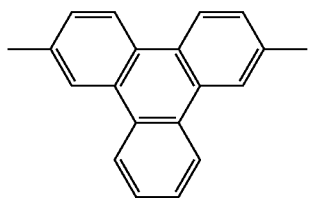
L-27
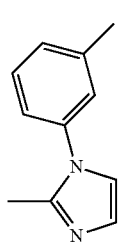
L-28
[Formula 11]
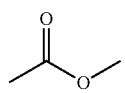
L-30
L-31
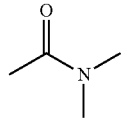
L-32
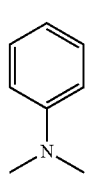
L-33
L-34
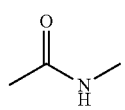
L-35
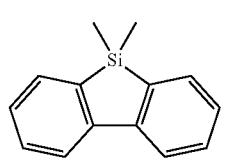
L-36
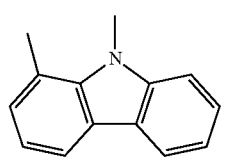
L-37
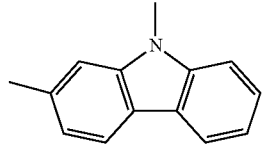
L-38
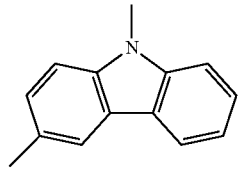
L-39
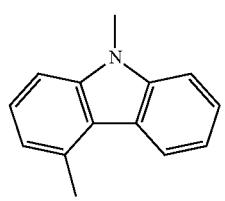
L-40

-continued
L-41
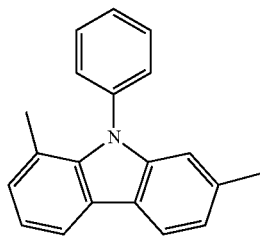
L-42
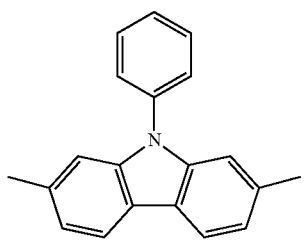
L-43
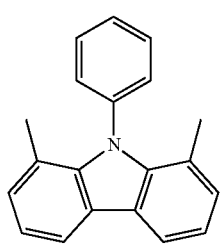
L-44
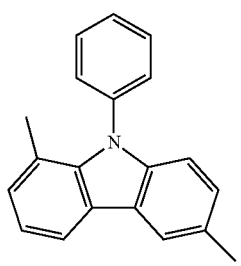
L-45
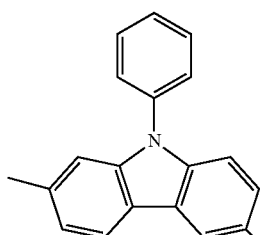
L-46
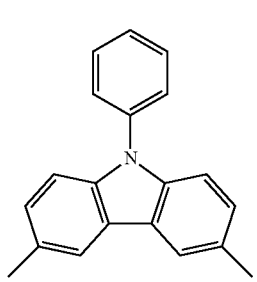
L-47
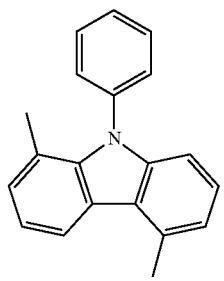
L-48
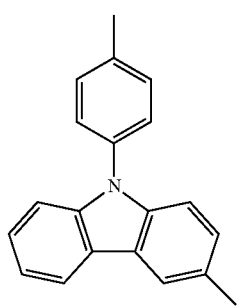
L-49
L-50
L-51

-continued
L-52 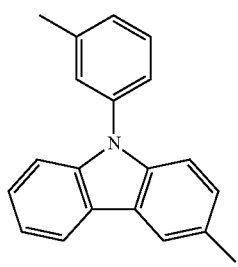
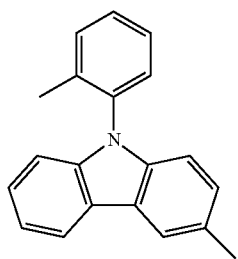
[Formula 12]
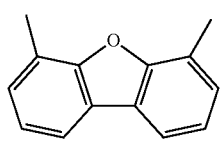
L-53
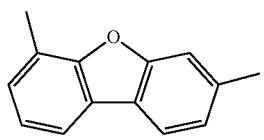
L-54
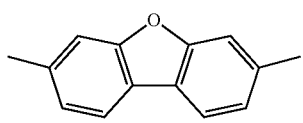
L-55
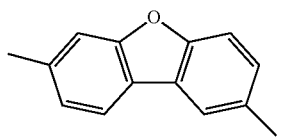
L-56
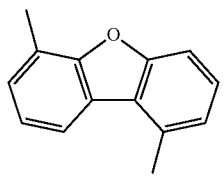
L-57
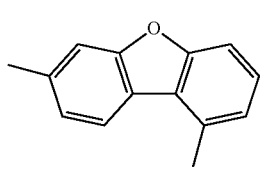
-continued
L-58 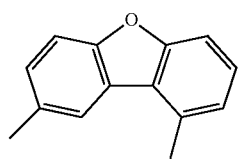
L-59 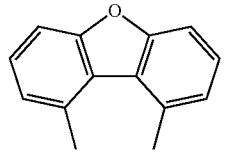
L-60 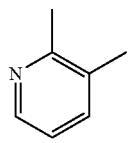
L-61 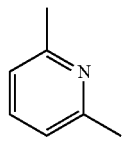
L-62
L-63
L-64 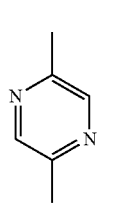
L-65 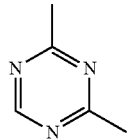
L-66 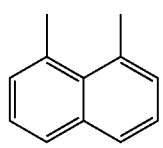
L-67
L-68
L-69 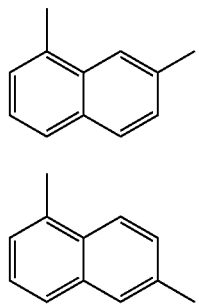

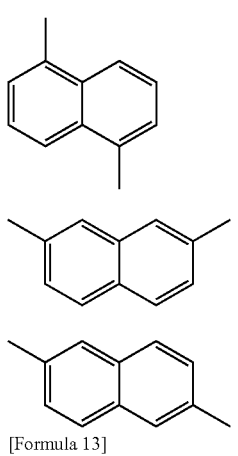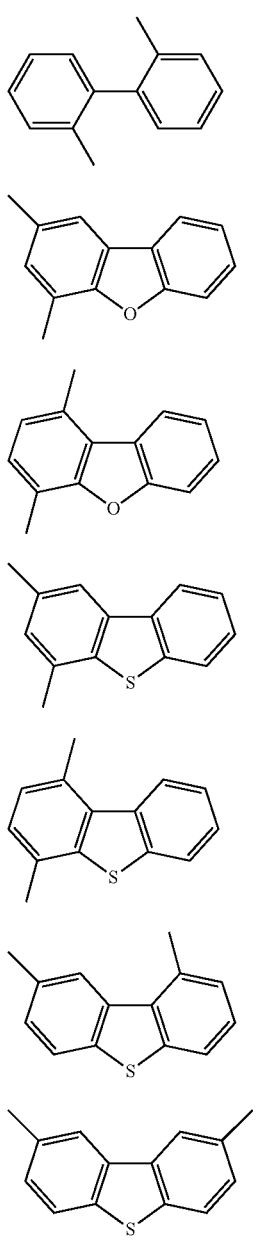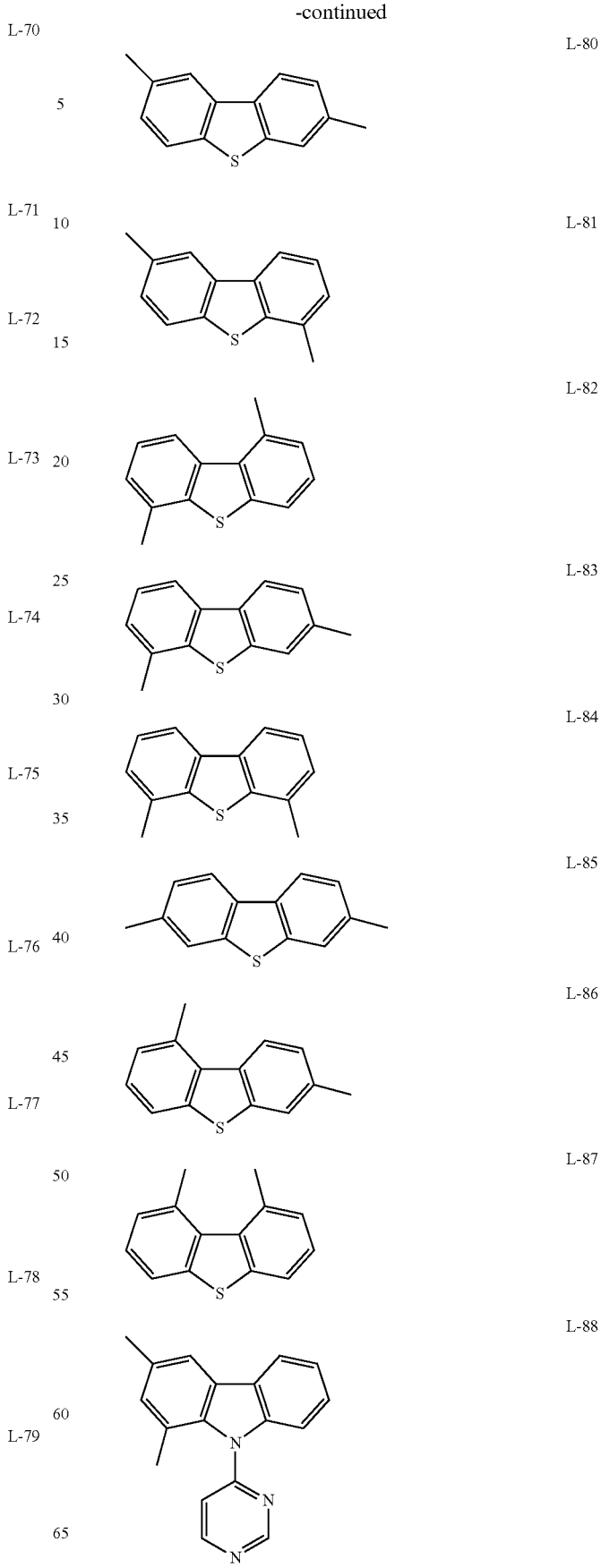

-continued

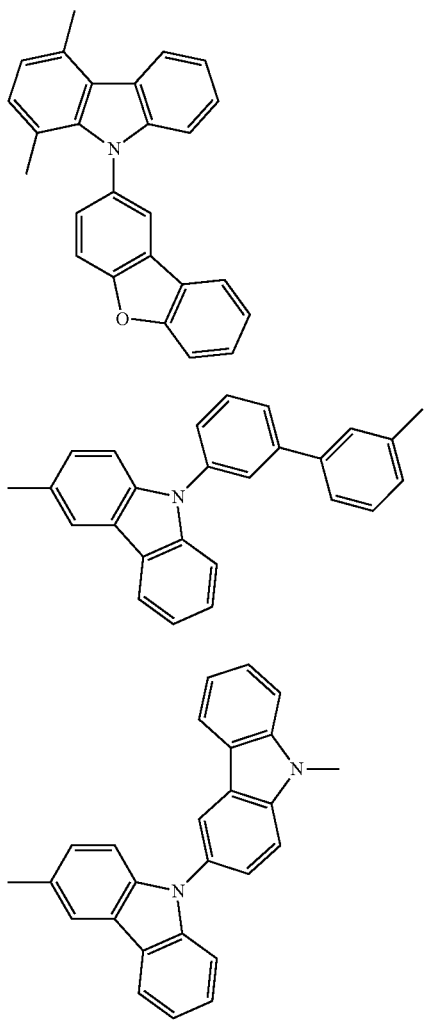

L-89

L-90

L-91

[Formula 14]

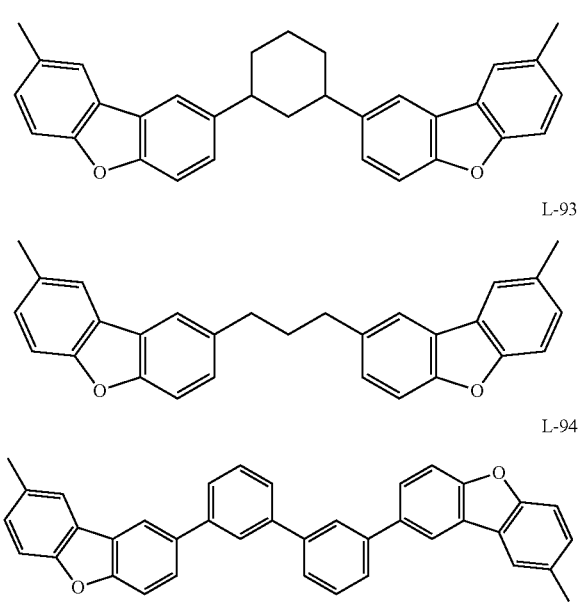

L-92

L-93

L-94

-continued

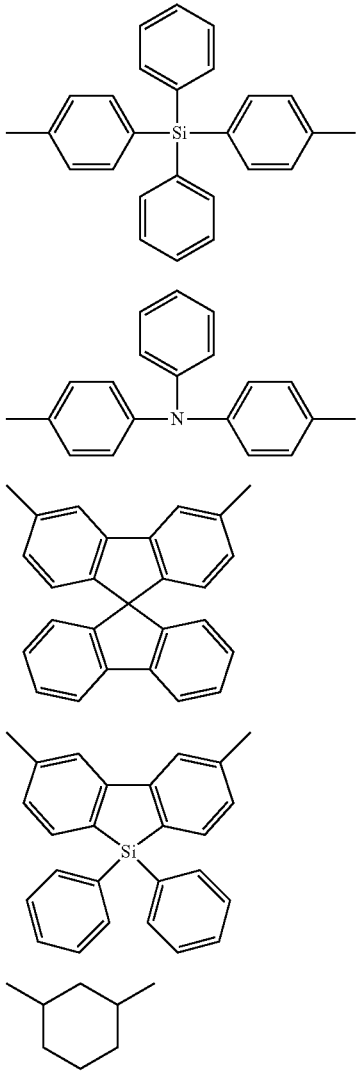

L-95

L-96

L-97

L-98

L-99

In Formula (1), $R_1$ to $R_3$ each independently represent a deuterium atom, a halogen atom, a cyano group, an alkyl group, an alkenyl group, an alkynyl group, an alkoxy group, a carbonyl group, an amino group, a silyl group, a hydroxy group, a thiol group, a phosphine oxide group, an aromatic hydrocarbon ring group, an aromatic heterocyclic group, a non-aromatic hydrocarbon ring group, or a non-aromatic heterocyclic group, and may further have an optional substituent; if pluralities of $R_1$'s to $R_3$'s are present, these substituents may be the same or different or may be bonded to each other to form a ring.

Preferred examples of the groups represented by $R_1$ to $R_3$ include a silyl group, an aromatic hydrocarbon ring group, and an aromatic heterocyclic group. Preferred examples of the aromatic hydrocarbon ring or the aromatic heterocyclic ring include a benzene ring, a carbazole ring, a dibenzofuran ring, a dibenzothiophene ring, a pyridine ring, a pyrazine ring, an indoloindole ring, an indole ring, a benzofuran ring, a benzothiophene ring, an imidazole ring, and a triazine ring.

Examples of the optional substituents included in $R_1$ to $R_3$ include a deuterium atom, a halogen atom, a cyano group, an alkyl group, an alkenyl group, an alkynyl group, an alkoxy group, a carbonyl group, an amino group, a silyl group, a hydroxy group, a thiol group, a phosphine oxide group, aromatic hydrocarbon ring groups, aromatic heterocyclic groups, non-aromatic hydrocarbon ring groups, non-aromatic heterocyclic groups, a phosphino group, a sulfonyl group, and a nitro group. These optional substitutes may be further substituted.

In Formula (1), n1 represents an integer of 0 to 8; n2 represents an integer of 0 to 3; n3 represents an integer of 0 to 4; n1+n2+n3 is 1 or more.

n1 is preferably 0 to 2, more preferably 0 or 1. At least one of n2 and n3 is 1. More preferably, n2 and n3 each are 0 or 1. Most preferably, n2+n3 is 1.

In Formula (1), Cbz represents a carbazolyl group. In Formula (1), $L_1$ and $R_1$ may be bonded to any biding site of a carbazole ring.

In Formula (1), at least one of $R_1$ to $R_3$ represents a group represented by Formula (2):

[Formula 15]

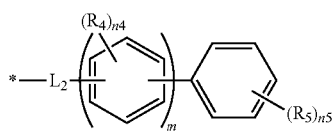

Formula (2)

In Formula (2), * represents a binding site to the structure represented by Formula (1).

In Formula (2), $R_4$ represents a substituent. Examples of the substituent represented by $R_4$ include the same as the optional substituents included in $R_1$ to $R_3$ listed above.

In Formula (2), $R_5$ represents an aromatic heterocyclic group, a non-aromatic hydrocarbon ring group, or a non-aromatic heterocyclic group bonded via a carbon atom to a deuterium atom, a halogen atom, a cyano group, an alkyl group, an alkenyl group, an alkynyl group, an alkoxy group, a carbonyl group, a silyl group, a phosphine oxide group, an aromatic hydrocarbon ring group, or a phenyl group; each $R_5$ may further have an optional substituent, and if two optional substituents are present, these optional substituents may be bonded to each other to form a ring.

The optional substituent (s) included in $R_5$ may be the same optional substituents included in $R_1$ to $R_3$ listed above.

If pluralities of $R_4$'s and $R_5$'s are present, these substituents may be the same or different provided that the $R_5$'s are not bonded to each other to form a ring.

In Formula (2), n4 represents an integer of 0 to 4, and is more preferably 0 or 1, most preferably 0.

In Formula (2), n5 represents an integer of 0 to 5, and is more preferably 0 or 1, most preferably 0.

In Formula (2), $L_2$ represents a single bond or a divalent linking group.

Examples of the divalent linking group represented by $L_2$ include the same divalent linking groups represented by $L_1$ in Formula (1) listed above.

In Formula (2), m represents an integer of 2 to 10.

The compound represented by Formula (1) is preferably a compound represented by Formula (3):

[Formula 16]

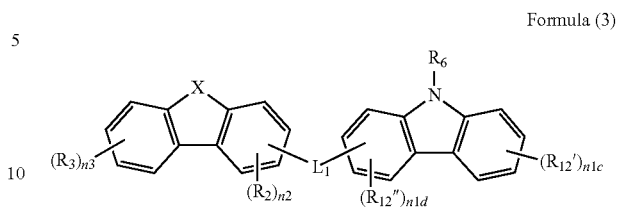

Formula (3)

where $R_2$, $R_3$, $R_6$, $R_{12}'$, and $R_{12}''$ each independently represent a deuterium atom, a halogen atom, a cyano group, an alkyl group, an alkenyl group, an alkynyl group, an alkoxy group, a carbonyl group, an amino group, a silyl group, a hydroxy group, a thiol group, a phosphine oxide group, an aromatic hydrocarbon ring group, an aromatic heterocyclic group, a non-aromatic hydrocarbon ring group, or a non-aromatic heterocyclic group, and may further have an optional substituent; if pluralities of $R_2$'s, $R_3$'s, $R_{12}''$'s, and $R_{12}'''$'s are present, these substituents may be the same or different, or may be bonded to each other to form a ring.

Preferred groups represented by $R_2$, $R_3$, $R_6$, $R_{12}'$, and $R_{12}''$ are the same as the preferred groups represented by $R_1$ to $R_3$ listed above.

The optional substituents included in $R_2$, $R_3$, $R_6$, $R_{12}'$, and $R_{12}''$ are the same as the optional substituents included in $R_1$ to $R_3$ listed above.

In Formula (3), n2 and n1d each represent an integer of 0 to 3, n3 and n1c each represent an integer of 0 to 4, and n2+n3+n1c+n1d is 1 or more.

At least one of n2 and n3 is preferably 1. More preferably, n2 and n3 each are 0 or 1. Most preferably, n2+n3 is 1. n1c and n1d each are preferably 0 or 1. More preferably, n1c+n1d is 1.

In Formula (3), $L_1$ and X are the same as $L_1$ and X defined in Formula (1).

In Formula (3), at least one of $R_2$, $R_3$, $R_6$, $R_{12}'$, and $R_{12}''$ represents a group represented by Formula (2).

The compound represented by Formula (3) is preferably a compound represented by Formula (6):

[Formula 17]

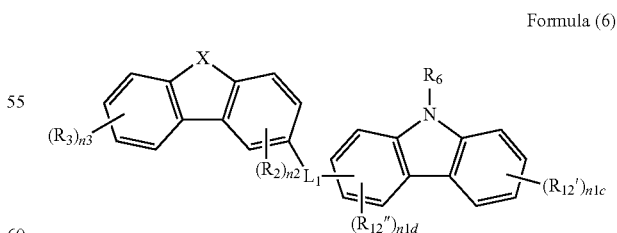

Formula (6)

where $R_2$, $R_3$, $R_6$, $R_{12}'$, $R_{12}''$, n2, n3, n1c, n1d, X, and $L_1$ are the same as $R_2$, $R_3$, $R_6$, $R_{12}'$, $R_{12}''$, n2, n3, n1c, n1d, X, and $L_1$ defined in the Formula (3).

The compound represented by Formula (1) is preferably a compound represented by Formula (4):

[Formula 18]

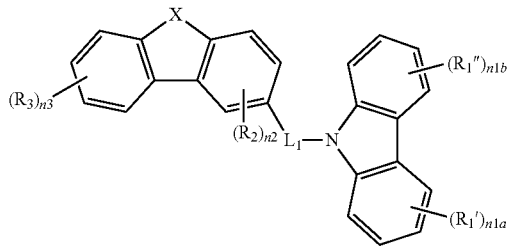

Formula (4)

where $R_2$, $R_3$, $R_1'$, and $R_1''$ each independently represent a deuterium atom, a halogen atom, a cyano group, an alkyl group, an alkenyl group, an alkynyl group, an alkoxy group, a carbonyl group, an amino group, a silyl group, a hydroxy group, a thiol group, a phosphine oxide group, an aromatic hydrocarbon ring group, an aromatic heterocyclic group, a non-aromatic hydrocarbon ring group, or a non-aromatic heterocyclic group, and may further have an optional substituent; if $R_2$'s, $R_3$'s, $R_1''$s, and $R_1'''$s are present, these substituents may be the same or different or may be bonded to each other to form a ring.

Preferred examples of $R_2$, $R_3$, $R_1'$, and $R_1''$ include are the same as the preferred groups represented by $R_1$ to $R_3$ in Formula (1) listed above.

The optional substituents included in $R_2$, $R_3$, $R_1'$, and $R_1''$ are the same as the optional substituents included in $R_1$ to $R_3$ in Formula (1) listed above.

In Formula (4), n2 represents an integer of 0 to 3; n3, n1a, and n1b each independently represent integer of 0 to 4; n2+n3+n1a+n1b is 1 or more.

Preferably at least one of n2 and n3 is 1. More preferably, n2 and n3 each are 0 or 1. Most preferably, n2+n3 is 1. n1a and n1b are preferably 0 or 1. More preferably, n1a+n1b is 1.

In Formula (4), $L_1$ and X are the same as $L_1$ and X defined in Formula (1).

In Formula (4), at least one of $R_2$, $R_3$, $R_1'$, and $R_1''$ represents a group represented by Formula (2).

The compound represented by Formula (4) is preferably a compound represented by Formula (7):

[Formula 19]

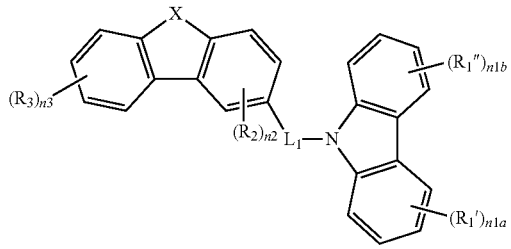

Formula (7)

where $R_2$, $R_3$, $R_1'$, $R_1''$, n2, n3, n1a, n1b, X, and $L_1$ are the same as $R_2$, $R_3$, $R_1'$, $R_1''$, n2, n3, n1a, n1b, X, and $L_1$ defined in the Formula (4).

The group represented by Formula (2) is preferably a group represented by Formula (5):

[Formula 20]

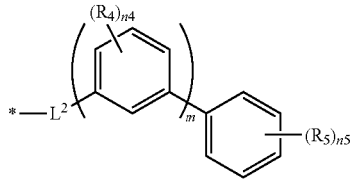

Formula (5)

where * represents a binding site to a structure represented by Formula (1), (3), (4), (6), or (7);

$L_2$, m, $R_4$, $R_5$, n4, and n5 are the same as $L_2$, m, $R_4$, $R_5$, n4, and n5 defined in Formula (2).

The group represented by Formula (5) has an aromatic ring bonded at a meta-position. Such a structure is more flexible than other linking structures. The present inventors infer that particularly a luminous host or a compound having such a flexible group represented by Formula (5) can be densely contained due to the interaction with a luminous dopant, and can significantly enhance the amorphousness of the layer.

In Formula (2) or (5), $L_2$ is preferably a single bond.

The single bond increases the proportion of the substituent represented by Formula (2) or (5) in the compound represented by each of Formulae (1) to (7) to enhance interaction of the compound with a dopant and attain a preferred dispersion state of the dopant. Such a compound can attain enhanced luminescence efficiency and a prolonged emission lifetime of the organic EL element. The single bond as the linking group can attain the highest electrical stability, which also attains enhanced luminescence efficiency and prolonged emission lifetime of the organic EL element.

In Formula (2) or (5), m is preferably an integer of 2 to 5. At m of 1 or less, the group represented by Formula (2) or (5) is no longer flexible, and the resulting compound cannot be readily formed into a thin film, which is readily crystallized during storage under high temperature and high humidity. Such a thin film with altered morphology degrades the performance of the organic EL element.

At m of 10 or more, the overall compound has a significantly large molecular weight, and readily decomposes under high temperature during deposition. Such a compound has remarkably low solubility, resulting in uneven coating. Accordingly, m of 2 to 10 attains a flexible compound, and m in the range of 2 to 5 most effectively attains a compound having flexibility, ability for deposition, and solubility.

In Formula (1), (3), (4), (6), or (7), $L_1$ is preferably a single bond.

In Formula (1), (3), (4), (6), or (7), X preferably represents an oxygen atom. The inventors infer that the oxygen atom enhances the toughness of the compounds represented by these formulae compared to a sulfur atom, in regard to X, attaining a significantly prolonged emission lifetime.

The host compound preferably has a high glass transition temperature (Tg) in the range of preferably 100° C. or more, more preferably 120° C. or more, most preferably 130° C. or more in view of long-term stability and effective production of organic EL elements.

In a combination of the compound represented by Formula (1) with a phosphorescent compound described later, the compound preferably has a minimum excited triplet energy ($T_1$) higher than that of the phosphorescent compound. $T_1$ is preferably 2.7 eV or more, more preferably 2.75 eV or more, most preferably 2.8 eV or more.
Specifically, non-limiting examples of the compounds represented by Formulae (1) to (7) include the following.
[Formula 21]
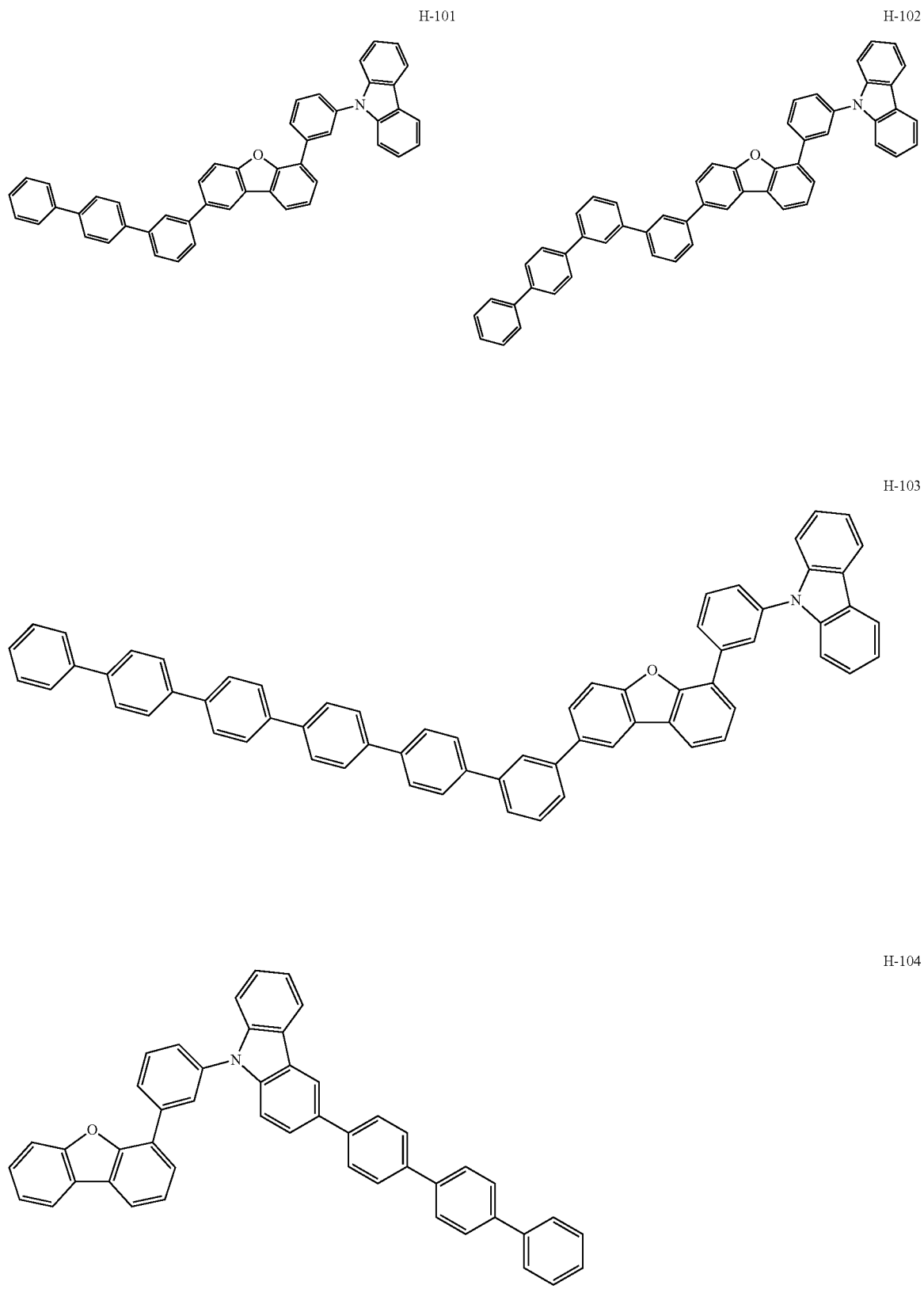

[Formula 22]
H-105
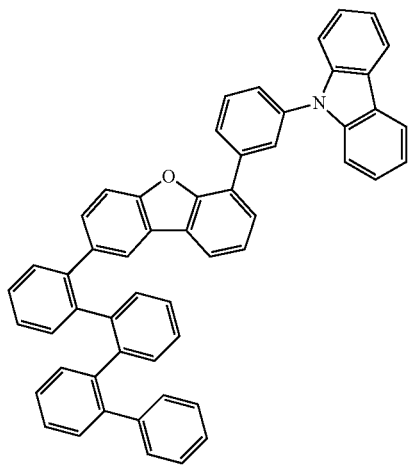
H-106
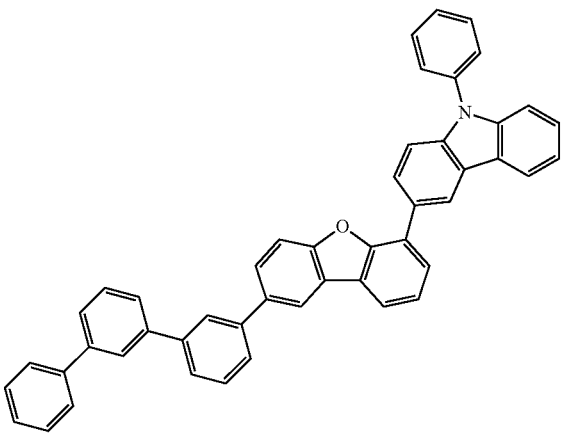
H-107
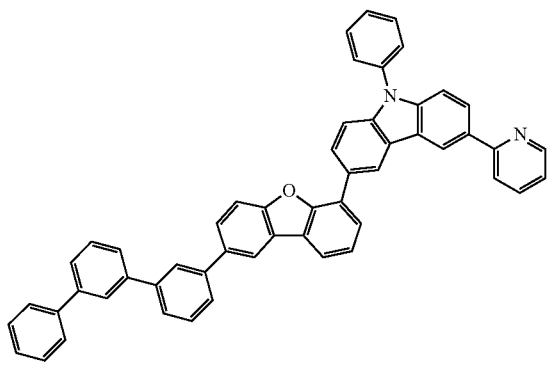
H-108
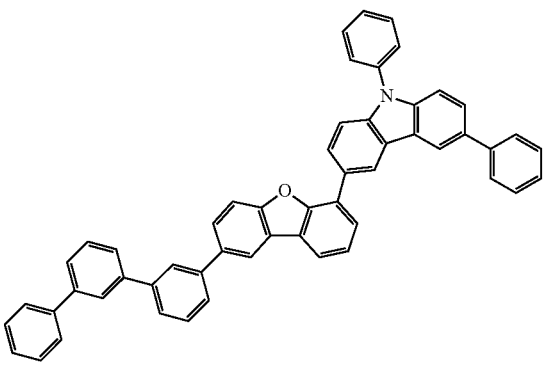
[Formula 23]
H-109
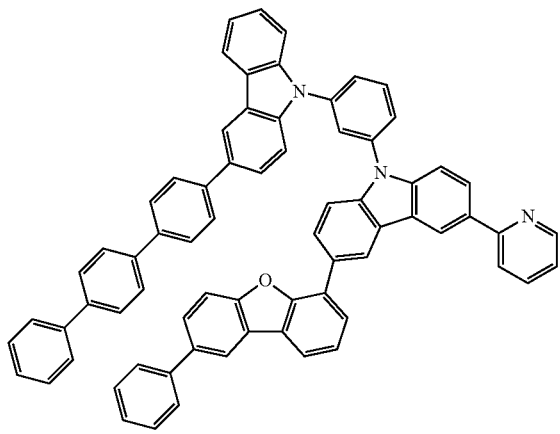
H-110
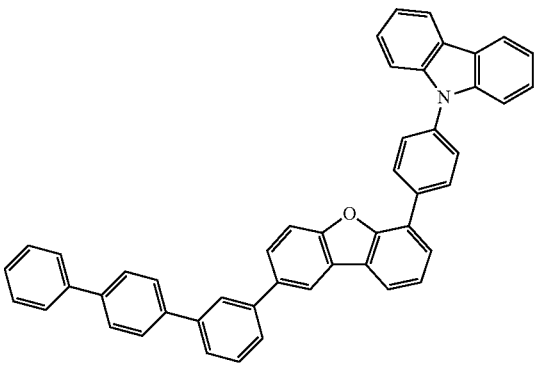

H-111
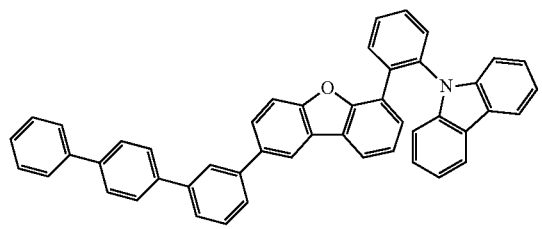
H-112
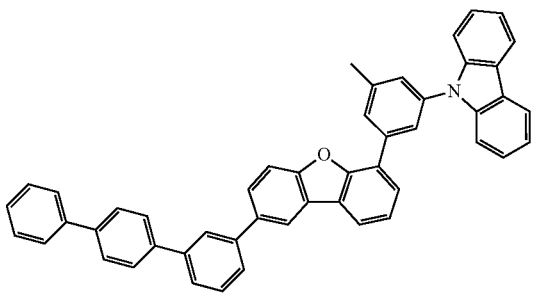
[Formula 24]
H-201
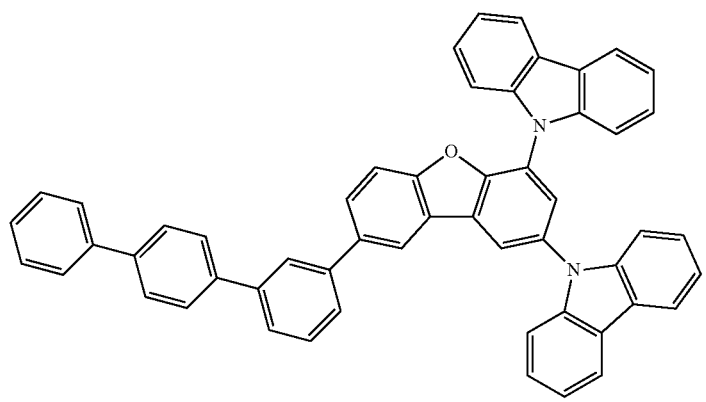
H-202
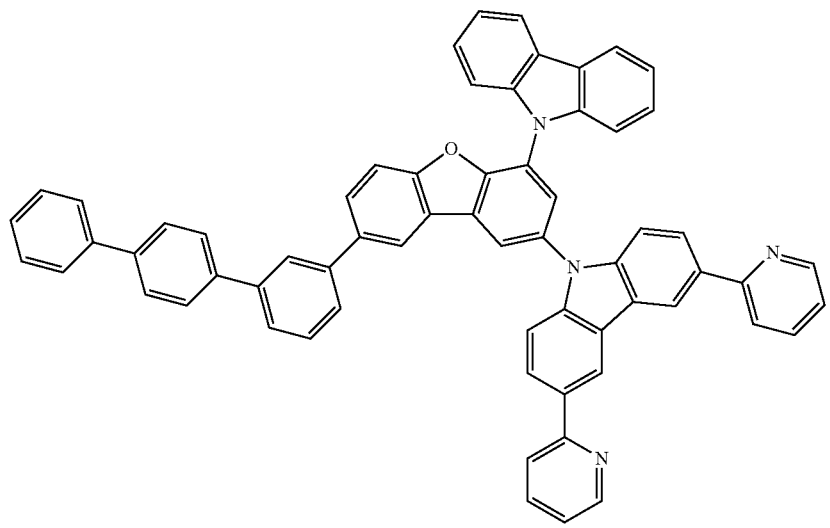

H-203
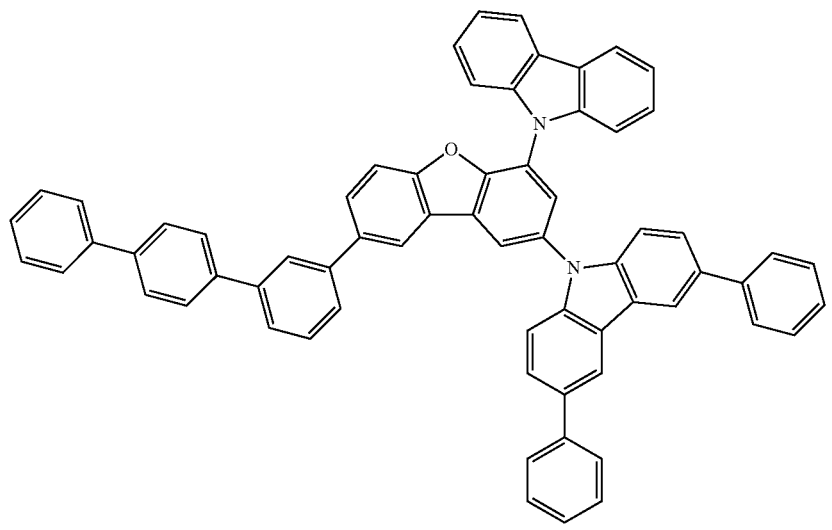
H-204
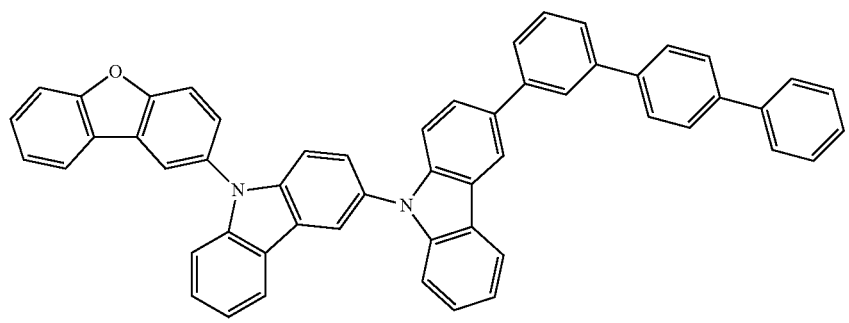
[Formula 25]
H-205
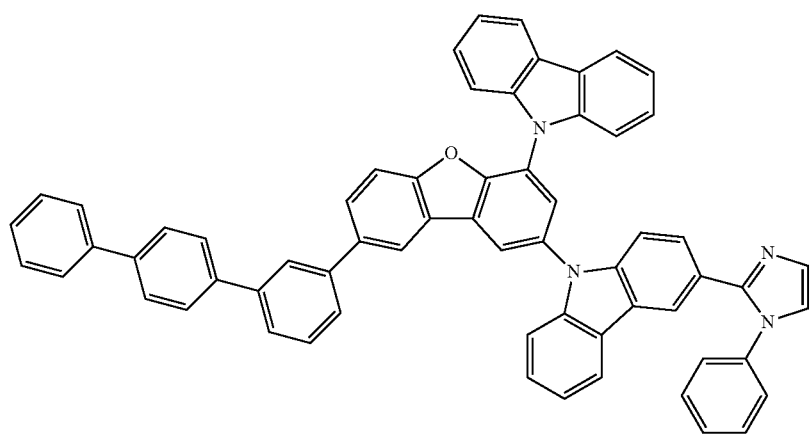

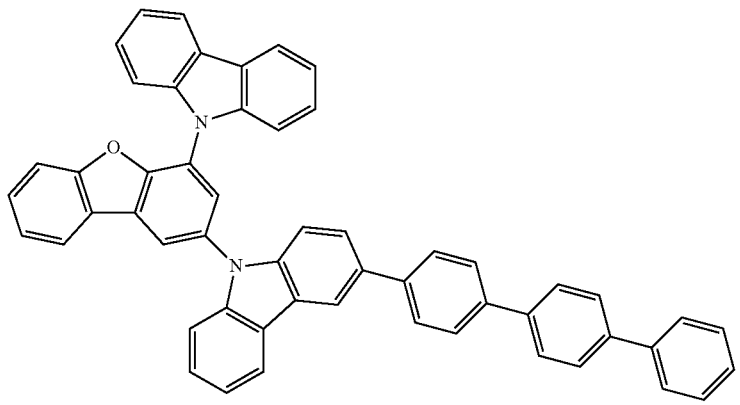
H-206
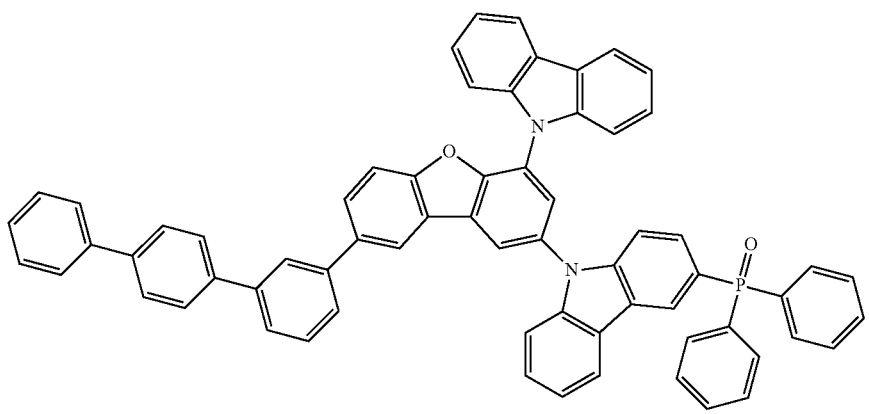
H-207
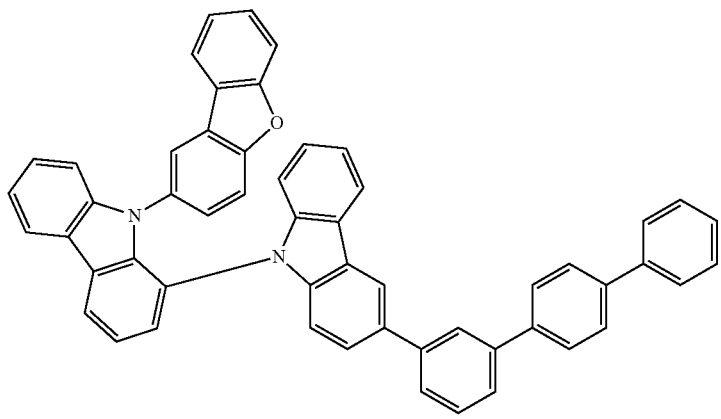
H-208

[Formula 26]
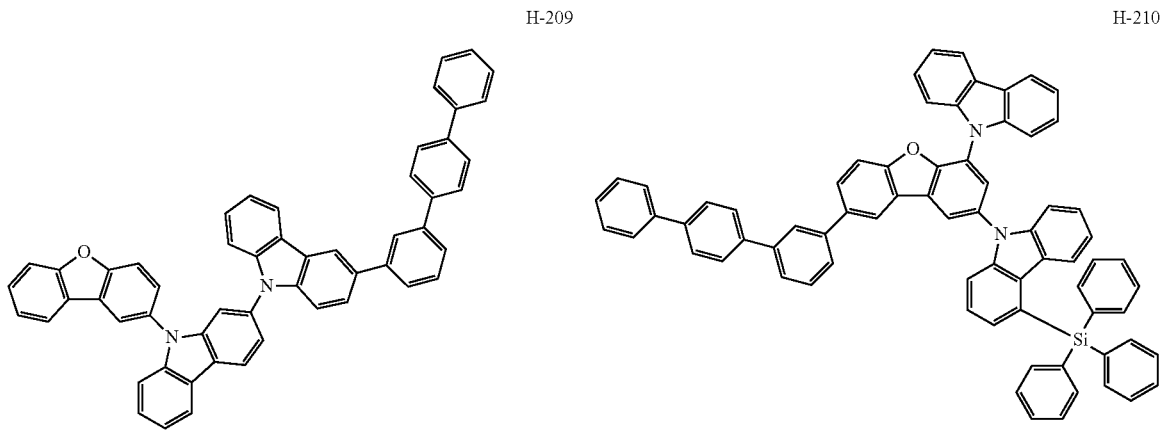
H-209
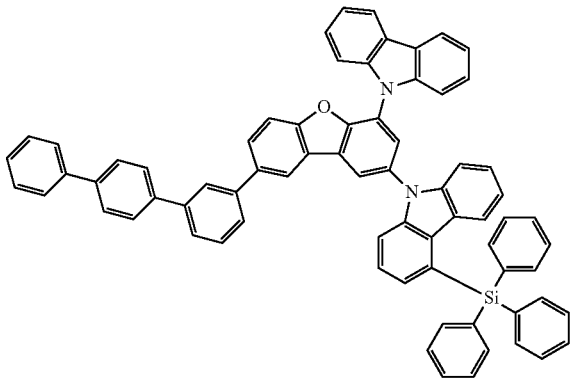
H-210
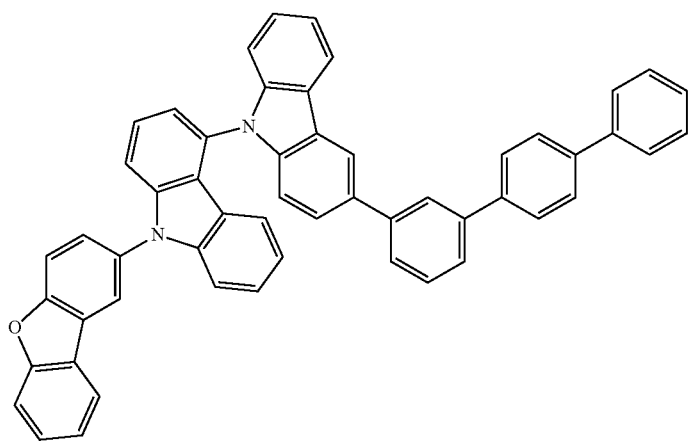
H-211
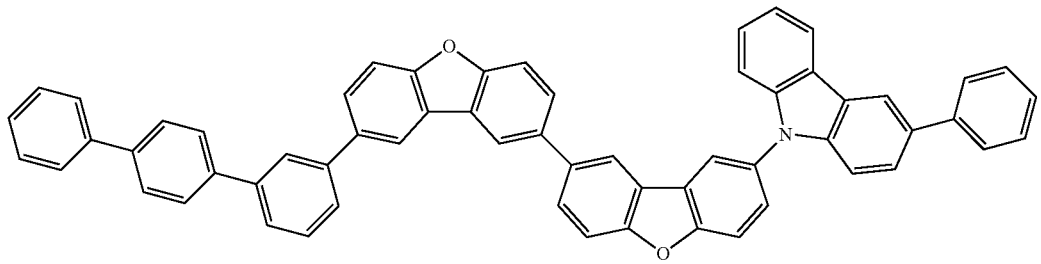
H-212
[Formula 27]
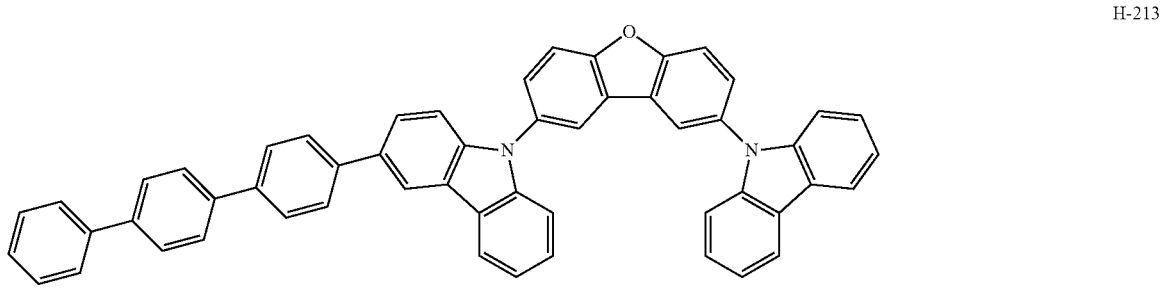
H-213

H-214
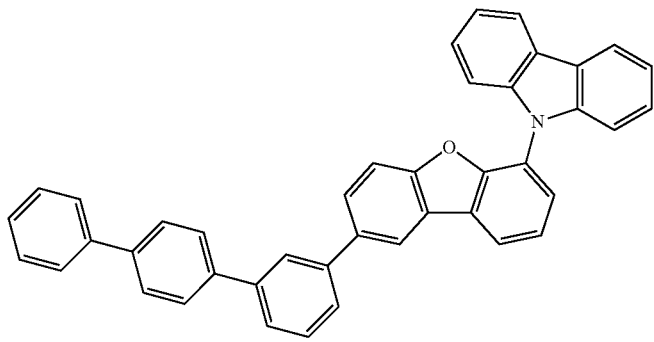
H-215
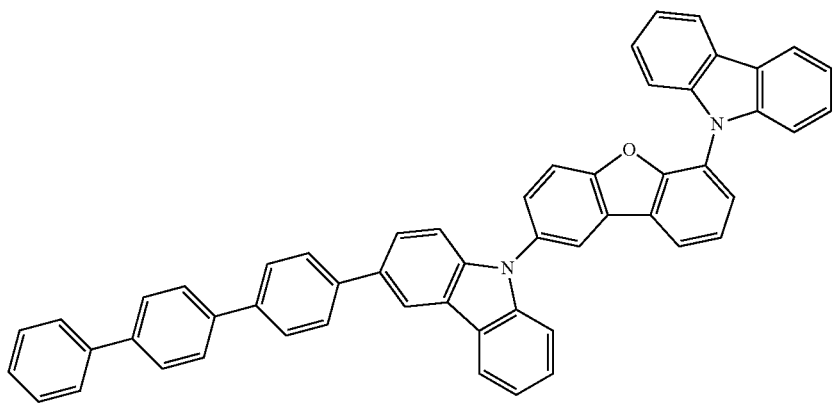
H-216
H-217
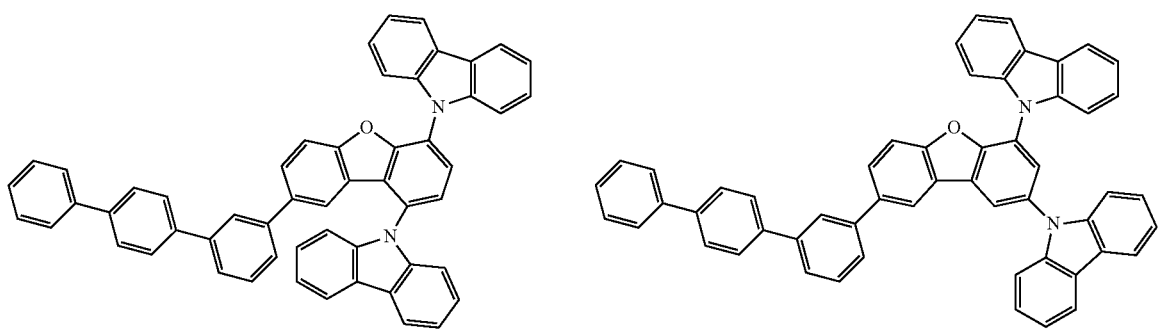
[Formula 28]
H-301
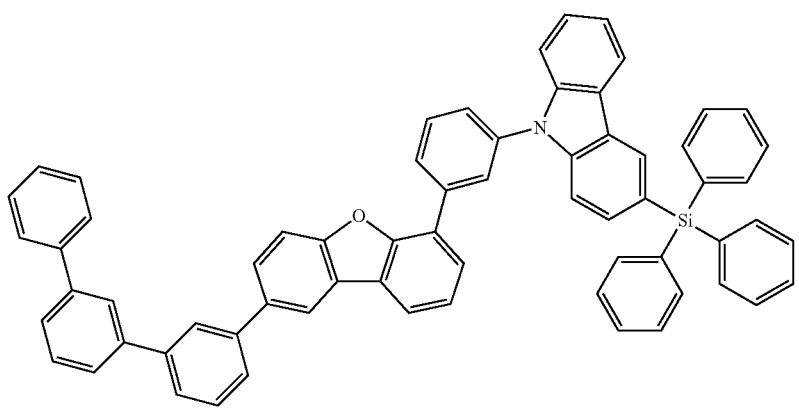

-continued
H-302
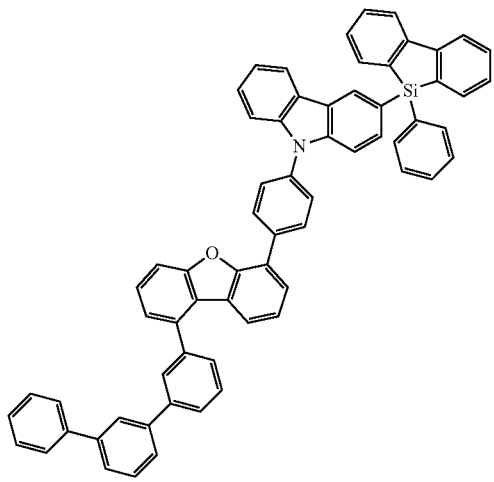
H-303
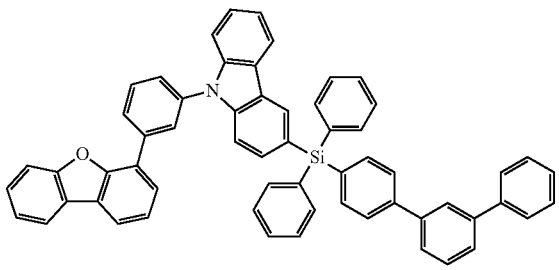
H-304
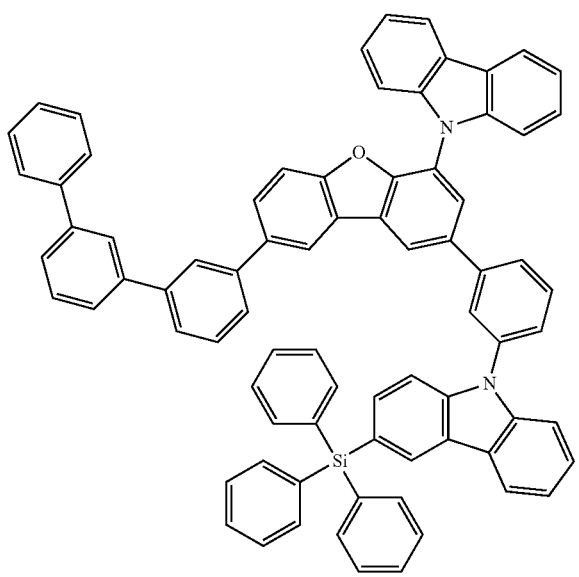
[Formula 29]
H-305
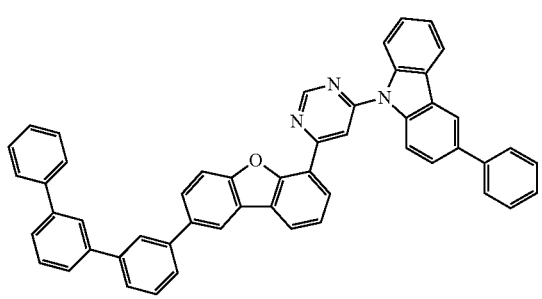
H-306
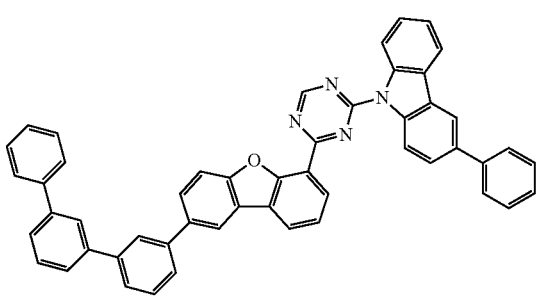

-continued
H-307
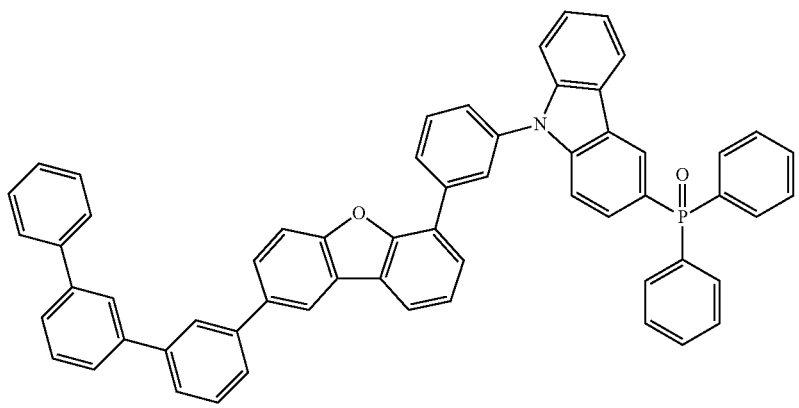
H-308
H-309
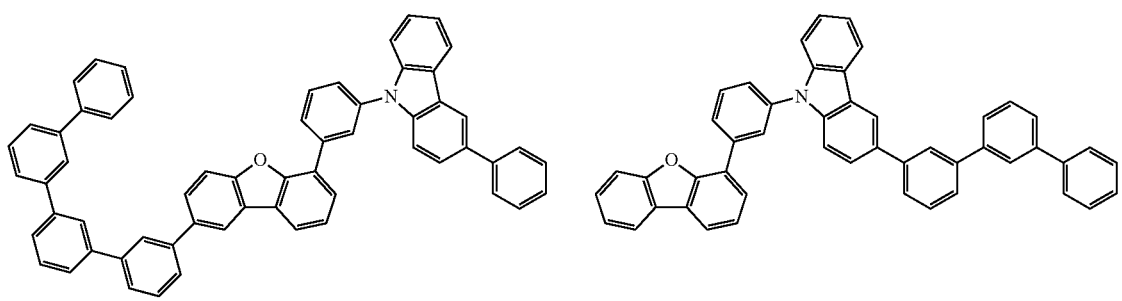
[Formula 30]
H-310
H-311
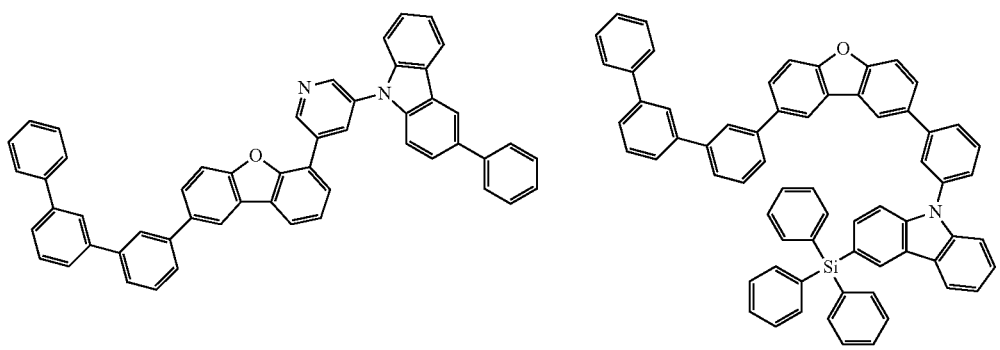
H-312
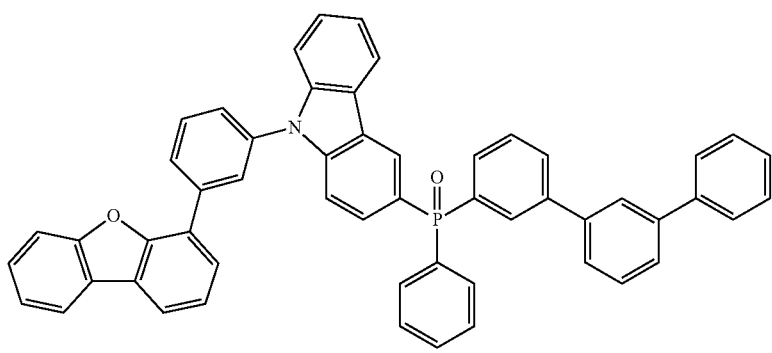

H-313
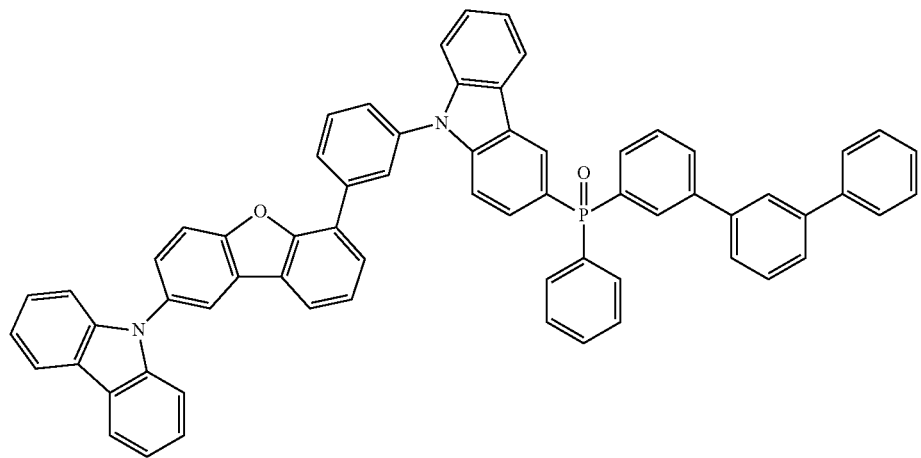
[Formula 31]
H-314
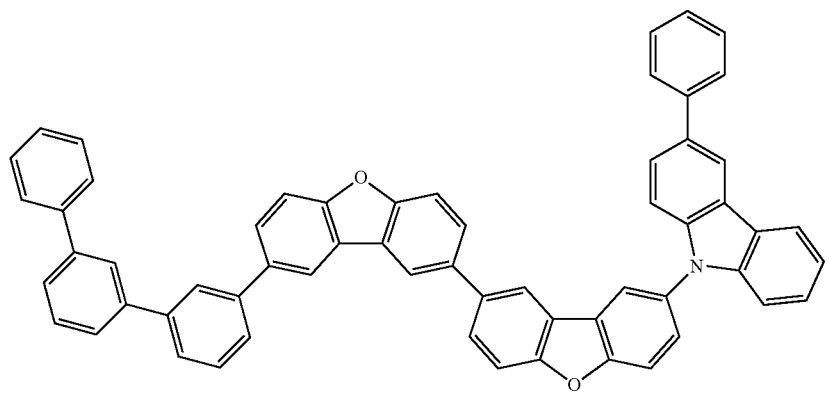
H-315
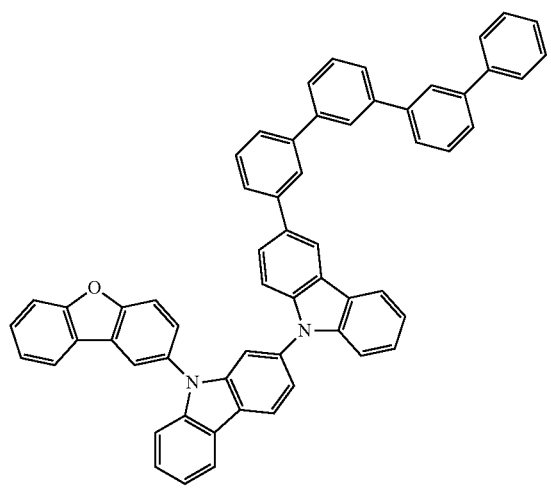
H-316
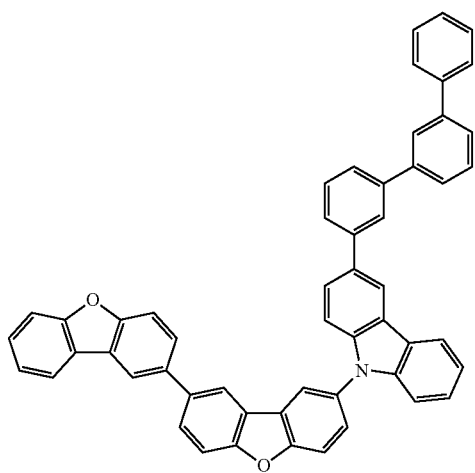

-continued
H-317 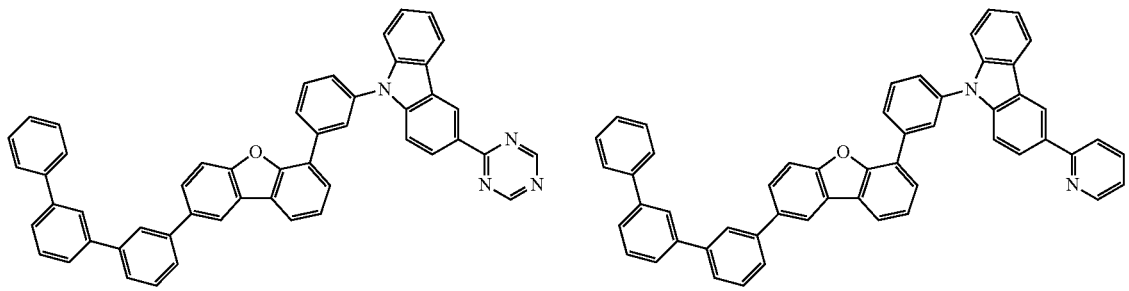 H-318
[Formula 32]
H-319
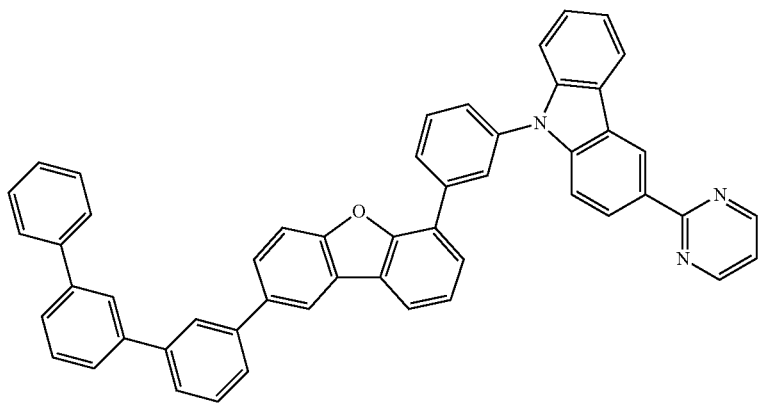
H-320
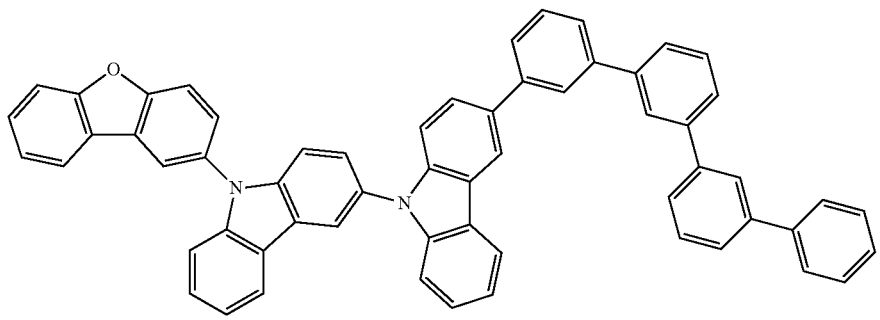
H-321
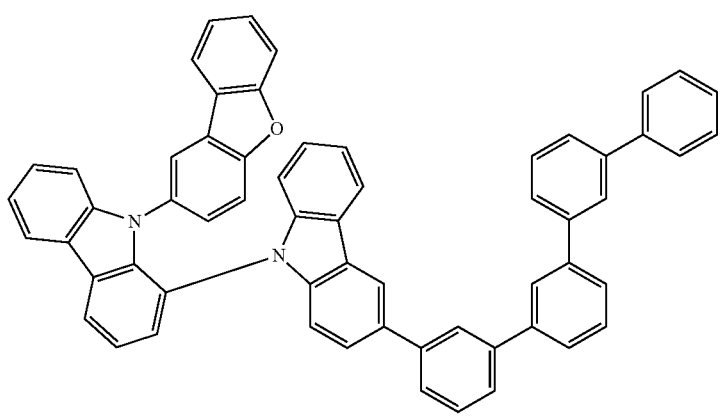

-continued
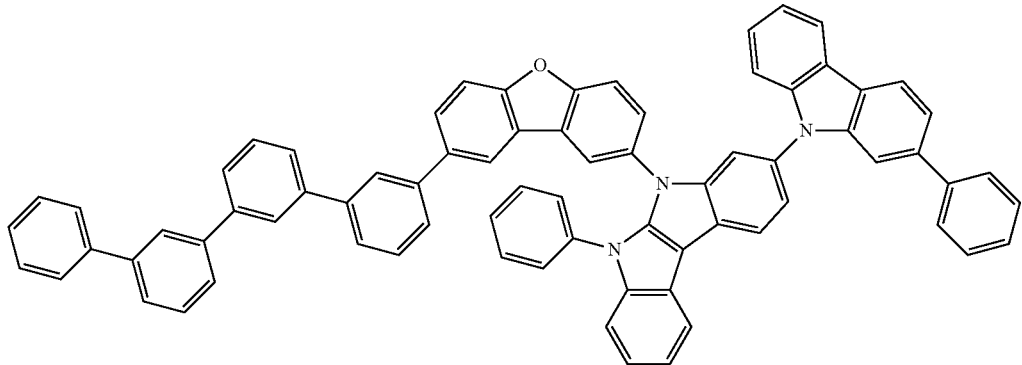
H-322
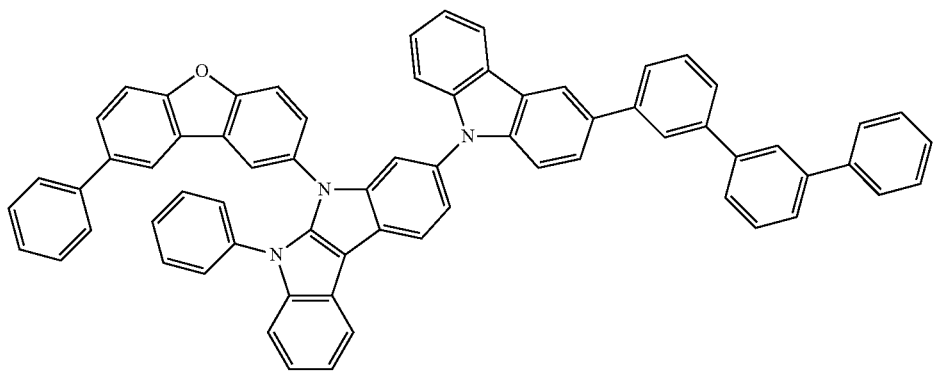
H-323
[Formula 33]
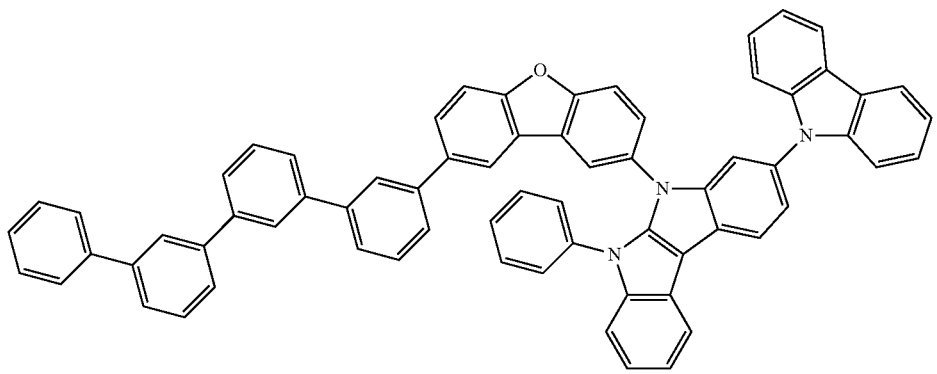
H-324

H-325
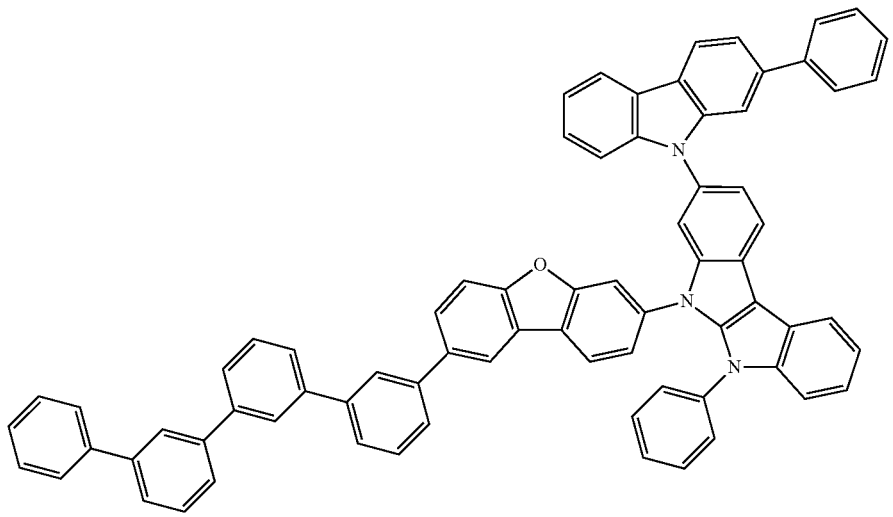
H-326
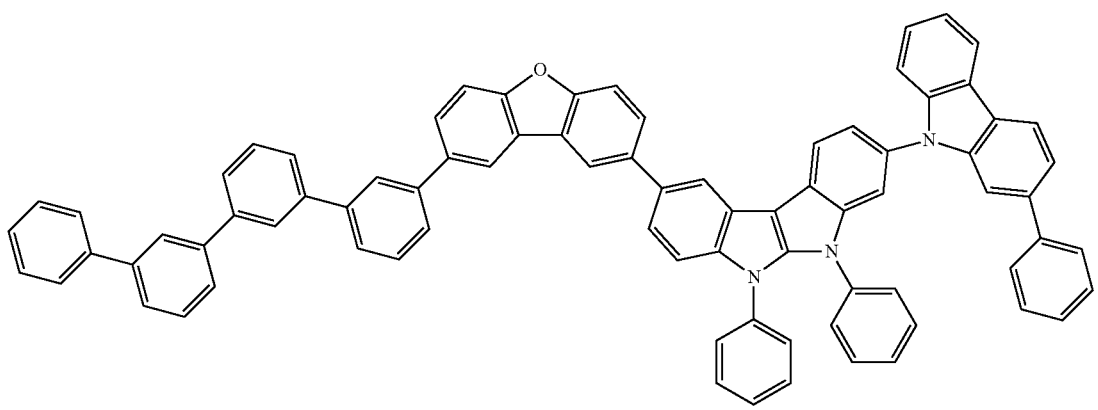
H-327
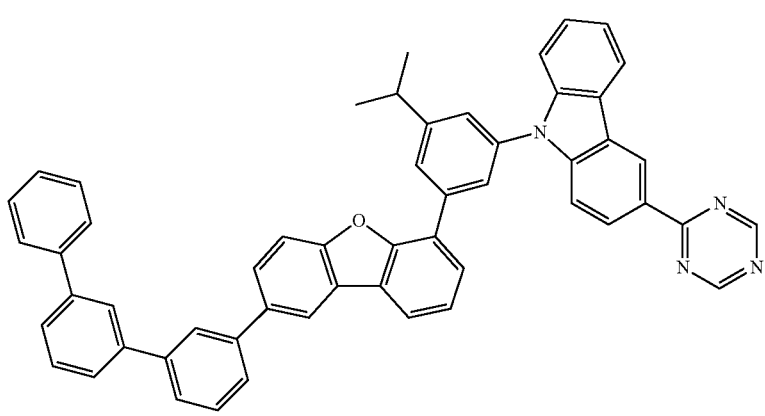

[Formula 34]
H-401
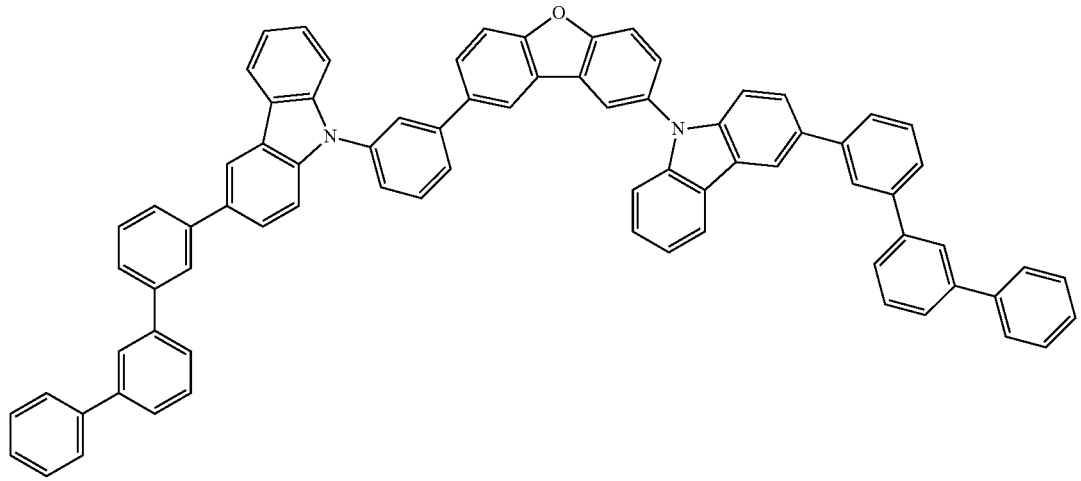
H-402
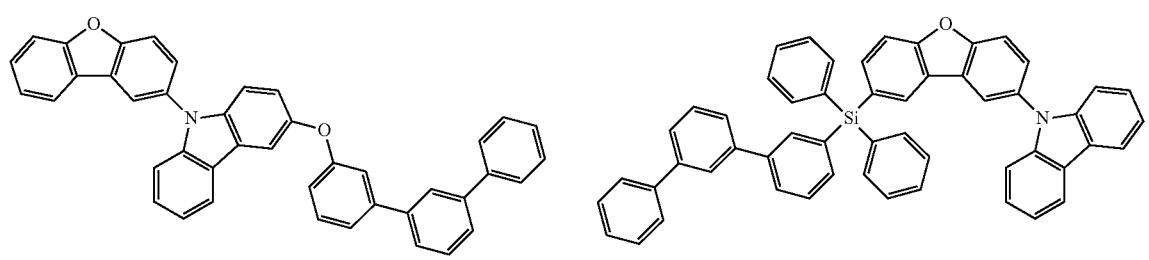
H-403
H-404
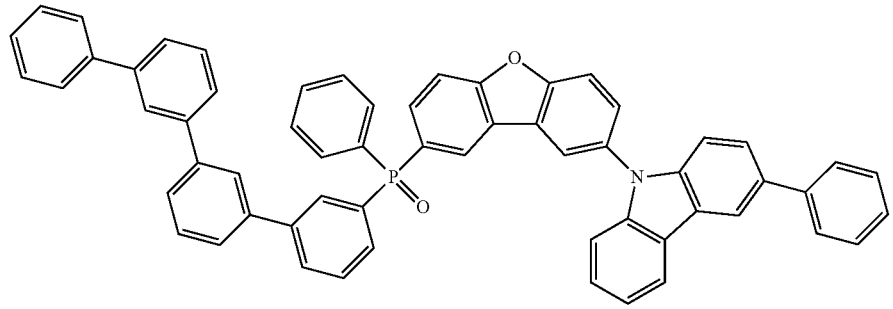
H-405
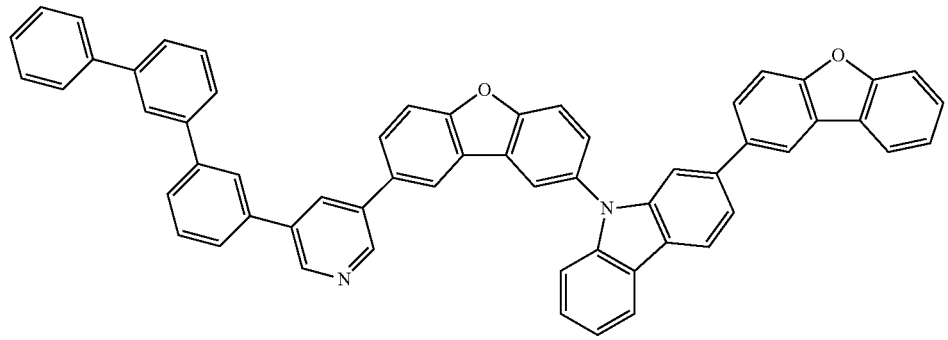

-continued
H-406
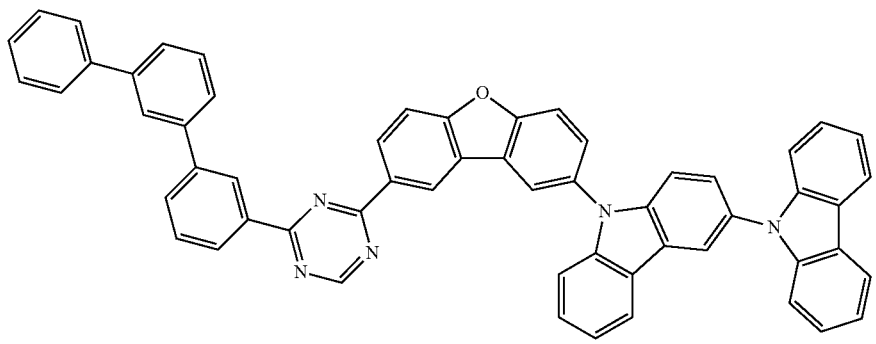
[Formula 35]
H-407
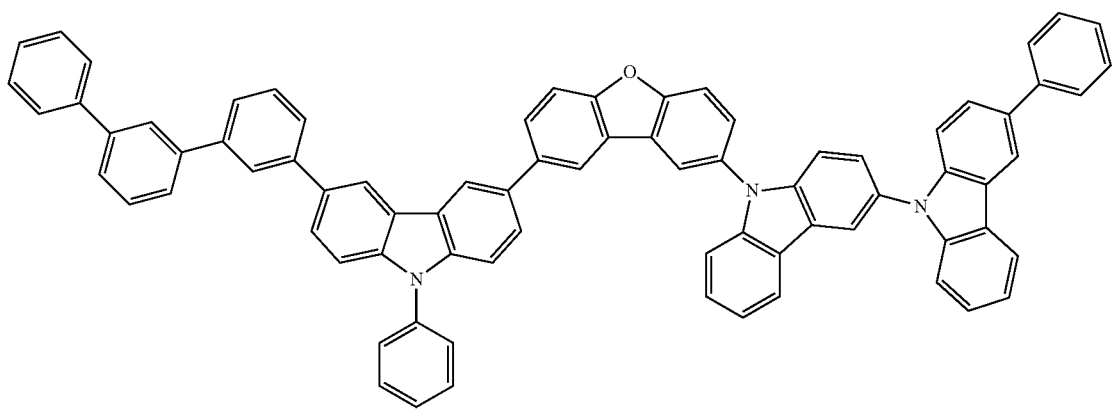
H-408
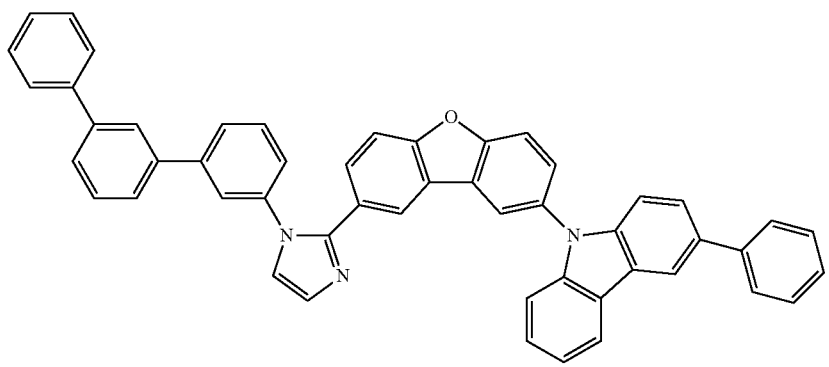
H-409
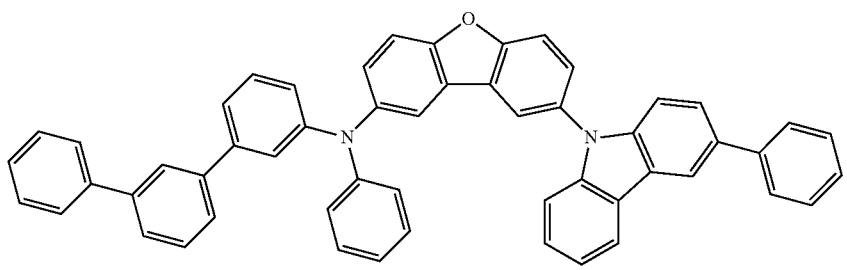

-continued
H-410
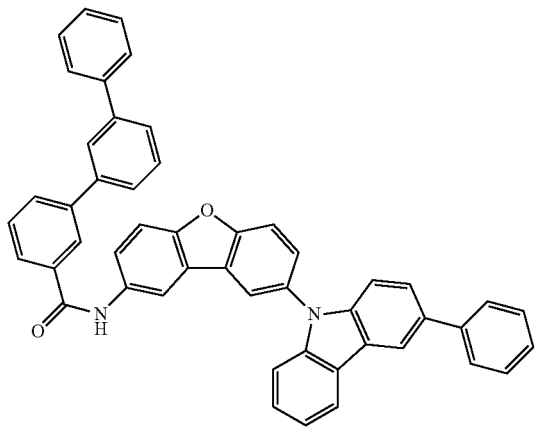
H-411
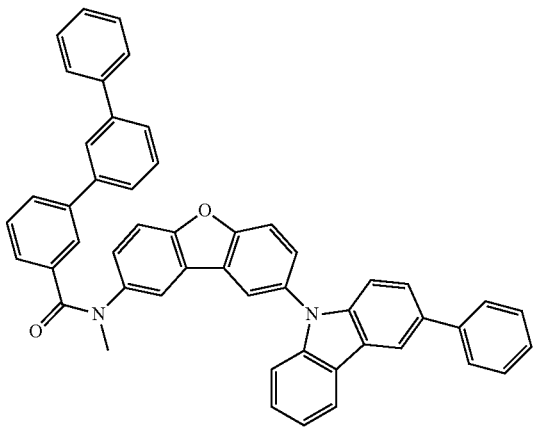
[Formula 36]
H-412
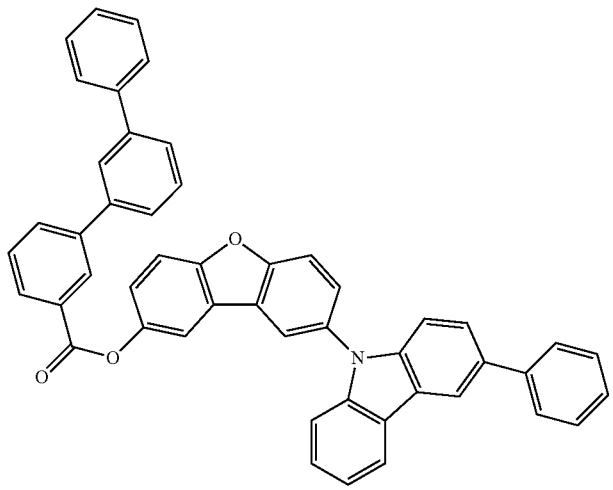
H-413
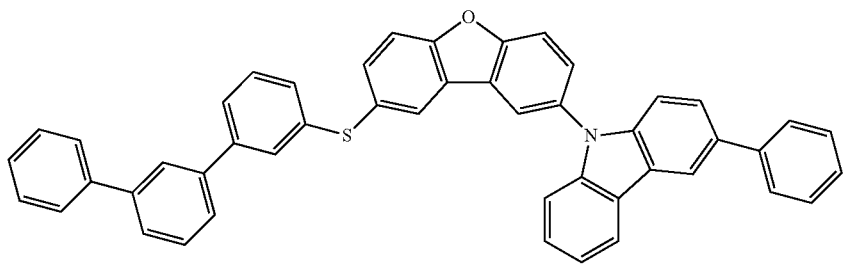
H-414
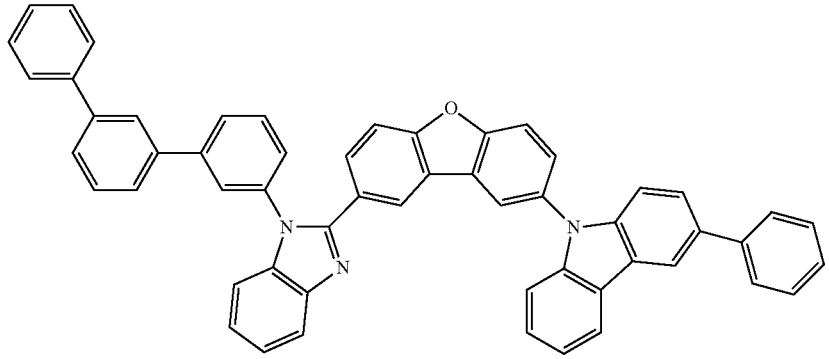

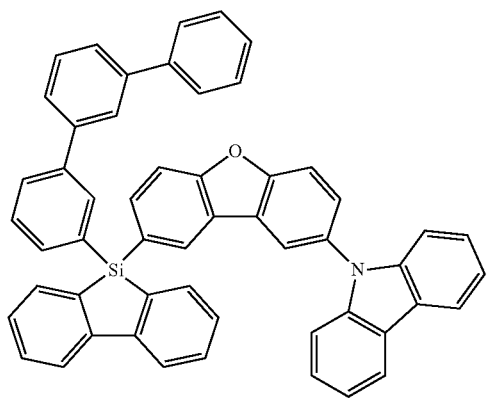
H-415
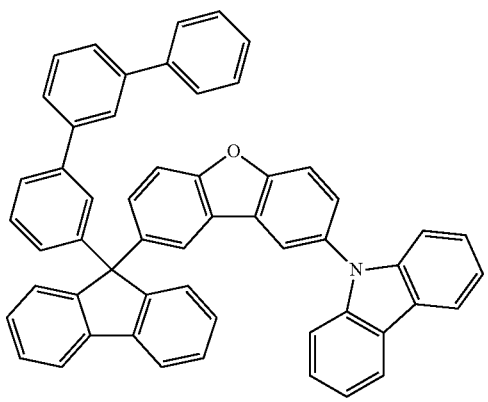
H-416
[Formula 37]
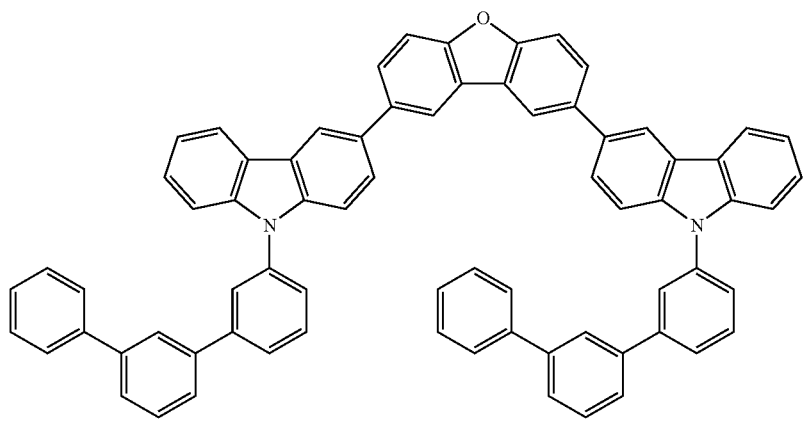
H-418
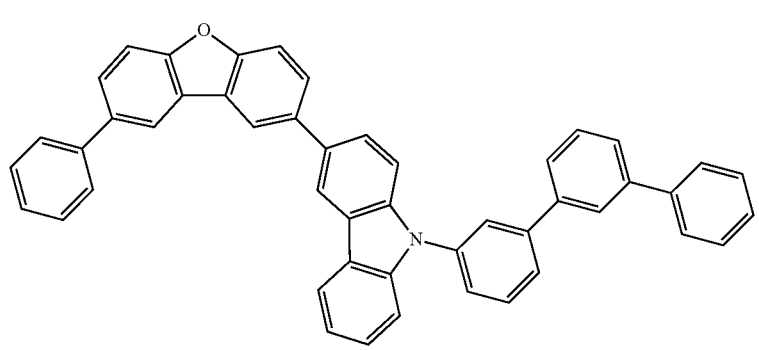
H-420

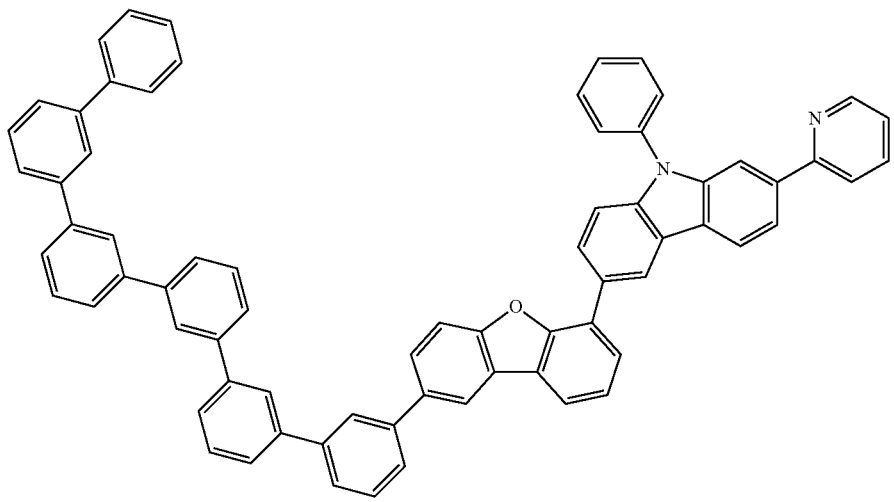
H-421
[Formula 38]
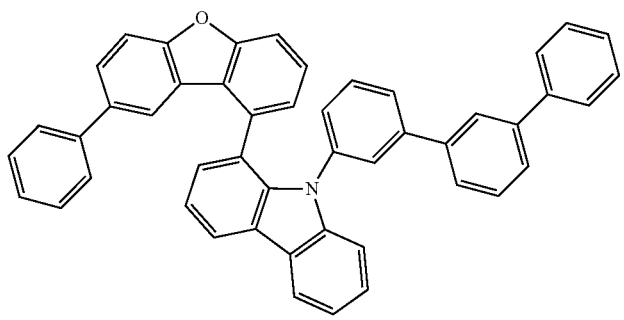
H-422
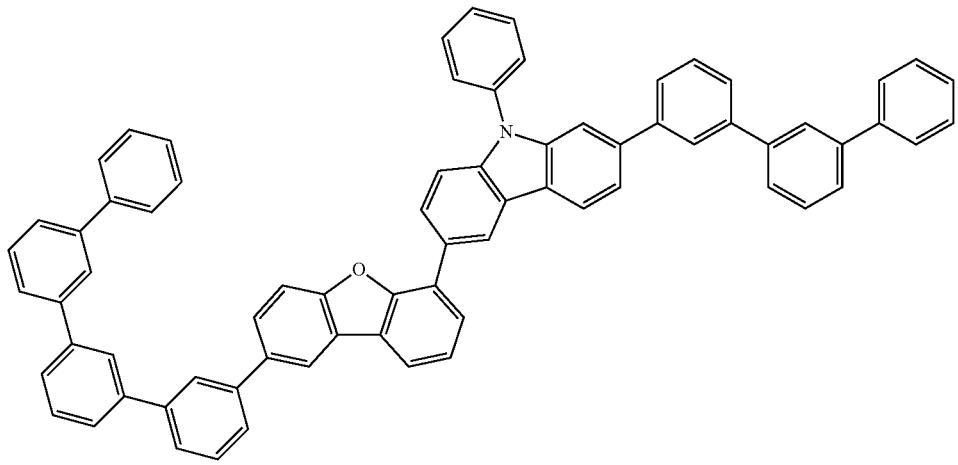
H-423

-continued
H-424
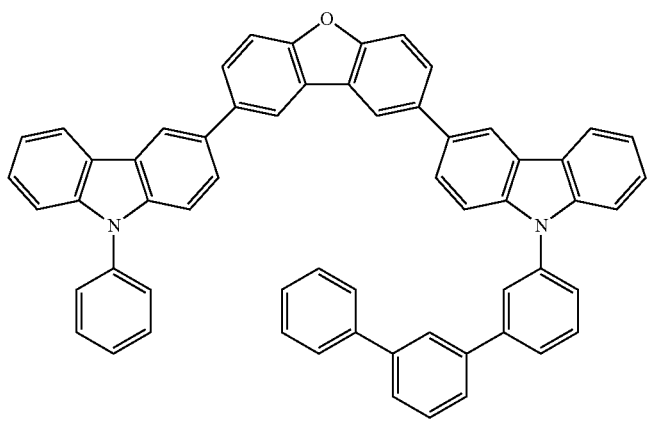
H-425
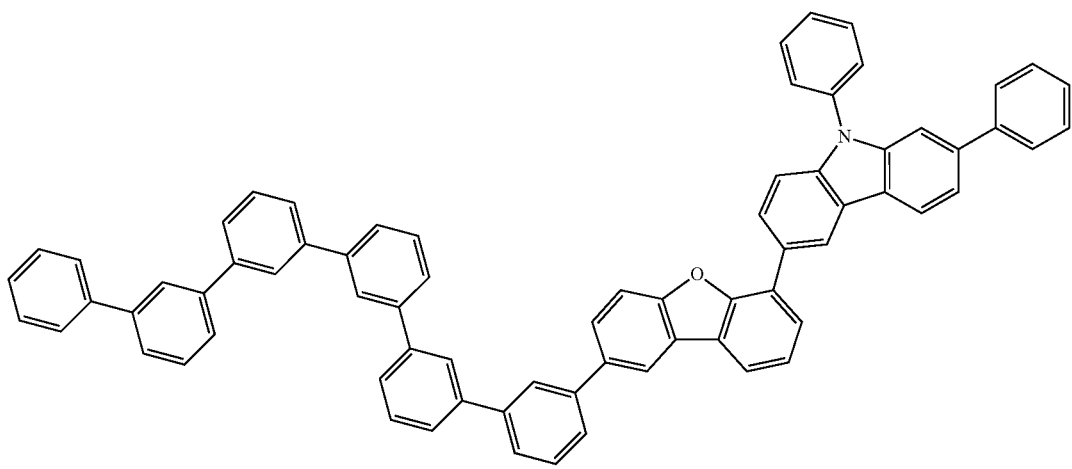
[Formula 39]
H-426 H-427
H-428 H-429
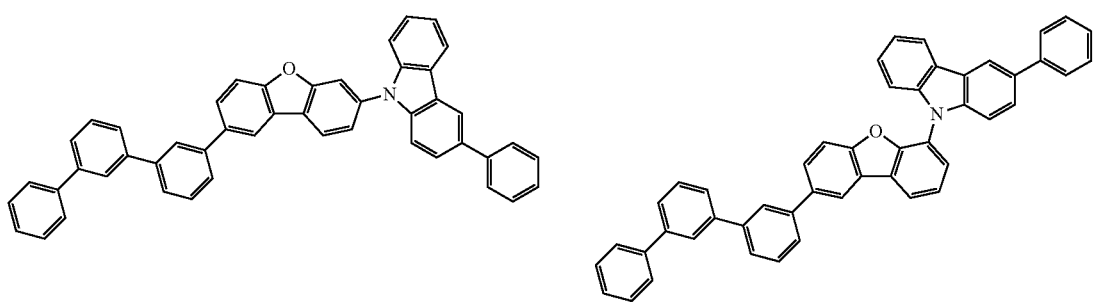
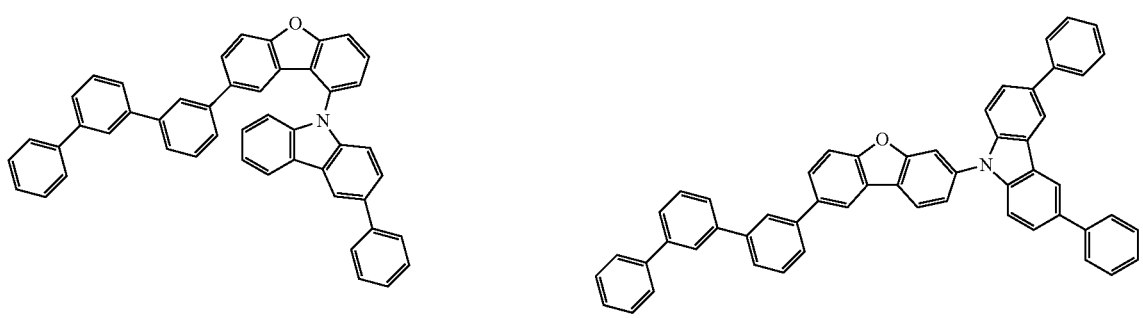

H-430
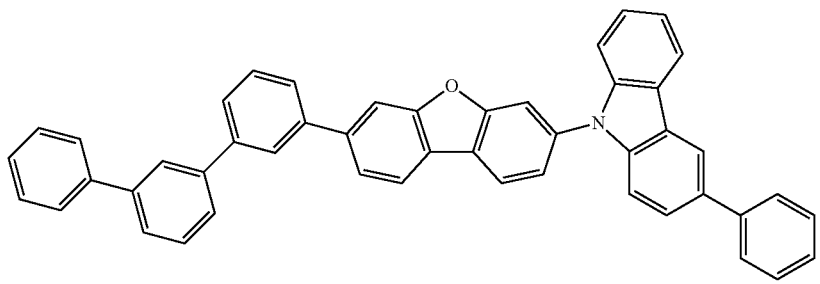
[Formula 40]
H-431
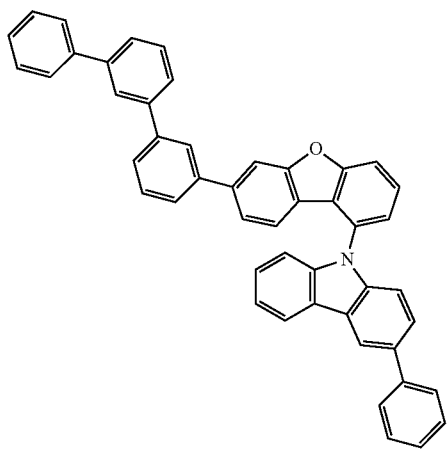
H-432
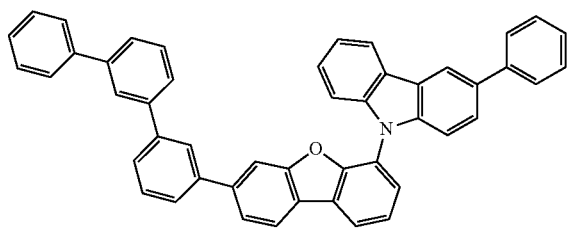
H-433
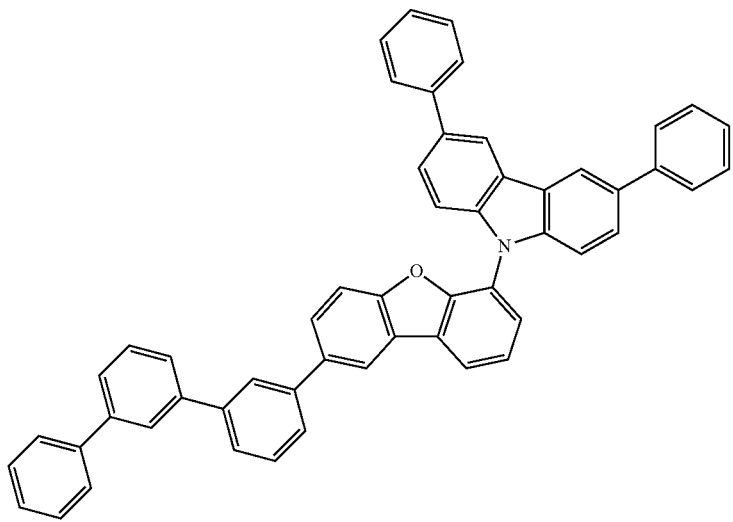

[Formula 41]
H-434
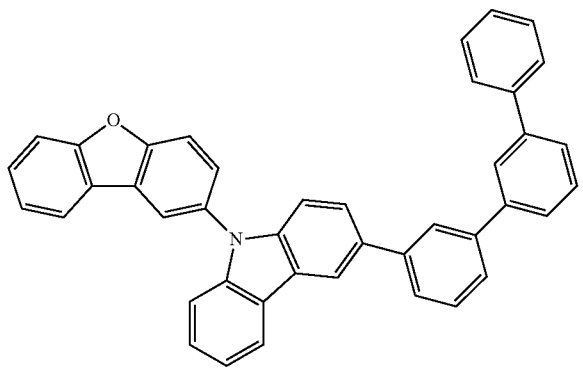
H-435
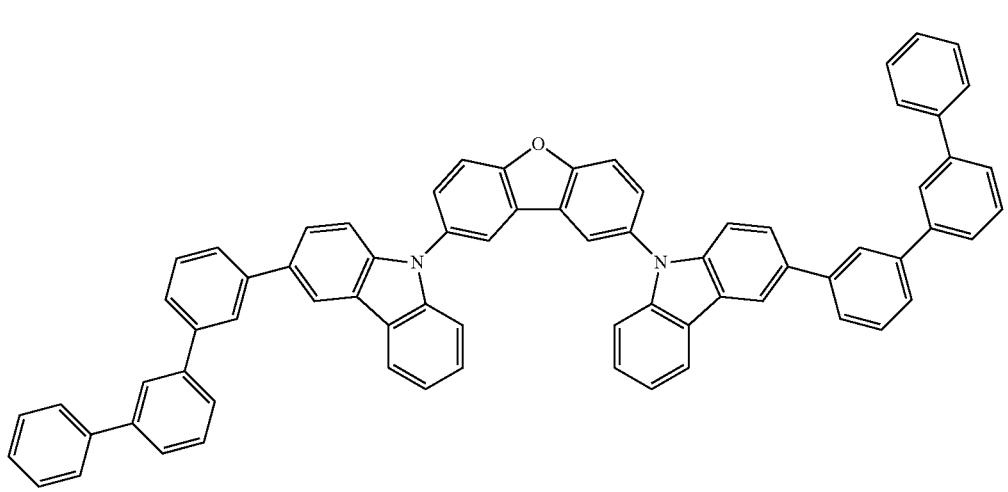
H-436
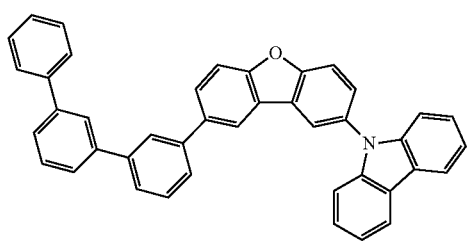
H-437
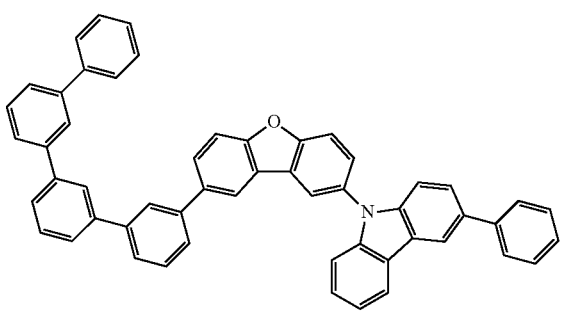
[Formula 42]
H-438
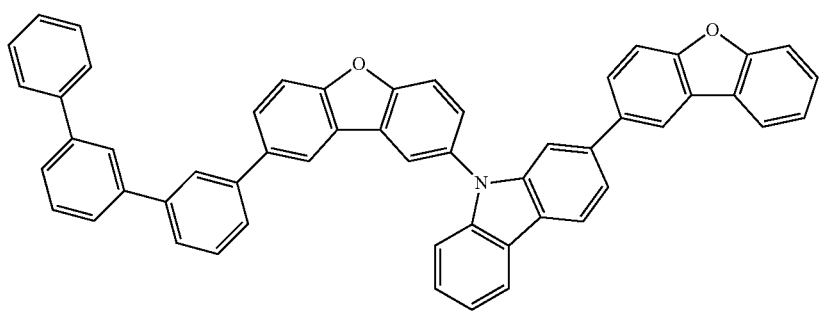

H-439
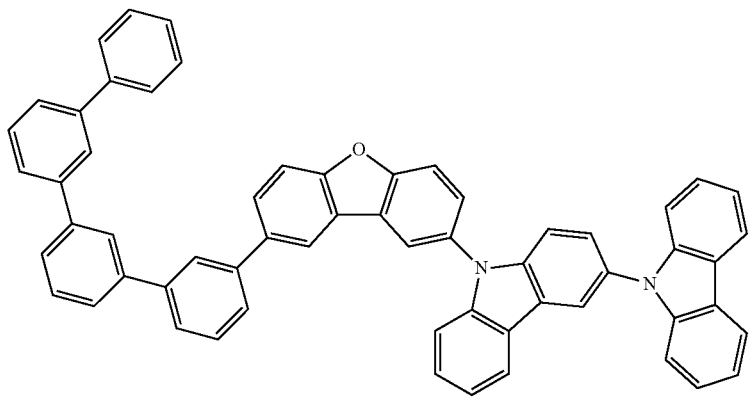
H-440
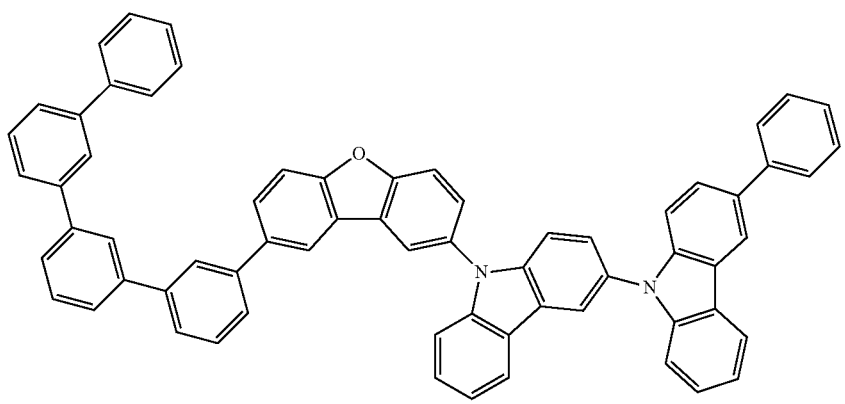
H-441
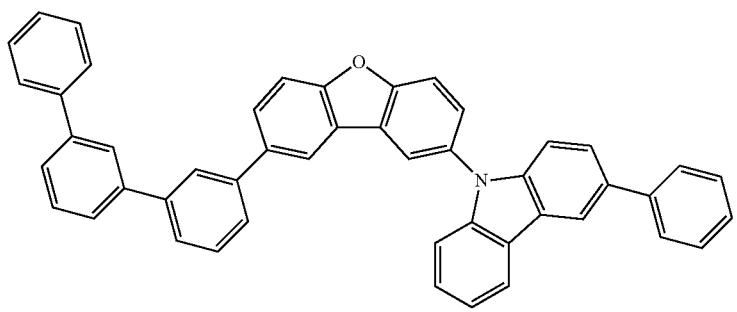
[Formula 43]
H-442
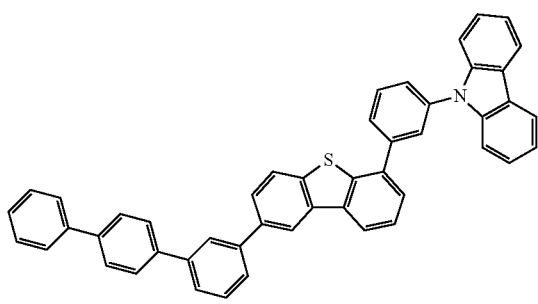
H-443
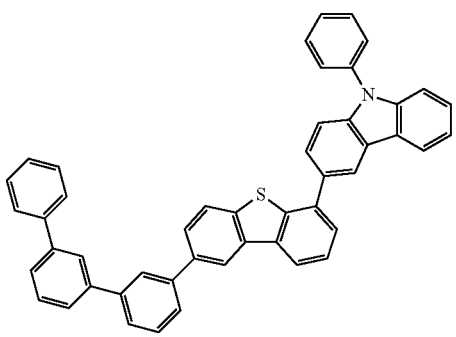

-continued
H-444
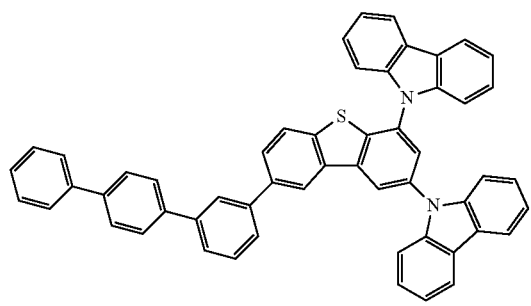
H-445
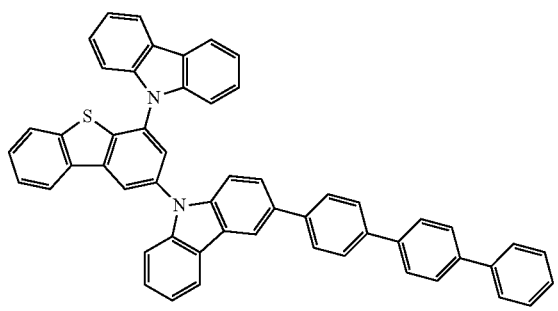
[Formula 44]
H-446
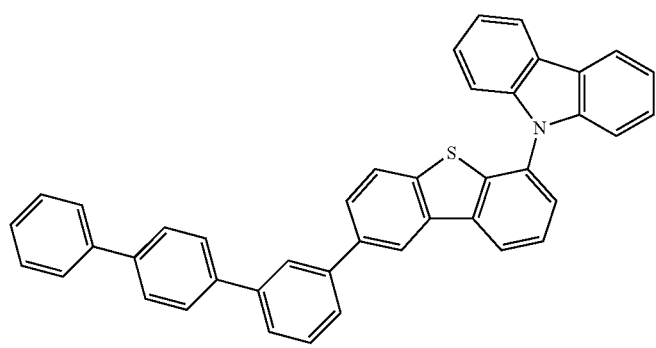
H-447
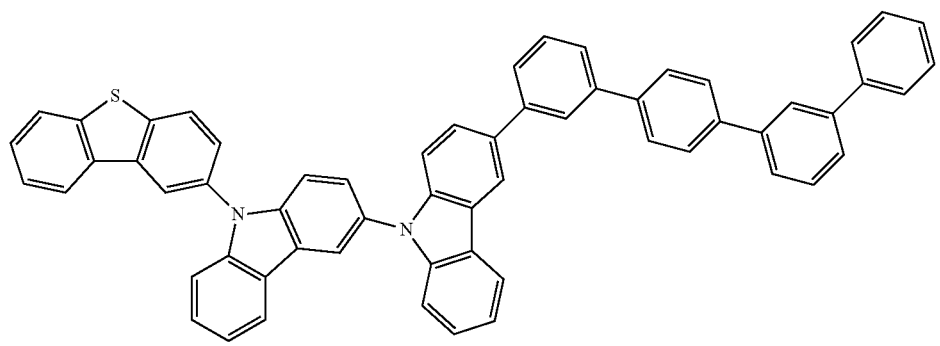
H-448
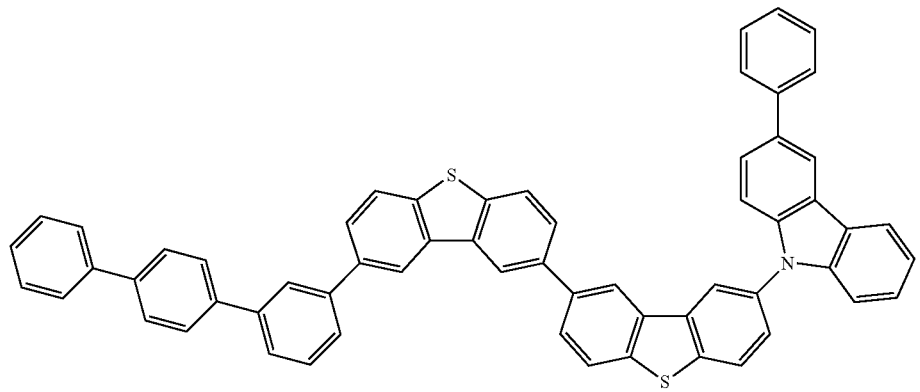

-continued
[Formula 45]
H-449
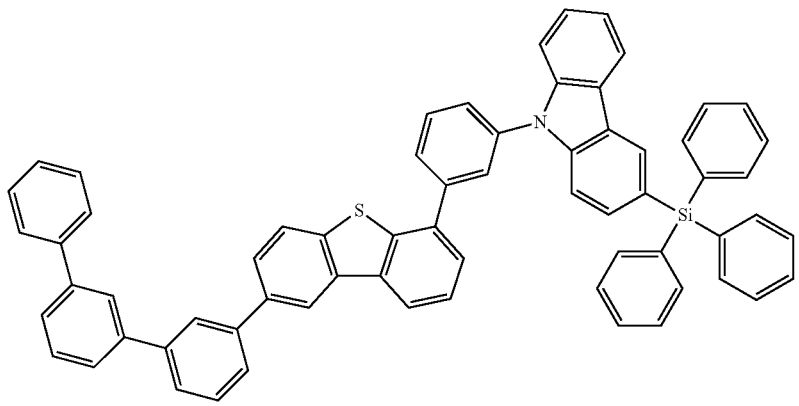
H-450
H-451
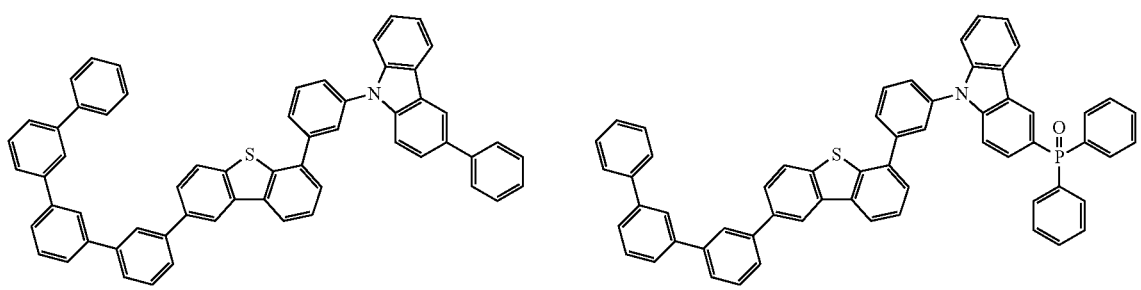
H-452
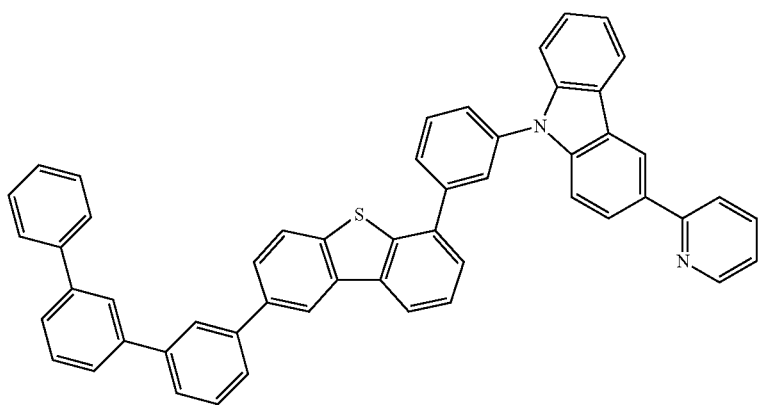
[Formula 46]
H-453
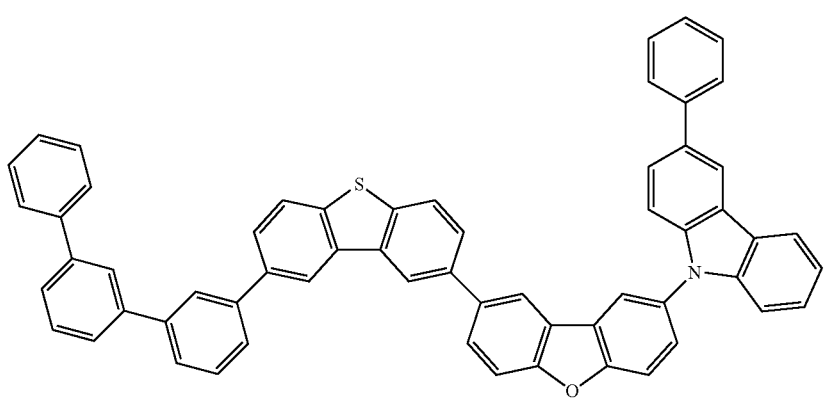

H-454
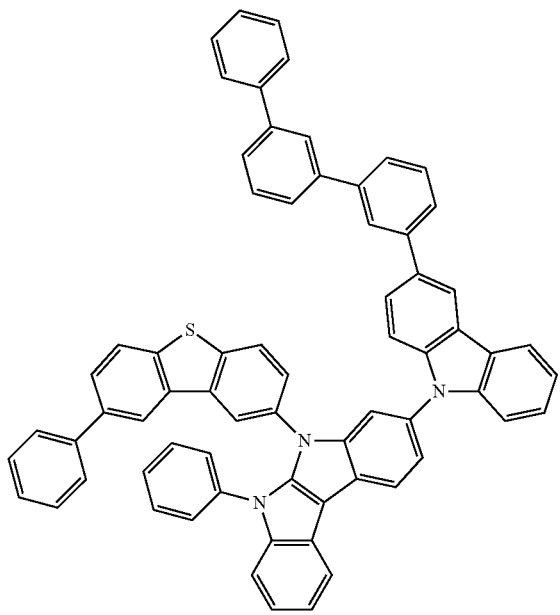
H-455
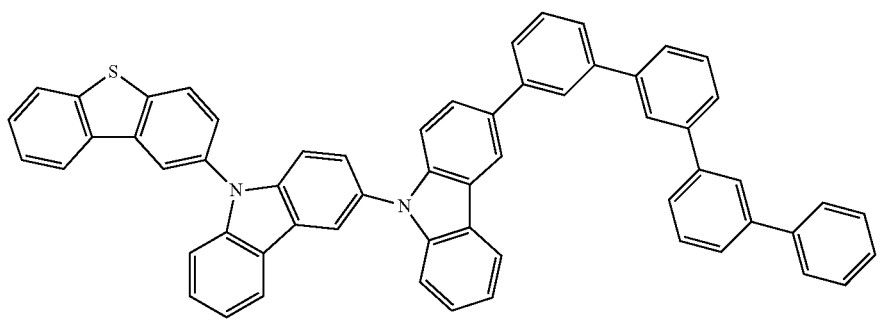
[Formula 47]
H-456 H-457
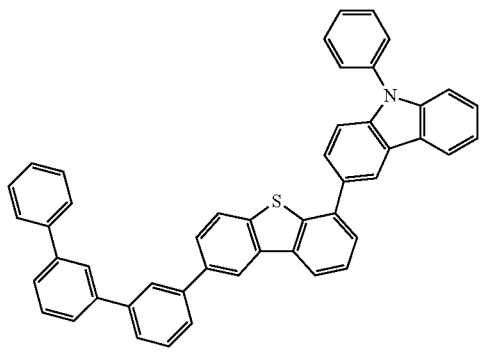 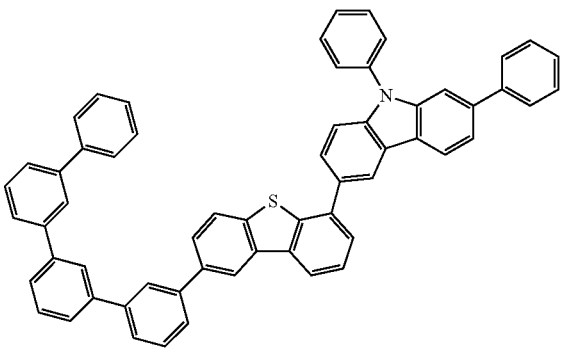

-continued
H-458  H-459
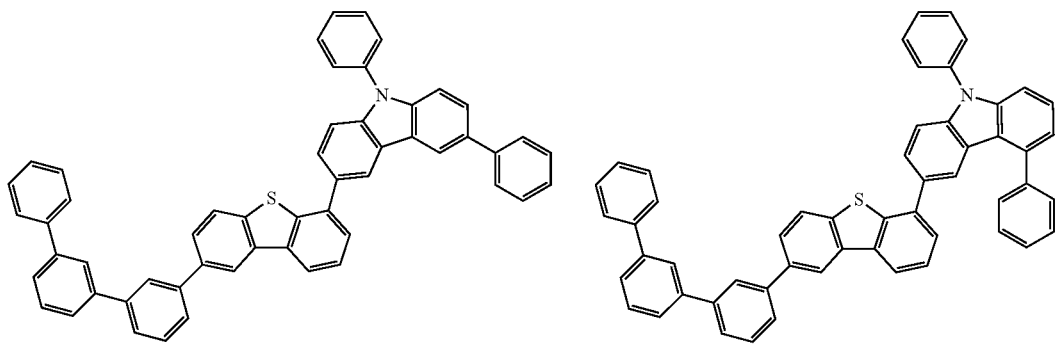
[Formula 48]
H-460  H-461
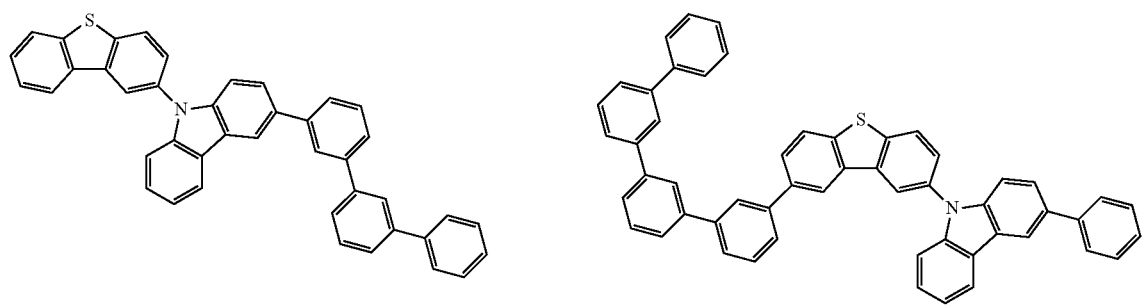
H-462  H-463
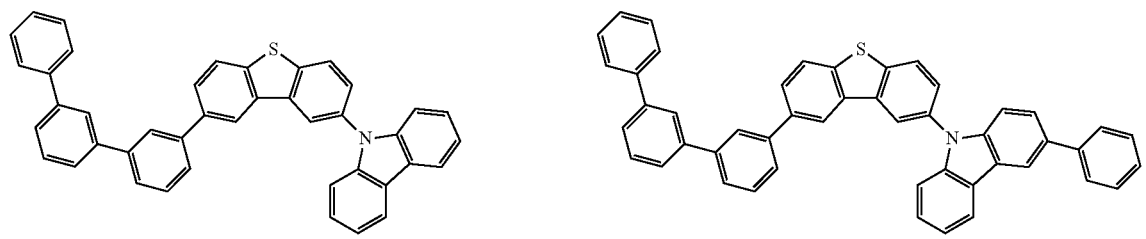
[Formula 49]
H-464  H-465
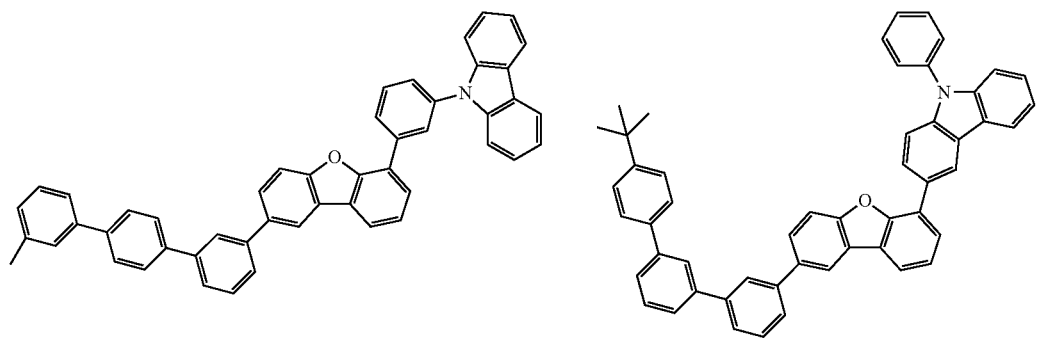

-continued
H-466
H-467
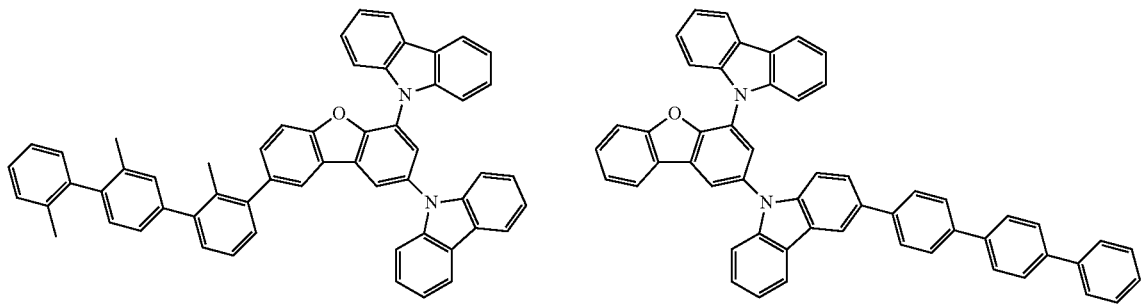
[Formula 50]
H-468
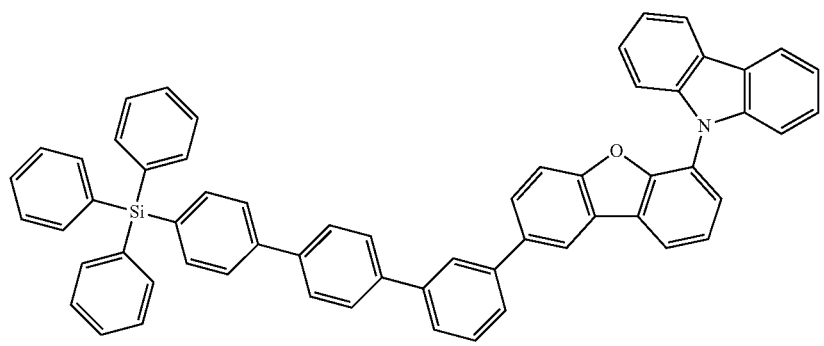
H-469
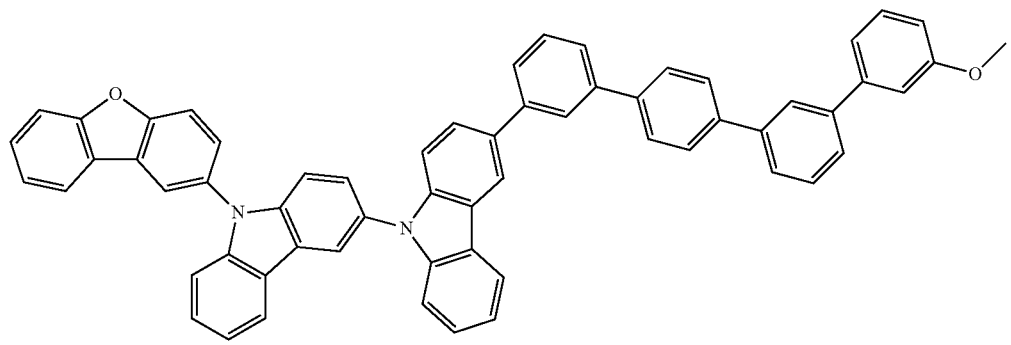
H-470
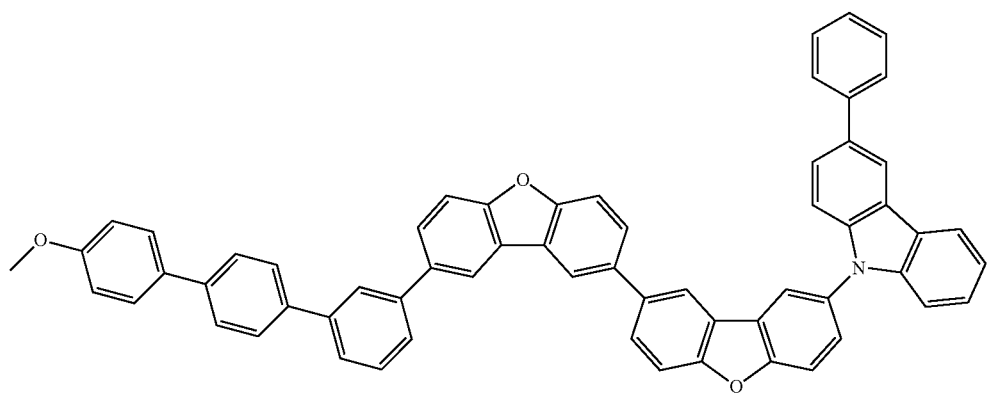

[Formula 51]
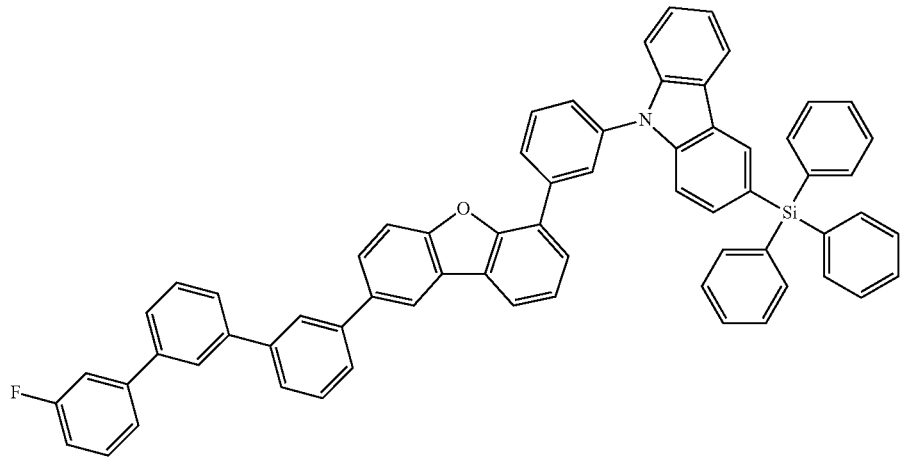
H-471
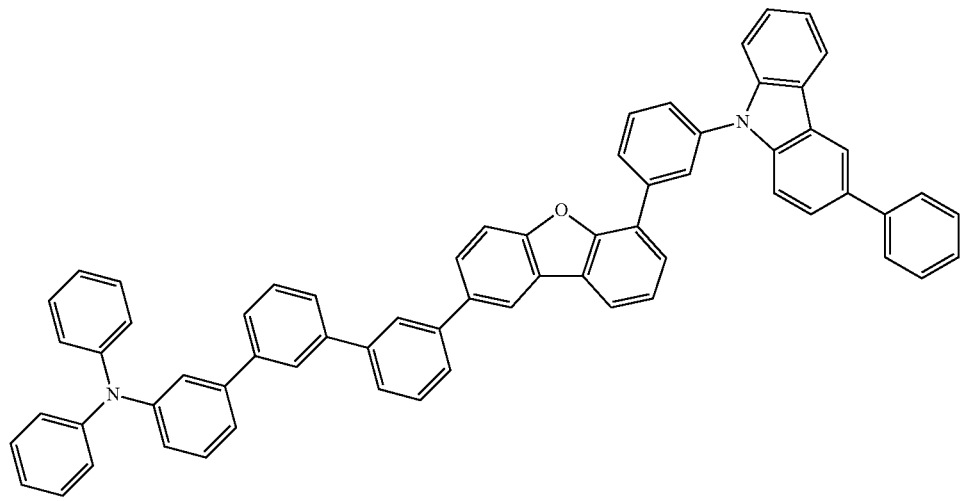
H-472
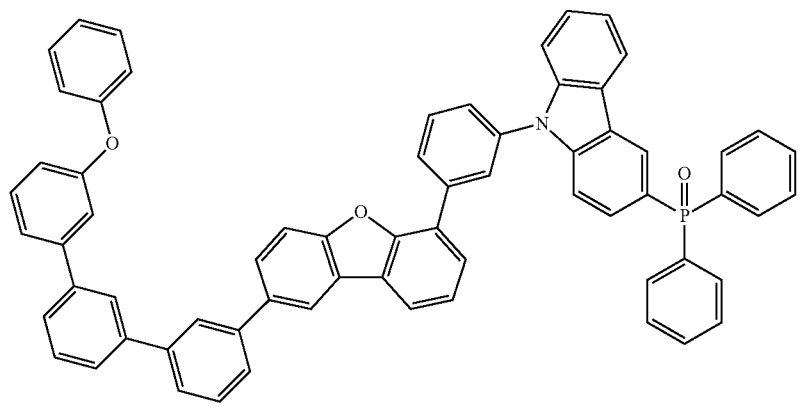
H-473

H-474
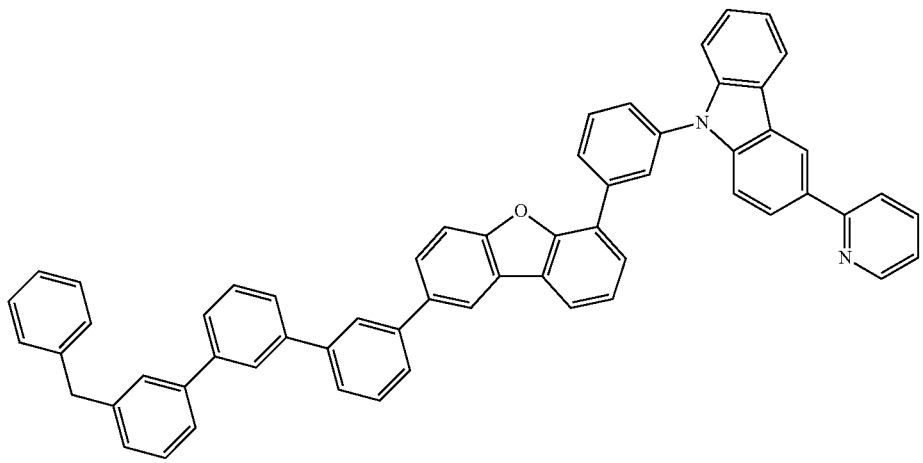
[Formula 52]
H-475
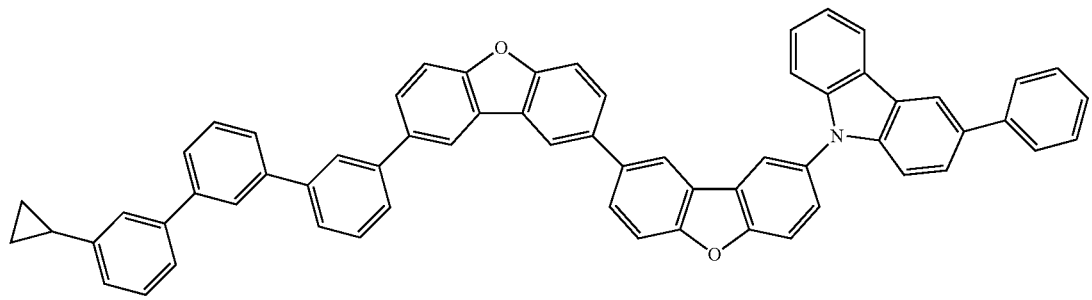
H-476
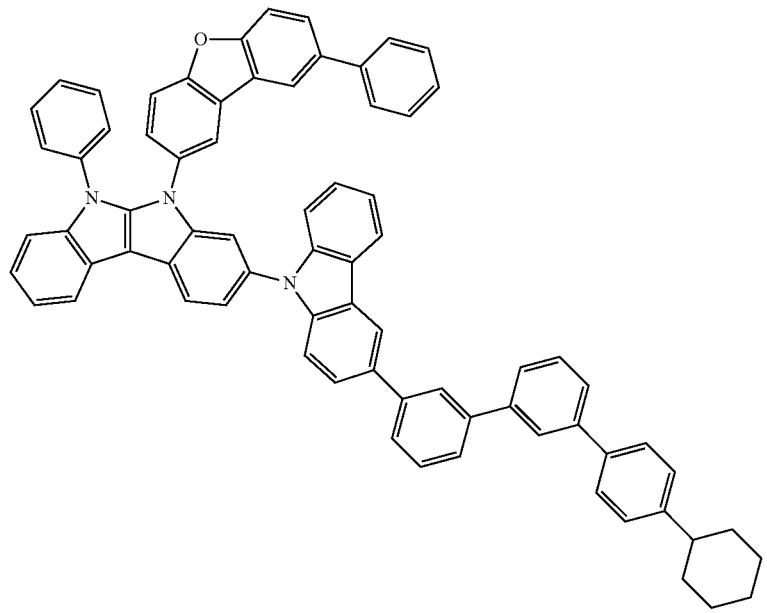

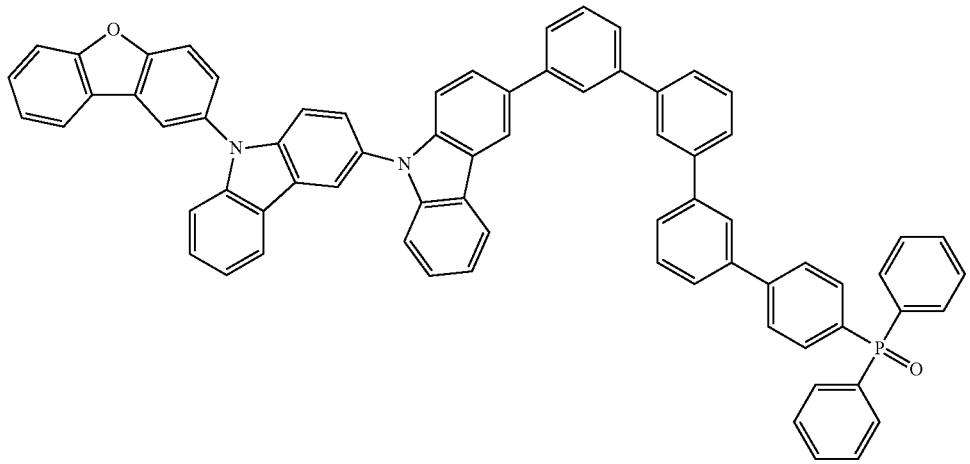
H-477
[Formula 53]
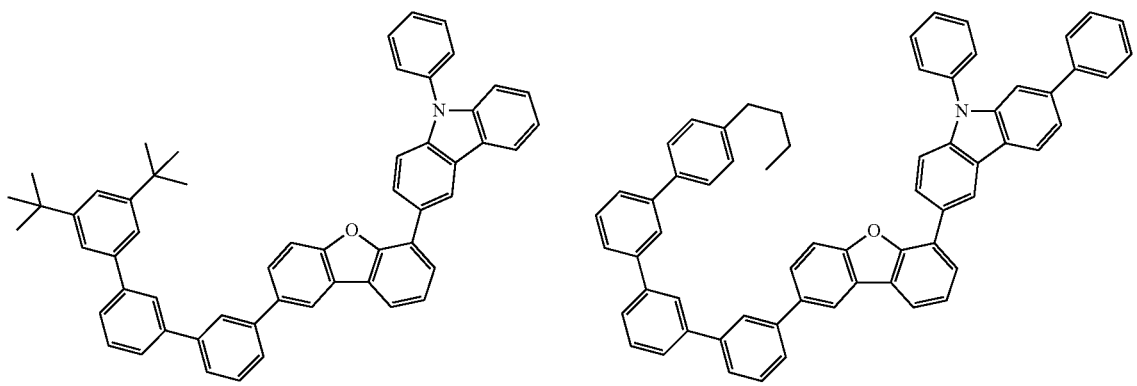
H-478  H-479
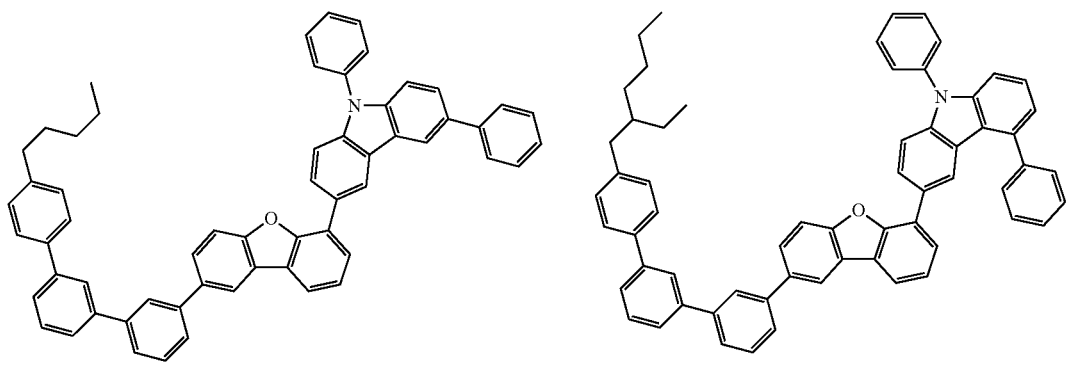
H-480  H-481

[Formula 54]
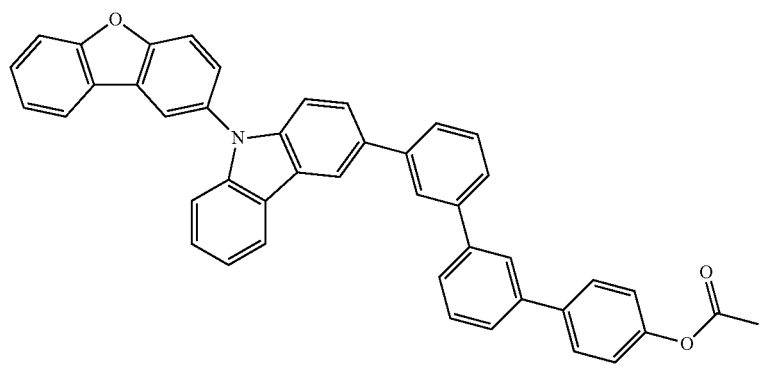
H-482
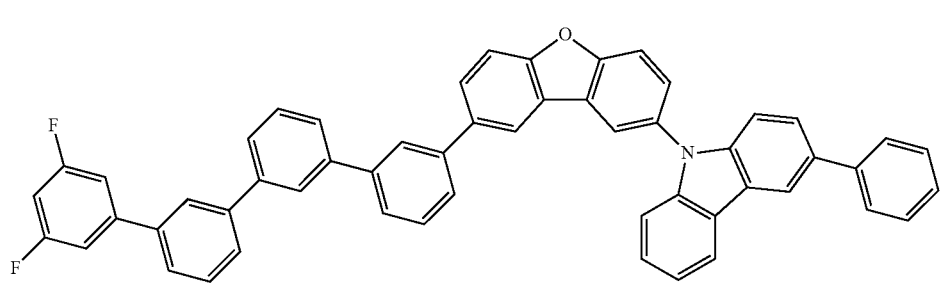
H-483
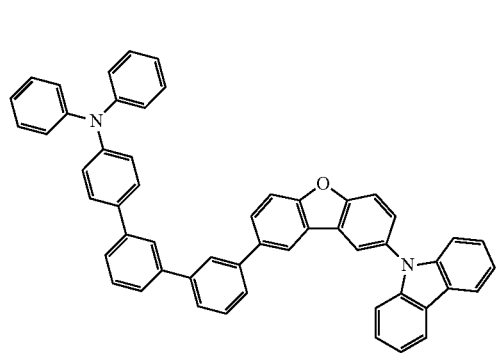
H-484
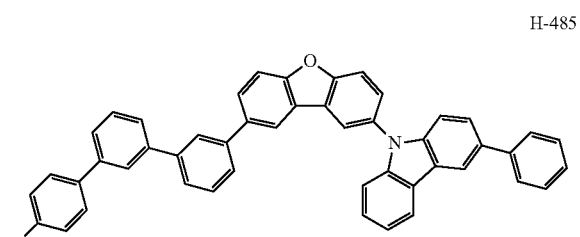
H-485
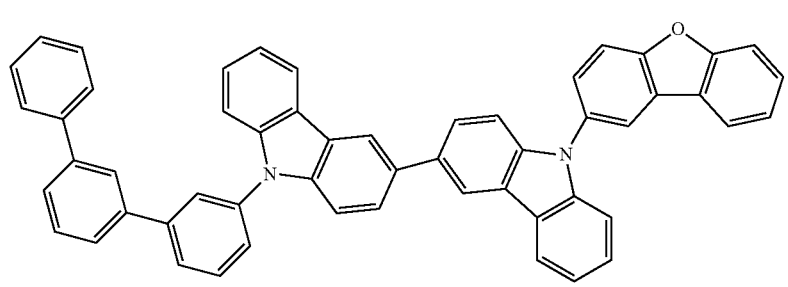
H-486

[Formula 55]
H-487
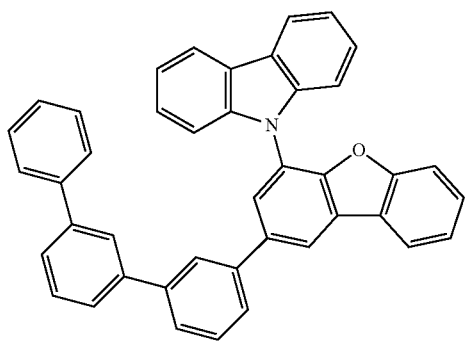
H-488
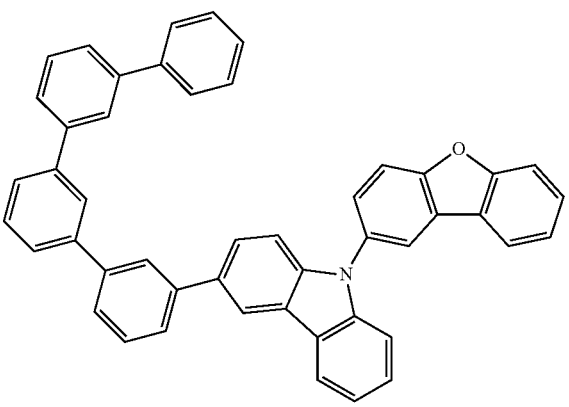
H-489
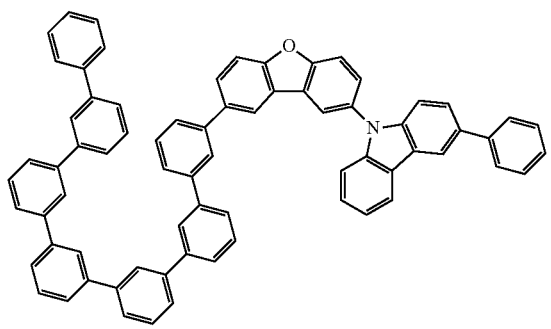
H-490
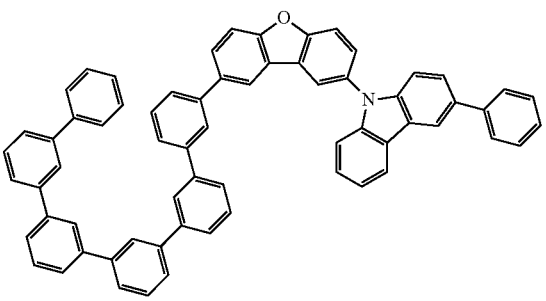
H-491
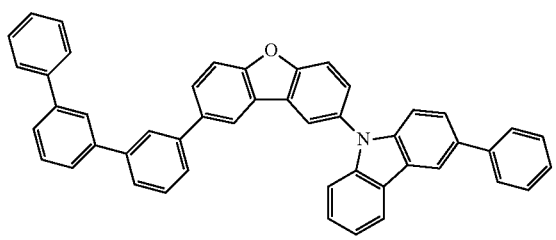
H-492
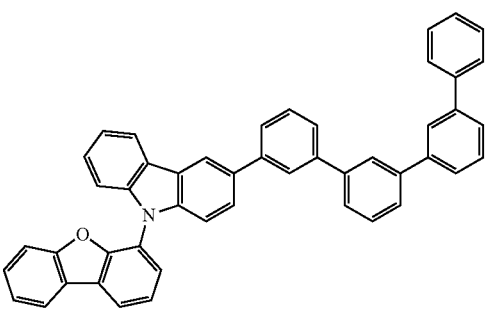

[Formula 56]
H-500
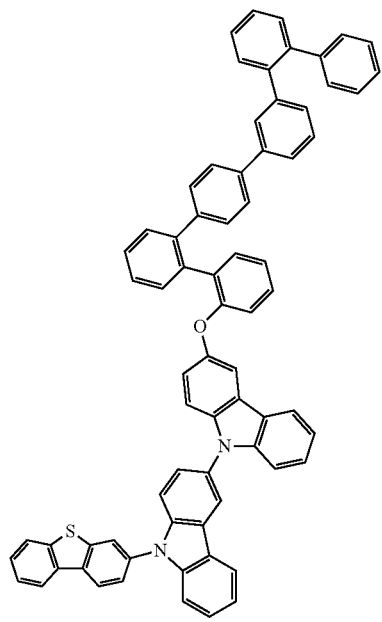
H-501
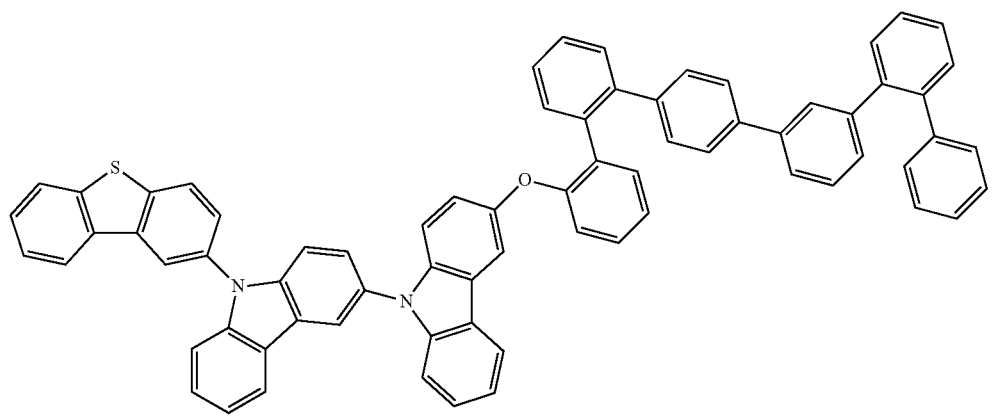
H-502
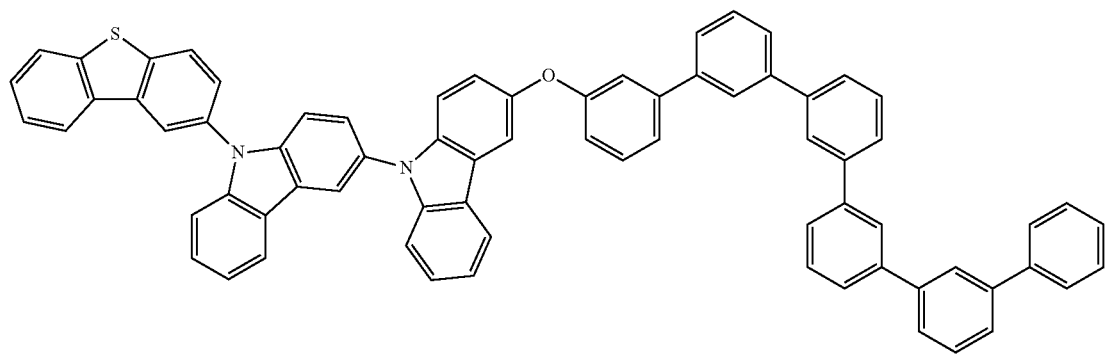

[Formula 57]
H-503
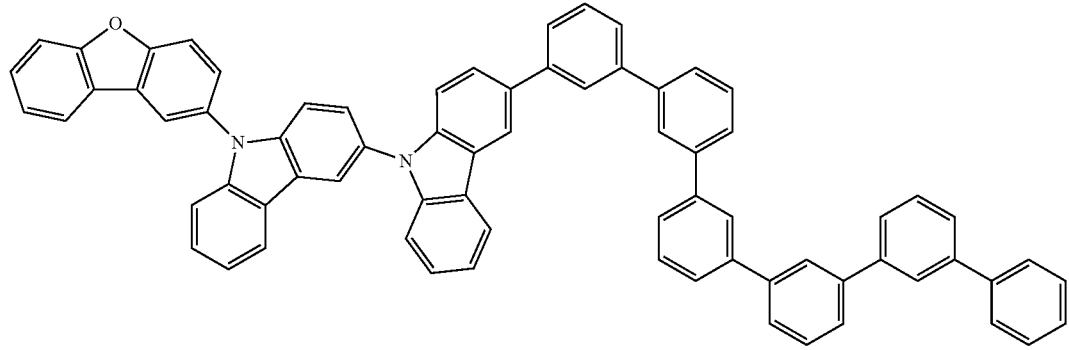
H-504
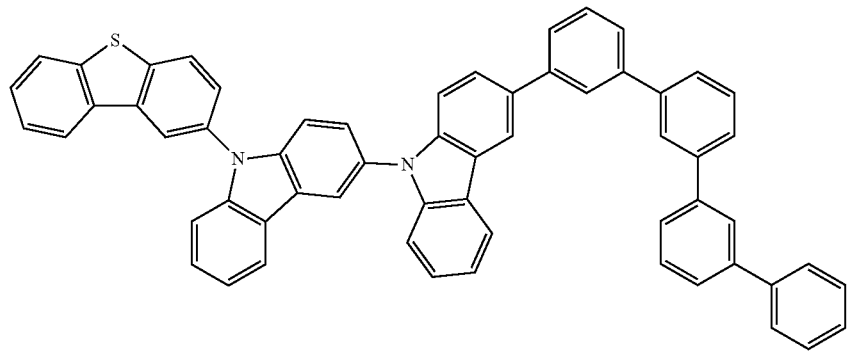
H-505
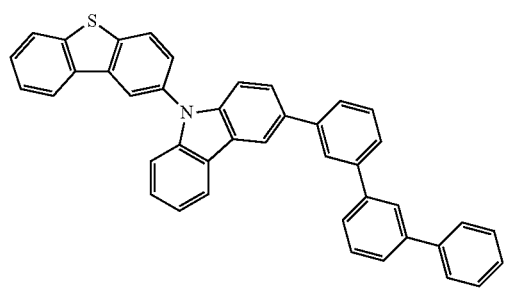
H-506
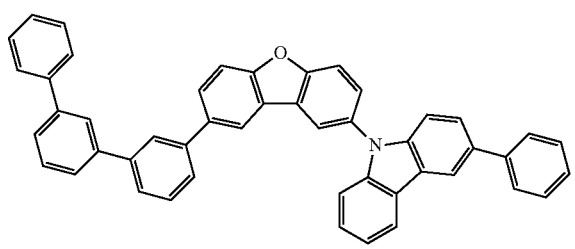

[Formula 58]
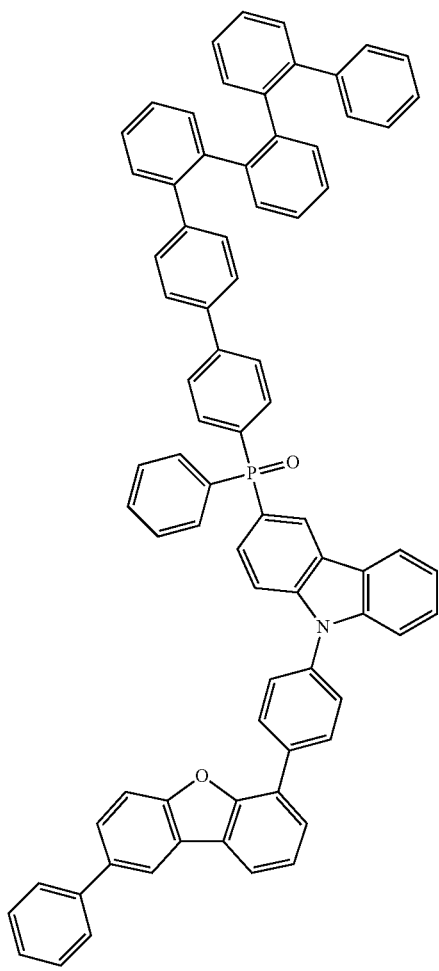
H-507
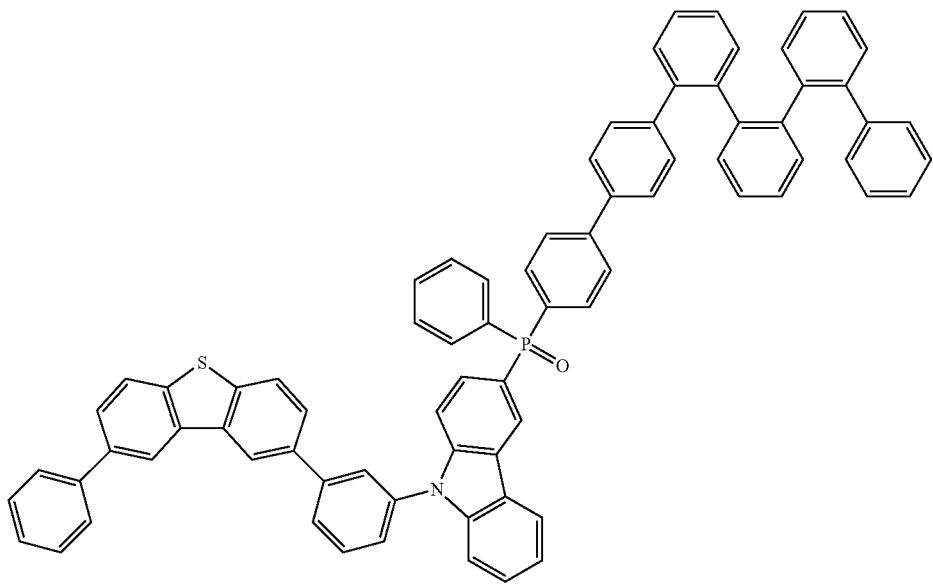
H-508

H-509
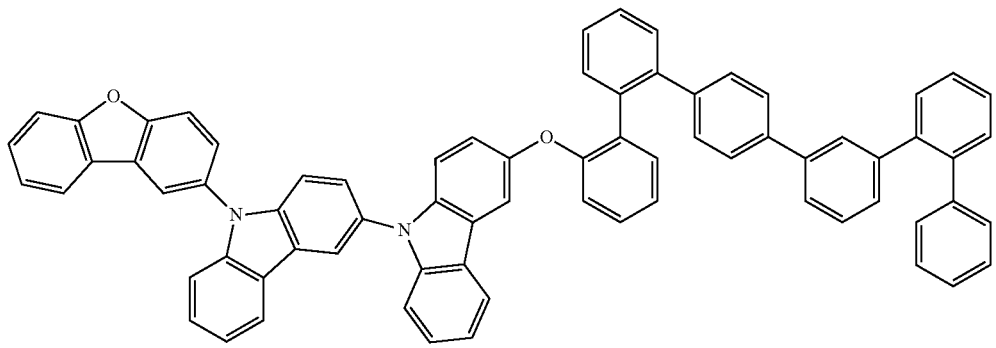
[Formula 59]
H-510
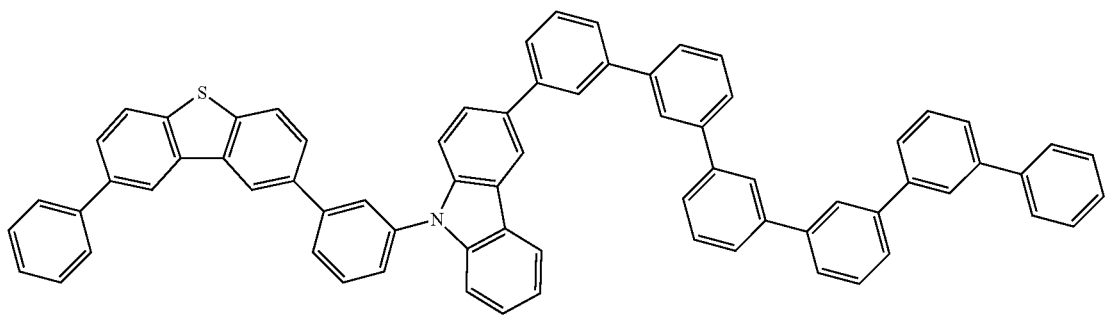
H-511 H-512
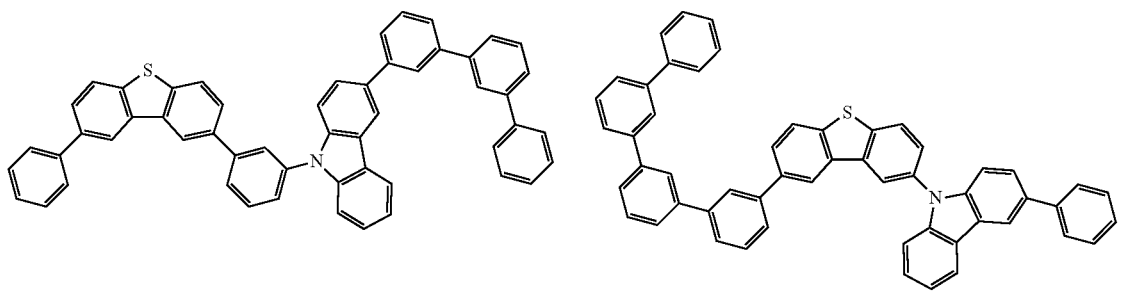
H-513
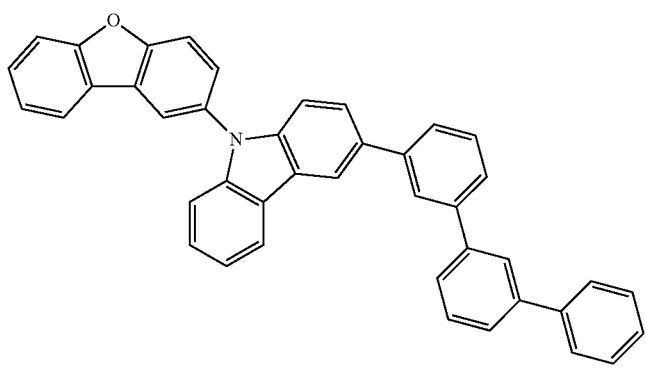

[Formula 60]
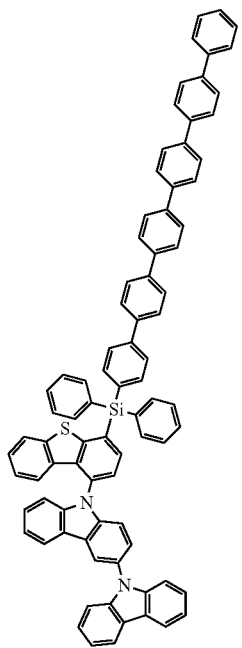
H-514
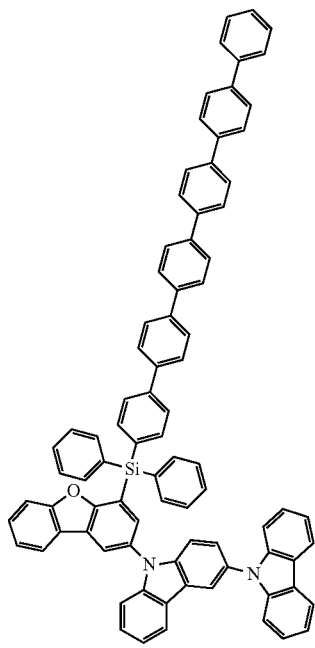
H-515
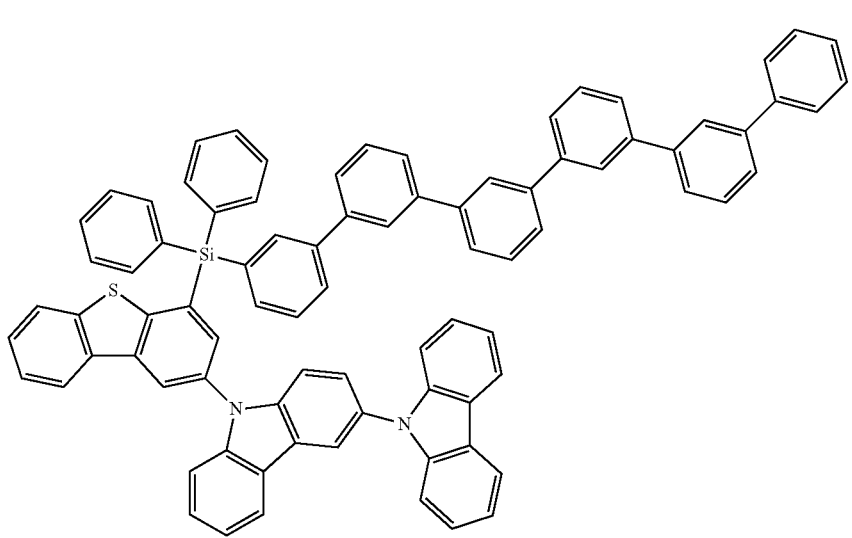
H-516

[Formula 61]
H-517
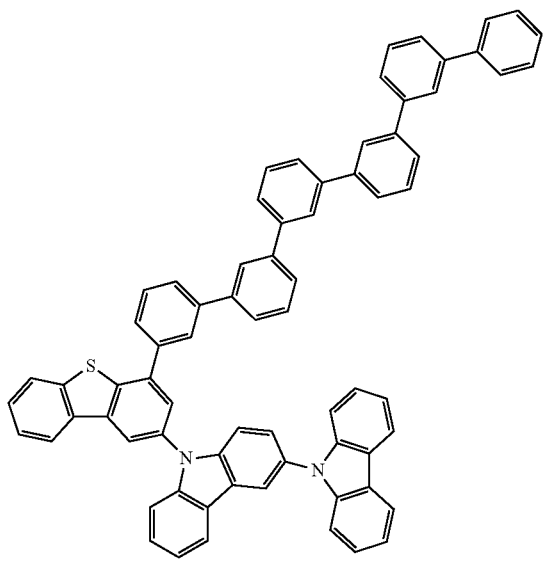
H-518
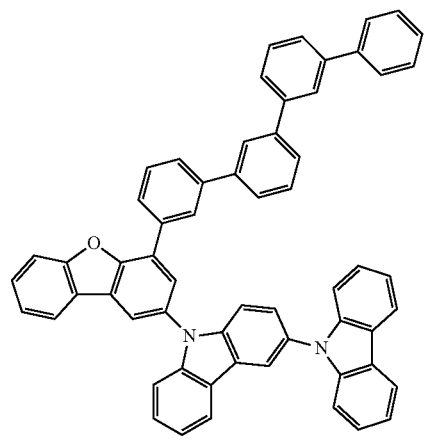
H-519
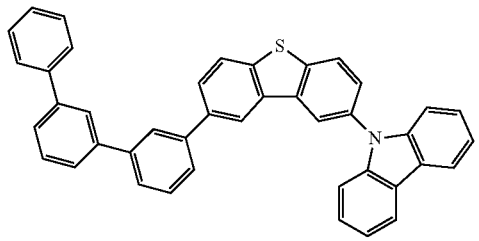
H-520
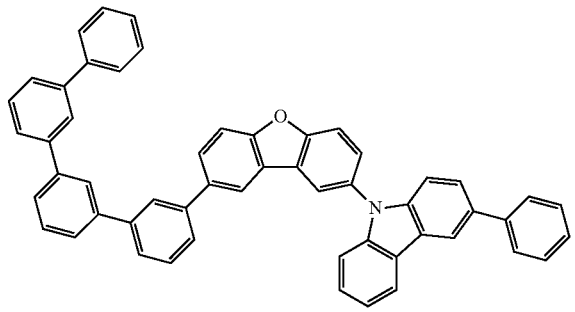
[Formula 62]
H-521
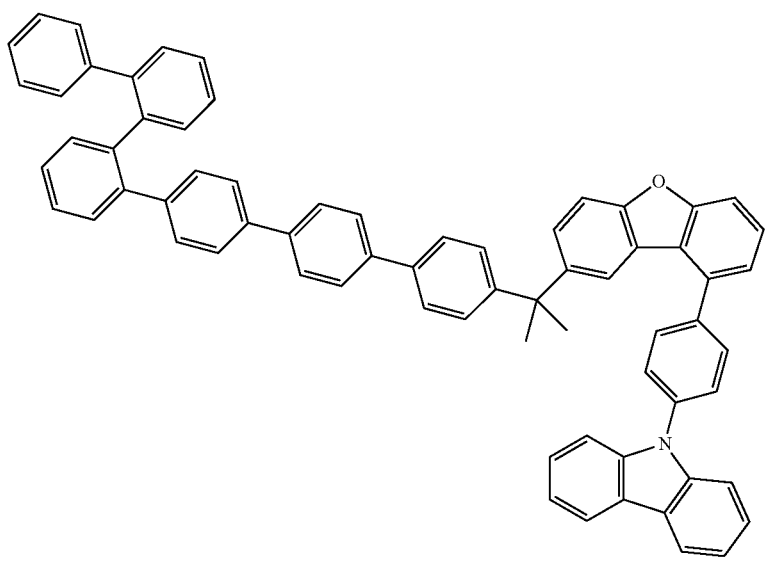

H-522
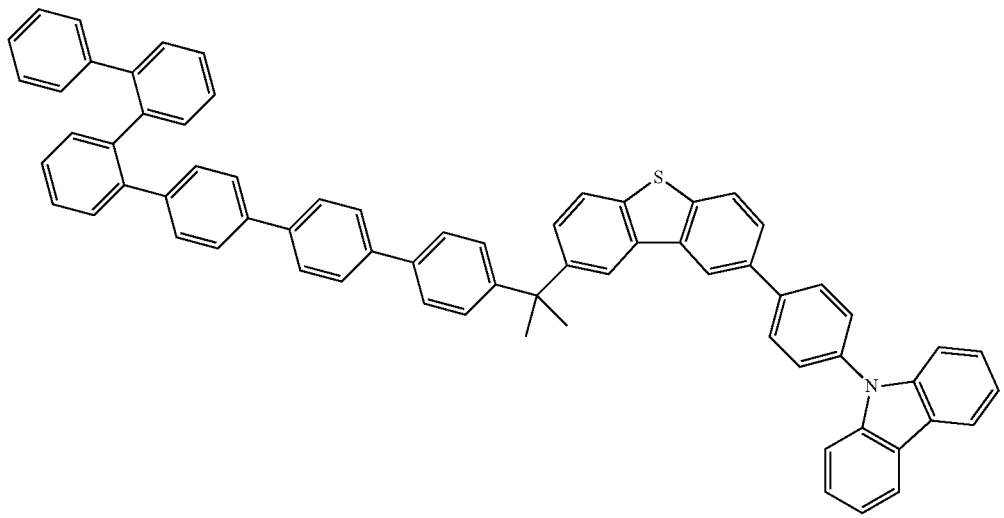
H-523
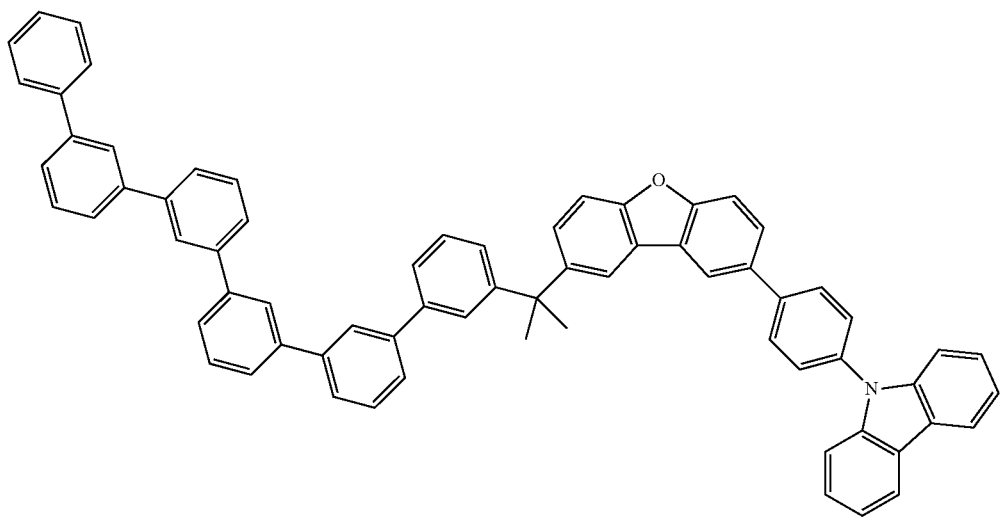
H-524
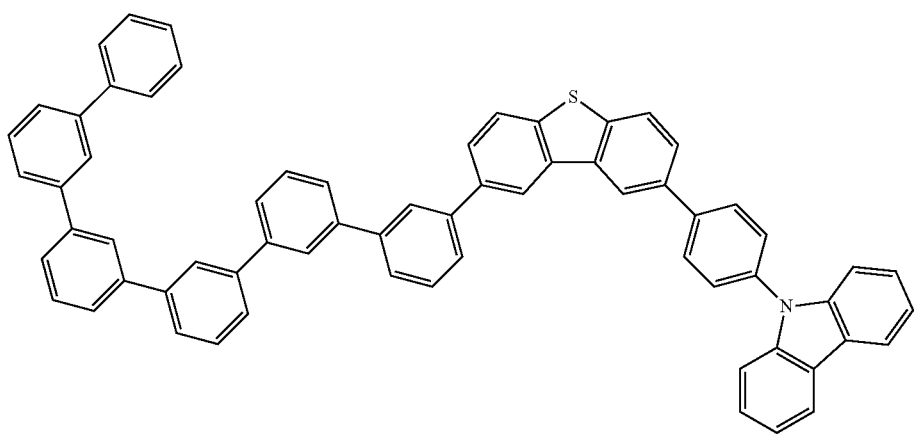

[Formula 63]
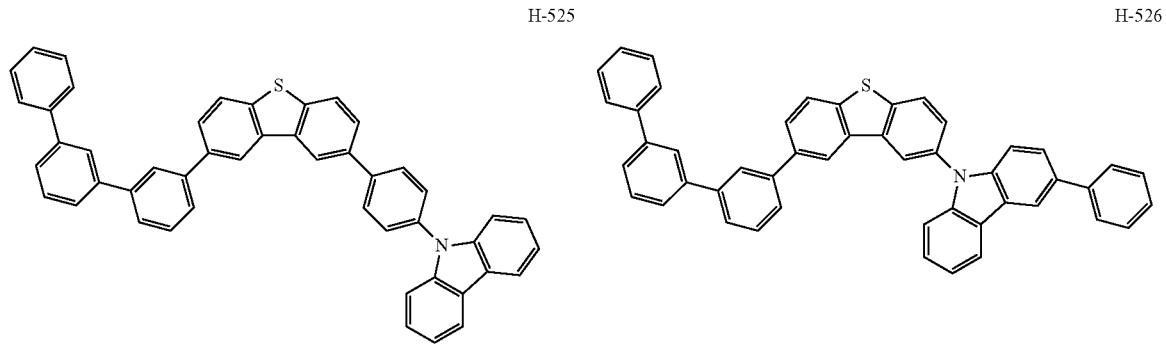
[Formula 64]
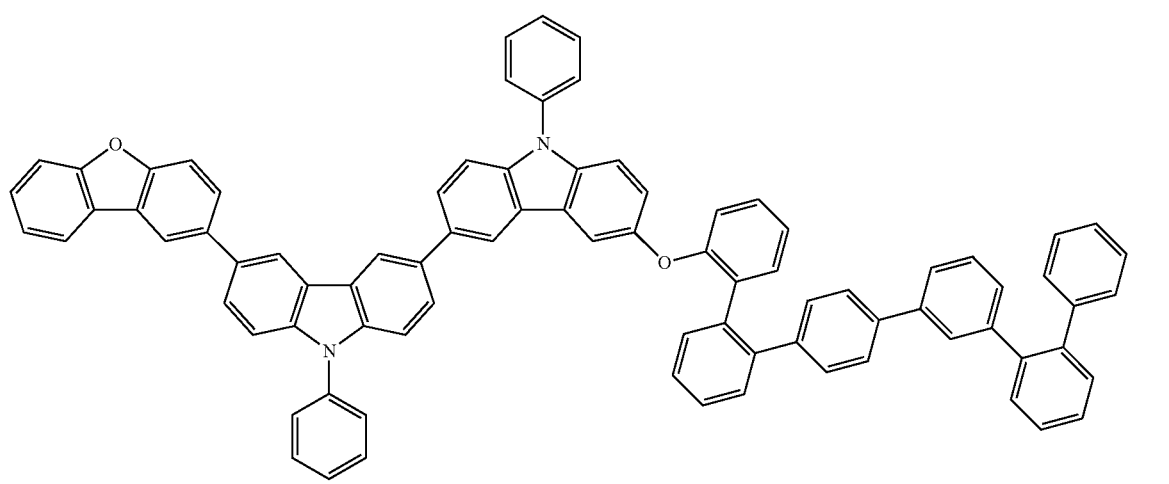

H-529
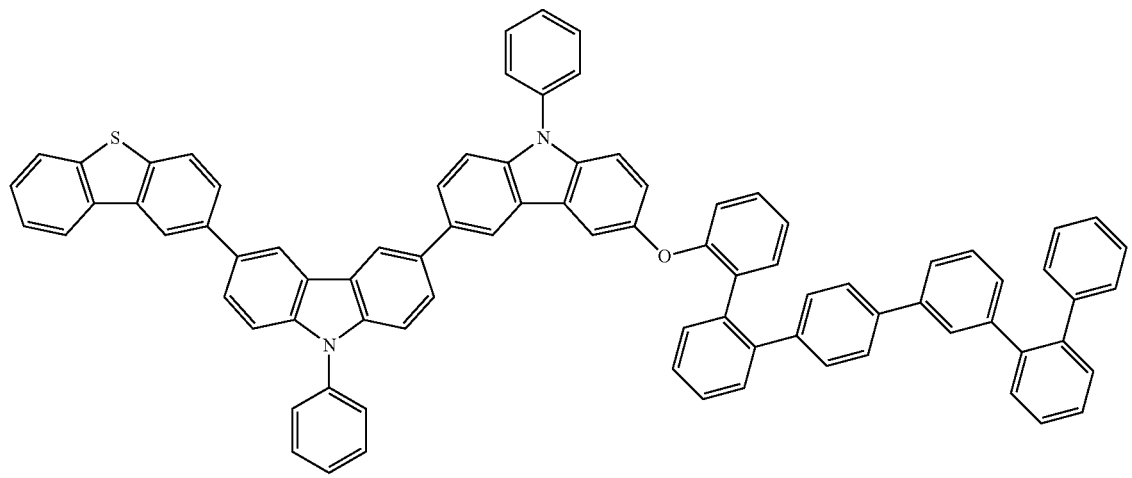
H-530
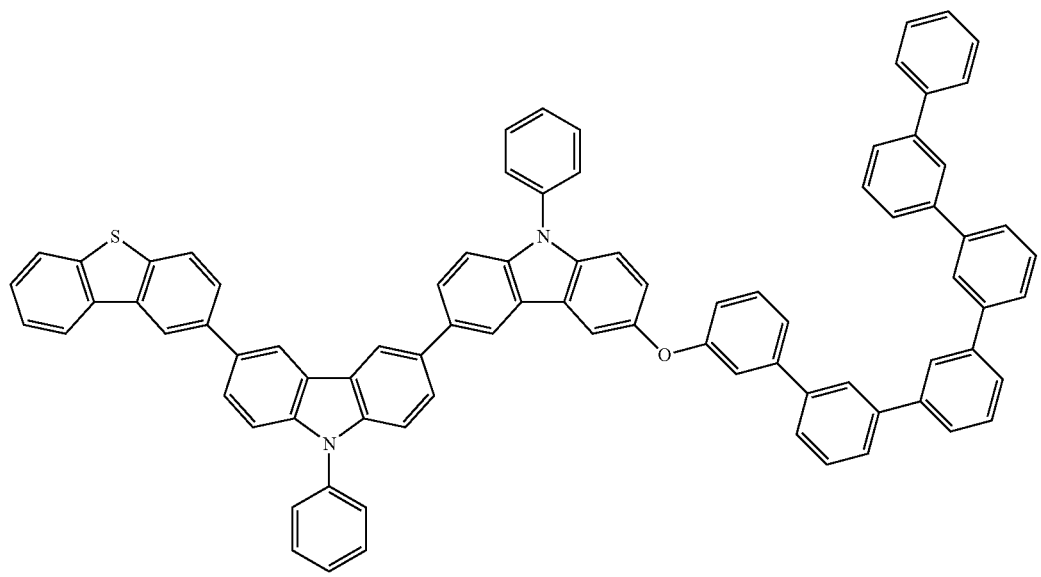
[Formula 65]
H-531
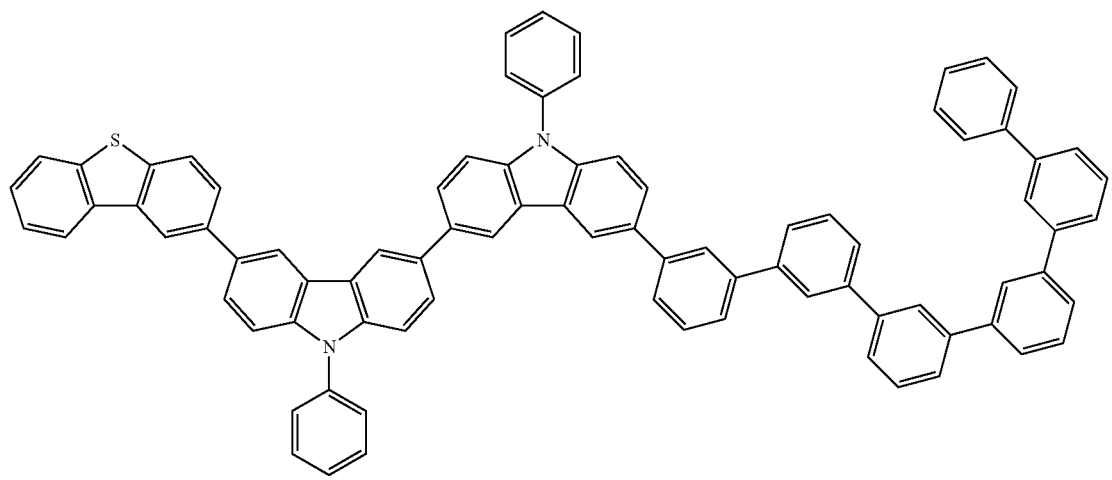

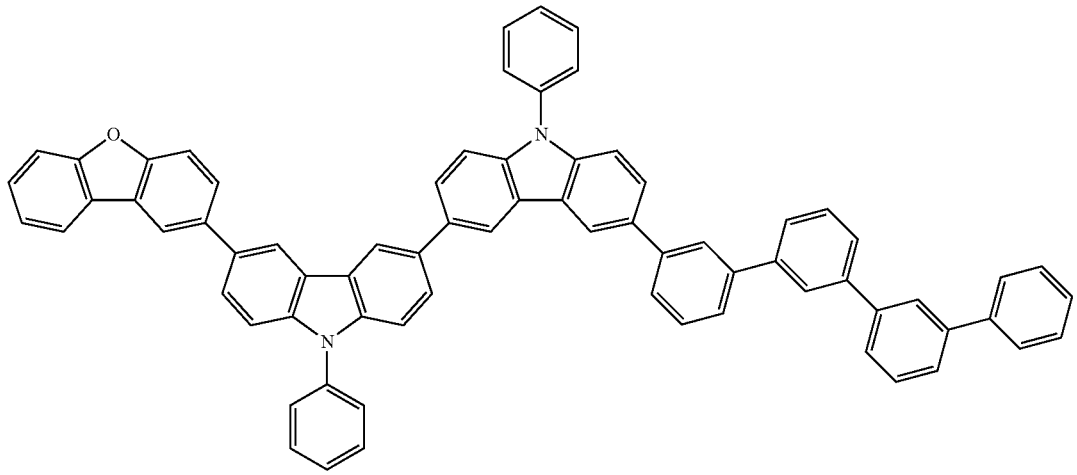
H-532
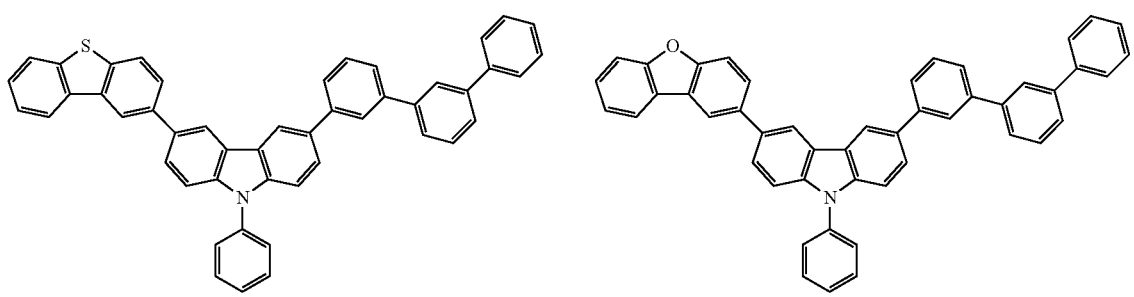
H-533   H-534
[Formula 66]
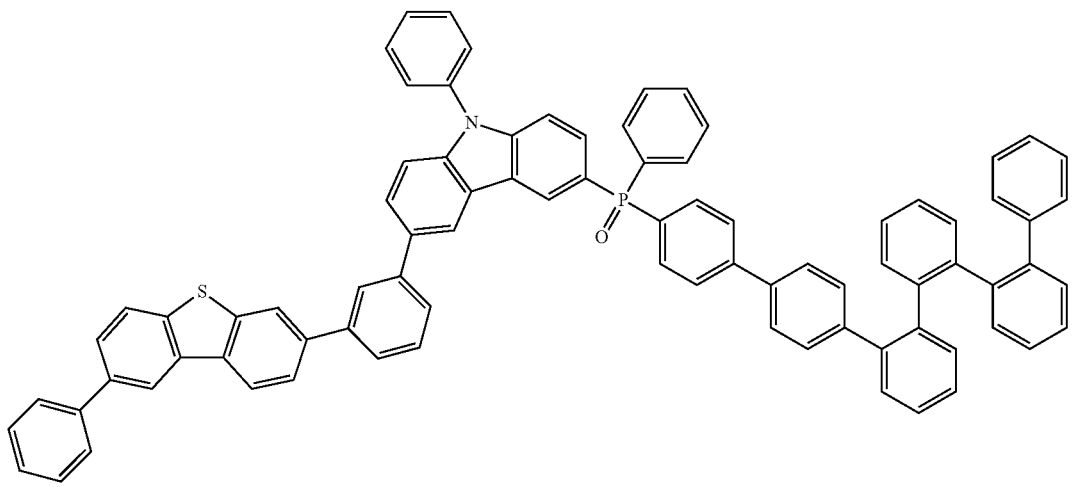
H-535

H-536
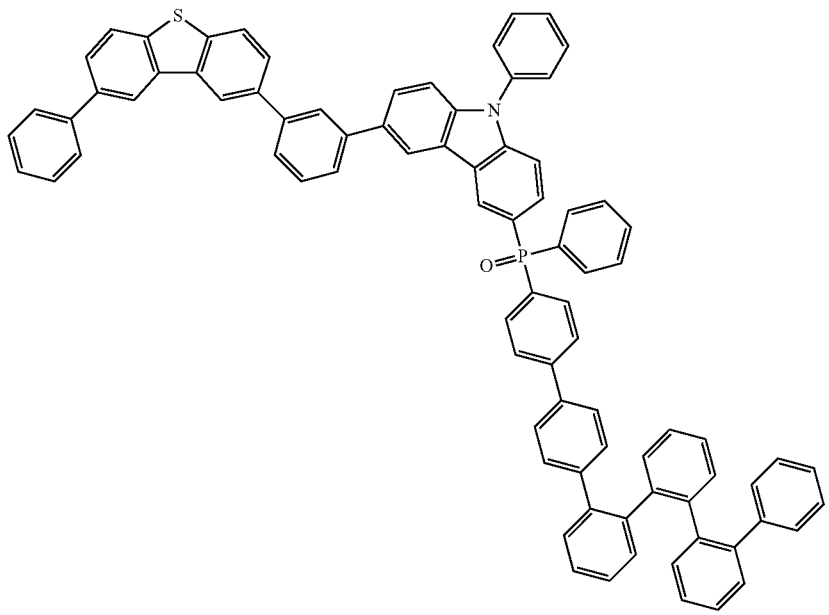
H-537
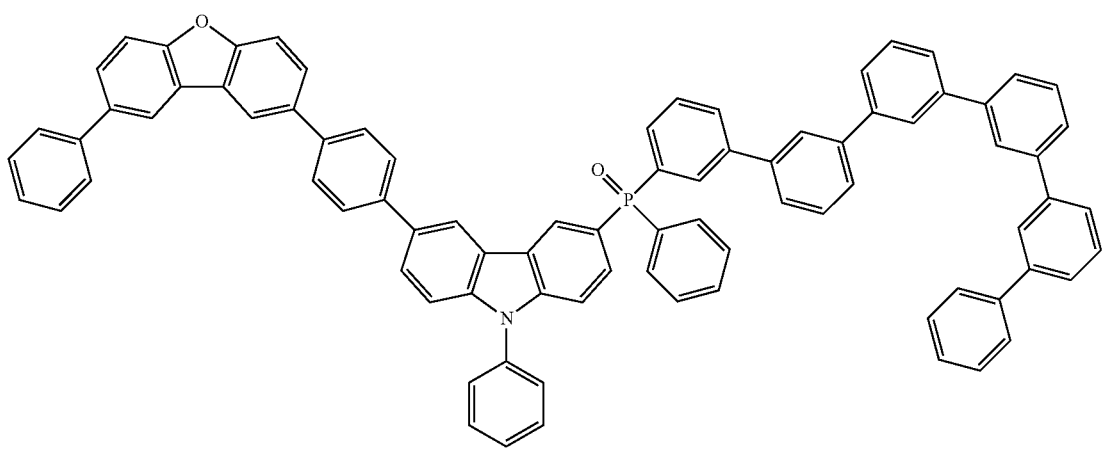
[Formula 67]
H-538
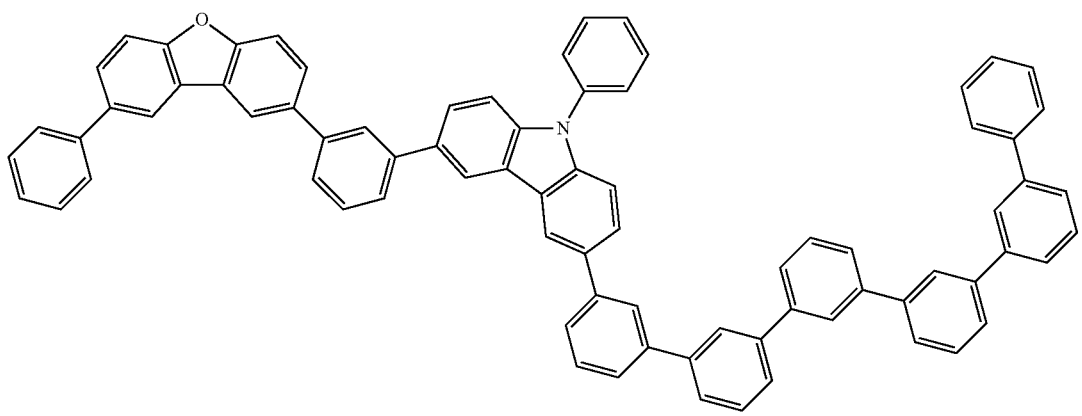

H-539
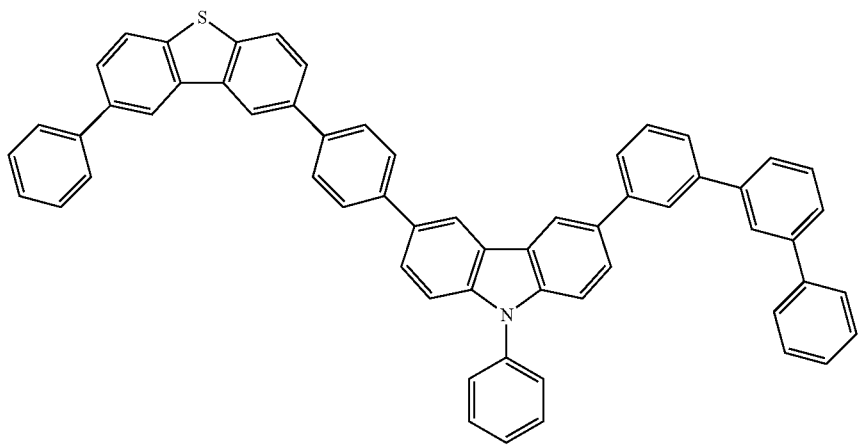
H-540
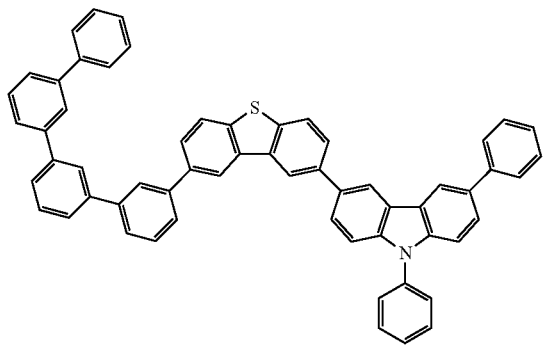
H-541
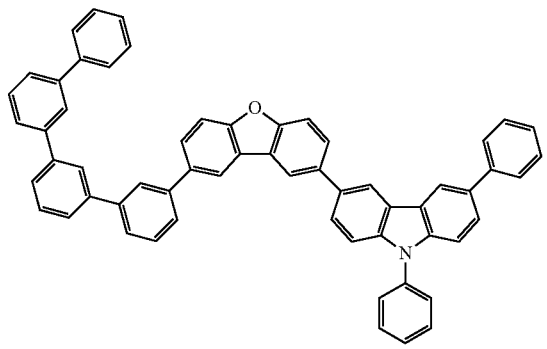
[Formula 68]
H-542
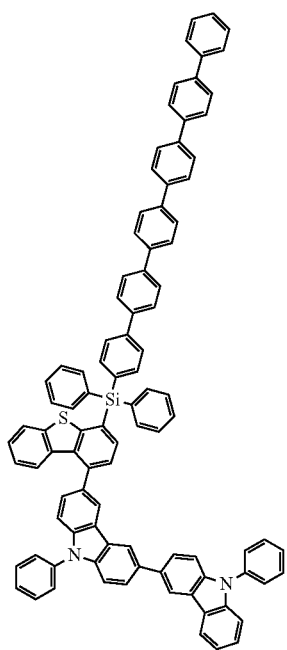
H-543
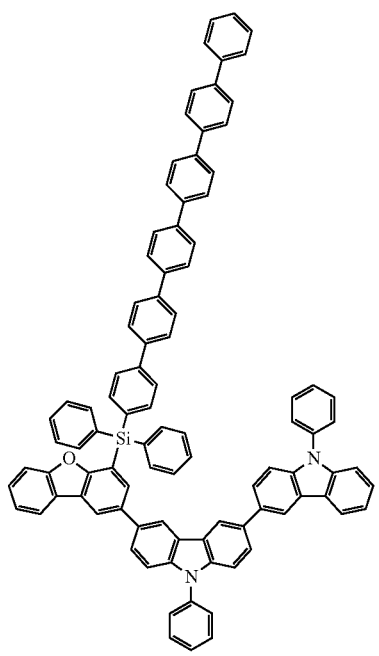

H-544
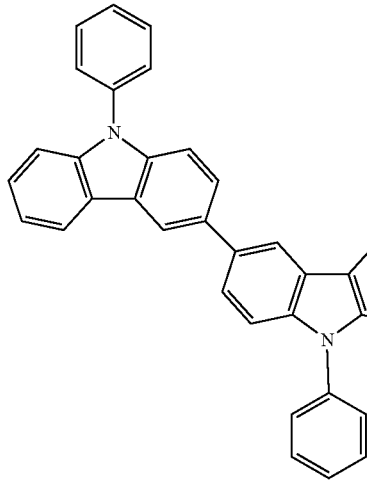
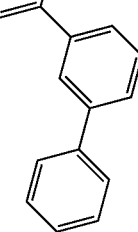
[Formula 69]
H-545                                   H-546
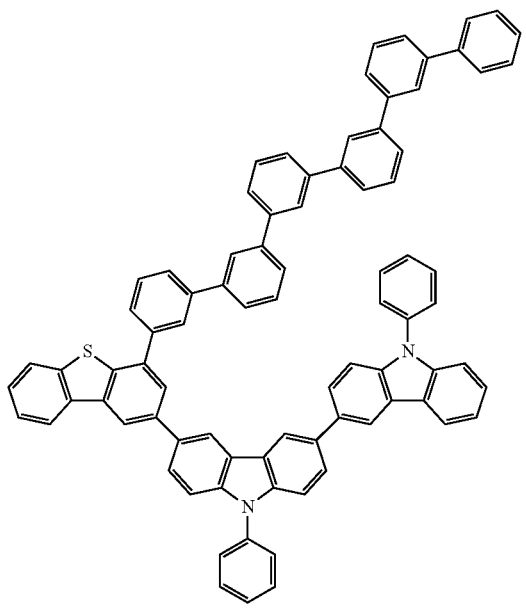
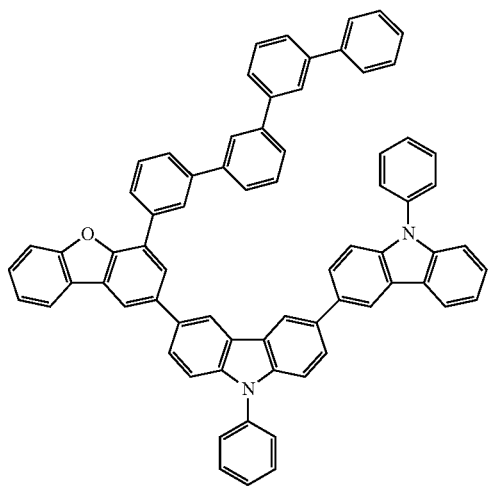
H-547                                   H-548
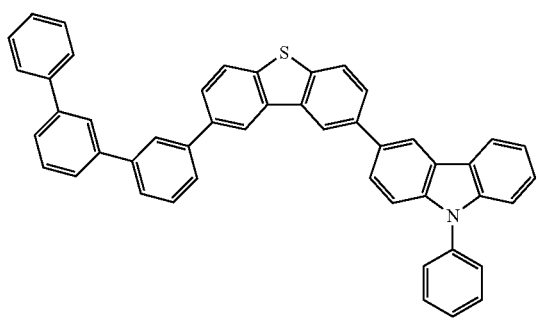
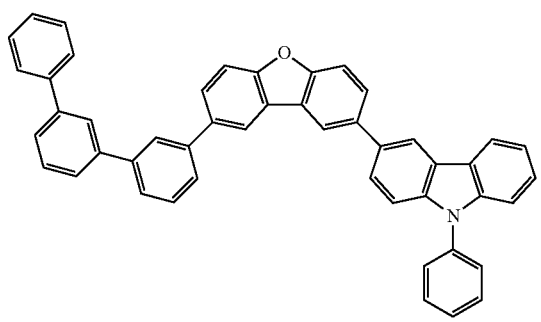

[Formula 70]
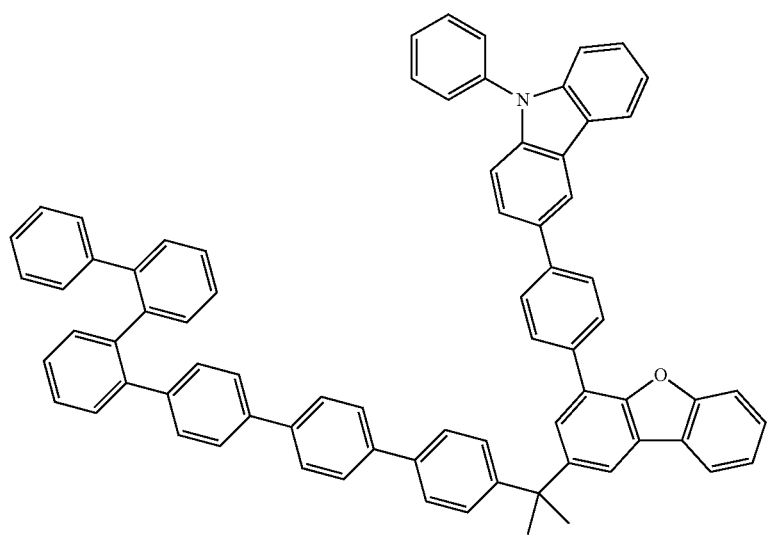
H-549
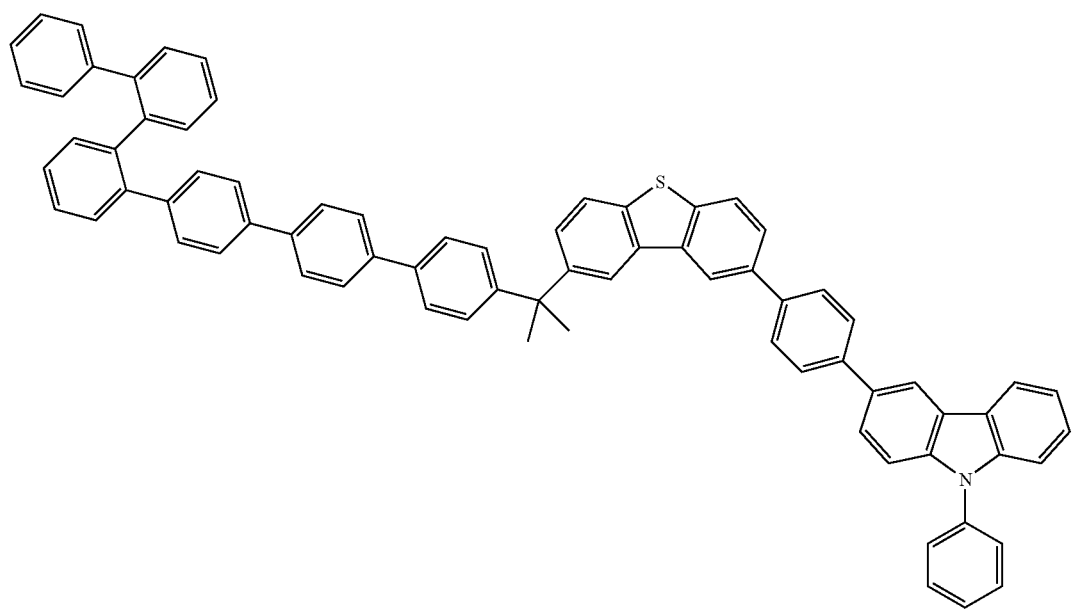
H-550

H-551
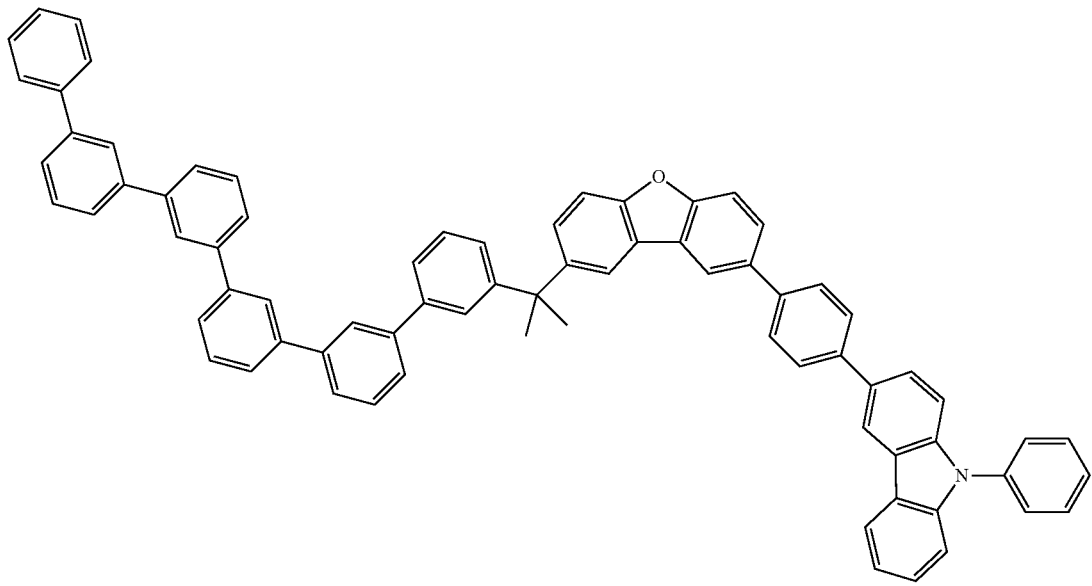
H-552
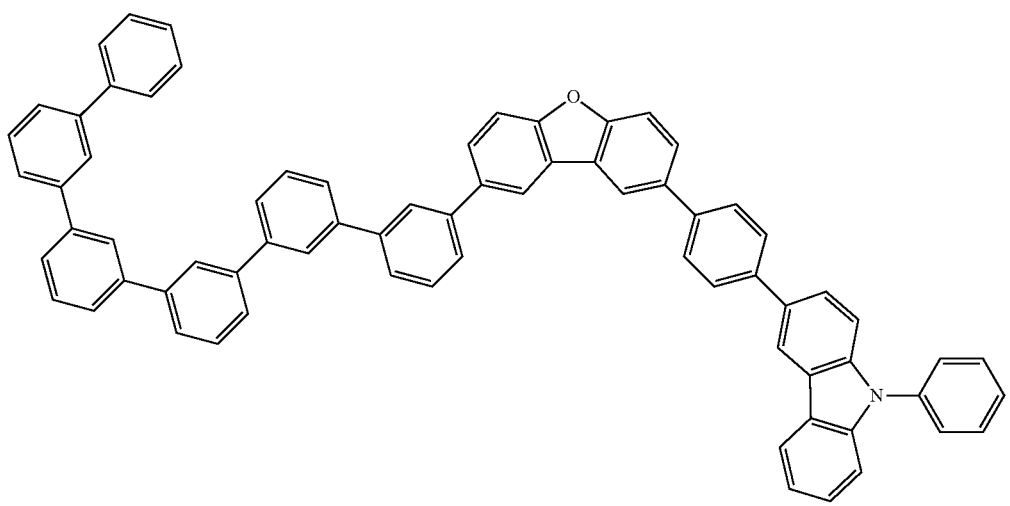
[Formula 71]
H-553  H-554
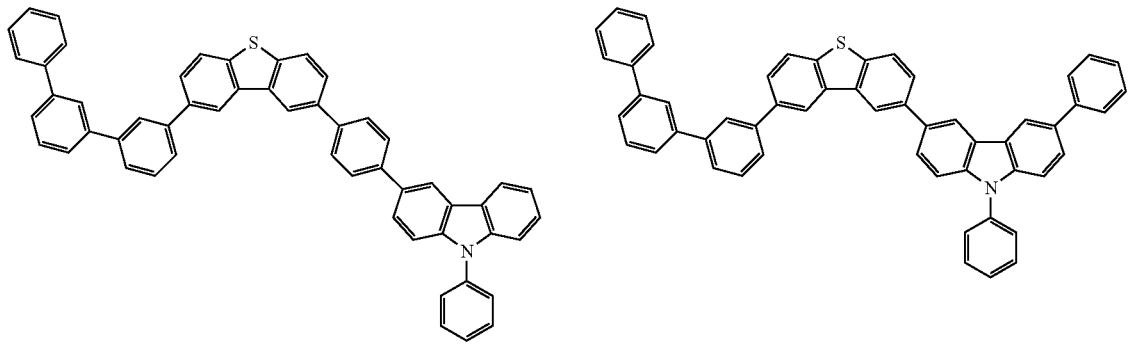

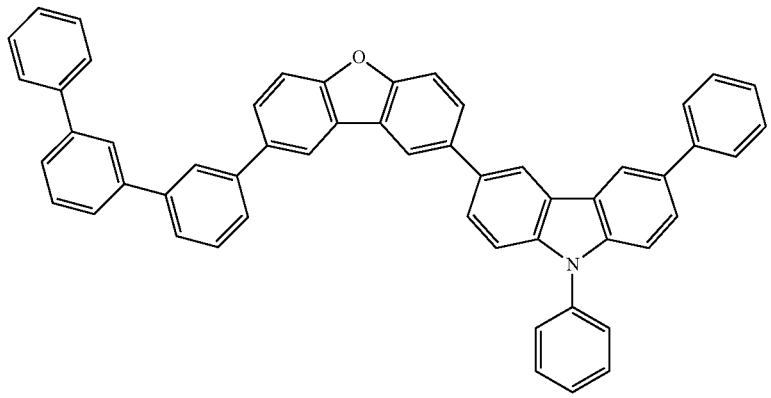
H-555
Non-limiting, Synthetic Examples of the compounds represented by Formulae (1) to (7) will now be described. Processes of preparing the compounds represented by Formulae (1) to (7) will be described by way of Compounds H-437 and H-486 to H-492.
A process of preparing Compound H-486 will be described.
[Formula 72]
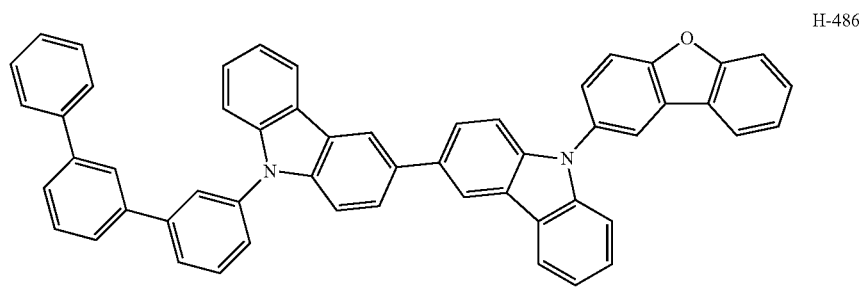
H-486
Compound H-486 can be prepared by the following scheme:
[Formula 73]
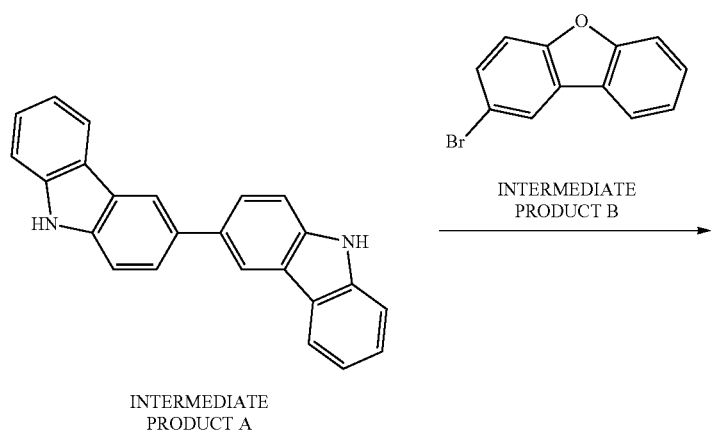

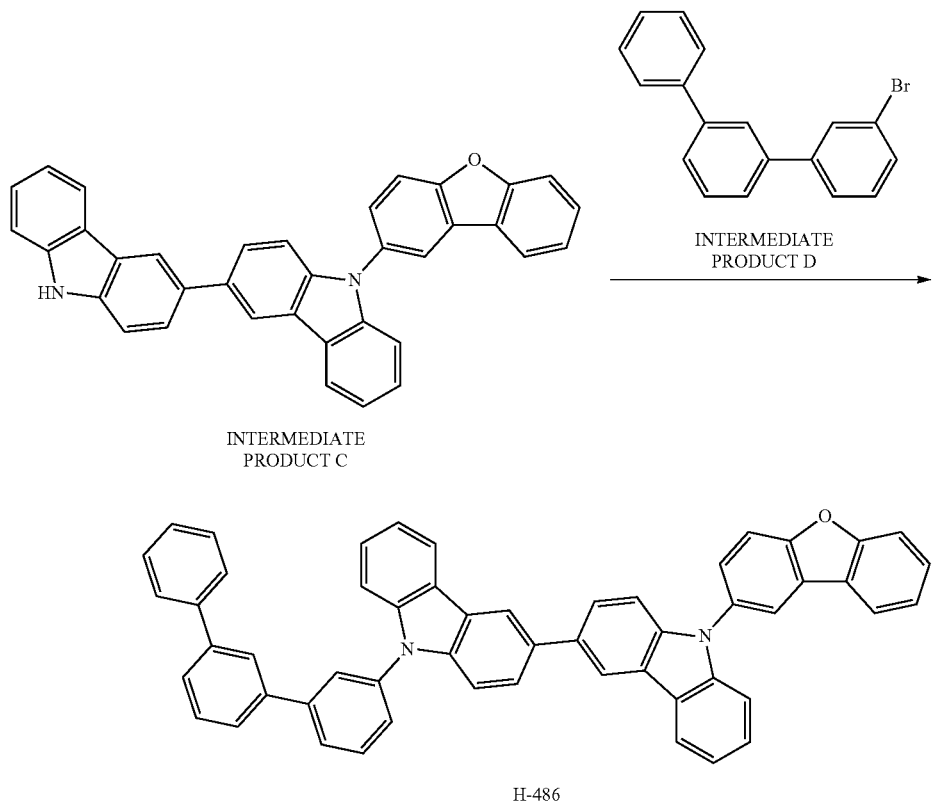

INTERMEDIATE
PRODUCT C

H-486

Intermediate product A was prepared with reference to The Journal of Organic Chemistry, 2009, 4490-4498.

Intermediate product B was prepared with reference to The Journal of Organic Chemistry, 1997, 1348-1355.

Intermediate product C was prepared by the following procedure.

Intermediate product A (3.32 g), Intermediate product B (2.47 g), S-phos (1.64 g), palladium acetate (0.224 g), and tripotassium phosphate (6.3 g) were placed in a 100 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Intermediate product D was prepared with reference to EP23041926.

Compound H-486 was prepared with Intermediate product C and Intermediate product D by the following procedure.

Intermediate product C (4.98 g), Intermediate product D (3.5 g), S-phos (1.64 g), palladium acetate (0.224 g), and tripotassium phosphate (6.3 g) were placed in a 100 ml three-necked flask sufficiently purged with nitrogen, and were dissolved in toluene (100 ml). The solution was refluxed with heating. After formation of the target product was confirmed, water (100 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

A process of preparing Compound H-487 will now be described.

[Formula 74]

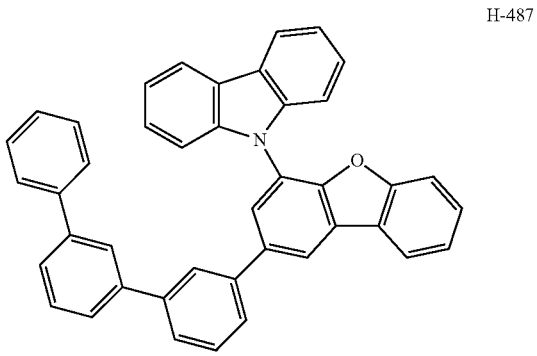

H-487

Compound H-487 can be prepared by the following scheme:

[Formula 75]

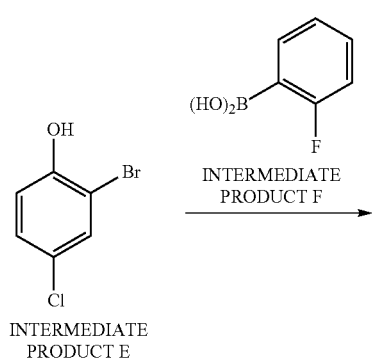

INTERMEDIATE PRODUCT E

INTERMEDIATE PRODUCT F

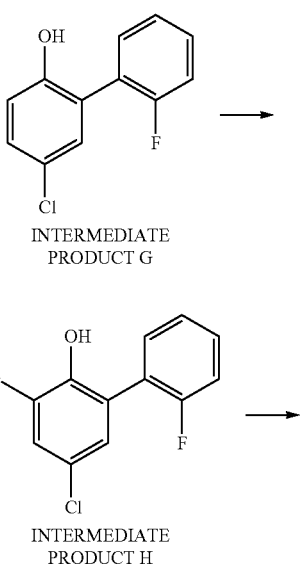

INTERMEDIATE PRODUCT G

INTERMEDIATE PRODUCT H

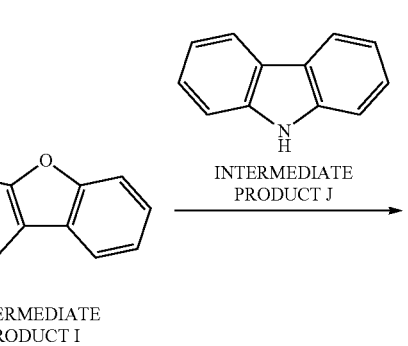

INTERMEDIATE PRODUCT I

INTERMEDIATE PRODUCT J

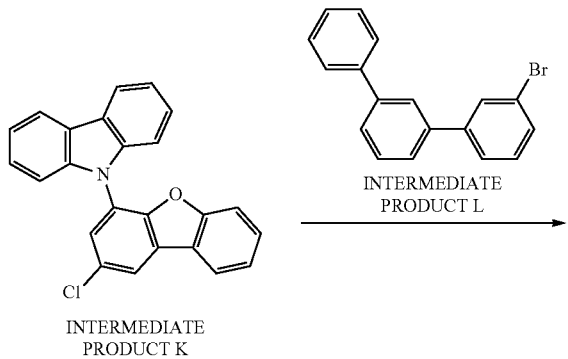

INTERMEDIATE PRODUCT K

INTERMEDIATE PRODUCT L

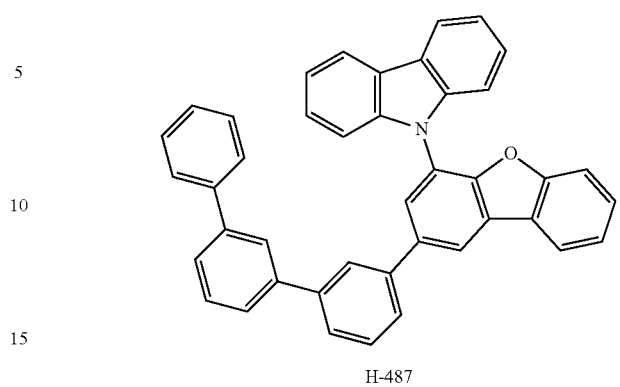

H-487

Intermediate product G was prepared by the following procedure.

Intermediate product E (2.07 g), Intermediate product F (1.4 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (100 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Intermediate product H was prepared by the following procedure.

Intermediate product G (2.22 g) was placed in a 200 ml three-necked flask sufficiently purged with nitrogen, was dissolved in DMF (100 ml), and was cooled with ice. NBS (1.8 g) was added to the solution, and was stirred at room temperature. After formation of the target product was confirmed, water (100 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Intermediate product I was prepared by the following procedure.

Intermediate product I (2.8 g) was placed in a 200 ml three-necked flask sufficiently purged with nitrogen, was dissolved in tetrahydrofuran (100 ml), and was cooled with ice. Sodium hydride (0.3 g) was added to the solution, and was stirred at room temperature. After formation of the target product was confirmed, water (100 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Intermediate product K was prepared by the following procedure.

Intermediate product I (2.81 g), carbazole (1.67 g), S-phos (1.64 g), palladium acetate (0.224 g), and tripotassium phosphate (6.3 g) were placed in a 100 ml three-necked flask sufficiently purged with nitrogen, and were dissolved in toluene (100 ml). The solution was refluxed with heating. After formation of the target product was confirmed, water (100 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Intermediate product L was prepared with reference to EP2301926.

Compound H-487 was prepared with Intermediate product K and Intermediate product L by the following procedure.

Intermediate product K (3.67 g), Intermediate product L (2.74 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (100 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

A process of preparing Compound H-488 will now be described.

[Formula 76]

H-488

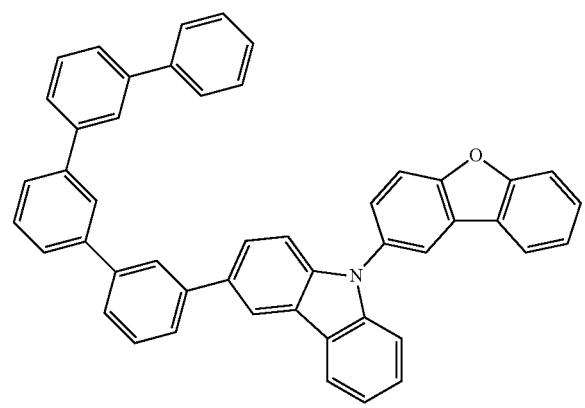

Compound H-488 can be prepared by the following scheme:

[Formula 77]

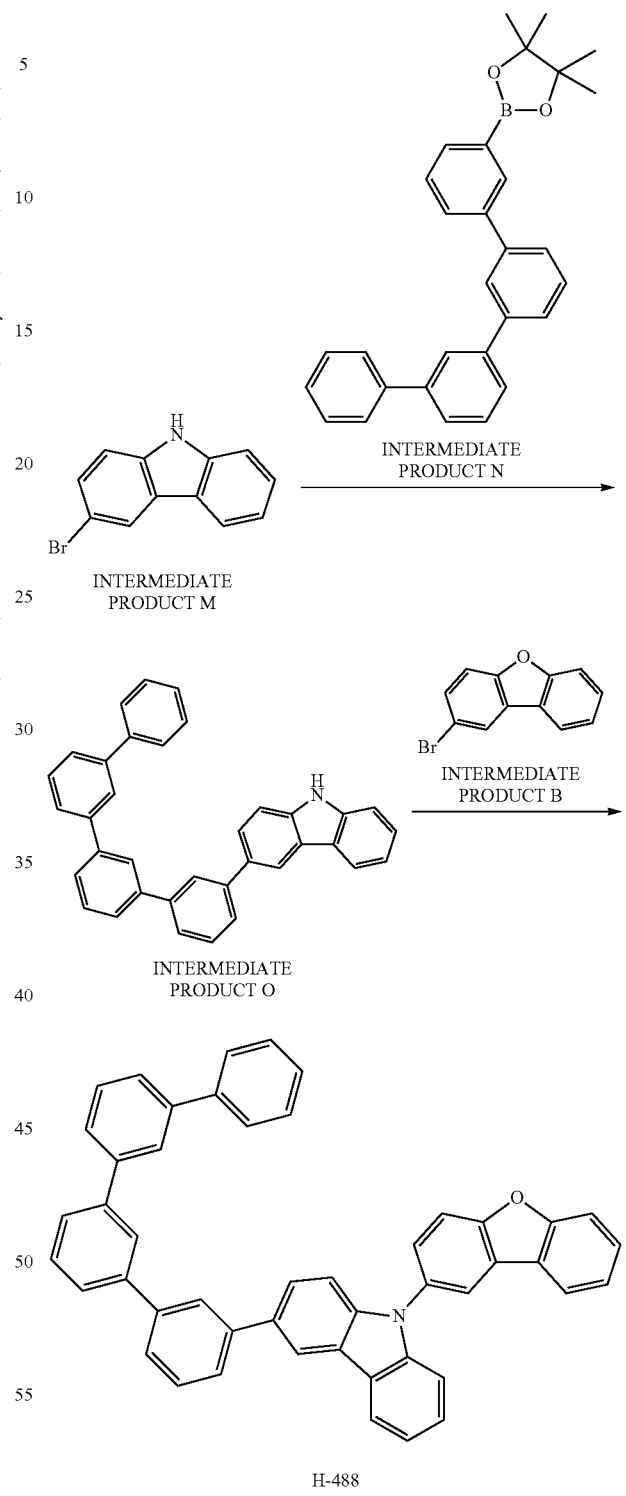

Intermediate product N was prepared as in Intermediate product L.

Intermediate product O was prepared by the following procedure.

Intermediate product M (2.46 g), Intermediate product N (4.32 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Compound H-488 was prepared with Intermediate product B and Intermediate product O by the following procedure.

Intermediate product O (4.7 g), Intermediate product B (2.47 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

A process of preparing Compound H-489 will now be described.

[Formula 78]

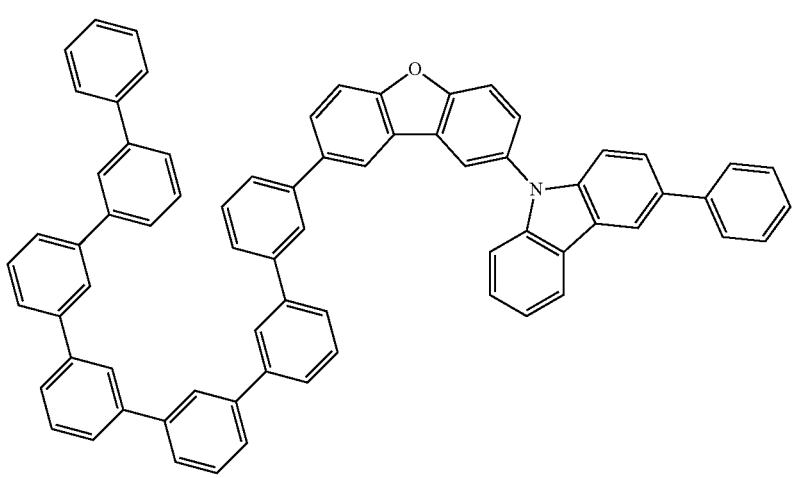

H-489

Compound H-489 can be prepared by the following scheme.

[Formula 79]

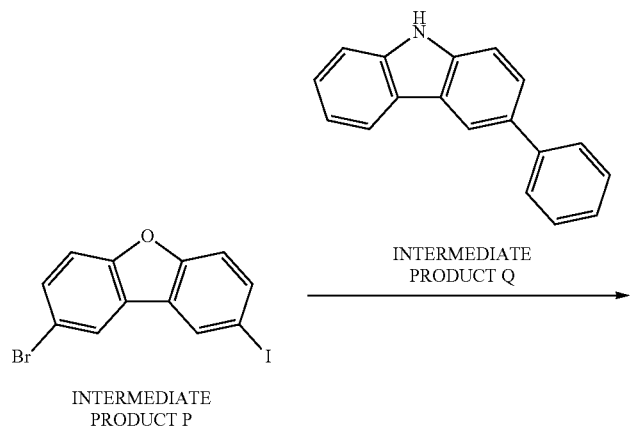

INTERMEDIATE PRODUCT P

INTERMEDIATE PRODUCT Q

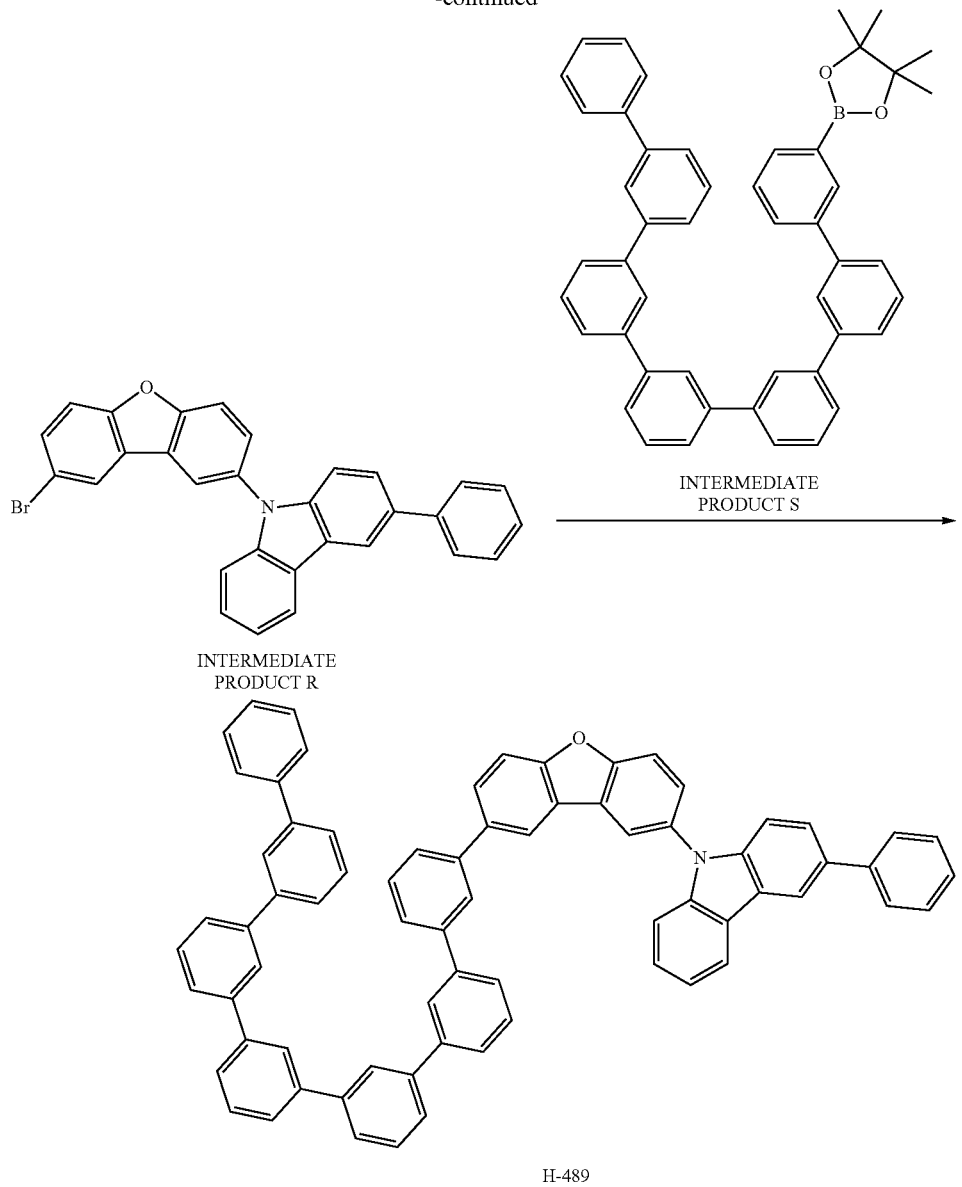

H-489

Intermediate product P was prepared with reference to US2009/131673.

Intermediate product Q was prepared with reference to US/2010/76201.

Intermediate product R was prepared by the following procedure.

Intermediate product P (3.73 g), Intermediate product Q (2.43 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Intermediate product S was prepared as in Intermediate product L.

Compound H-489 was prepared with Intermediate product R and Intermediate product S by the following procedure.

Intermediate product R (4.88 g), Intermediate product S (6.60 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

A process of preparing Compound H-490 will now be described.
[Formula 80]
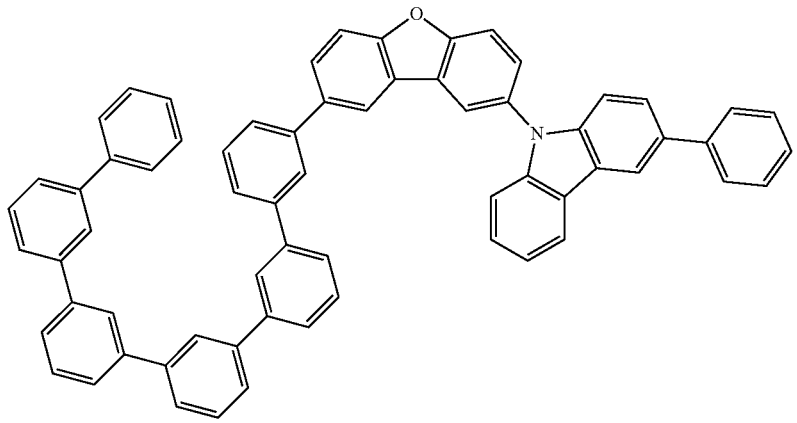
H-490
Compound H-490 can be prepared by the following scheme.
[Formula 81]
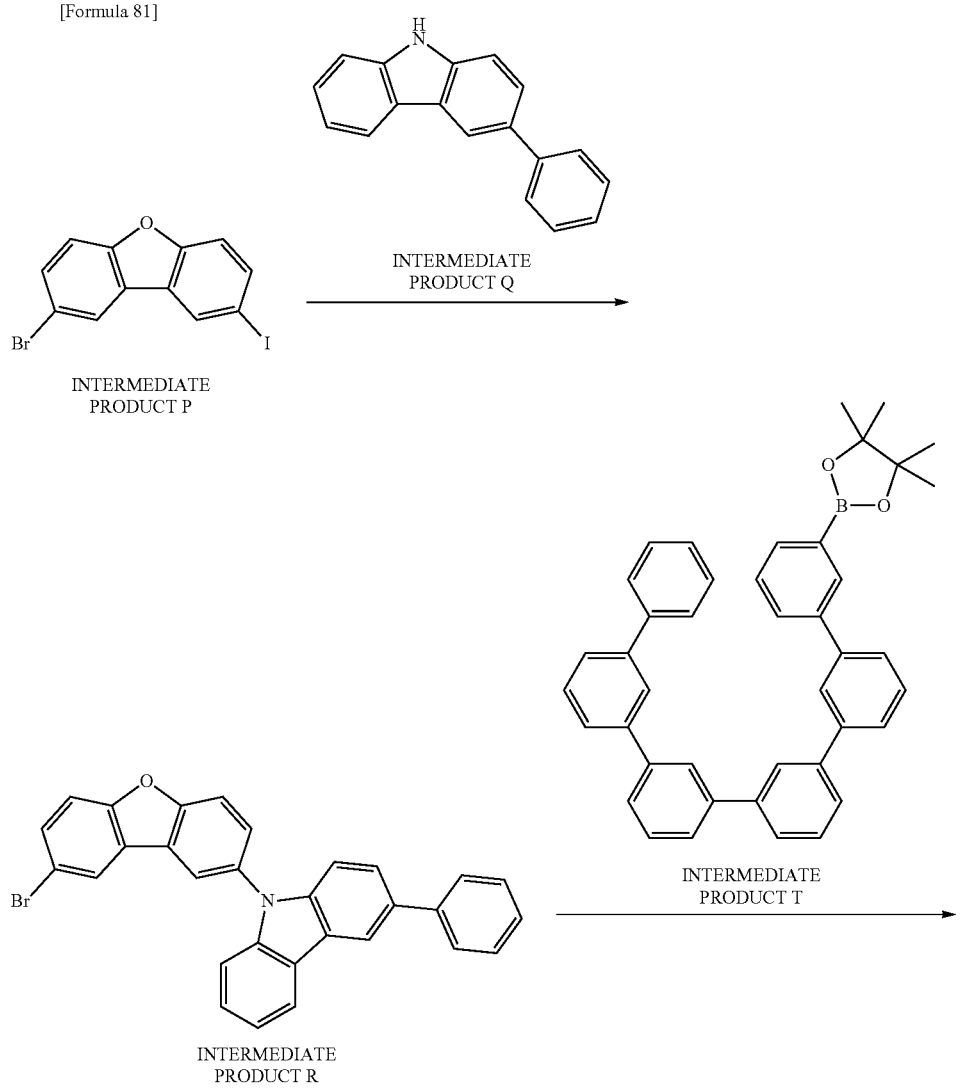

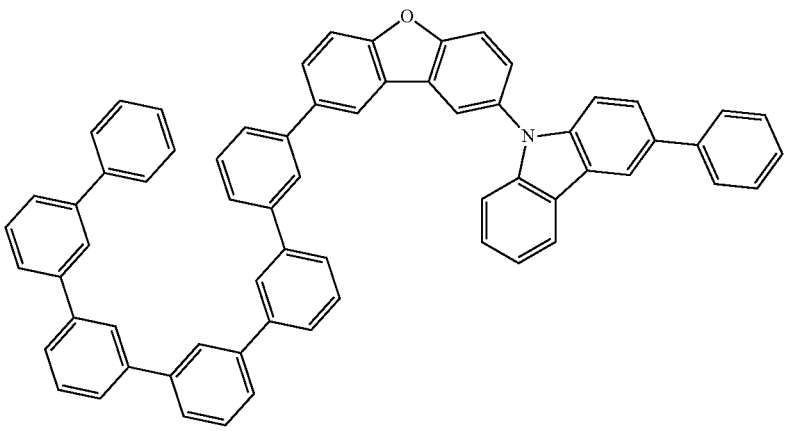

H-490

Intermediate product T was prepared as in Intermediate product L.

Compound H-490 was prepared with Intermediate product R and Intermediate product T by the following procedure.

Intermediate product R (4.88 g), Intermediate product T (5.84 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

A process of preparing Compound H-437 will now be described.

[Formula 82]

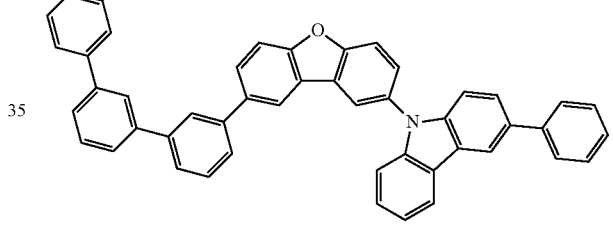

H-437

Compound H-437 can be prepared by the following scheme:

[Formula 83]

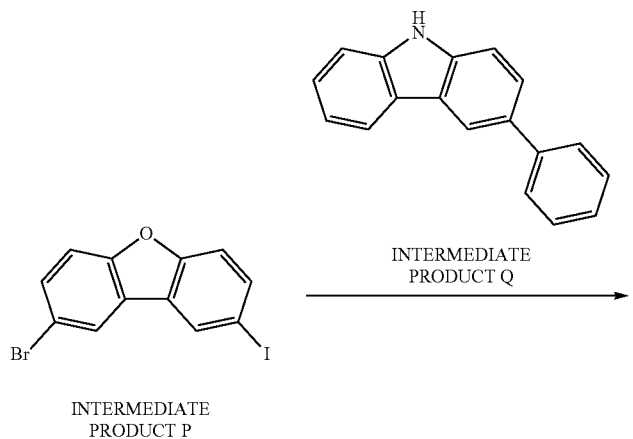

-continued

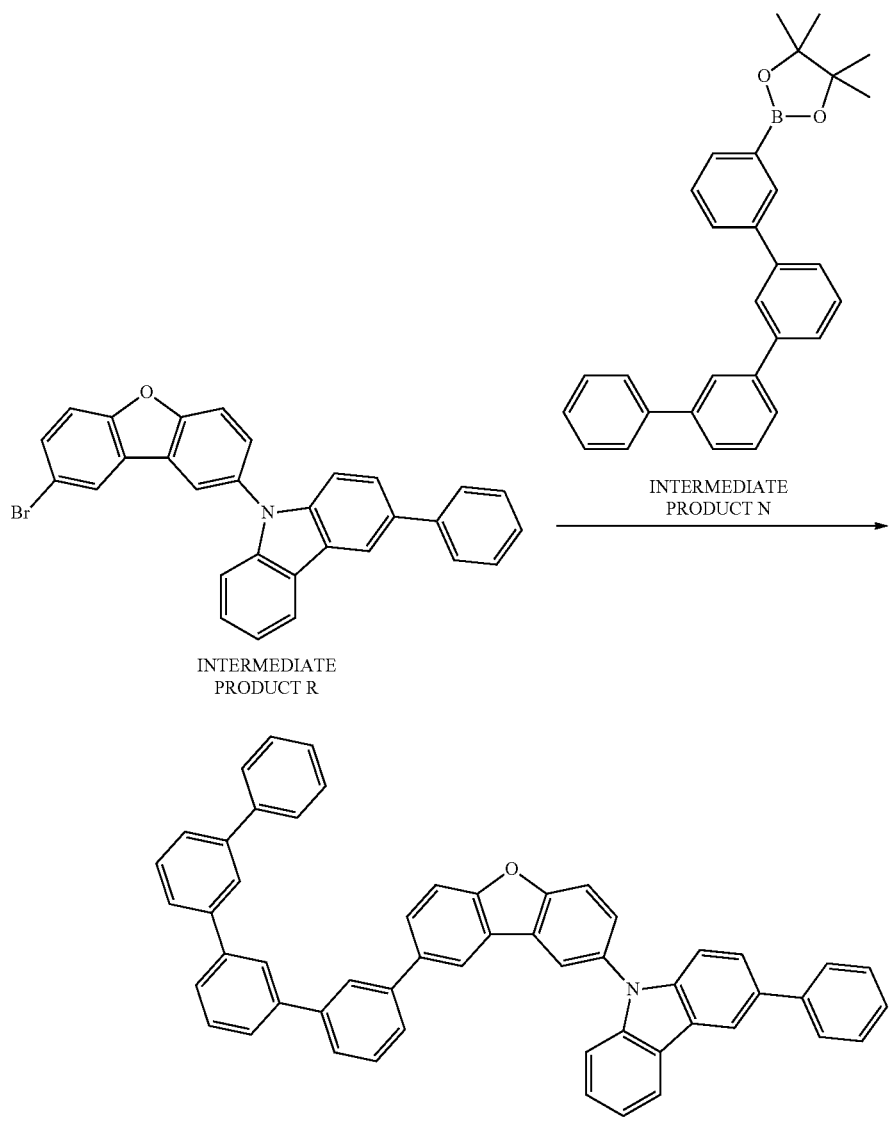

INTERMEDIATE PRODUCT R

INTERMEDIATE PRODUCT N

H-437

Compound H-437 was prepared with Intermediate product R and Intermediate product N by the following procedure.

Intermediate product R (4.88 g), Intermediate product N (4.32 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

A process of preparing Compound H-491 will now be described.

[Formula 84]

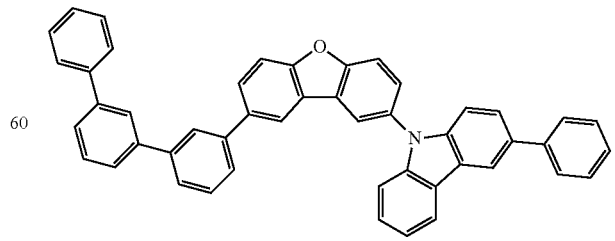

H-491

Compound H-491 can be prepared by the following scheme:

139

[Formula 85]

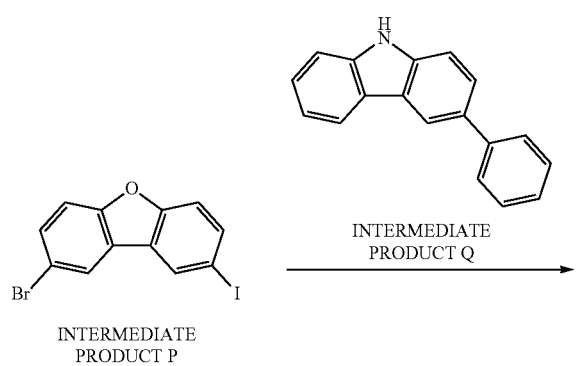

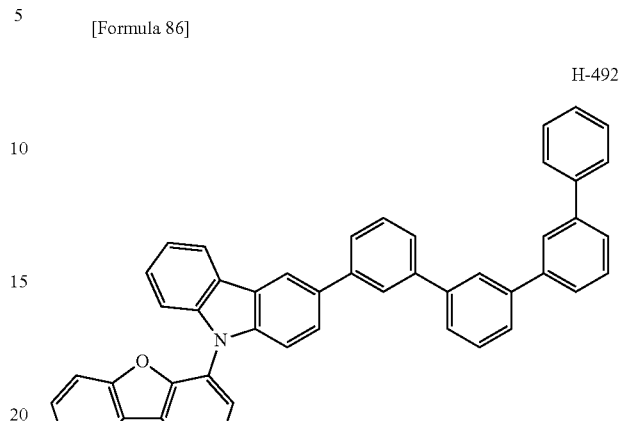

Intermediate product V was prepared as in Intermediate product L.

Compound H-491 was prepared with Intermediate product R and Intermediate product V by the following procedure.

Intermediate product R (4.88 g), Intermediate product V (3.56 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

140

A process of preparing Compound H-492 will now be described.

[Formula 86]

Compound H-492 can be prepared by the following scheme.

[Formula 87]

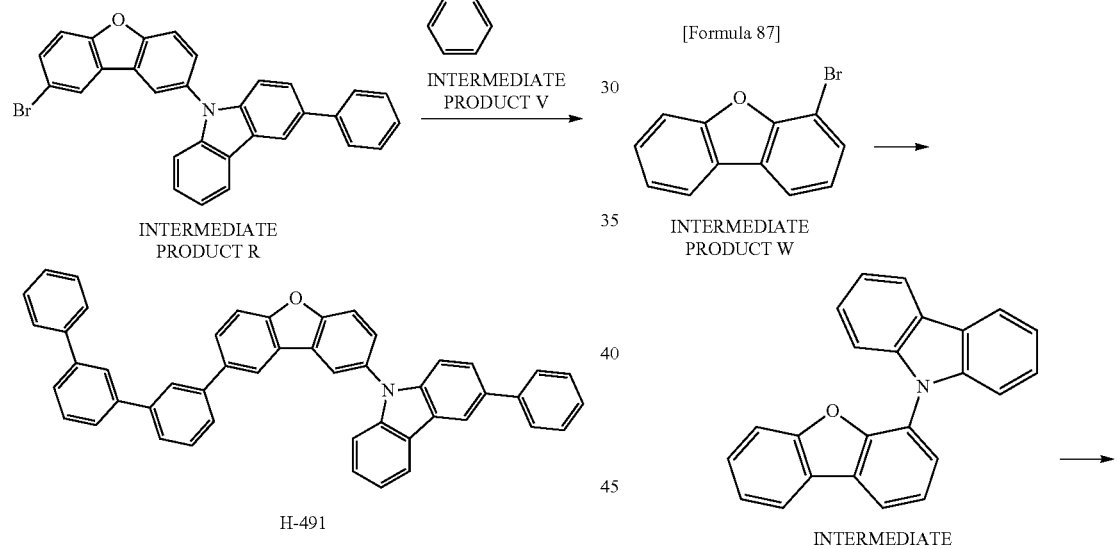

-continued

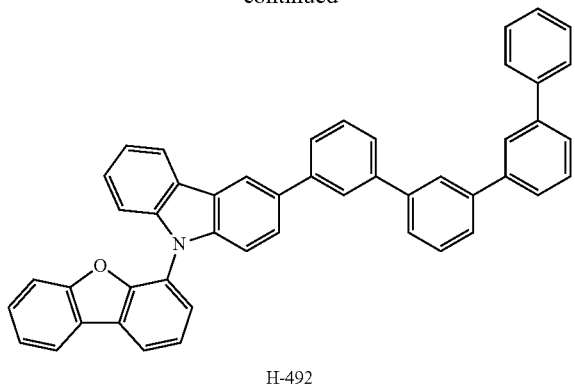

H-492

Intermediate product W was prepared with reference to Angewandte Chemie International Edition, 2010, 10214-10216.

Intermediate product X was prepared by the following procedure.

Intermediate product W (2.47 g), carbazole (1.67 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Intermediate product Y was prepared by the following procedure.

Intermediate product X (3.33 g) was placed in a 200 ml three-necked flask sufficiently purged with nitrogen, was dissolved in DMF (100 ml), and was cooled with ice. NBS (1.8 g) was added to the solution, and was stirred at room temperature. After formation of the target product was confirmed, water (100 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

Intermediate product U was prepared as in Intermediate product L.

Compound H-492 was prepared with Intermediate product Y and Intermediate product U by the following procedure.

Intermediate product Y (4.12 g), Intermediate product U (4.32 g), S-phos (1.64 g), palladium acetate (0.224 g), and tripotassium phosphate (6.3 g) were placed in a 200 ml three-necked flask sufficiently purged with nitrogen, and were dissolved in toluene (100 ml). The solution was refluxed with heating. After formation of the target product was confirmed, water (200 ml) was added, and the product was extracted with toluene. The extracted organic layer was cleaned with saturated brine. Magnesium sulfate was added, and the solution was stirred for 10 minutes. Insoluble substances were removed through filtration, and the solvent was distilled off under reduced pressure. The residue was purified by column chromatography to recover the target product.

<<Phosphorescent Compound Preferably Used in Organic EL Element According to the Present Invention>>

Phosphorescent compounds preferably used in the organic EL element according to the present invention will now be described.

The phosphorescent compounds preferably used in the organic EL element according to the present invention are represented by Formula (DP). The phosphorescent compounds represented by Formula (DP) are preferably contained together with the material for an organic EL element represented in Formula (1) in the luminous layer.

[Formula 88]

Formula (DP)

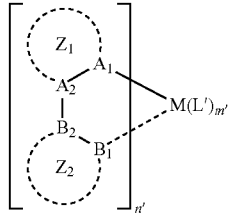

where M represents Ir, Pt, Rh, Ru, Ag, Cu, or Os; $A_1$, $A_2$, $B_1$, and $B_2$ each independently represent a carbon atom or a nitrogen atom; ring $Z_1$ represents a 6-membered aromatic hydrocarbon ring or a 5- or 6-membered aromatic heterocyclic ring including $A_1$ and $A_2$; ring $Z_2$ represents a 5- or 6-membered aromatic heterocyclic ring including $B_1$ and $B_2$; ring $Z_1$ and ring $Z_2$ may have optional substituents, and the optional substituents may be bonded to form a fused ring structure; substituents in ligands may be bonded to each other to link the ligands; at least one of $B_1$ and $B_2$ is preferably a nitrogen atom, and ring $Z_2$ is preferably a 5-membered aromatic heterocyclic ring.

In Formula (DP), L' represents a monoanionic bidentate ligand coordinated with M; m' represents an integer of 0 to 2; n' represents an integer of 1 to 3; m'+n' is 2 or 3. If m' and n' both are 1 or more, ligands represented by ring $Z_1$ and ring $Z_2$ each may be the same as or different from L'. Examples of the optional substituents included in ring $Z_1$ and ring $Z_2$ include a hydrogen atom, a deuterium atom, a halogen atom, a cyano group, an alkyl group, an alkenyl group, an alkynyl group, an alkoxy group, a hydroxyl group, a thiol group, a carbonyl group, an amino group, a silyl group, a phosphine oxide group, an arylalkyl group, an aryl group, a heteroaryl group, aromatic hydrocarbon ring groups, aromatic heterocyclic groups, non-aromatic hydrocarbon ring groups, or non-aromatic heterocyclic groups. These substituents may form fused ring structures, and may further have an optional substituent.

The compound represented by Formula (DP) is preferably represented by Formula (DP-1):

[Formula 89]

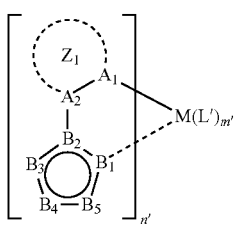

Formula (DP-1)

where M, $A_1$, $A_2$, $B_1$, $B_2$, ring $Z_1$, L', m', and n' are the same as M, $A_1$, $A_2$, $B_1$, $B_2$, ring $Z_1$, L', m', and n' defined in Formula (DP).

In Formula (DP-1), $B_3$ to $B_5$ represent a group of atoms forming an aromatic heterocyclic ring, and each represent a carbon atom, a nitrogen atom, an oxygen atom, or a sulfur atom having an optional substituent.

The optional substituent included in $B_3$ to $B_5$ are the same optional substituents as those included in ring $Z_1$ and ring $Z_2$ in Formula (DP).

In Formula (DP-1), an aromatic heterocyclic ring composed of $B_1$ to $B_5$ is preferably represented by any one of Formulae (DP-1a), (DP-1b), and (DP-1c):

[Formula 90]

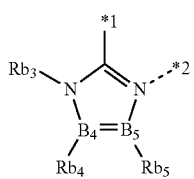

Formula (DP-1a)

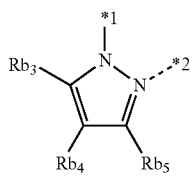

Formula (DP-1b)

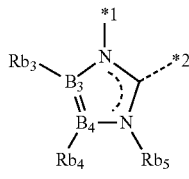

Formula (DP-1c)

In Formulae (DP-1a), (DP-1b), and (DP-1c), *1 represents a binding site to $A_2$ in Formula (DP-1), and *2 represents a binding site to M in Formula (DP-1).

In Formulae (DP-1a), (DP-1b), and (DP-1c), $Rb_3$ to $Rb_5$ each represent a hydrogen atom or a substituent. The substituents represented by $Rb_3$ to $Rb_5$ are the same optional substituents as those included in ring $Z_1$ and ring $Z_2$ in Formula (DP).

In Formula (DP-1a), $B_4$ and $B_5$ each independently represent a carbon atom or a nitrogen atom. More preferably, at least one of $B_4$ and $B_5$ represents a carbon atom.

In Formula (DP-1c), $B_3$ and $B_4$ each independently represent a carbon atom or a nitrogen atom. More preferably, at least one of $B_3$ and $B_4$ represents a carbon atom.

The compound represented by Formula (DP) is preferably a compound represented by Formula (DP-2):

[Formula 91]

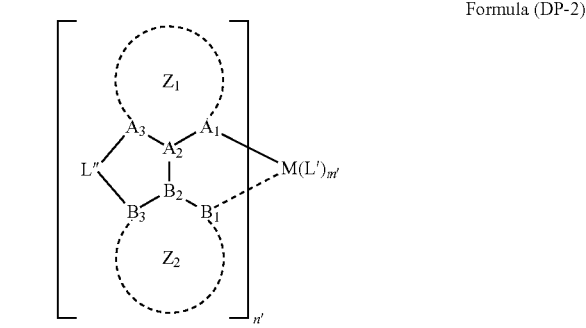

Formula (DP-2)

where M, $A_1$, $A_2$, $B_1$, $B_2$, ring $Z_1$, L', m', and n' are the same as M, $A_1$, $A_2$, $B_1$, $B_2$, ring $Z_1$, L', m', and n' defined in Formula (DP).

In Formula (DP-2), ring $Z_2$ represents a 5-membered aromatic heterocyclic ring including $B_1$ to $B_3$.

In Formula (DP-2), $A_3$ and $B_3$ each independently represent a carbon atom or a nitrogen atom; and L" represents a divalent linking group.

Examples of the divalent linking group represented by L" include an alkylene group, an alkenylene group, an arylene group, a heteroarylene group, a divalent heterocyclic group, —O—, —S—, or linking groups in any combination thereof.

The compound represented by Formula (DP-2) is preferably represented by Formula (DP-2a):

[Formula 92]

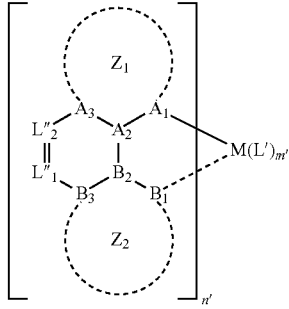

Formula (DP-2a)

where M, $A_1$, $A_2$, $A_3$, $B_1$, $B_2$, $B_3$, ring $Z_1$, ring $Z_2$, L', m', and n' are the same as M, $A_1$, $A_2$, $A_3$, $B_1$, $B_2$, $B_3$, ring $Z_1$, ring $Z_2$, L', m', and n' defined in Formula (DP-2).

In Formula (DP-2a), $L''_1$ and $L''_2$ each independently represent C—Rb6 or a nitrogen atom, and Rb6 represents a hydrogen atom or a substituent. If $L''_1$ and $L''_2$ both represent C-Rb6's, Rb6's may be bonded to each other to form a ring.

In Formula (DP), (DP-1), (DP-2), or (DP-2a), $A_2$ preferably represents a carbon atom. More preferably, $A_1$ represents a carbon atom. Ring $Z_1$ preferably represents a substituted or unsubstituted benzene or pyridine ring, more preferably represents a benzene ring.

Non-limiting, specific examples of the phosphorescent compounds represented by Formulae (DP), (DP-1), (DP-2), and (DP-2a) are listed below:

[Formula 93]
DP-1 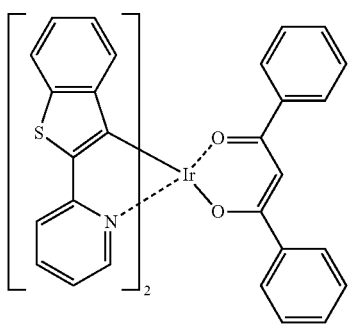
DP-2 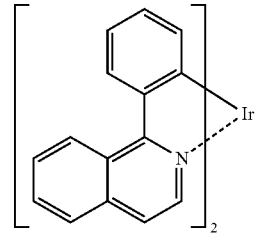
DP-3 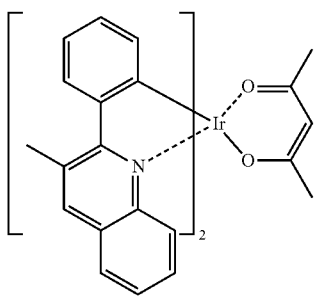
DP-4 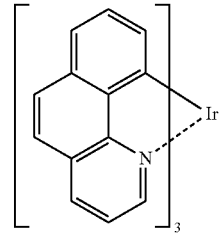
DP-5 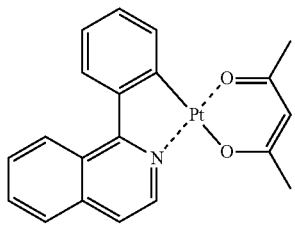
DP-6 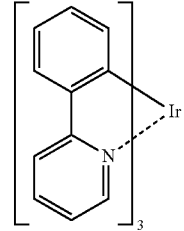
DP-7 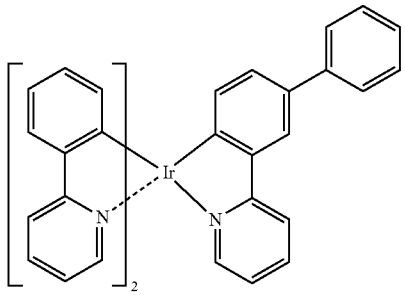
DP-8 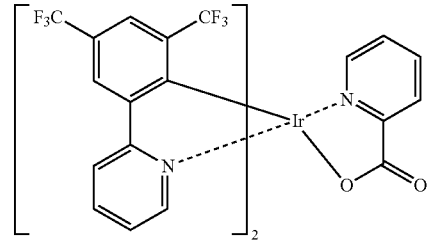
DP-9 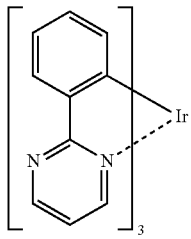
DP-10 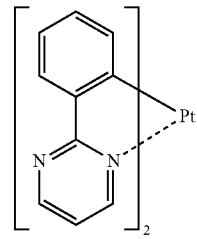

-continued
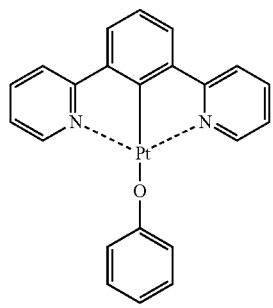
DP-11
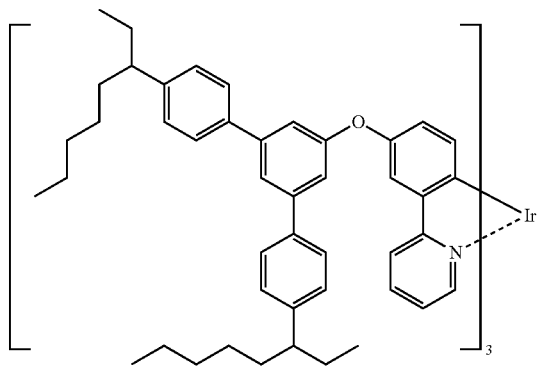
DP-12
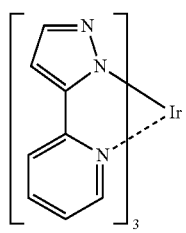
DP-13
[Formula 94]
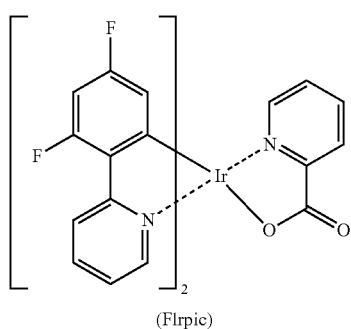
(FIrpic)
DP-14
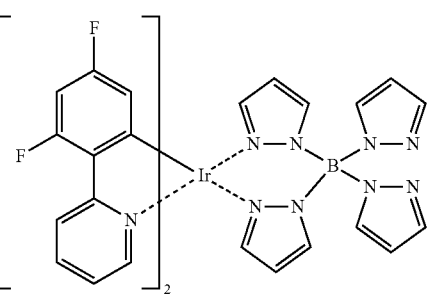
DP-15
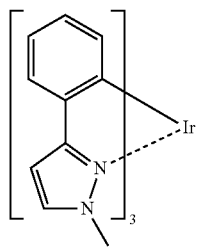
DP-17
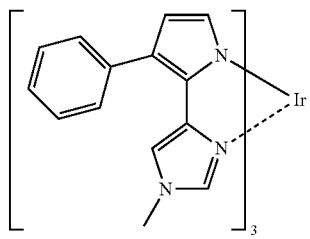
DP-18
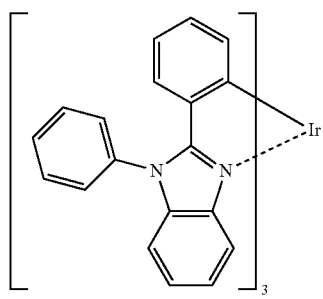
DP-19
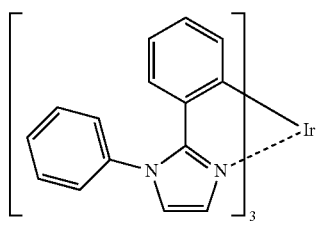
DP-20

-continued
DP-21
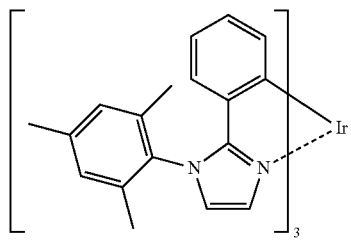
DP-22
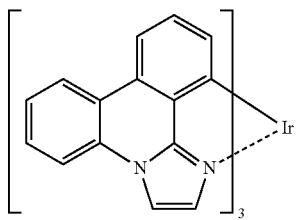
DP-23
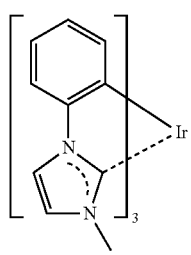
DP-24
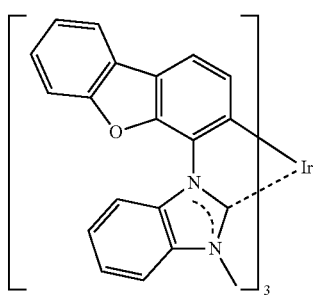
DP-25
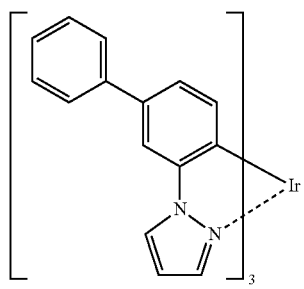
DP-26
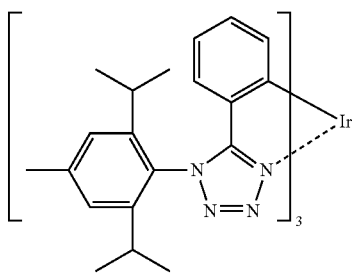
[Formula 95]
DP-27
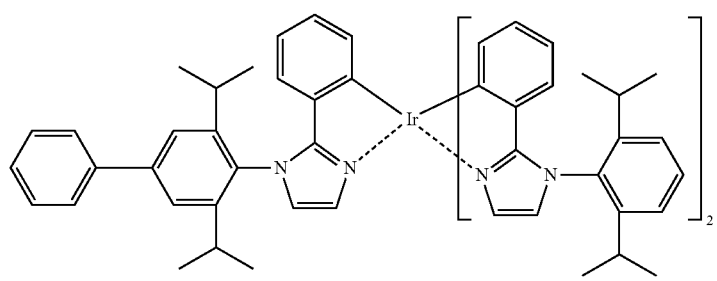
DP-28
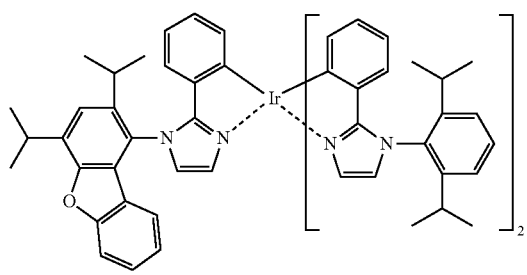
DP-29
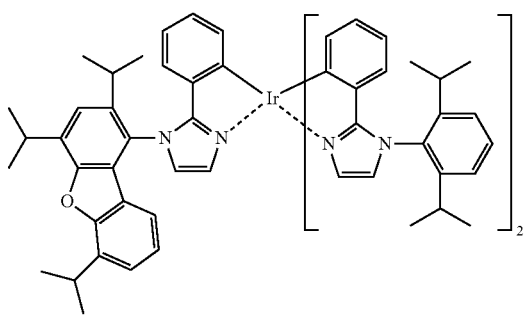

DP-30
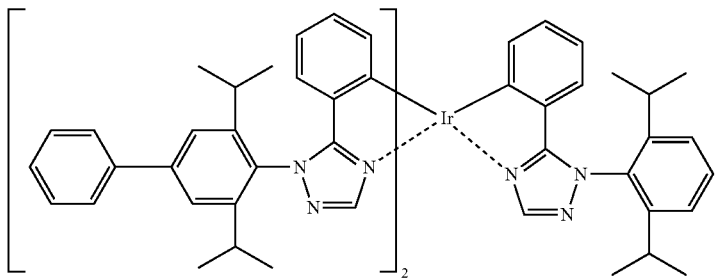
DP-31
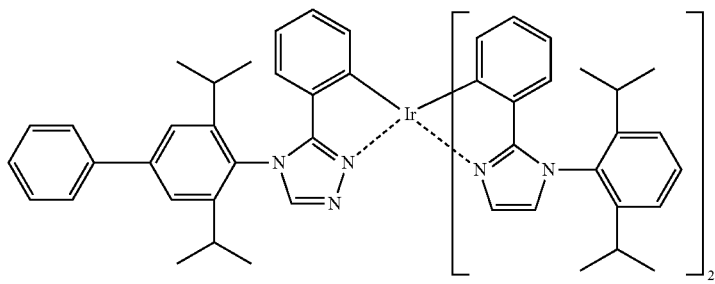
[Formula 96]
DP-32
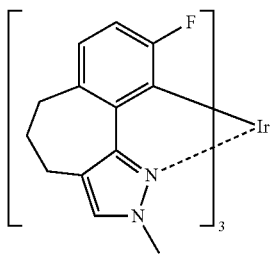
DP-33
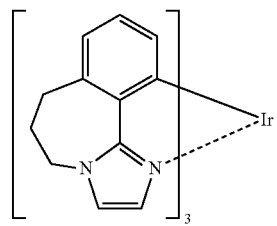
DP-34
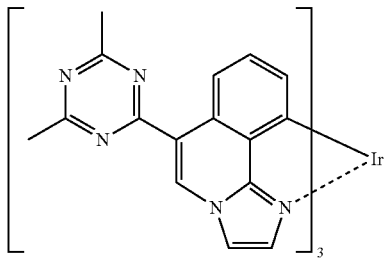
DP-35
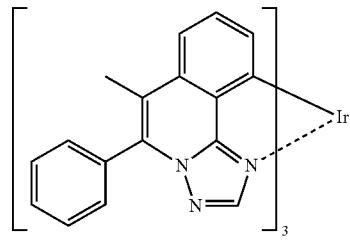
DP-36
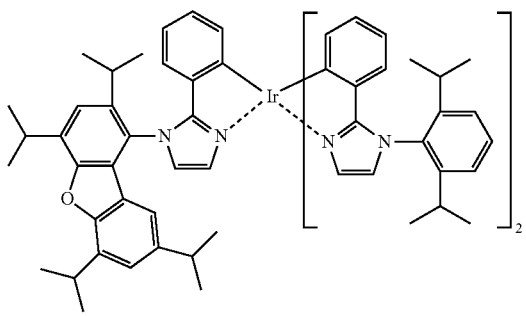
DP-37
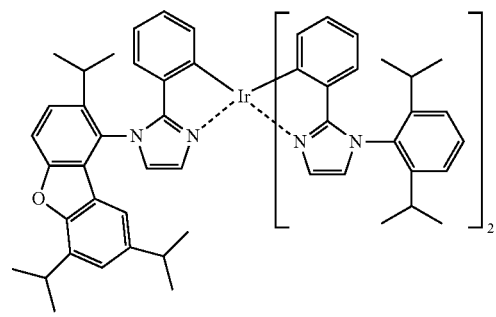

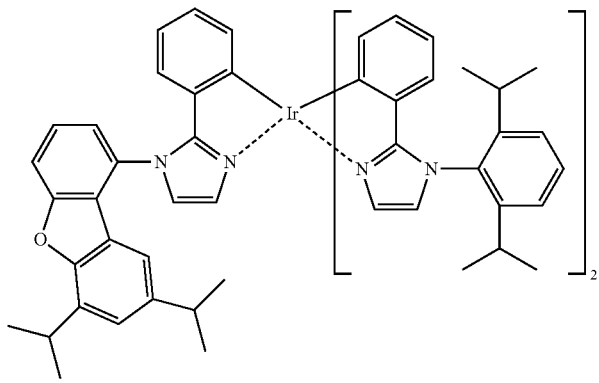
DP-38
[Formula 97]
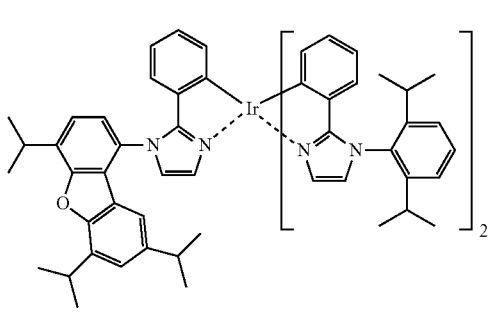
DP-39
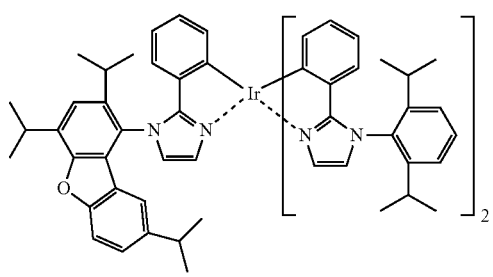
DP-40
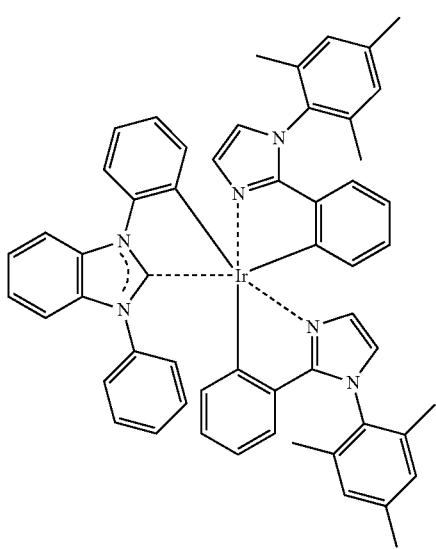
DP-41

-continued
DP-42
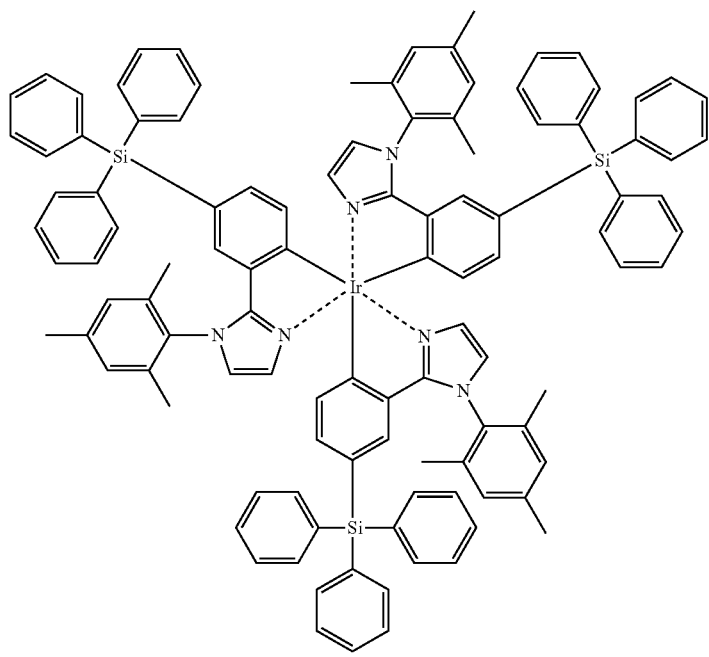
[Formula 98]
DP-43
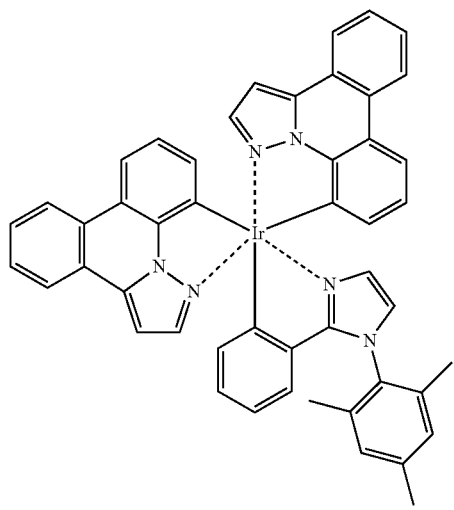
DP-44
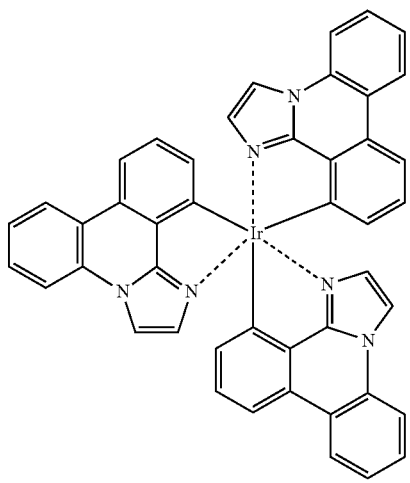
DP-45
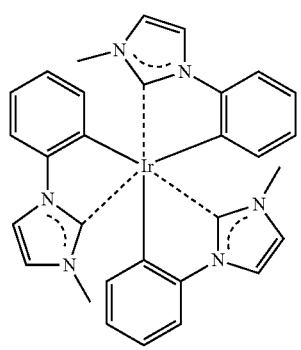
DP-46
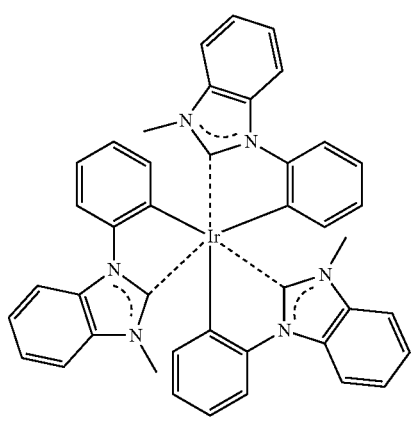

DP-47
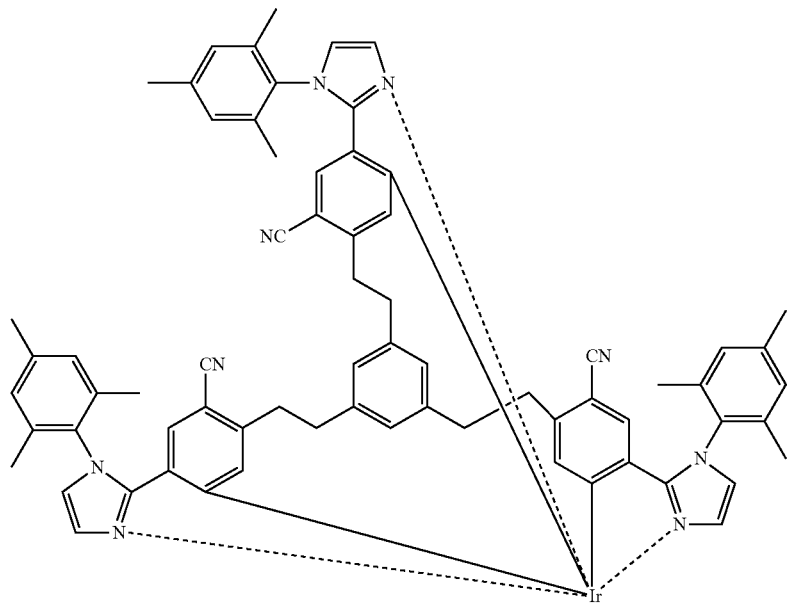
[Formula 99]
DP-48
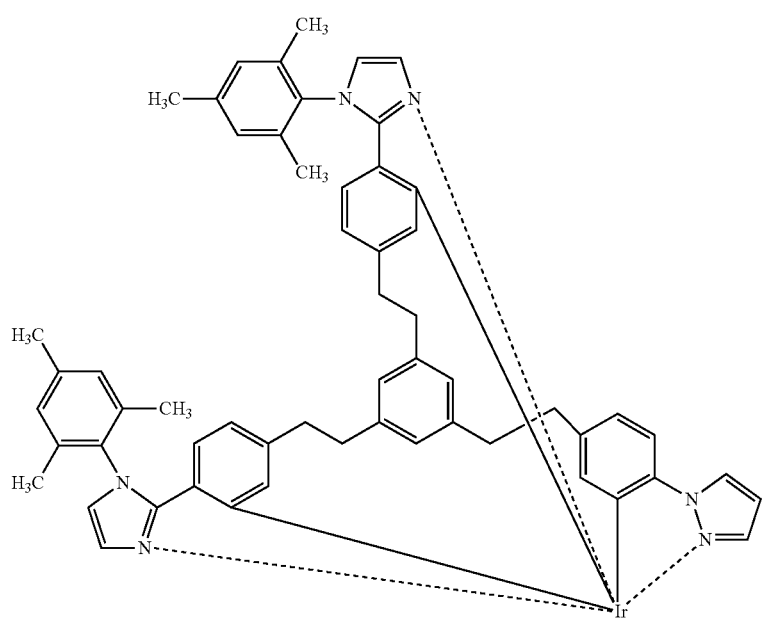

DP-49
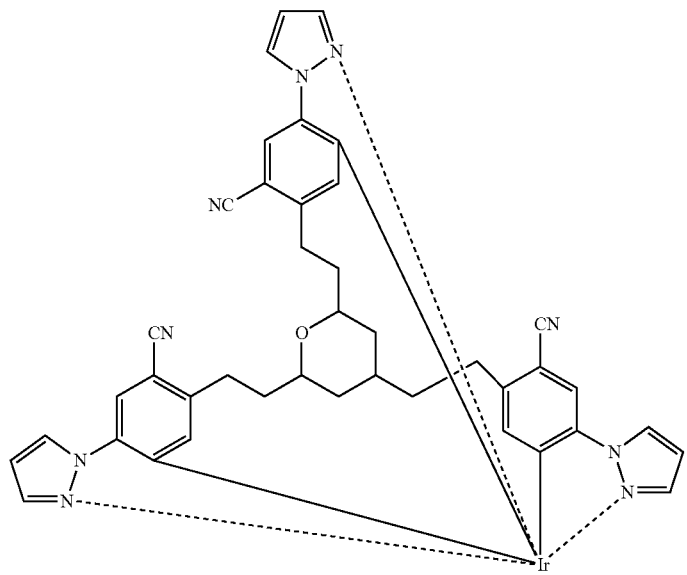
DP-50
DP-51
[Formula 100]
DP-52
DP-53
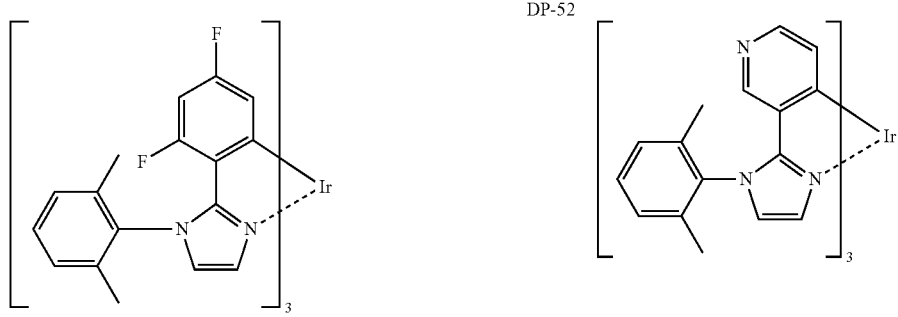
DP-54
DP-55
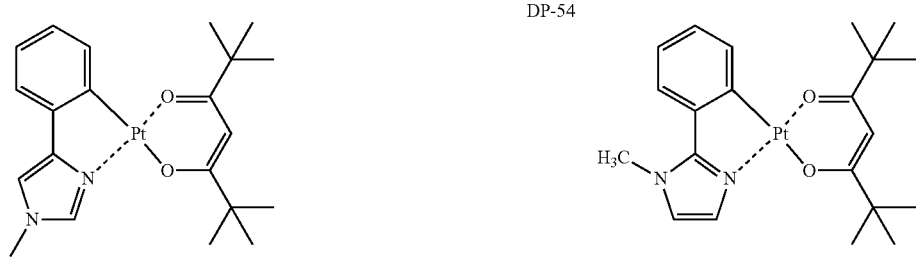

-continued

DP-56

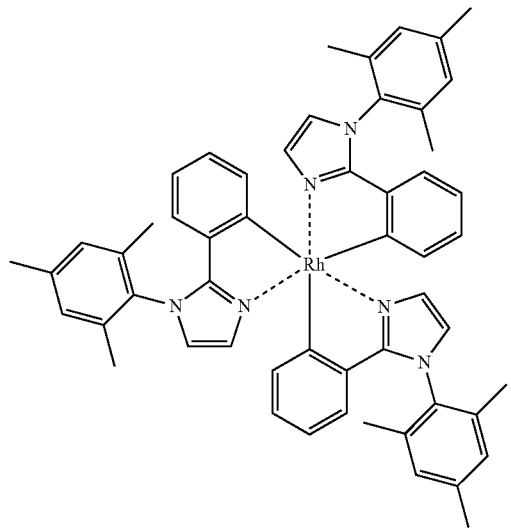

DP-57

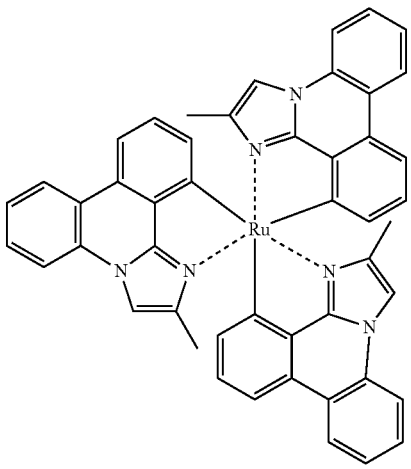

DP-58

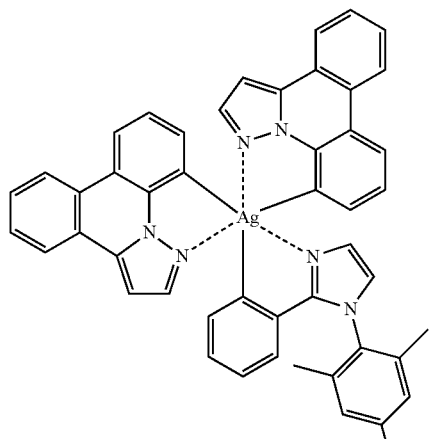

DP-59

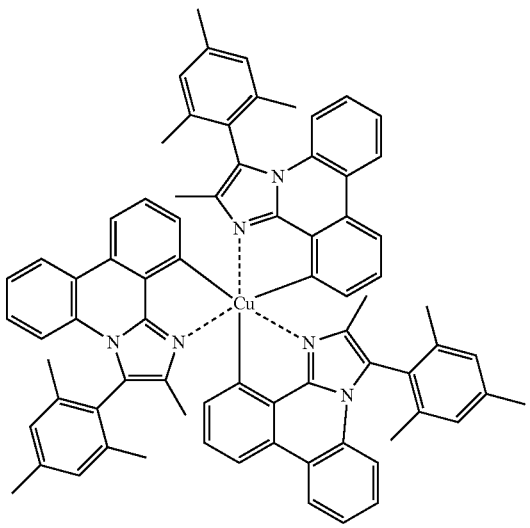

<<Layer Configuration of Organic EL Element>>

The layer configuration of the organic EL element according to the present invention will be described. The organic EL element according to the present invention includes different types of organic layers disposed between an anode and a cathode. Non-limiting, preferred examples of the layers and the layer configuration are listed below:
(i) Anode/luminous layer unit/electron transporting layer/cathode
(ii) Anode/hole transporting layer/luminous layer unit/electron transporting layer/cathode
(iii) Anode/hole transporting layer/luminous layer unit/hole blocking layer/electron transporting layer/cathode
(iv) Anode/hole transporting layer/luminous layer unit/electron transporting layer/electron injecting layer/cathode
(v) Anode/hole injecting layer/hole transporting layer/luminous layer unit/electron transporting layer/electron injecting layer/cathode
(vi) Anode/hole transporting layer/luminous layer unit/hole blocking layer/electron transporting layer/electron injecting layer/cathode
(vii) Anode/hole injecting layer/hole transporting layer/luminous layer unit/hole blocking layer/electron transporting layer/electron injecting layer/cathode.

Besides the hole blocking layers, electron blocking layers are also used as blocking layers.

The luminous layer unit (hereinafter merely referred to as luminous layer) may be composed of one luminous layer, or may be composed of two or more luminous layers. The luminous layer unit may further include a non-luminous intermediate layer between any adjacent luminous layers. Alternatively, the luminous layer unit may have a multiphoton unit configuration, the intermediate layer of which is a charge generating layer. In this case, examples of the charge generating layer include inorganic layers composed of conductive inorganic compounds, such as indium.tin oxide (ITO), indium.zinc oxide (IZO), $ZnO_2$, TiN, ZrN, HfN, TiOx, VOx, CuI, InN, GaN, $CuAlO_2$, $CuGaO_2$, $SrCu_2O_2$, $LaB_6$, and $RuO_2$; double-layer films, such as $Au/Bi_2O_3$ films; multi-layer films, such as $SnO_2/Ag/SnO_2$, $ZnO/Ag/ZnO$, $Bi_2O_3/Au/Bi_2O_3$, $TiO_2/TiN/TiO_2$, and $TiO_2/ZrN/TiO_2$ films; and organic layers composed of conductive organic compounds, such as fullerenes (such as C60), oligothiophene, metal phthalocyanines, metal-free phthalocyanines, metal porphyrins, and metal-free porphyrins.

In the organic EL element according to the present invention, a preferred luminous layer is a white luminous layer. Illumination devices including white luminous layers are preferred. In other words, the organic EL element preferably emits white light.

The individual layers in the organic EL element according to the present invention will now be described.

<<Luminous Layer>>

The luminous layer emits light through recombination of electrons and holes, which are injected from electrodes or the electron transporting layer and the hole transporting layer. The site of light emission may be the interior of the luminous layer or the interface between the luminous layer and its adjoining layer.

The entire luminous layer can have any thickness. The thickness is adjusted to the range of preferably 2 to 5000 nm, more preferably 2 to 200 nm, most preferably 5 to 100 nm in order to achieve high uniformity of the film, luminescence at relatively low voltage applied to the luminous layer, and stable color light emission regardless of a variation in driving current.

The luminous layer can be prepared with a luminous dopant and a host compound described later by a vacuum evaporation process or a wet process (e.g., spin coating, casting, die coating, blade coating, roll coating, ink jetting, printing, spray coating, curtain coating, and Langmuir-Blodgett (LB) coating).

In the organic EL element according to the present invention, the luminous layer preferably contains a luminous dopant (such as phosphorescent dopants (also referred to as phosphorescent dopant group) and fluorescent dopants) compound and a luminous host compound.

(1) Luminous Dopant

The luminous dopant (also referred to as merely dopant) will be described. Examples of usable luminous dopants include fluorescent dopants (also referred to as fluorescent compounds) and phosphorescent dopants (also referred to as phosphorescent substances or compounds).

(1.1) Phosphorescent Dopant

The phosphorescent dopant usable in the present invention will now be described.

The phosphorescent dopant according to the present invention emits light from the excited triplet state. Specifically, the phosphorescent dopant according to the present invention is defined as a compound emitting phosphorescent light at room temperature (25° C.) and having a phosphorescent quantum yield of 0.01 or more at 25° C. A preferred phosphorescent quantum yield is 0.1 or more.

The phosphorescent quantum yield is determined by the method described in page 398 of Bunko II of Jikken Kagaku Koza 7 (Spectroscopy II, Experimental Chemistry 7) (4th Edition, 1992, published by Maruzen Company, Limited). The phosphorescent quantum yield in a solution can be determined with any suitable solvent. The phosphorescent dopant usable in the present invention has a phosphorescent quantum yield of 0.01 or more determined with an appropriate solvent.

There are two types of light emission mechanisms of the phosphorescent dopant: The first one is energy-transfer emission. Carriers transported to the host compound are recombined therein to excite the luminous host compound, and the energy of the excited luminous host compound is transferred to the phosphorescent dopant to emit light from the phosphorescent dopant. The second one is carrier-trap emission. The phosphorescent dopant serves as a carrier trap to recombine carriers trapped on the phosphorescent dopant to emit light. In both cases, the excitation energy of the phosphorescent dopant should be lower than the excitation energy of the host compound.

The organic EL element according to the present invention preferably contains a phosphorescent compound represented by any one of Formulae (DP), (DP-1), (DP-2), and (DP-2a).

The luminous layer usable in the present invention can be used in combination with the compounds disclosed in the following patent publications:

WO00/70655, Japanese Patent Application Laid-Open Nos. 2002-280178, 2001-181616, 2002-280179, 2001-181617, 2002-280180, 2001-247859, 2002-299060, 2001-313178, 2002-302671, 2001-345183, and 2002-324679, WO02/15645, Japanese Patent Application Laid-Open Nos. 2002-332291, 2002-50484, 2002-332292, and 2002-83684, Japanese Unexamined Patent Application Publication (Tokuhyou) No. 2002-540572, Japanese Patent Application Laid-Open Nos. 2002-117978, 2002-338588, 2002-170684, and 2002-352960, WO01/93642, Japanese Patent Application Laid-Open Nos. 2002-50483, 2002-100476, 2002-173674, 2002-359082, 2002-175884, 2002-363552, 2002-184582, and 2003-7469, Japanese Unexamined Patent Application Publication (Tokuhyou) No. 2002-525808, Japanese Patent Application Laid-Open No. 2003-7471, Japanese Unexamined Patent Application Publication (Tokuhyou) No. 2002-525833, Japanese Patent Application Laid-Open Nos. 2003-31366, 2002-226495, 2002-234894, 2002-235076, 2002-241751, 2001-319779, 2001-319780, 2002-62824, 2002-100474, 2002-203679, 2002-343572, and 2002-203678.

(1.2) Fluorescent Dopant

Examples of fluorescent dopants (also referred to as fluorescent compounds) include coumarin dyes, pyran dyes, cyanine dyes, croconium dyes, squarylium dyes, oxobenzanthracene dyes, fluorescein dyes, rhodamine dyes, pyrylium dyes, perylene dyes, stilbene dyes, polythiophene dyes, fluorescent rare earth element complexes, and compounds having high fluorescent quantum yields, such as laser dyes.

(1.3) Luminous Dopant in Combination with Traditional Dopants

The luminous dopants usable in the present invention may be a combination of two or more compounds, for example, a combination of phosphorescent dopants having different structures or a combination of a phosphorescent dopant with a fluorescent dopant.

Non-limiting, specific examples of traditional phosphorescent dopants usable in combination with the compound represented by Formula (1) according to the present invention are listed below:

[Formula 101]

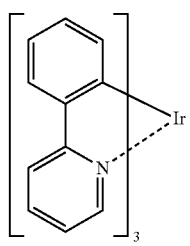

D-1

D-2 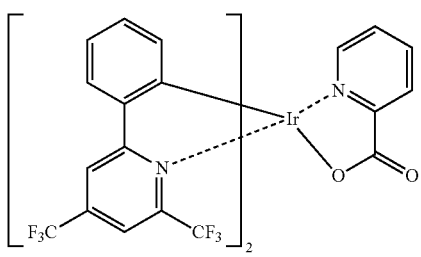
D-3 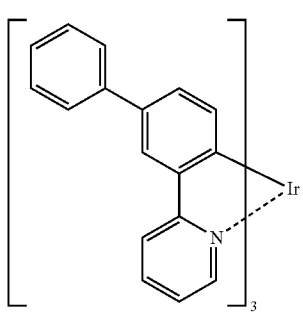
D-4 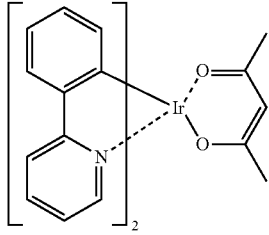
D-5 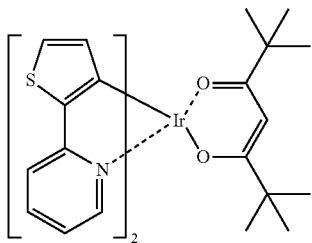
D-6 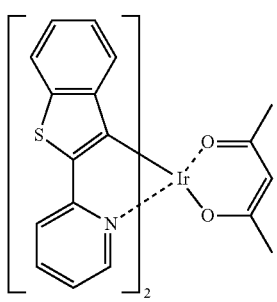
D-7 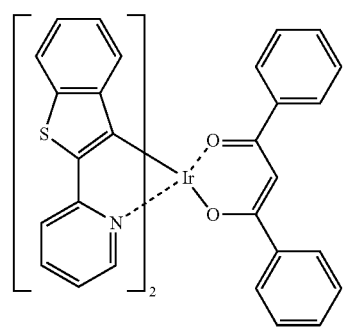
D-8 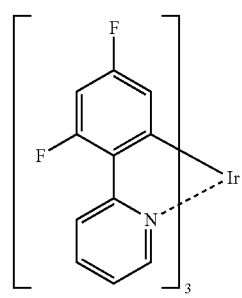
D-9 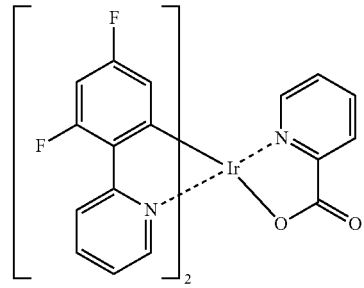
D-10 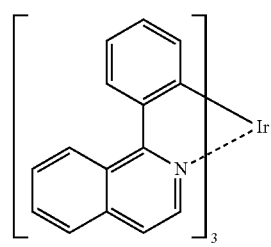
D-11 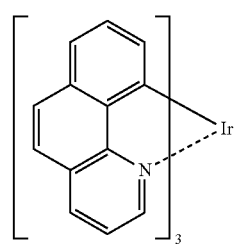

D-12
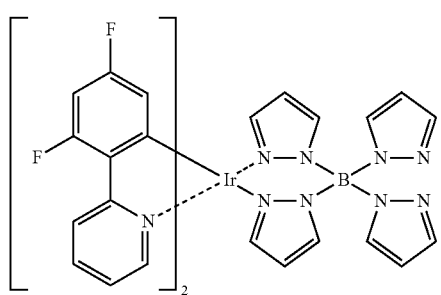
[Formula 102]
D-13
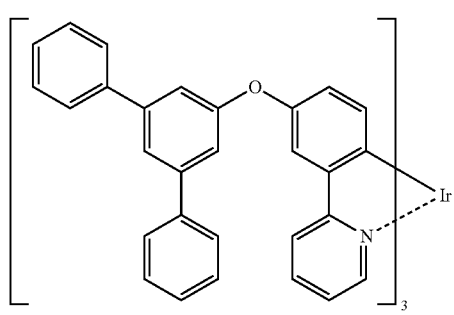
D-14
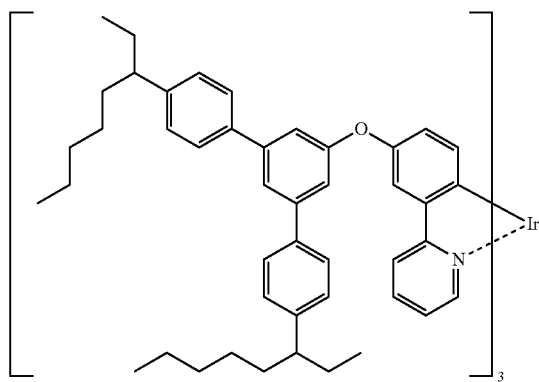
D-15
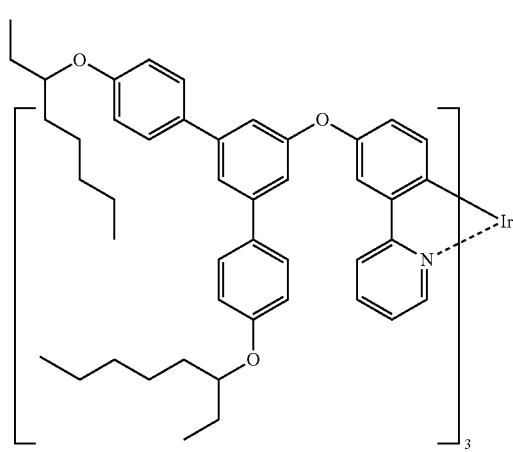
D-16
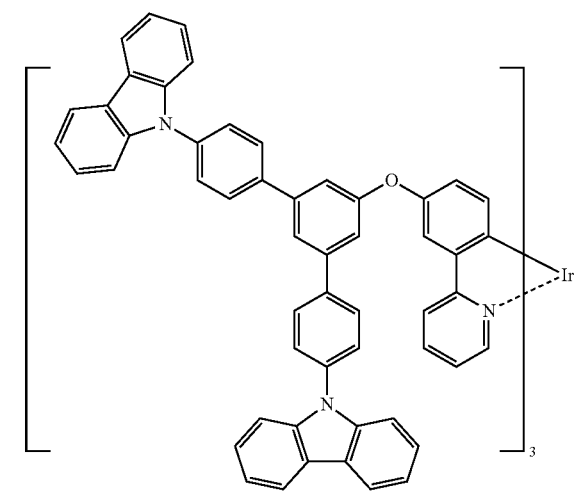
D-17
(bottom portion of img_3)
[Formula 103]
D-18
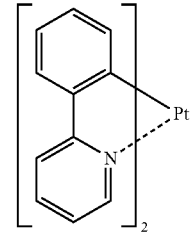
D-19
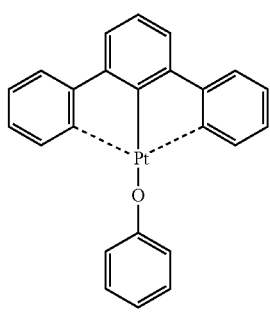

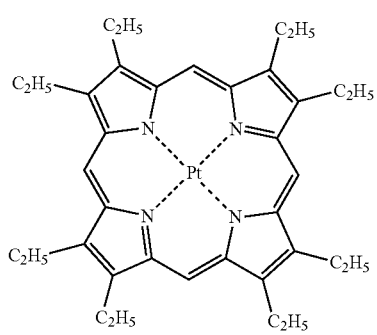
D-20
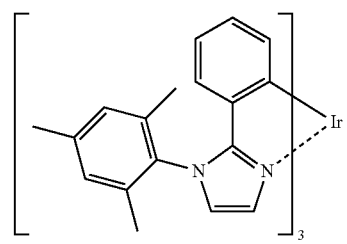
D-26
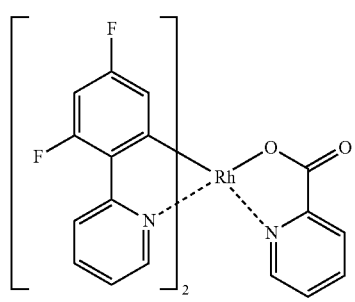
D-21
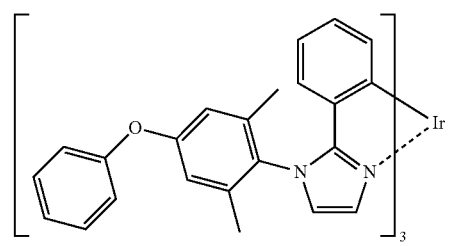
D-27
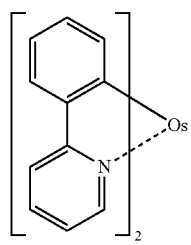
D-22
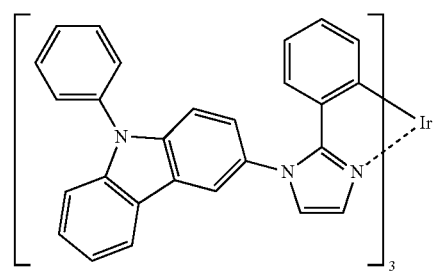
D-28
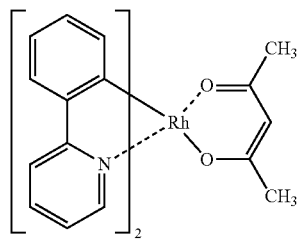
D-23
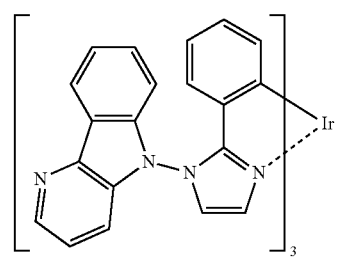
D-29
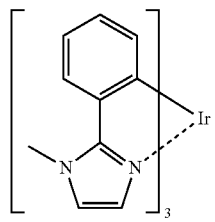
D-24
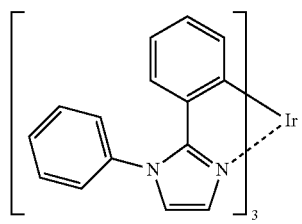
D-25
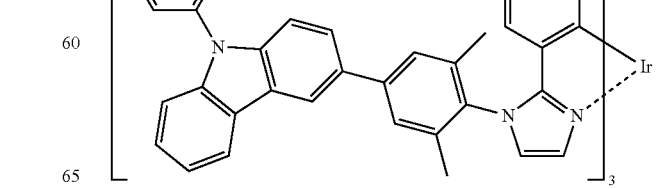
D-30

[Formula 104]
D-31
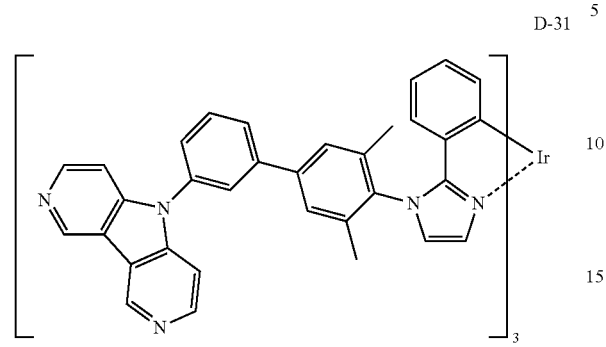
D-32
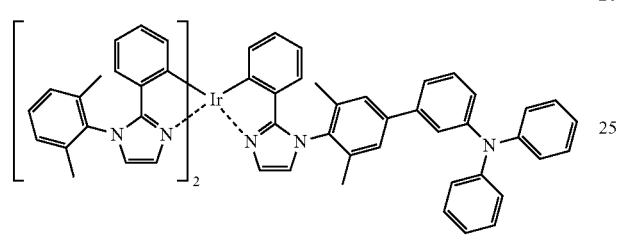
D-33
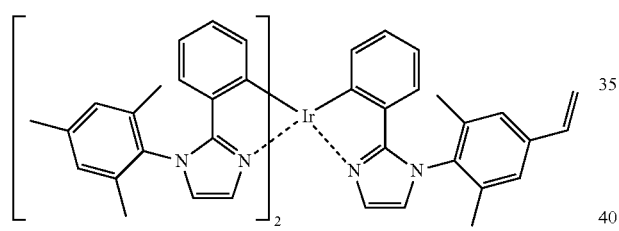
D-34
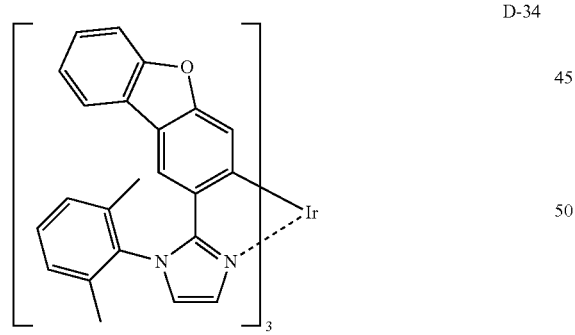
D-35
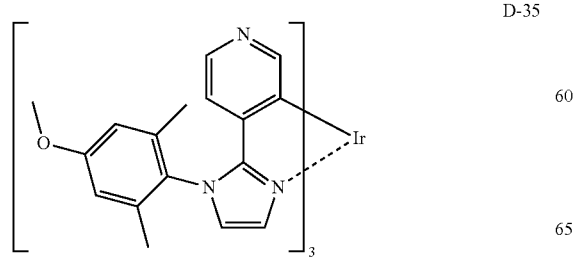
D-36
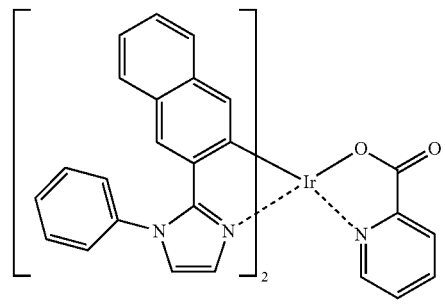
D-37
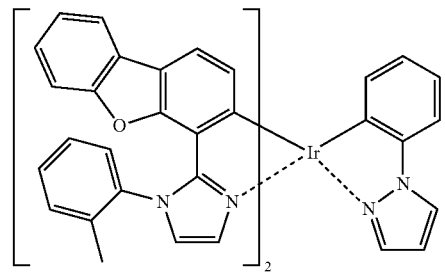
D-38
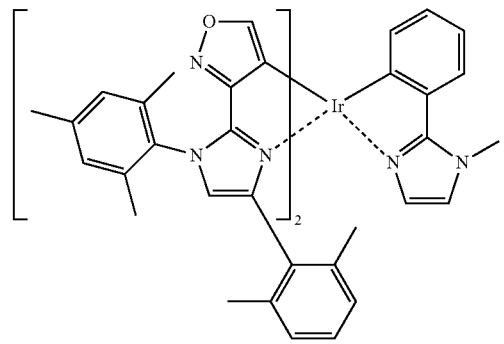
[Formula 105]
D-39
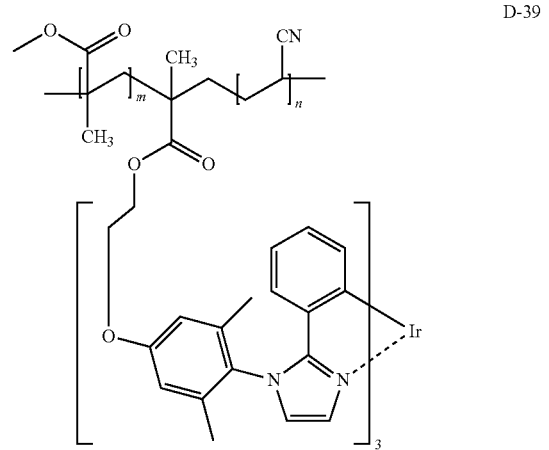

-continued
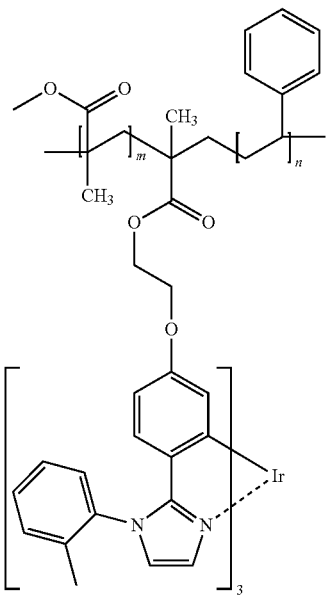
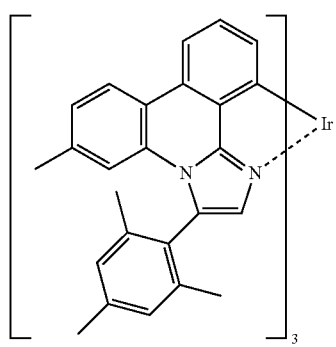
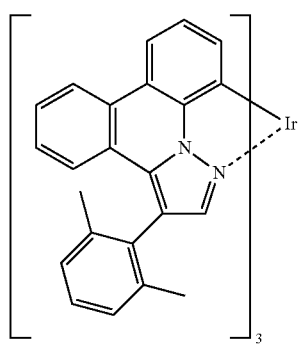
-continued
D-40
D-41
D-42
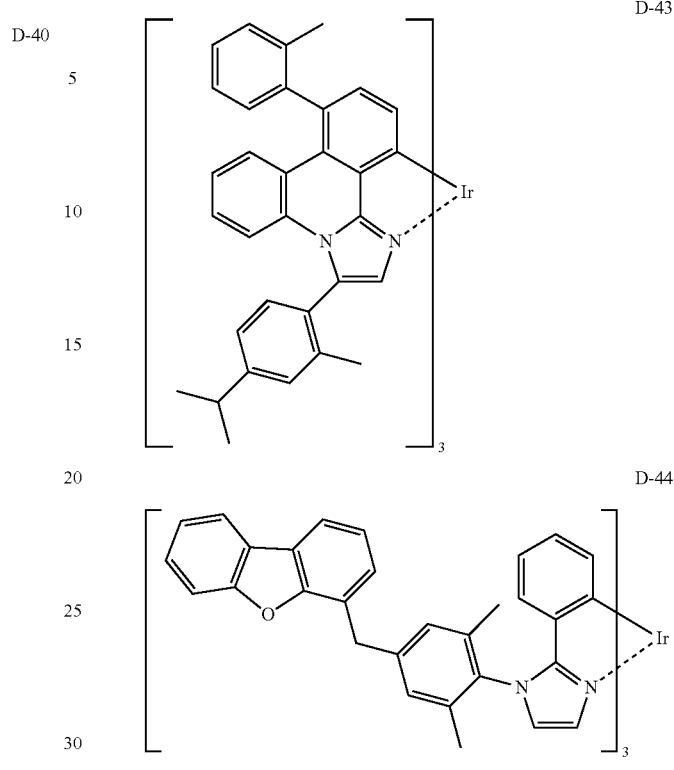
D-43
D-44
D-45
[Formula 106]
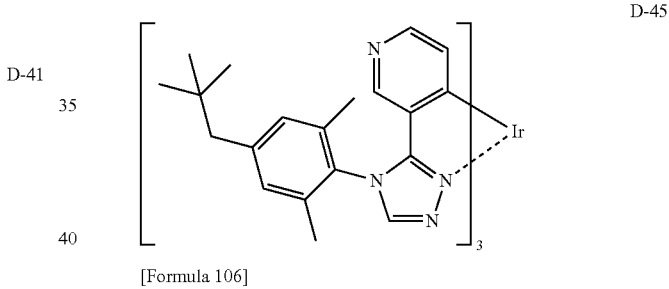
D-46
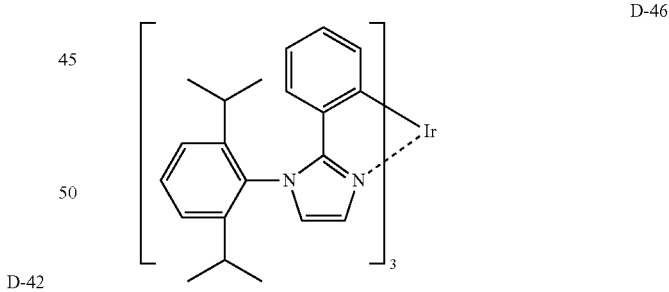
D-47
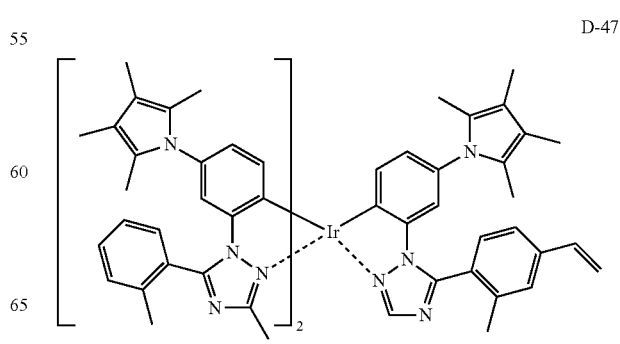

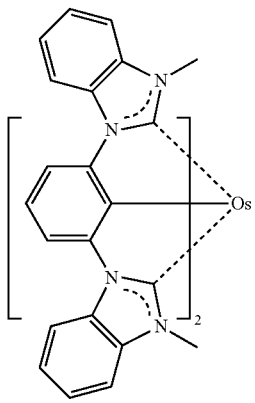

D-48

(2) Luminous Host Compound

In the present invention, the luminous host compound (also referred to as luminous host, host compound, or host material) is defined as a compound contained in the luminous layer in a content of 20% or more, and emitting phosphorescence having a phosphorescent quantum yield of less than 0.1 at room temperature (25° C.). Preferably, the phosphorescent quantum yield is less than 0.01. The content of the luminous host compound in the luminous layer is preferably 50% or more.

Any compound typically used in organic EL elements can be used as the luminous host in the present invention. A preferred host compound used in the organic EL element according to the present invention is the material for an organic EL element represented in Formula (1) according to the present invention described above.

The host compound represented by Formula (1) according to the present invention can be used in combination with traditional host compounds. Typical examples of such traditional compounds include compounds having basic skeletons, such as carbazole derivatives, triarylamine derivatives, aromatic derivatives, heterocyclic compounds containing nitrogen, thiophene derivatives, furan derivatives, and oligoarylene compounds; or carboline derivatives and diazacarbazole derivatives (where the diazacarbazole derivative indicates a carboline derivative having a carboline ring in which at least one carbon atom in a hydrocarbon ring is replaced with a nitrogen atom).

Preferred luminous hosts usable in the present invention are known compounds that have hole transportation ability and electron transportation ability, do not cause a shift of light emission toward longer wavelengths, and have high glass transition temperature (Tg).

In the organic EL element according to the present invention, the material for an organic EL element represented by Formula (1) or a known host compound may be used alone, or these host compounds can be used in combination. A combination of several host compounds can control charge transfer to improve the efficiency of the organic EL element. A combination of several phosphorescent compounds represented by Formula (DP) and known phosphorescent dopants listed above can emit light of any color through mixing of light components.

The luminous host used in the present invention may be a low-molecular compound or a high-molecular compound having repeating units, or may be a low-molecular compound having a polymerizable group, such as a vinyl or epoxy group, (polymerizable luminous host). These compounds can be used alone or in combination.

Specific examples of the known luminous hosts include compounds described in the following documents:

Japanese Patent Application Laid-Open Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, and 2002-308837.

<<Injecting Layers: Hole Injecting Layer (Anode Buffer Layer), Electron Injecting Layer (Cathode Buffer Layer)>>

The injecting layer is disposed when necessary, and classified into an electron injecting layer and a hole injecting layer. As shown in the layer configuration above, the injecting layer can be disposed between the anode and the hole transporting layer, between the cathode and the electron transporting layer, between the anode and the luminous layer, or between the cathode and the luminous layer.

The injecting layer is disposed between the electrode and the organic layer to reduce driving voltage and enhance the luminance of emitted light. The detailed description is found in Chapter 2 "Denkyoku zairyo (Electrode material)" (pp. 123 to 166) of Yuki EL Soshi to Sonokougyouka Saizensen (Organic EL elements and Their Frontiers of Industrial Applications) vol. 2 (Nov. 30, 1998, published by NTS Inc.). The injecting layer is classified into a hole injecting layer (anode buffer layer) and an electron injecting layer (cathode buffer layer).

The anode buffer layer (hole injecting layer) is described in detail in Japanese Patent Application Laid-Open Nos. 9-45479, 9-260062, and 8-288069. Specific examples thereof include phthalocyanine buffer layers composed of phthalocyanine compounds, such as copper phthalocyanine; hexaazatriphenylene derivative buffer layers described in Japanese Unexamined Patent Application Publication (Tokuhyou) No. 2003-519432 and Japanese Patent Application Laid-Open No. 2006-135145; oxide buffer layers composed of oxides, such as vanadium oxide; amorphous carbon buffer layers; polymer buffer layers composed of conductive polymers, such as polyaniline (emeraldine) and polythiophene; and orthometalated complex layers composed of orthometalated complexes, such as a tris(2-phenylpyridine) iridium complex.

The cathode buffer layer (electron injecting layer) is described in detail in Japanese Patent Application Laid-Open Nos. 6-325871, 9-17574, and 10-74586. Specific examples thereof include metal buffer layers composed of metals, such as strontium and aluminum; alkali metal compound buffer layers composed of alkali metal compounds, such as lithium fluoride and potassium fluoride; alkaline earth metal compound buffer layers composed of alkaline earth metals, such as magnesium fluoride and cesium fluoride; and oxide buffer layers composed of oxides, such as aluminum oxide. The buffer layer (injecting layer) is desirably a very thin film. The thickness, which depends on materials, preferably ranges from 0.1 to 5000 nm.

<<Blocking Layer: Hole Blocking Layer, Electron Blocking Layer>>

The blocking layer is an optional layer added to the basic configuration of the organic layer described above. Examples of the blocking layer include hole blocking layers described in Japanese Patent Application Laid-Open Nos. 11-204258 and 11-204359, and page 237 of Yuki EL Soshi to Sonokougyouka Saizensen (Organic EL elements and Their Frontiers of Industrial Applications) (Nov. 30, 1998, published by NTS Inc.).

The hole blocking layer in a broad sense is composed of a hole blocking material having significantly low hole transportation ability while having electron transportation ability. Such a hole blocking layer blocks holes while transporting electrons, thereby increasing the opportunity of the recombination of electrons and holes.

Alternatively, the electron transporting layer described later can be used as the hole blocking layer when necessary.

In the organic EL element according to the present invention, the hole blocking layer is preferably disposed adjacent to the luminous layer.

Examples of usable hole blocking materials include carbazole derivatives, carboline derivatives, and diazacarbazole derivatives (where the diazacarbazole derivative indicates a carboline ring of which one of carbon atoms is replaced with a nitrogen atom) listed as the host compound above. The material for an organic EL element represented in Formula (1) can also be preferably used.

In the present invention, if two or more luminous layers emitting light beams of different colors are disposed, a luminous layer, among all of the luminous layers, emitting a light beam having a local maximum at the shortest wavelength (shortest-wavelength luminous layer) is preferably disposed nearest to the anode. In this case, the hole blocking layer is preferably disposed between the shortest wavelength layer and the luminous layer nearest to the anode second to the above shortest wavelength layer. More preferably, the hole blocking layer disposed in this position contains 50 mass % or more compound having an ionization potential that is 0.3 eV or more greater than that of the host compound contained in the shortest wavelength luminous layer.

The ionization potential is defined as energy required for release of electrons at the highest occupied molecular orbit (HOMO) level of a compound to the vacuum level, and can be determined by the following methods:

(1) The ionization potential can be determined with Gaussian 98 software for molecular orbit calculation (Revision A.11.4, M. J. Frisch, et al., available from Gaussian, Inc., Pittsburgh Pa., the United States, 2002.) as a value (in eV unit) calculated through optimization of the structure with a keyword B3LYP/6-31G*. The effectiveness of the calculated value is verified by a high correlation between the calculated value and the experimental value.

(2) The ionization potential can also be directly determined by photoelectric spectroscopy. For example, the ionization potential can be preferably determined with a low-energy electron spectrometer "Model AC-1" available from Riken Keiki Co., Ltd. or by ultraviolet photoelectron spectroscopy.

The electron blocking layer in a broad sense is composed of a material having remarkably low electron transportation ability while having hole transportation ability. The electron blocking layer can block electrons while transporting holes, thereby increasing the opportunity of recombination of electrons and holes.

Alternatively, the hole transporting layer described later can be used as the electron blocking layer, when necessary. The hole blocking layer and the electron blocking layer usable in the present invention each have a thickness of preferably 3 to 100 nm, more preferably 5 to 30 nm.

<<Hole Transporting Layer>>

The hole transporting layer is composed of a hole transporting material having hole transportation ability, and in a broad sense, includes the hole injecting layer and the electron blocking layer. The hole transporting layer can have a single-layer or multi-layer configuration.

The hole transporting material can be an organic or inorganic substance that have hole injection ability, hole transportation ability, or electron blocking ability. Examples thereof include triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline copolymers, and conductive higher oligomers, particularly thiophene oligomers.

Azatriphenylene derivatives described in Japanese Unexamined Patent Application Publication (Tokuhyou) Nos. 2003-519432 and 2006-135145 can also be used as hole transporting materials.

Although these hole transporting materials can be used, preferred are porphyrin compounds, aromatic tertiary amine compounds, and styrylamine compounds, and particularly preferred are aromatic tertiary amine compounds.

Typical examples of aromatic tertiary amine compounds and styrylamine compounds include N,N,N',N'-tetraphenyl-4,4'-diaminophenyl; N,N'-diphenyl-N,N'-bis(3-methylphenyl)-[1,1'-biphenyl]-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminodiphenyl ether; 4,4'-bis(diphenylamino)quadriphenyl; N,N,N-trip-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostilbene; N-phenylcarbazole; compounds having two fused aromatic rings in the molecule described in U.S. Pat. No. 5,061,569, such as 4,4'-bis[N-(1-naphthyl)-N-phenylamino]biphenyl (NPD); compounds having three triphenylamine units linked in a star burst form described in Japanese Patent Application Laid-Open No. 4-308688, such as 4,4',4"-tris[N-(3-methylphenyl)-N-phenylamino]triphenylamine (MTDATA).

Polymer materials having these materials in their polymer chains or having main chains mainly composed of these materials can also be used.

Inorganic compounds, such as p-type Si and p-type SiC, can also be used as the hole injecting material and the hole transporting material.

The p-type hole transporting materials described in Japanese Patent Application Laid-Open No. 11-251067 and a document written by J. Huang et al. (Applied Physics Letters 80(2002), p. 139) can also be used. In the present invention, these materials are preferred for enhancement in luminescent efficiency of the light-emitting element.

The hole transporting material can be formed into a thin film by any method, such as vacuum evaporation, spin coating, casting, printing including inkjet printing, or Langmuir Blodgett (LB) deposition to prepare a hole transporting layer.

The hole transporting layer can have any thickness. The thickness is usually about 5 to 5000 nm, preferably 5 to 200 nm. The hole transporting layer may have a single-layer structure composed of one or more of these materials listed above.

Alternatively, a hole transporting layer doped with an impurity to enhance p-properties can also be used. Examples thereof include hole transporting layers described in Japanese Patent Application Laid-Open Nos. 4-297076, 2000-196140, and 2001-102175, and J. Appl. Phys., 95, 5773 (2004).

In the present invention, such a hole transporting layer having enhanced p-properties can be preferably used to reduce power consumption of the resulting organic EL element.

Non-limiting, specific examples of compounds preferably used for formation of the hole injecting layer and the hole transporting layer in the organic EL element according to the present invention are listed below:

[Formula 107]

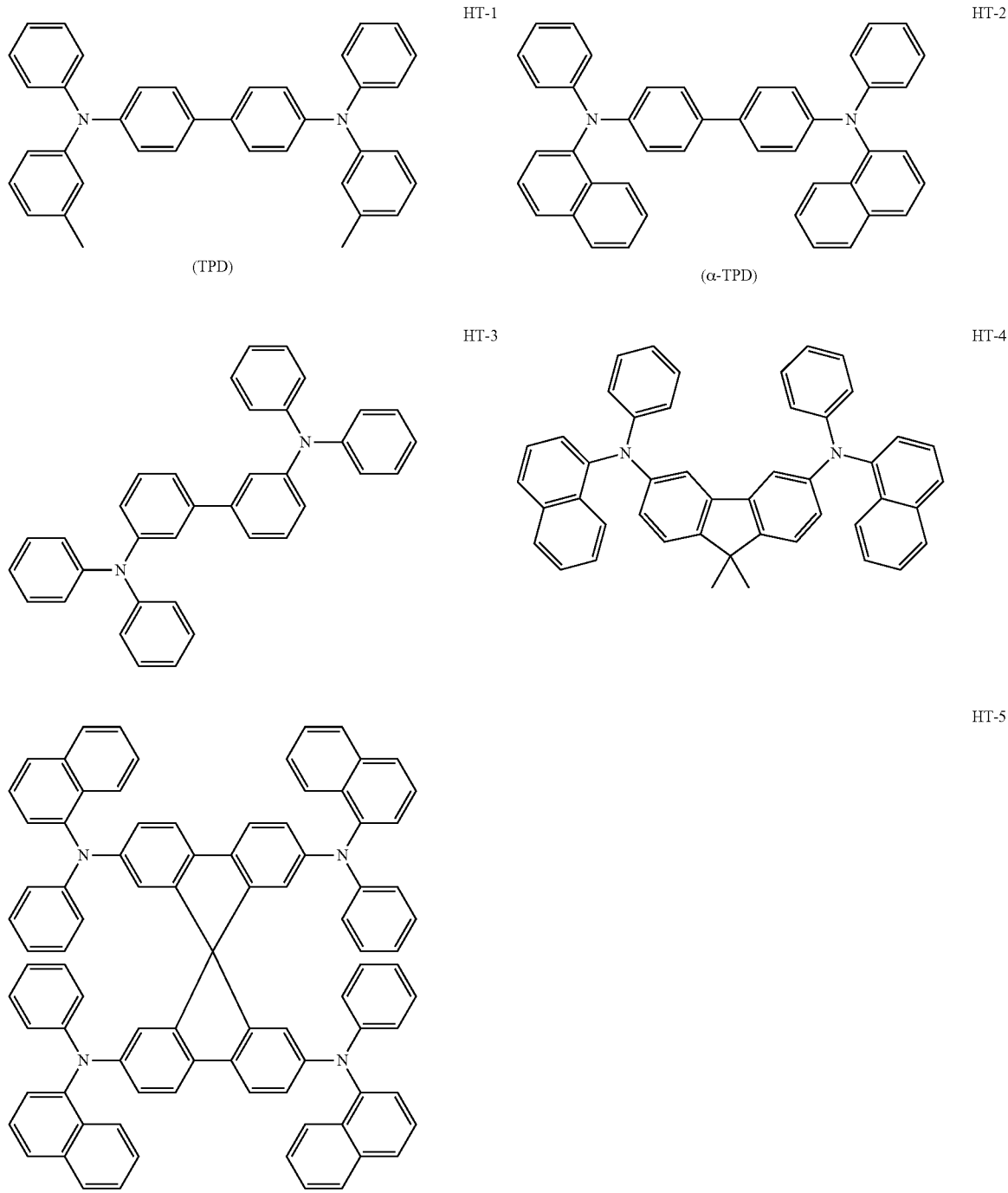

-continued
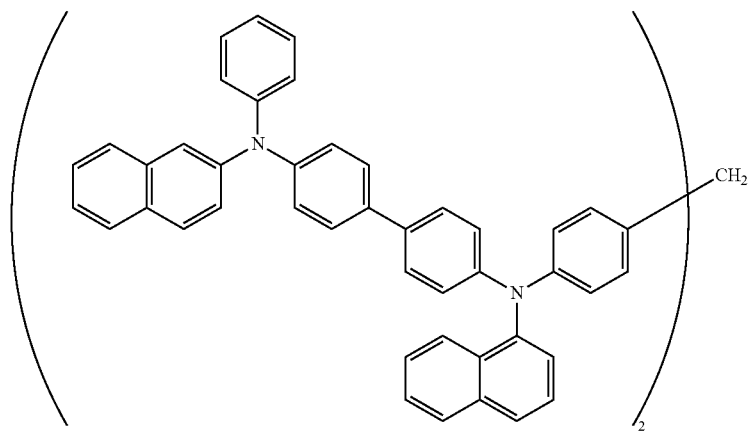
HT-6
[Formula 108]
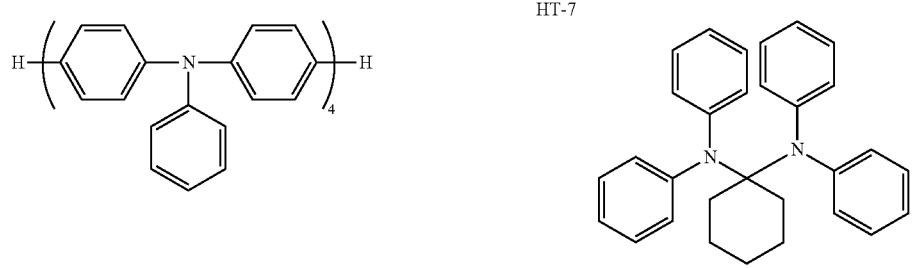
HT-7
HT-8
HT-9
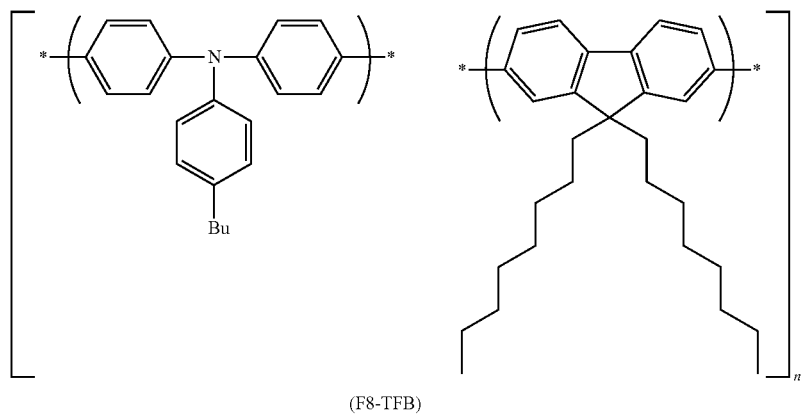
(F8-TFB)
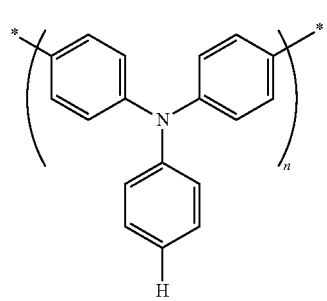
HT-10
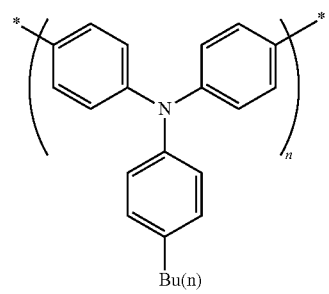
HT-11

HT-12
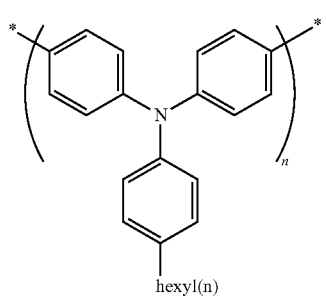
[Formula 109]
HT-13
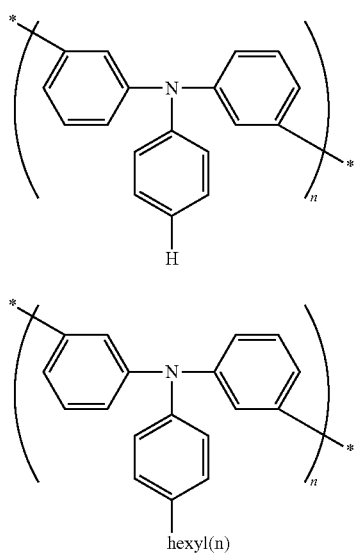
HT-14
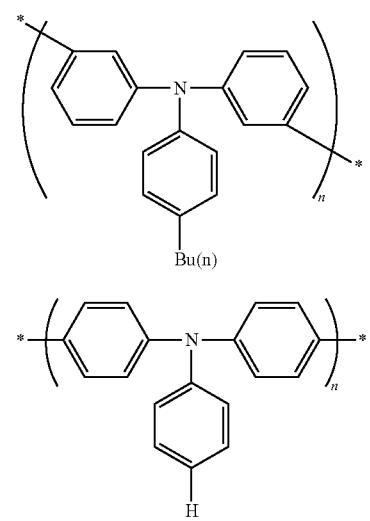
HT-15
HT-16
HT-17
HT-18
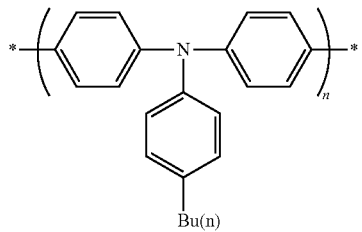
HT-19
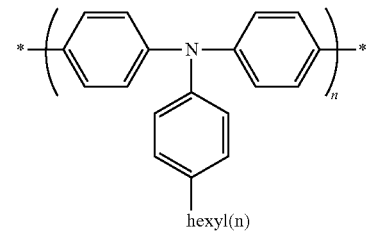
HT-20
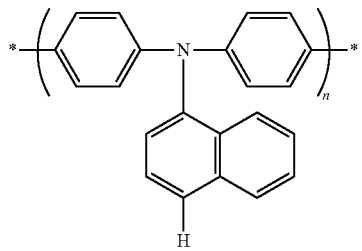
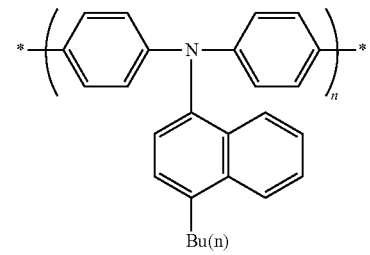
HT-21
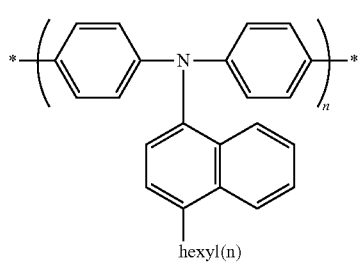

[Formula 110]
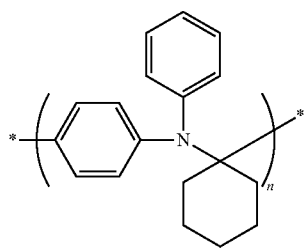
HT-22 HT-23
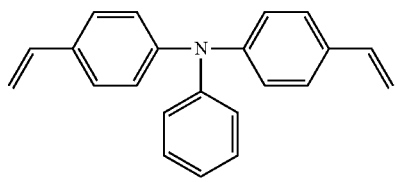
HT-24 HT-25
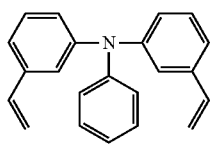 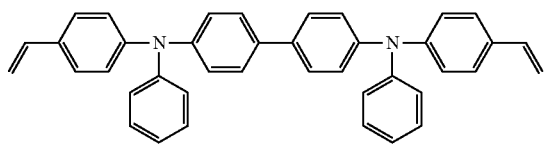
HT-26 HT-27
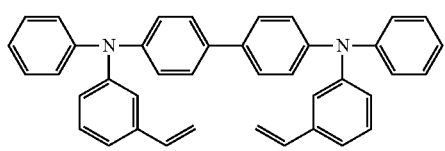 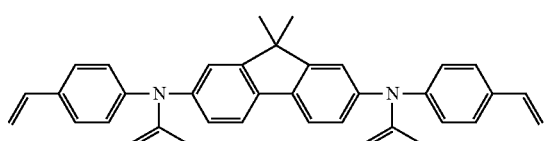
HT-28 HT-29
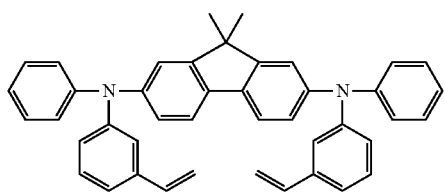 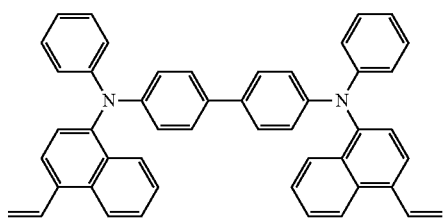
[Formula 111]
HT-30 HT-31
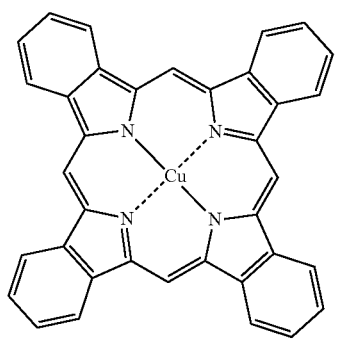 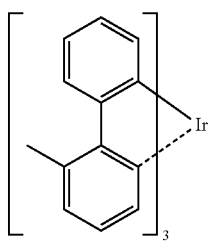
─[CH$_x$F$_y$]$_n$─
HT-32 HT-33
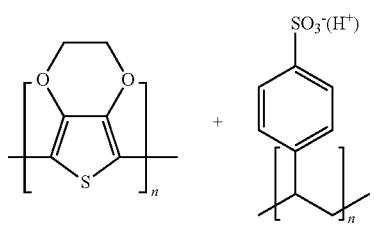

HT-34 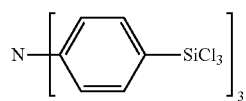
HT-35 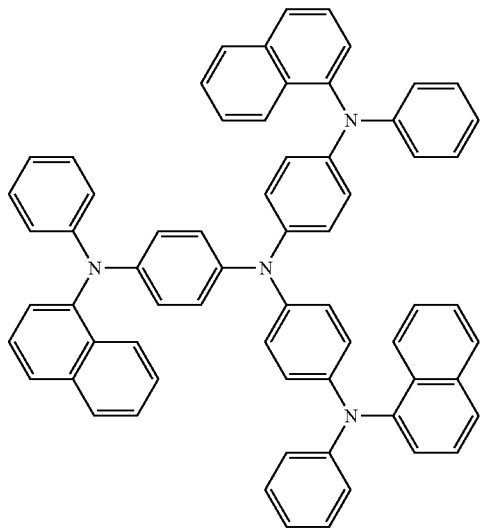
HT-36 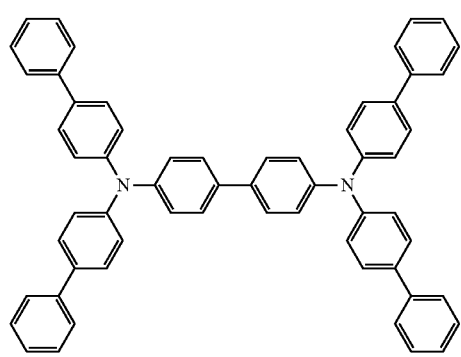
HT-37 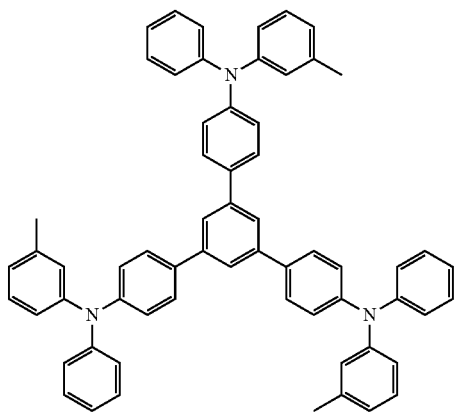
[Formula 112]
HT-38 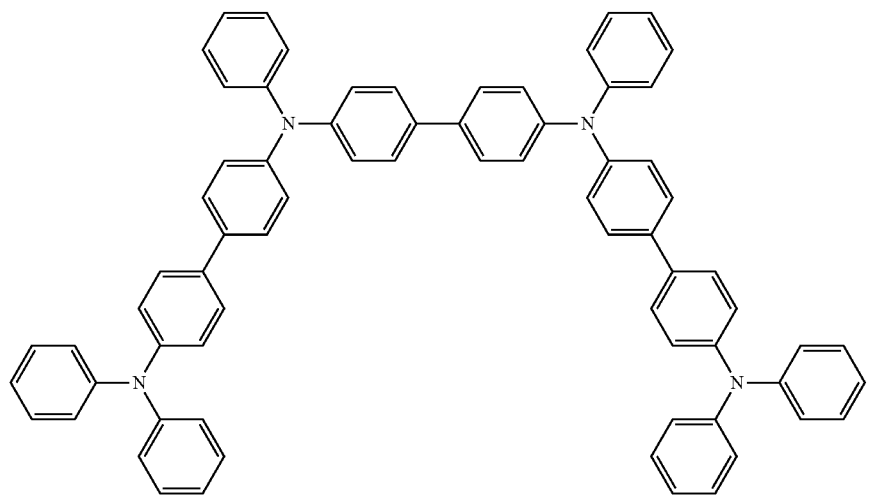

HT-39
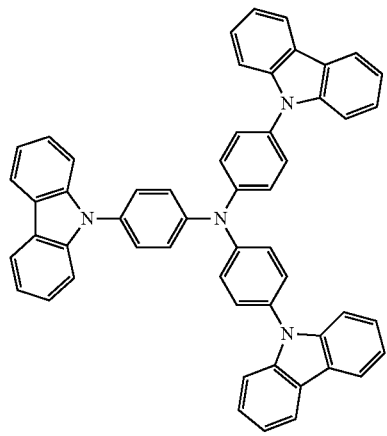
HT-40
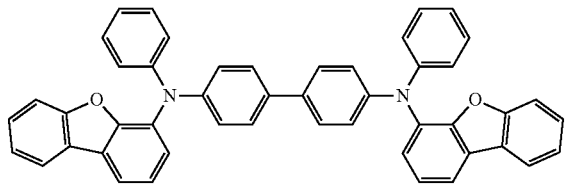
HT-41
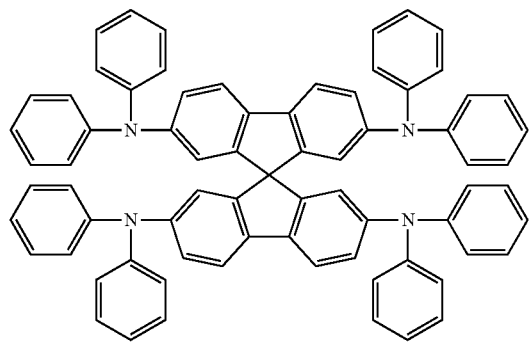
HT-42
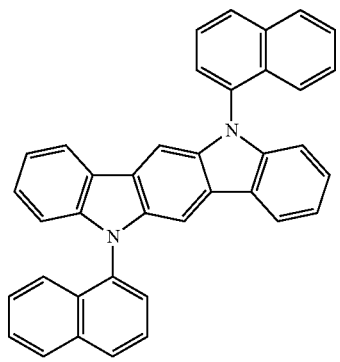
[Formula 113]
HT-43
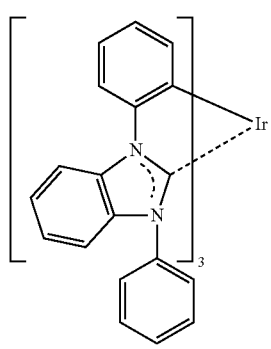
HT-44
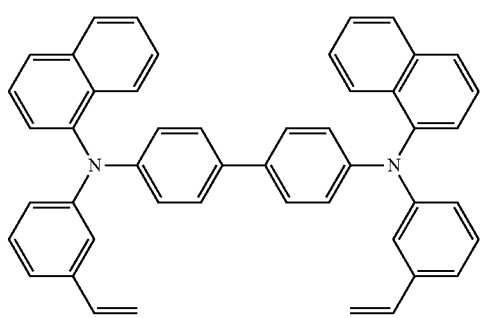
HT-45
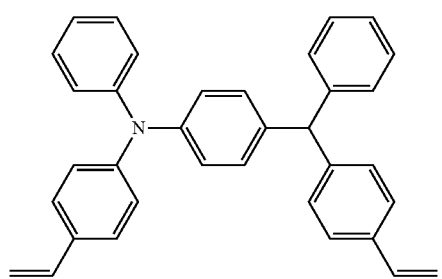

<<Electron Transporting Layer>>

The electron transporting layer is composed of a material having electron transportation ability and, in a broad sense, includes the electron injecting layer and the hole blocking layer. The electron transporting layer can have a single layer or multi-layer configuration.

The electron transporting layer transfers electrons injected from the cathode to the luminous layer. The material for the electron transporting layer can be selected from known compounds. These compounds can also be used in combination.

Examples of the known material for the electron transporting layer (hereinafter referred to as electron transporting material) include polycyclic aromatic hydrocarbons, such as nitro-substituted fluorene derivatives, diphenylquinone derivatives, thiopyran dioxide derivatives, naphthalene, and perylene; heterocyclic tetracarboxylic anhydrides; carbodiimide; fluorenylidenemethane derivatives; anthraquinodimethane and anthrone derivatives; oxadiazole derivatives; derivatives with a ring structure such as carboline derivatives or carboline derivatives having carboline rings in which at least one of carbon atoms of the hydrocarbon ring is replaced with a nitrogen atom; or hexaazatriphenylene derivatives.

Examples of usable electron transporting materials also include thiadiazole derivatives derived from the oxadiazole derivatives by replacement of the oxygen atom in the oxadiazole ring with a sulfur atom; and quinoxaline derivatives having a quinoxaline ring known as an electron-attractive group.

Polymer materials containing these materials in their polymer chains or having main chains composed of these materials can also be used.

The following electron transporting material can also be used: metal complexes of 8-quinolinol derivatives, such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, and bis(8-quinolinol)zinc (Znq), or these metal complexes in which the central metal is In, Mg, Cu, Ca, Sn, Ga, or Pb.

Metal-free or metal phthalocyanine or these phthalocyanines having an alkyl or sulfonate group at their terminals can also be used as electron transporting materials. Inorganic semiconductors, such as n-type Si and n-type SiC, can also be used as electron transporting materials.

The electron transporting layer can preferably be prepared with the electron transporting material by a vacuum evaporation process or a wet process (such as spin coating, casting, die coating, blade coating, roll coating, inkjet printing, printing, spray coating, curtain coating, and Langmuir Blodgett (LB) coating).

The electron transporting layer can have any thickness. The thickness is usually about 5 to 5000 nm, preferably 5 to 200 nm. The electron transporting layer may have a single-layer structure composed of one or more of these materials listed above.

The electron transporting layer can be doped with an n-type dopant, which is a metal complex or a metal compound (such as halogenated metals).

Non-limiting, specific examples of known compounds (electron transporting materials) preferably used in formation of the electron transporting layer of the organic EL element according to the present invention are listed below:

[Formula 114]

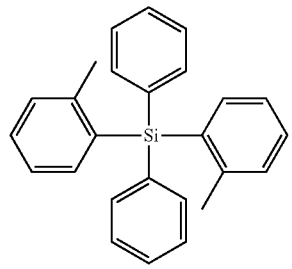

ET-1

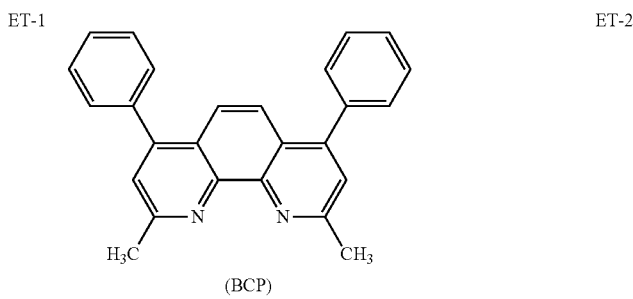

(BCP) ET-2

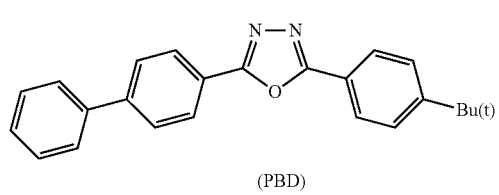

(PBD) ET-3

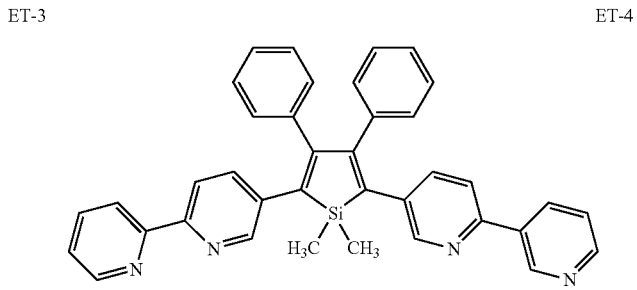

ET-4

-continued
ET-5
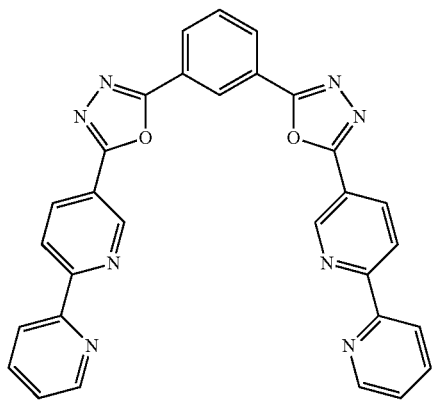
ET-6
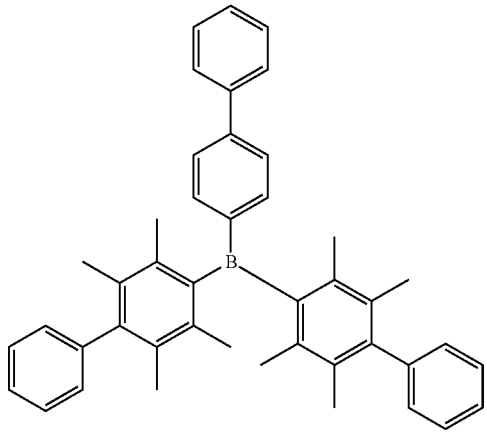
ET-7
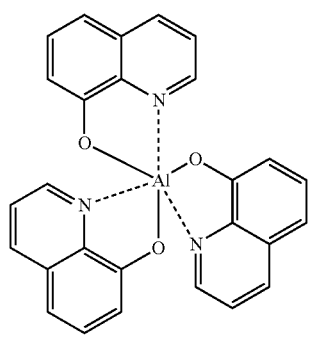
(Alq₃)
ET-8
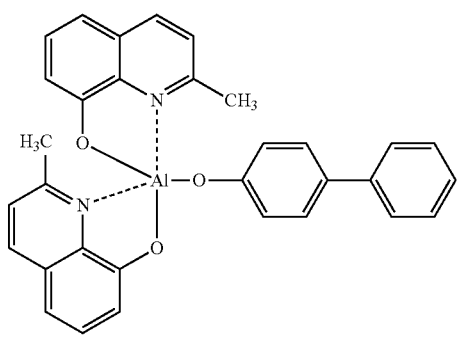
(BAlq)
[Formula 115]
ET-9
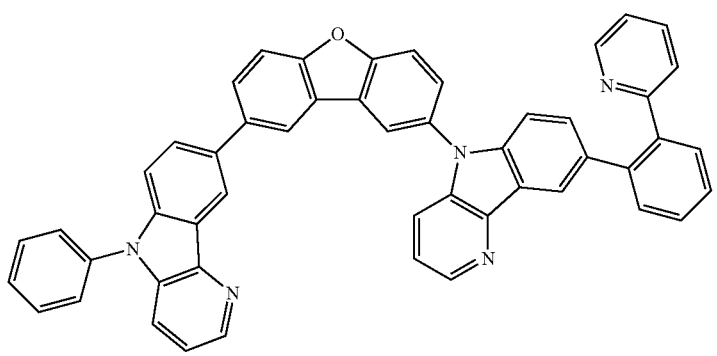
ET-10
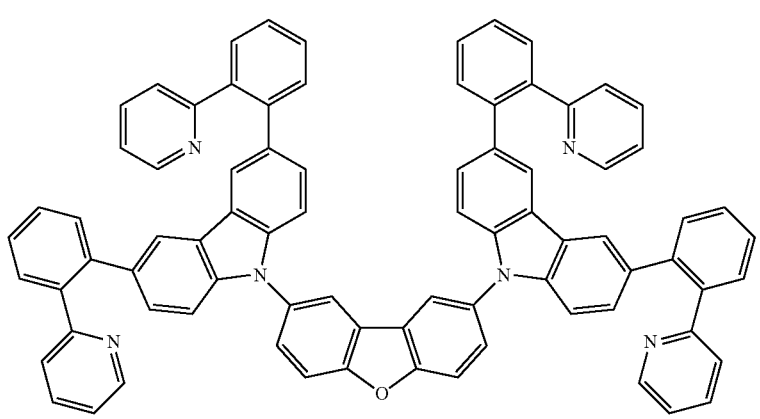

ET-11
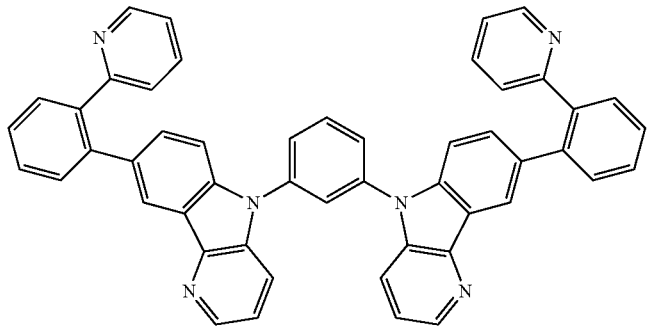
[Formula 116]
ET-12  ET-13
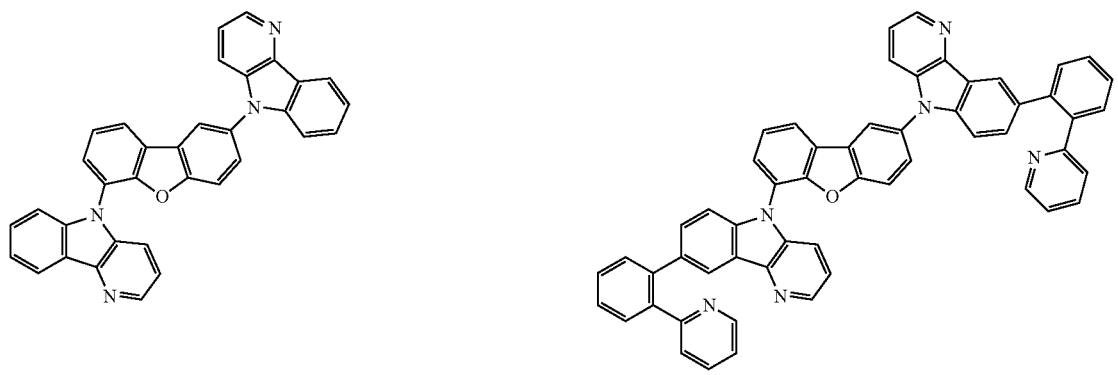
ET-14  ET-15
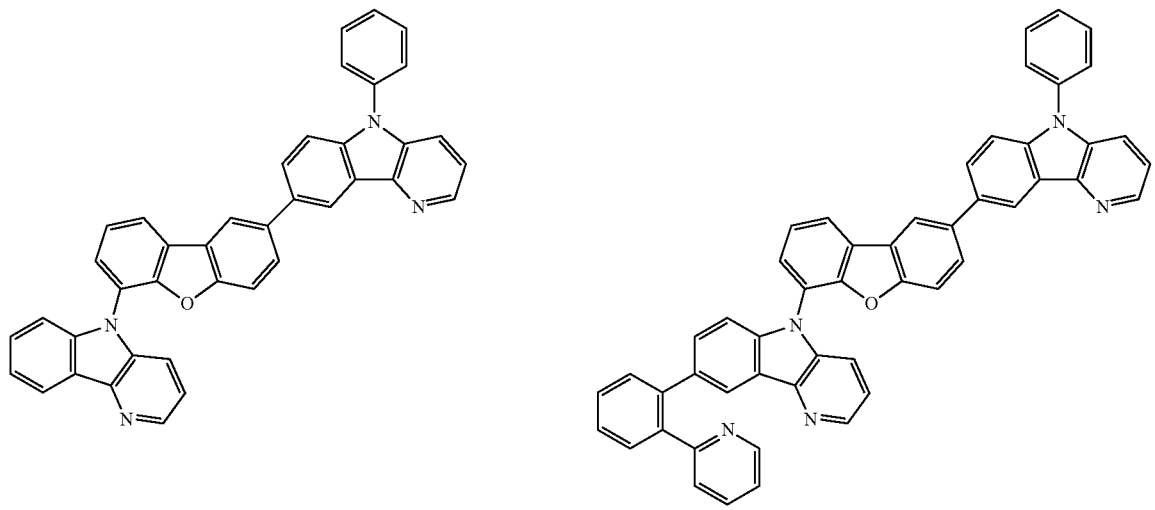

-continued
ET-16
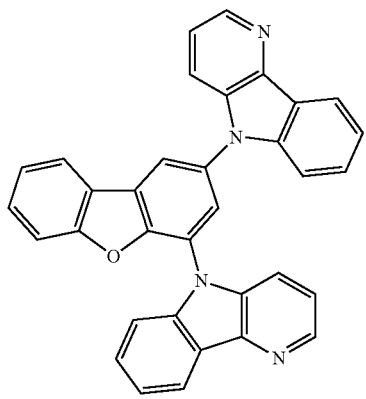
[Formula 117]
ET-18
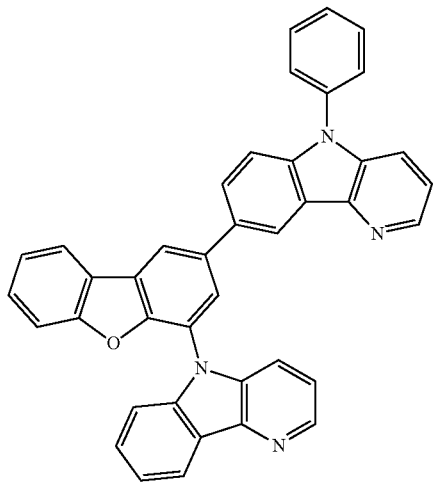
ET-20
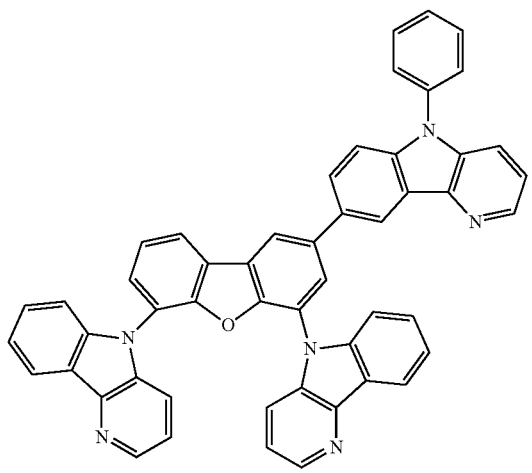
ET-17
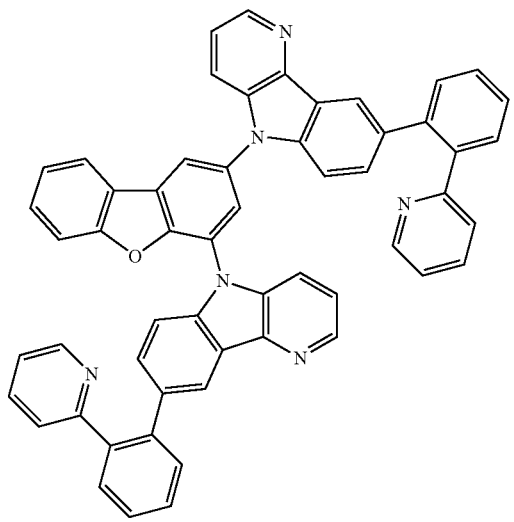
ET-19
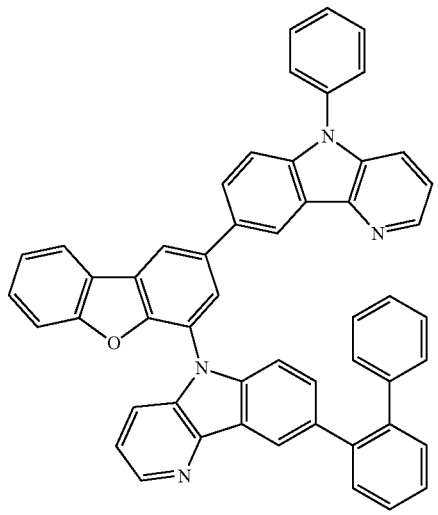
ET-21
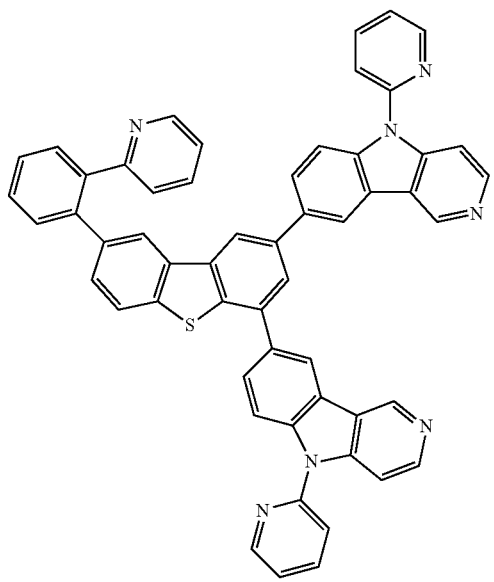

ET-22
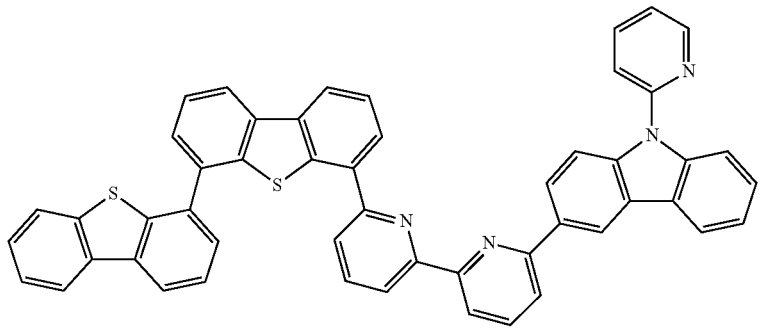
[Formula 118]
ET-23
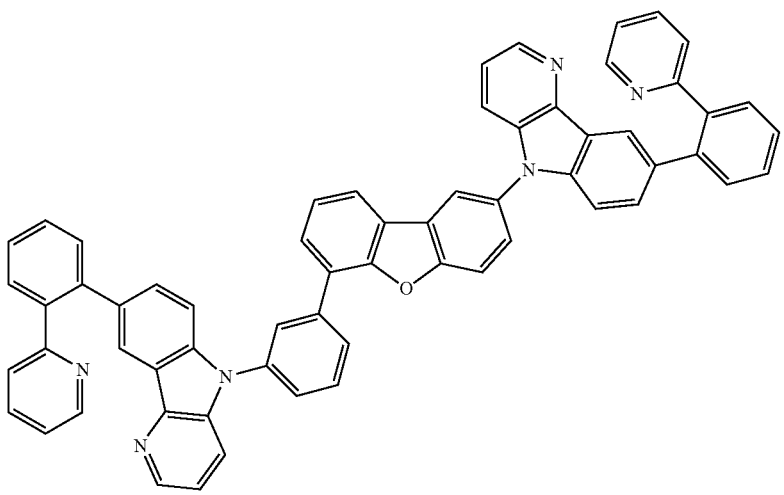
ET-24
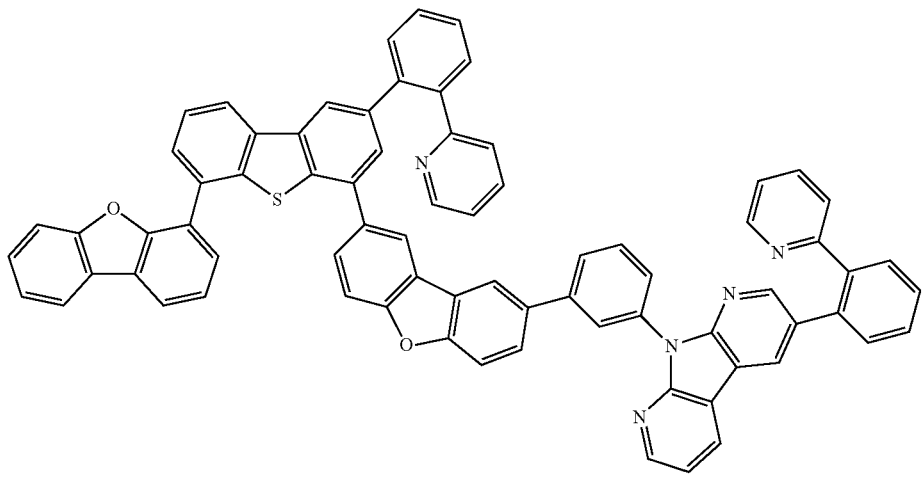

ET-25
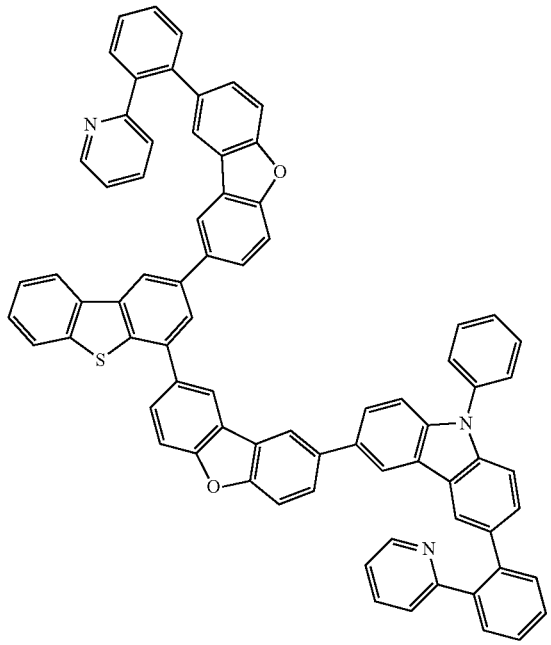
[Formula 119]
ET-26
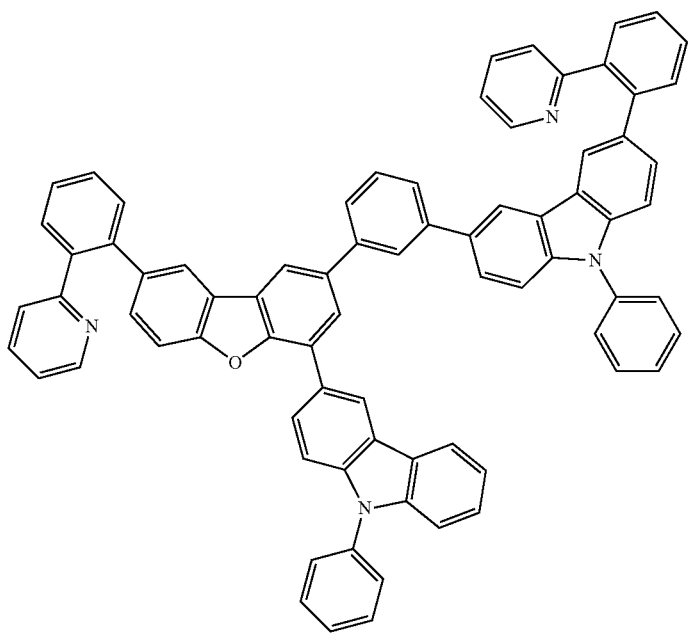

-continued
ET-27
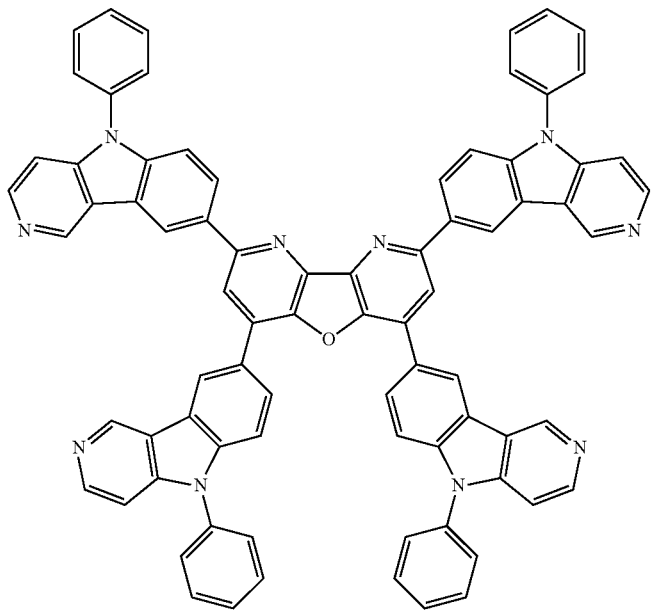
ET-28
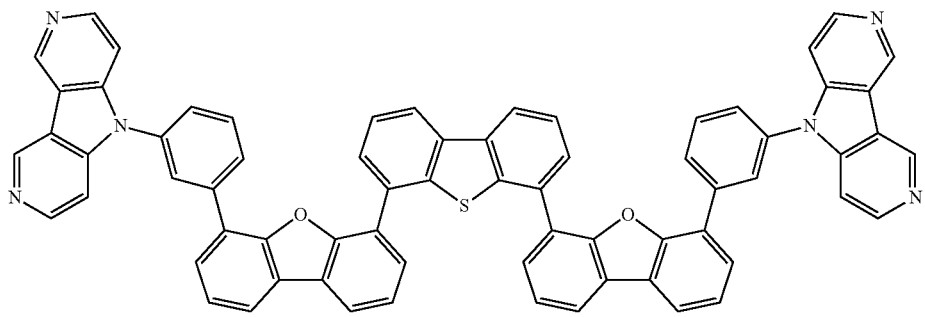
[Formula 120]
ET-29
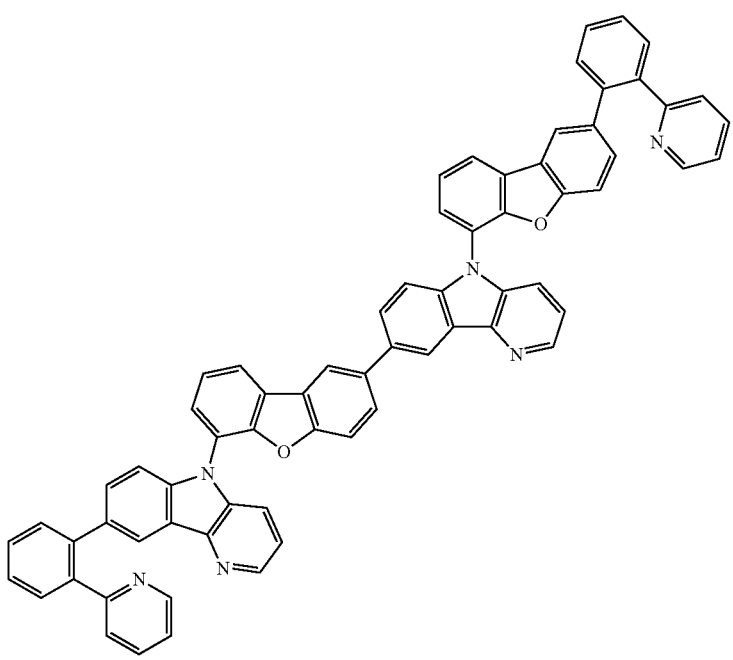

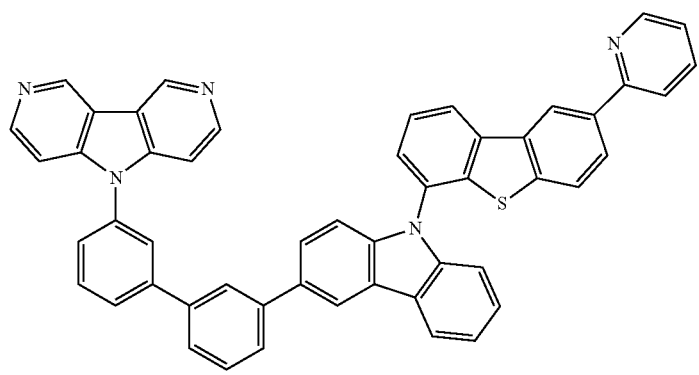
ET-30
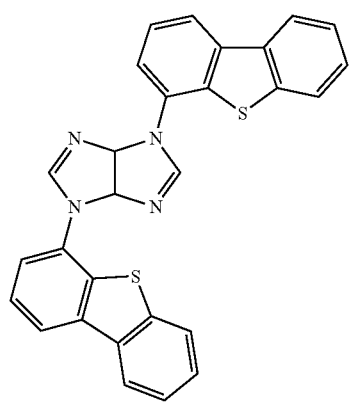
ET-31
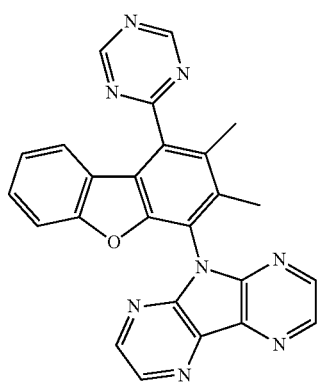
ET-32
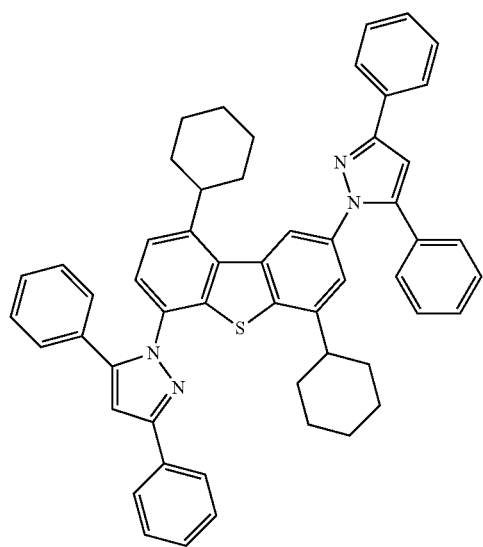
ET-33

[Formula 121]
ET-34
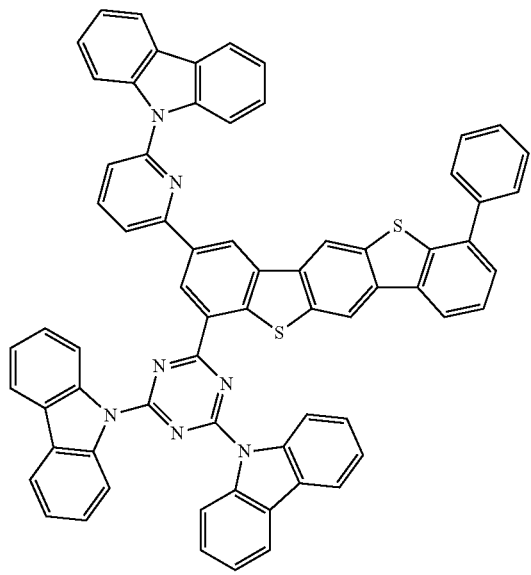
ET-35
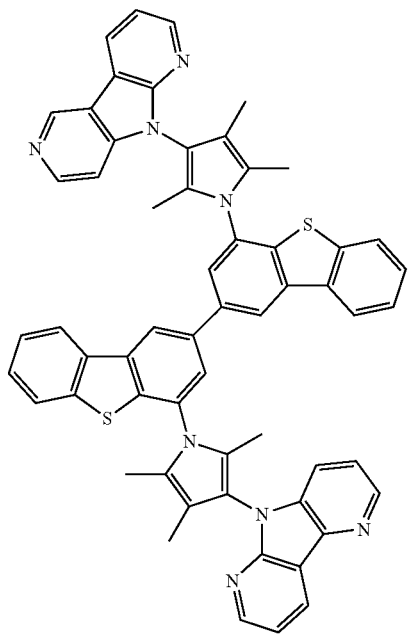
ET-36
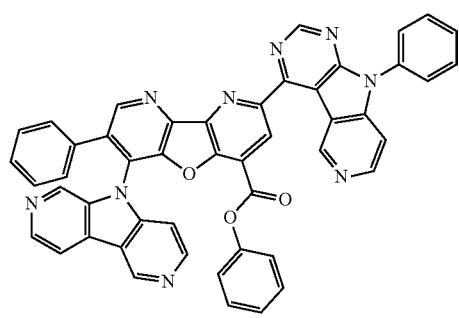
ET-37
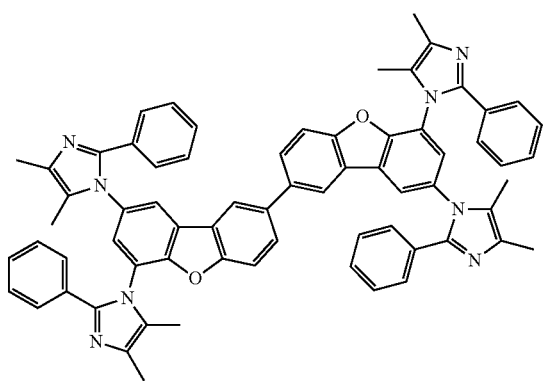

[Formula 122]
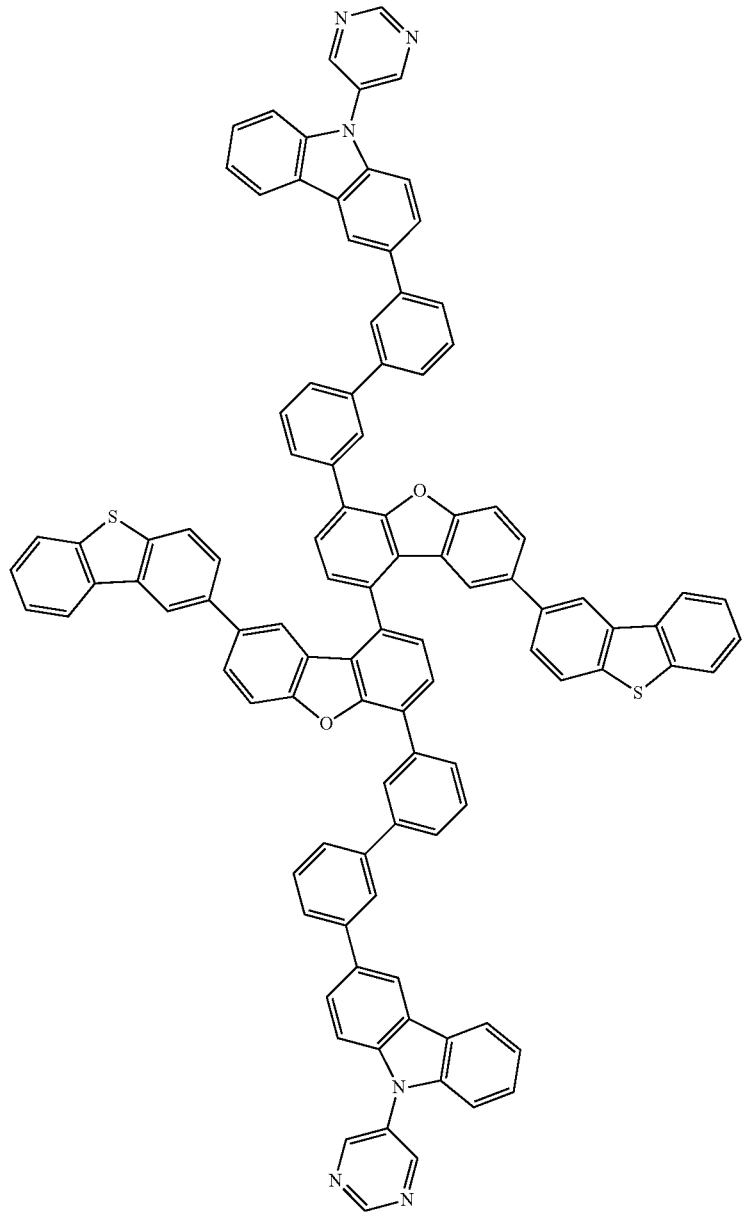
ET-38

-continued
ET-39
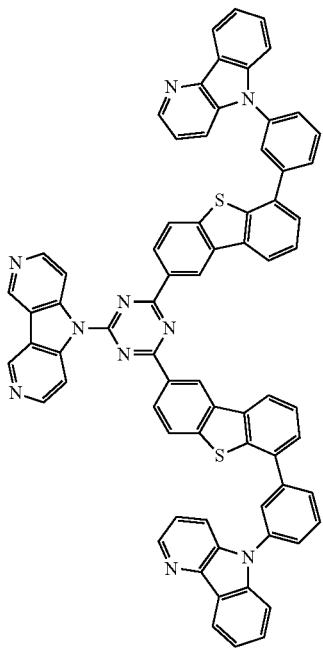
[Formula 123]
ET-40
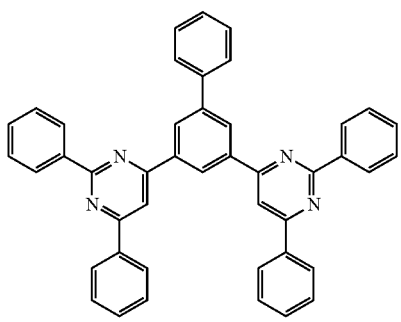
ET-41
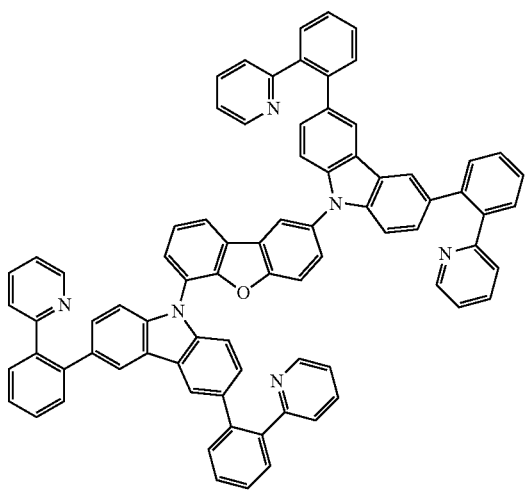
ET-42
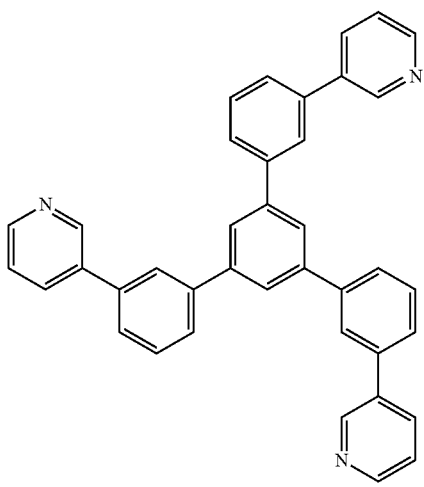
ET-43
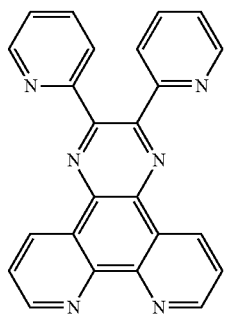

<<Anode>>

Preferred electrode substances used in the anode of the organic EL element are metals, alloys, conductive compounds having large work functions (4 eV or more), and mixtures thereof. Specific examples of the electrode substances include metals, such as Au; and conductive transparent materials, such as CuI, indium tin oxide (ITO), $SnO_2$, and ZnO.

Materials formable into amorphous transparent conductive films, such as IDIXO ($In_2O_3$—ZnO), can also be used in the anode. The anode can be prepared as follows: A thin film is prepared with any one of the electrode substances by deposition or sputtering, and is optionally patterned by photolithography. If a high-precision pattern is not required (about 100 μm or more), the film may be patterned through a mask having a desired pattern during deposition or sputtering of the electrode substance.

Alternatively, the anode can be prepared with a coatable substance, such as organic conductive compounds, by a wet process, such as printing and coating.

The anode desirably has a transmittance of more than 10% for extraction of emitted light. The anode preferably has a sheet resistance of several hundreds ohms per square or less. The thickness, which depends on the material, is determined in the range of usually 10 to 1000 nm, preferably 10 to 200 nm.

<<Cathode>>

Preferred electrode substances used in the cathode are metals (referred to as electron injecting metals), alloys, conductive compounds having small work functions (4 eV or less), and mixtures thereof. Specific examples of such electrode substances include sodium, sodium-potassium alloys, magnesium, lithium, mixtures of magnesium/copper, mixtures of magnesium/silver, mixtures of magnesium/aluminum, mixtures of magnesium/indium, mixtures of aluminum/aluminum oxide ($Al_2O_3$), indium, mixtures of lithium/aluminum, and rare earth element metals. Among these, preferred are mixtures of electron injecting metals and stable second metals having large work functions, such as mixtures of magnesium/silver, mixtures of magnesium/aluminum, mixtures of magnesium/indium, mixtures of aluminum/aluminum oxide ($Al_2O_3$), mixtures of lithium/aluminum, and aluminum in view of electron injection and durability against oxidation.

The cathode can be prepared with the electrode substance by deposition or sputtering. The cathode has a sheet resistance of preferably several hundreds ohms per square or less. The thickness is determined within the range of usually 10 to 5000 nm, preferably 50 to 200 nm.

To transmit emitted light, one of the anode and the cathode in the organic EL element is preferably transparent or translucent. Such an electrode enhances the luminance of the emitted light.

A transparent or translucent cathode can be prepared as follows: a cathode having a thickness of 1 to 20 nm is prepared with the metal listed above, and one of the conductive transparent materials listed as the materials for the anode is disposed on the cathode. An element having a light-transmissive anode and a light-transmissive cathode can also be prepared by this process.

<<Support Substrate>>

Any support substrate (hereinafter also referred to as base, substrate, base plate, or support) can be used in the organic EL element according to the present invention. The substrate can be composed of any material, such as glass or plastics, and may be transparent or opaque. Preferred is a transparent support substrate in view of extraction of light from the support substrate side. Preferred examples of the materials for the transparent support substrate include glass, quartz, and transparent resin films. Particularly preferred are resin films which can give flexibility to the organic EL element.

Examples of the materials for such resin films include polyesters, such as poly(ethylene terephthalate) (PET) and poly(ethylene naphthalate) (PEN); polyethylene; polypropylene; cellophane; cellulose esters, such as cellulose diacetate, cellulose triacetate, cellulose acetate butyrate, cellulose acetate propionate (CAP), cellulose acetate phthalate (TAC), and cellulose nitrate, and their derivatives; poly(vinylidene chloride); poly(vinyl alcohol); poly(ethylene-vinyl alcohol); syndiotactic polystyrene; polycarbonates; norbornene resins; polymethylpentene; polyether ketones; polyimides; polyether sulfones (PESs); poly(phenylene sulfide); polysulfones; polyether imides; polyether ketone imides; polyamides; fluorinated resins; nylons; poly(methylmethacrylate); acrylates or polyarylates; and cycloolefin resins, such as ARTON (trade name, available from JSR Corporation) or APEL (trade name, available from Mitsui Chemicals, Inc.).

The surfaces of the resin films can be coated with an inorganic, organic, or hybrid coating film. Such a coating film is preferably a barrier film having a water vapor permeation rate (25±0.5° C., relative humidity (90±2)% RH) of 0.01 g/($m^2 \cdot 24$ h) or less determined by a method in accordance with JIS K 7129-1992. The coating film is more preferably a high barrier film having an oxygen permeation rate of $10^{-3}$ ml/($m^2 \cdot 24$ h·atm) or less and a water vapor permeation rate of $10^{-5}$ g/($m^2 \cdot 24$ h) or less, which are determined by a method in accordance with JIS K 7126-1987.

Such a barrier film can be composed of any material which blocks invasion of substances degrading the organic EL element, such as moisture or oxygen. Usable materials for the barrier film are silicon oxide, silicon dioxide, and silicon nitride, for example. To improve the fragility of the barrier film, the barrier film more preferably has a laminate structure of an inorganic layer composed of the inorganic material and an organic layer composed of an organic material. The inorganic layer and the organic layer can be disposed in any order. Preferred is an alternating lamination of the inorganic layer and the organic layer.

The barrier film can be formed by any process, such as vacuum evaporation, sputtering, reactive sputtering, molecular beam epitaxy, cluster ion beaming, ion plating, plasma polymerization, atmospheric-pressure plasma enhanced polymerization, plasma enhanced chemical vapor deposition (CVD), laser CVD, thermal CVD, and coating. Particularly preferred is atmospheric-pressure plasma enhanced polymerization described in Japanese Patent Application Laid-Open No. 2004-68143.

Examples of opaque support substrates include metal plates composed of aluminum or stainless steel; films; opaque resin substrates; and ceramic substrates.

The organic EL element according to the present invention should preferably have a light external extraction efficiency of 1% or more, more preferably 5% or more, at room temperature. The light out-coupling efficiency is defined by Expression:

external extraction quantum efficiency (%)={(the number of photons emitted to the outside of organic EL element)/(the number of electrons flowing into organic EL element)}×100.

The substrate may be provided with a hue improving filter, such as a color filter, or a color converting filter for converting the color of light emitted from the organic EL element through a fluorescent substance. The color converting filter is suitable for an organic EL element that emits light at λmax of 480 nm or less.

<<Sealing>>

Examples of sealing methods used in the present invention include bonding an electrode and a support substrate to a sealing member with an adhesive.

The sealing member is disposed so as to cover the display area of the organic EL element, and may be a recessed plate or a flat plate. The sealing member can have any transparency and electrical insulation.

Specific examples thereof include glass plates, polymer plates and films, and metal plates and films. Examples of the glass plates include soda lime glass, glass containing barium or strontium, lead glass, aluminosilicate glass, borosilicate glass, barium borosilicate glass, and quartz.

Examples of the polymer plates include plates composed of polycarbonates, acrylics, polyethylene terephthalate), polyether sulfides, and polysulfones.

Examples of the metal plates include plates composed of one or more metals selected from the group consisting of stainless steel, iron, copper, aluminum, magnesium, nickel, zinc, chromium, titanium, molybdenum, silicon, germanium, and tantalum, and alloys thereof.

In the present invention, preferred are polymer films and metal films, which can attain a thin organic EL element.

These polymer films preferably have an oxygen permeation rate of $1 \times 10^{-3}$ ml/(m$^2 \cdot$24 h·atm) or less determined by a method in accordance with JIS K 7126-1987 and a water vapor permeation rate (25±0.5° C., relative humidity (90±2)% RH) of $1 \times 10^{-3}$ g/(m$^2 \cdot$24 h) or less determined by a method in accordance with JIS K 7129-1992.

A recessed sealing member is prepared by sand blasting or chemical etching.

Specific examples of the adhesive include photocurable or thermosetting adhesives having reactive vinyl groups, such as adhesives of oligomers of acrylic acid and methacrylic acid; and moisture-curable adhesives, such as 2-cyanoacrylate ester adhesives. Other examples thereof include thermally or chemically curable (two-component) adhesives, such as epoxy adhesives. Examples thereof also include hot-melt adhesives, such as polyamide, polyester, and polyolefin adhesives. Examples thereof also include cationic, ultraviolet light-curable epoxy resin adhesives.

Preferred are adhesives curable at a temperature from room temperature to 80° C. to prevent degradation of the organic EL element by a heat treatment. The adhesive may contain a desiccant dispersed therein. The adhesive can be applied to bonding portions of the sealing member with a commercially available dispenser, or can be printed thereon by screen printing.

A sealing film composed of an inorganic layer and an organic layer can also be suitably disposed on the support substrate and over the electrode remote from the support substrate to cover the electrode and the organic layer. In this case, the sealing film can be composed of any material which blocks invasion of substances degrading the organic EL element, such as moisture or oxygen. Usable materials are silicon oxide, silicon dioxide, and silicon nitride, for example.

To improve the fragility of the sealing film, the film preferably has a laminate structure composed of an inorganic layer composed of the inorganic material and an organic layer composed of an organic material. The sealing film can be formed by any method, such as vacuum evaporation, sputtering, reactive sputtering, molecular beam epitaxy, cluster ion beaming, ion plating, plasma polymerization, atmospheric pressure plasma polymerization, plasma CVD, laser CVD, thermal CVD, and coating.

The space between the sealing member and the display area of the organic EL element preferably contains an inert gas, such as nitrogen and argon, or an inert liquid, such as fluorohydrocarbon and silicone oil. The space can be in vacuum. A moisture absorbing compound can also be encapsulated in the space.

Examples of the moisture absorbing compound include metal oxides (such as sodium oxide, potassium oxide, calcium oxide, barium oxide, magnesium oxide, and aluminum oxide), sulfuric acid salts (such as sodium sulfate, calcium sulfate, magnesium sulfate, and cobalt sulfate), metal halides (such as calcium chloride, magnesium chloride, cesium fluoride, tantalum fluoride, cerium bromide, magnesium bromide, barium iodide, and magnesium iodide), perchloric acids (such as barium perchlorate and magnesium perchlorate). Preferred are anhydrides of sulfuric acid salts, metal halides, and perchloric acids.

<<Protective Film, Protective Plate>>

A protective film or plate may be disposed on or over the sealing film remote from the support substrate to enhance the mechanical strength of the organic EL element. Such a protective film or plate is particularly preferably disposed in an organic EL element sealed with the sealing film, which does not have sufficient mechanical strength. Materials usable in the protective film or plate are the same glass plates, polymer plates and films, and metal plates and films as those used for sealing. Preferred are polymer films in order to attain light and thin films.

<<Extraction of Light>>

In the organic EL element, light is emitted inside a luminous layer having a refractive index (refractive index of about 1.7 to 2.1) higher than that of air, and in general, only about 15% to 20% of the light emitted in the luminous layer is extracted. Such low extraction of the light is explained by the following reasons: light components incident on the interface (interface between transparent substrate and air) at an angle θ equal to or larger than a critical angle is totally reflected, and cannot be extracted from the organic EL element. Moreover, light components are totally reflected between the transparent electrode or luminous layer and the transparent substrate, and are transmitted through the transparent electrode or the luminous layer, escaping toward the sides of the organic EL element.

Examples of the measures to enhance the light out-coupling efficiency include use of a transparent substrate having an irregular surface to prevent total reflection of light at the interface between the transparent substrate and air (U.S. Pat. No. 4,774,435), use of a light-condensing substrate to enhance the out-coupling efficiency (Japanese Patent Application Laid-Open No. 63-314795), formation of reflecting surfaces on side surfaces of an organic EL element (Japanese Patent Application Laid-Open No. 1-220394), disposition of a flat layer between a substrate and a luminous layer, the flat antireflective layer having a middle refractive index between that of the substrate and that of the luminous member (Japanese Patent Application Laid-Open No. 62-172691), disposition of a flat layer between a substrate and a luminous layer, the flat layer having a refractive index lower than that of the substrate (Japanese Patent Application Laid-Open No. 2001-202827), and disposition of a diffraction grating between any two adjacent layers of a substrate, a transparent electrode layer, and a luminous layer (including between the substrate and the outside) (Japanese Patent Application Laid-Open No. 11-283751).

In the present invention, these measures can be applied to the organic EL element according to the present invention. Preferred is disposition of a flat layer between a substrate and a luminous member, the flat layer having a refractive index lower than the substrate, or disposition of a diffraction grating between any two adjacent layers of a substrate, a transparent electrode layer, and a luminous layer (including between the substrate and the outside).

In the present invention, a combination of these measures can further enhance the luminance and durability of the organic EL element.

A medium having a low refractive index and an optical thickness larger than the wavelength of light is disposed between a transparent electrode and a transparent substrate. In this configuration, as the medium has a lower refractive index, the light traveling from the transparent electrode is extracted to the outside at higher extraction efficiency.

Examples of low refractive index layers include layers composed of aerogel, porous silica, magnesium fluoride, and fluorine polymers. Since the transparent substrate usually has a refractive index of about 1.5 to 1.7, the low refractive index layer preferably has a refractive index of about 1.5 or less. The low refractive index layer more preferably has a reflective index of 1.35 or less.

The optical thickness of the low refractive index medium should desirably be at least twice the wavelength of light in the medium. If the optical thickness of the low refractive index medium is substantially equal to the wavelength of light, the advantageous effect of the low refractive index layer is reduced because such a thickness allows invasion of evanescent electromagnetic waves into the substrate.

A diffraction grating provided at an interface or any medium which totally reflects light can significantly enhance the light extraction efficiency. The diffraction grating can orient light by Bragg diffraction, such as primary diffraction or secondary diffraction, to a specific direction different from refraction. In this method, such features of the diffraction grating are utilized to extract light. Specifically, the diffraction grating is disposed at the interface between any two adjacent layers or inside any medium (inside the transparent substrate or the transparent electrode) to diffract the light beams which are generated in the luminous layer but cannot be extracted due to total reflection.

The diffraction grating desirably has a two-dimensional periodic pattern in a refractive index. The light emitted in the luminous layer is emitted in random directions. A typical one-dimensional diffraction grating having a periodic refractive index distribution in one direction, however, diffracts only the light traveling in one specific direction, and does not significantly contribute to the light extraction efficiency of the light emitted in random directions.

In contrast, a diffraction grating having two-dimensional distribution of the refractive index diffracts the light traveling in every direction to enhance the light extraction efficiency.

As described above, the diffraction grating may be disposed at the interface between any two adjacent layers or inside any medium (inside the transparent substrate or transparent electrode), and desirably is disposed on the organic luminous layer which emits light or on any other adjacent layer in the vicinity of the luminous layer.

At this time, the period of the diffraction grating is preferably about half to triple the wavelength of the light inside the medium.

The diffraction grating preferably has a two-dimensional repeating pattern, such as a square lattice, a triangular lattice, or a honeycomb lattice.

<<Light-Condensing Sheet>>

In the organic EL element according to the present invention, the light extracting surface of the substrate may be provided with a microlens array structure or combined with a light-condensing sheet to condense light in a specific direction, for example, the front of the luminous surface of the element. The luminance in the specific direction can be thereby enhanced.

In an exemplified microlens array, quadrangular pyramids measuring 30 µm per side and having an apex angle of 90 degrees are two-dimensionally arranged on the light-extracting surface of the substrate. The side has a thickness of preferably 10 µm to 100 µm. A side less than 10 µm causes coloring due to diffraction. A side more than 100 µm increases the thickness of the microlens array.

Examples of usable light-condensing sheets include those used in LED backlights of liquid crystal display devices. Examples of such light-condensing or prism sheets include a brightness enhancing film (BEF) available from Sumitomo 3M Limited. An exemplary prism sheet may be composed of a base plate and stripes consisting of pyramidal prisms having an apex angle of 90 degrees and a pitch of 50 µm. The prisms may have round apices or may be arrayed at randomized pitches. Alternatively, the prisms may have any other shape.

To control the emission angle of the light from the light-emitting element, a light diffusion plate or film can be used in combination with the light-condensing sheet. A light diffusion film LIGHT-UP available from Kimoto Co., Ltd. can be used, for example.

<<Process of Preparing Organic EL Element>>

An exemplary process of preparing an organic EL element will now be described that includes an anode, a hole injecting layer (anode buffer layer), a hole transporting layer, a luminous layer, a hole blocking layer, an electron transporting layer, an electron injecting layer, a cathode buffer layer, and a cathode.

A substance suitable for an anode is applied onto an appropriate substrate into a thin film having a thickness of 1 µm or less, preferably 10 to 200 nm. An anode is prepared.

Thin layers, such as a hole injecting layer, a hole transporting layer, a luminous layer, a hole blocking layer, an electron transporting layer, and an electron injecting layer, are sequentially disposed on the anode using organic compounds suitable for the components of these layers.

The thin layers can be formed by a vacuum evaporation process or a wet process.

Examples of the wet process include spin coating, casting, die coating, blade coating, roll coating, inkjet printing, printing, spray coating, curtain coating, and LB coating. Preferred are processes suitable for a roll-to-roll process, such as die coating, roll coating, inkjet printing, and spray coating, which can form precise thin films with high productivity. These layers can be formed by different processes.

Organic EL materials usable in the present invention can be dissolved or dispersed in the following solvents: ketones, such as methyl ethyl ketone and cyclohexanone; fatty acid esters, such as ethyl acetate; halogenated hydrocarbons, such as dichlorobenzene; aromatic hydrocarbons, such as toluene, xylene, mesitylene, and cyclohexyl benzene; aliphatic hydrocarbons, such as cyclohexane, decalin, and dodecane; and organic solvents, such as DMF and DMSO.

The EL materials can be dispersed by ultrasonic waves, high shear force dispersion, or media dispersion.

After formation of these layers, a substance for a cathode is applied onto the top of the workpiece to form a thin film having a thickness in the range of 1 μm or less, preferably 50 to 200 nm. A desired organic EL element is thereby prepared.

An organic EL element can be prepared in the reverse order, that is, by sequentially disposing a cathode, an electron injecting layer, an electron transporting layer, a hole blocking layer, a luminous layer, a hole transporting layer, a hole injecting layer, and an anode.

During preparation of the organic EL element according to the present invention, the layers from the hole injecting layer to the cathode are preferably prepared by a single vacuum operation. Alternatively, the workpiece may be taken out of the apparatus midway and be subjected to a different deposition process. At this time, the workpiece is preferably taken out under a dry inert gas atmosphere.

<<Applications>>

The organic EL element according to the present invention can be applied to display devices, displays, and light emitting sources. Examples of the light emitting sources include, but should not be limited to, illumination devices (house lightings, car interior lightings), backlights for clocks and liquid crystal devices, advertising signs, traffic signals, and light sources for optical storage media, electrophotographic copiers, optical communication processors, and optical sensors. The organic EL element according to the present invention can be particularly suitable for backlights for liquid crystal display devices and light sources for illumination devices.

The organic EL element according to the present invention may be patterned through a metal mask or by inkjet printing when necessary during formation of the film. The patterning may be performed only on the electrode, on the electrode and the luminous layer, or on all of the layers of the element. The organic EL element can be prepared by a traditional process.

Figure 4:
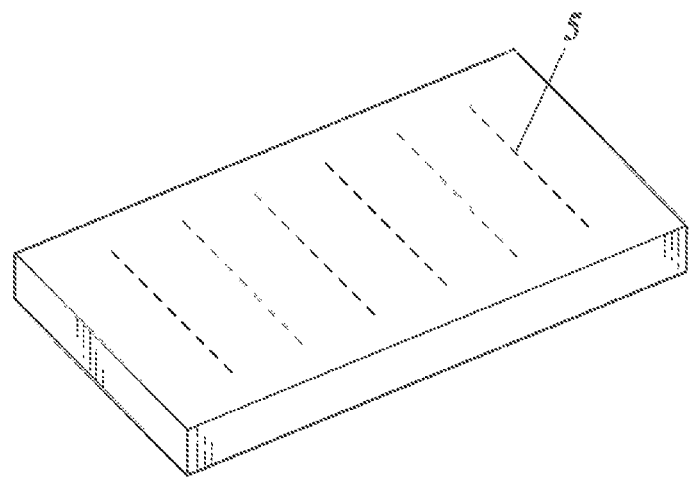
FIG. 4 is a schematic view illustrating a passive-matrix full-color display device.
Figure 4:
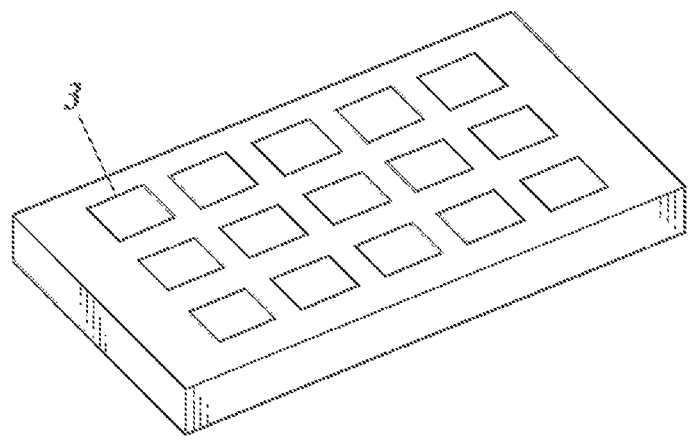
Figure 4:
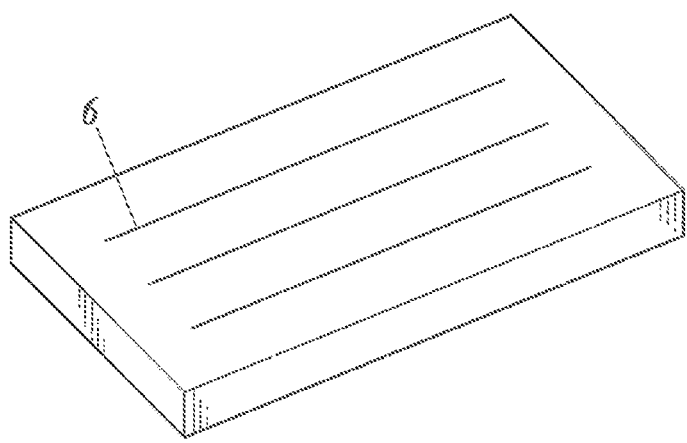

The color of light emitted from the organic EL element according to the present invention or the compound according to the present invention is determined from the results of the measurement with a spectroradiometric luminance meter CS-1000 (available from Konica Minolta Sensing, Inc.) applied to the CIE chromaticity coordinates shown in FIG. 4.16 in page 108 of "Shinpen Shikisai Kagaku Handobukku (New Scientific Handbook of Color)" (edited by the Color Science Association of Japan, published by University of Tokyo Press, 1985).

In the organic EL element according to the present invention emitting white light, the term "white" indicates that the chromaticity at 1000 cd/m$^2$ in the CIE1931 color system is within the region defined by X=0.33±0.07 and Y=0.33±0.1 in the measurement of the front luminance at a view angle of 2 degrees by the above method.

<<Display Device>>

The display device according to the present invention will now be described. The display device according to the present invention includes the organic EL element according to the present invention. The display device according to the present invention may be a monochromatic or polychromatic display device. A polychromatic display device will now be described.

In the polychromatic display device, a luminous layer is formed over an underlying layer through a shadow mask by deposition, casting, spin coating, inkjet printing, or printing.

If only the luminous layer is patterned, preferred examples of the patterning method include, but should not be limited to, deposition, an inkjet method, spin coating, or a printing method.

The organic EL element included in the display device has a desired configuration selected from the exemplified configurations of the organic EL element.

The process of preparing an organic EL element has been described as one aspect of the process of preparing the organic EL element according to the present invention.

When a DC voltage of about 2 V to 40 V is applied between the anode (positive polarity) and the cathode (negative polarity) to such a polychromatic display device, the device emits light. If voltage is applied to a display device having inverted polarities of the electrodes, however, current does not flow, and thus no light emission occurs. Application of AC voltage causes light emission only if the anode is positive and the cathode is negative. The AC voltage to be applied may have any waveform.

The polychromatic display device can be used as display devices, displays, and light emitting sources. Display devices and displays can display full-color images by way of three organic EL elements emitting blue light, red light, and green light, respectively.

Examples of the display devices and the displays include televisions, personal computers, mobile apparatuses, AV apparatuses, displays for text broadcasting receivers, and car-mount displays. In particular, the polychromatic display device can be used for reproducing still pictures and moving pictures. In reproduction of moving pictures, the display device can be driven in a simple matrix (passive matrix) mode or in an active matrix mode.

Examples of the light emitting sources include, but should not be limited to, house lightings, car interior lightings, backlights for clocks and liquid crystal devices, advertising signs, traffic signals, and light sources for optical storage media, electrophotographic copiers, optical communication processors, and optical sensors.

An exemplary display device including the organic EL element according to the present invention will now be described with reference to the drawings.

FIG. 1 is a schematic view illustrating an exemplary display device including an organic EL element. FIG. 1 schematically shows a display device which displays image information through the light emission of the organic EL element, such as a display for a mobile phone.

A display 1 includes a display unit A having a plurality of pixels, and a control unit B for scanning an image on the display unit A based on image information. The control unit B is electrically connected to the display unit A. The control unit B transmits scanning signals and image data signals to the respective pixels based on external image information. In response to the scanning signals, the pixels on the corresponding scanning lines sequentially emit light according to the image data signals. The image information thereby appears on the display unit A.

Figure 2:
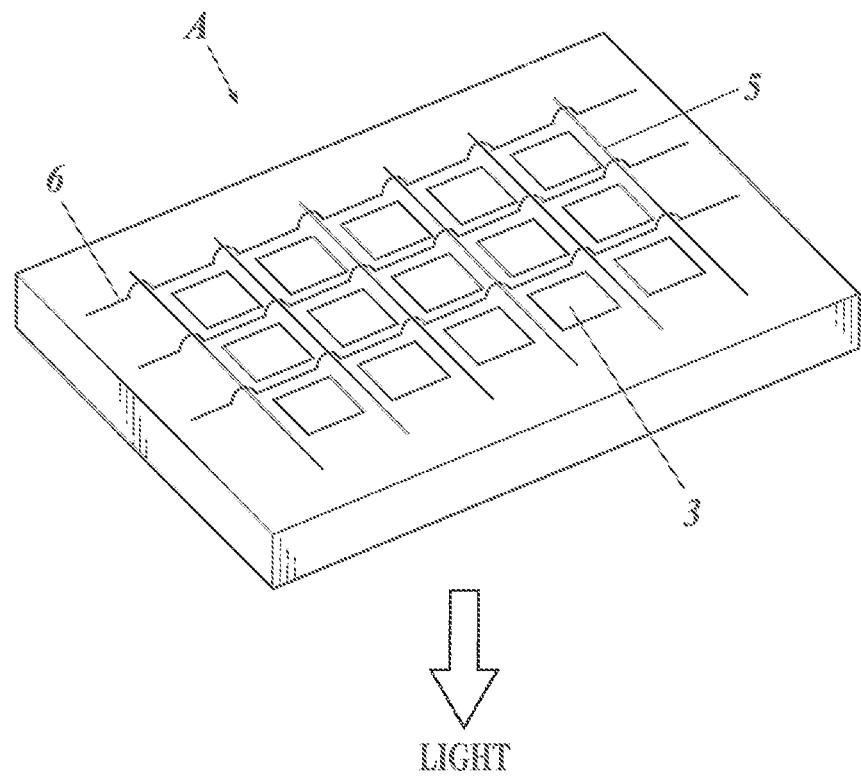
FIG. 2 is a schematic view illustrating a display unit A in FIG. 1.

FIG. 2 is a schematic view illustrating the display unit A.

The display unit A includes a substrate, a line unit including a plurality of scanning lines 5 and data lines 6, and a plurality of pixels 3. The line unit and the pixels are disposed on the substrate. The main components of the display unit A will now be described.

In FIG. 2, the light emission from the pixels 3 is extracted as expressed by the blank arrow (downward in the drawing).

The scanning lines 5 and the data lines 6 in the line unit are composed of a conductive material. The scanning lines 5 intersect orthogonally to the data lines 6 in the form of a lattice. The intersections are connected to the pixels 3 (details are not shown).

Each of the pixels 3 receives a scanning signal from the corresponding scanning line 5, and receives an image data signal from the corresponding data line 6. The pixels 3 emit light according to the received image data. The pixels emitting light in a red region, those emitting light in a green region, and those emitting light in a blue region are regularly disposed on the substrate to achieve full-color display of images.

Figure 3:
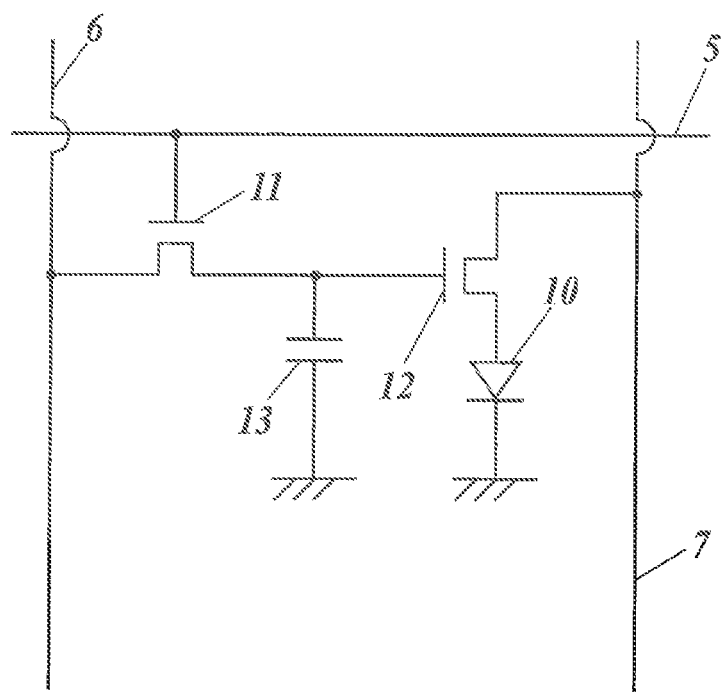
FIG. 3 is a schematic view illustrating pixels.

The process of emitting light from pixels will now be described. FIG. 3 is a schematic view illustrating a pixel. The pixel includes an organic EL element 10, a switching transistor 11, a driving transistor 12, and a capacitor 13. Red, green, and blue organic EL elements 10 can be disposed in the pixels on the substrate for full-color display of images.

In FIG. 3, an image data signal is fed from the control unit B through the data line 6 to the drain of the switching transistor 11. A scanning signal is fed from the control unit B through the scanning line 5 to the gate of the switching transistor 11. The switching transistor 11 is then turned on to transmit the image data signal in the drain to the capacitor 13 and the gate of the driving transistor 12.

In response to the transmission of the image data signal, the capacitor 13 is charged according to the potential of the image data signal while the driving transistor 12 is turned on. In the driving transistor 12, the drain is connected to a power supply line 7, and the source is connected to the electrode of the organic EL element 10. According to the potential of the image data signal in the gate of the driving transistor 12, current is fed to the organic EL element 10 from the power supply line 7.

The scanning signal is fed to the next scanning line 5 as a result of sequential scanning by the control unit B, and the switching transistor 11 is then turned off. Even after the switching transistor 11 is turned off, the capacitor 13 keeps the charge applied according to the potential of the image data signal and the driving transistor 12 is kept on. The organic EL element 10 continuously emits light until the transmission of the next scanning signal. The next scanning signal is fed by sequential scanning. The driving transistor 12 is driven according to the potential of the next image data signal in synchronization with the feed of the scanning signal, so that the organic EL element 10 emits light.

In short, the pixels each include the organic EL element 10, and active elements, i.e., the switching transistor 11 and the driving transistor 12, which control the light emission of the organic EL element 10 in each pixel 3. Such a process of light emission is called an active matrix mode.

The light emission of the organic EL element 10 may have gradations derived from a multi-valued image data signal having a plurality of gradation potentials, or may be controlled by switching on/off of a predetermined amount of light emission by a binary image data signal. The capacitor 13 may keep the charged potential until the next scanning signal is applied, or may discharge immediately before the next scanning signal is applied.

In the present invention, the display mode may be a passive matrix mode to control the organic EL element to emit light according to the data signal only while the scanning signal is being fed, instead of the active matrix mode described above.

FIG. 4 is a schematic view illustrating a passive matrix display device. In FIG. 4, a plurality of scanning lines 5, a plurality of pixels 3, and a plurality of image data lines 6 are disposed in sequence. The scanning lines 5 and the image data lines 6 are disposed in the form of a lattice. The scanning signal is fed from the scanning line 5 as a result of sequential scanning, and the pixel 3 connected to the scanning line 5 then emits light according to the image data signal. In the passive matrix mode, the pixel 3 has no active element and thus can be produced at low cost.

<<Illumination Device>>

The illumination device according to the present invention will now be described. The illumination device according to the present invention includes an organic EL element according to the present invention. The organic EL element according to the present invention may have a resonator structure. Such an organic EL element having a resonator structure can be used in light sources for optical storage media, electrophotographic copiers, optical communication processors, and optical sensors, but these applications should not be construed to limit the invention. The organic EL element according to the present invention causing laser oscillation can also be used in these applications.

The organic EL element according to the present invention can also be used as a lamp for illumination and a light source for exposure, or can also be used in a projector for projecting the image or a display device (display) for directly displaying still pictures and moving pictures. The organic EL element according to the present invention used as a display device for reproducing moving pictures can be driven in a simple matrix (passive matrix) mode or an active matrix mode. Use of two or more organic EL elements according to the present invention emitting light of different colors can attain a full-color display device.

The organic EL material according to the present invention can be used to prepare organic EL elements for illumination devices emitting substantially white light. White light emission is attained through mixing of different colors of light beams emitted from two or more luminous materials at the same time. The light beams of such a color combination may have three local maximum wavelengths corresponding to three primary colors, red, green, and blue, or may have two local maximum wavelengths corresponding to complementary colors, such as blue and yellow, or blue green and orange.

The combination of luminous materials emitting light beams of different colors can be selected from combinations of two or more phosphorescent or fluorescent materials and combinations of fluorescent or phosphorescent luminous materials with dyes emitting excitation light based on the light emitted from the luminous materials. In the present invention, a white organic EL element emitting white light by mixing of different colors of light beams can be achieved by a combination of luminous dopants.

Such white organic EL elements can be prepared by the following simple process: These luminous materials are separately applied through a mask in the deposition process of a luminous layer, a hole transporting layer, or an electron transporting layer. Other common layers, such as electrode layers, can be disposed over the entire underlying layers by deposition, casting, spin coating, inkjet printing, or printing without patterning through a mask, at high productivity. An organic EL element itself produced through this process emits white light, unlike white organic EL devices including arrays of light-emitting elements emitting light beams of different colors. The luminous layer can be prepared with any luminous material. For example, white light in a backlight for a liquid crystal display element can be produced by any combination of materials selected from the metal complex according to the present invention and known luminous materials so as to match wavelength ranges with desired color filter (CF) properties.

<<An Embodiment of Illumination Device According to the Present Invention>>

An embodiment of the illumination device according to the present invention including the organic EL element according to the present invention will now be described.

The organic EL element according to the present invention is disposed on a glass sealing substrate having a thickness of 300 μm. An epoxy photocurable adhesive (Laxtrack LC0629B available from TOAGOSEI CO., LTD.) is applied around the organic EL element, and a glass case is disposed over the cathode to cover the non-light emitting surface of the organic EL element according to the present invention. The glass cover is bonded to the glass sealing substrate, and the glass sealing substrate is irradiated with UV light to seal the organic EL element. An illumination device illustrated in FIGS. 5 and 6 is prepared.

Figure 5:
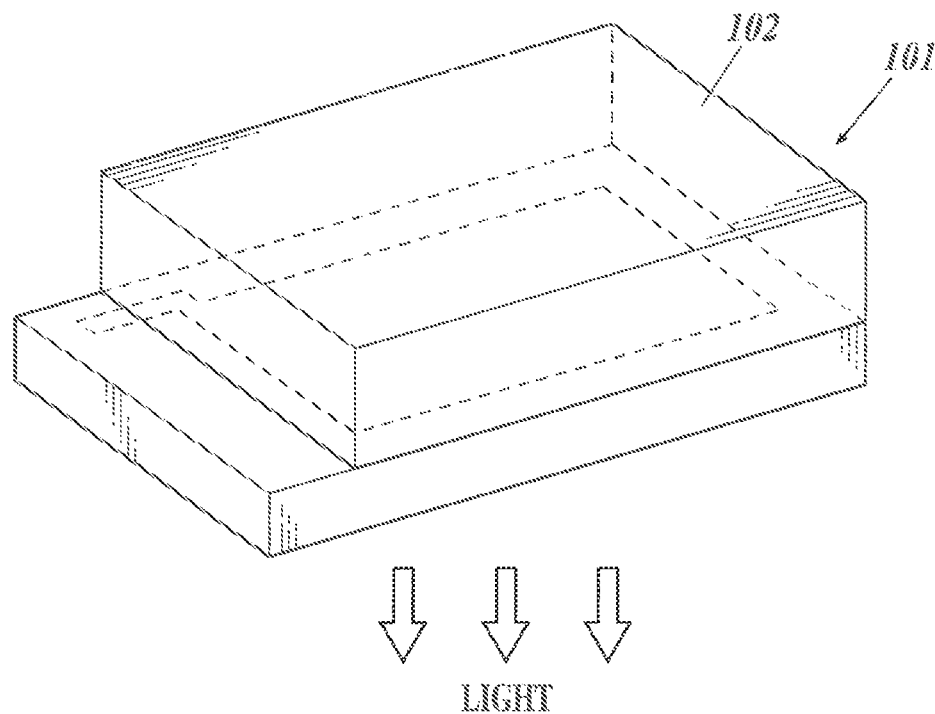
FIG. 5 is a schematic view illustrating an illumination device.

FIG. 5 is a schematic view illustrating an illumination device. The organic EL element 101 according to the present invention is covered with a glass cover 102 (sealing with the glass cover is performed under a nitrogen atmosphere (under an atmosphere of high purity nitrogen gas (purity: 99.999% or more) in a glovebox so as not to contact the organic EL element 101 with air).

Figure 6:
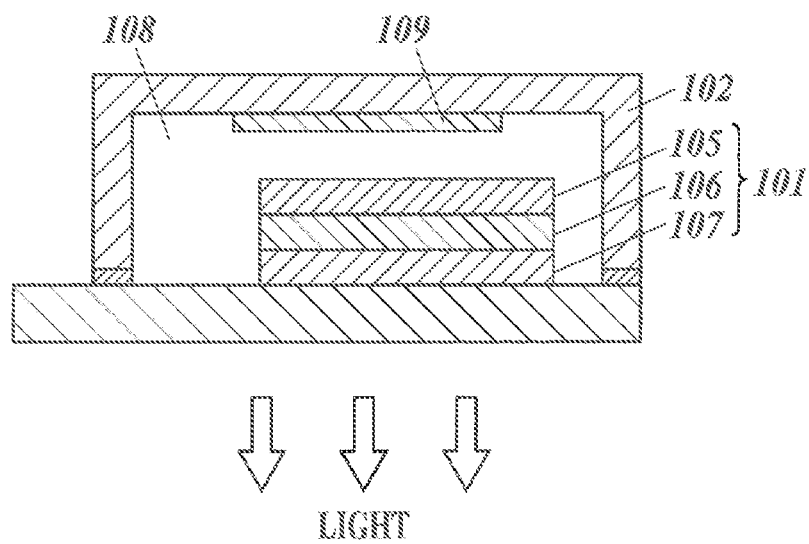
FIG. 6 is a schematic view illustrating an illumination device.

FIG. 6 is a sectional view illustrating an illumination device. FIG. 6 illustrates a cathode 105, an organic EL layer 106, and a glass substrate with a transparent electrode 107. The interior of the glass cover 102 (see FIG. 5) is filled with nitrogen gas 108, and contains a water getter 109.

EXAMPLES

The present invention will now be described in more detail by way of non-limiting Examples.

The structures of the compounds used in Examples are listed below. Compounds 3-1-1 to 4-7-2 correspond to the materials for organic EL elements represented by Formulae (1) to (7).

[Formula 124]

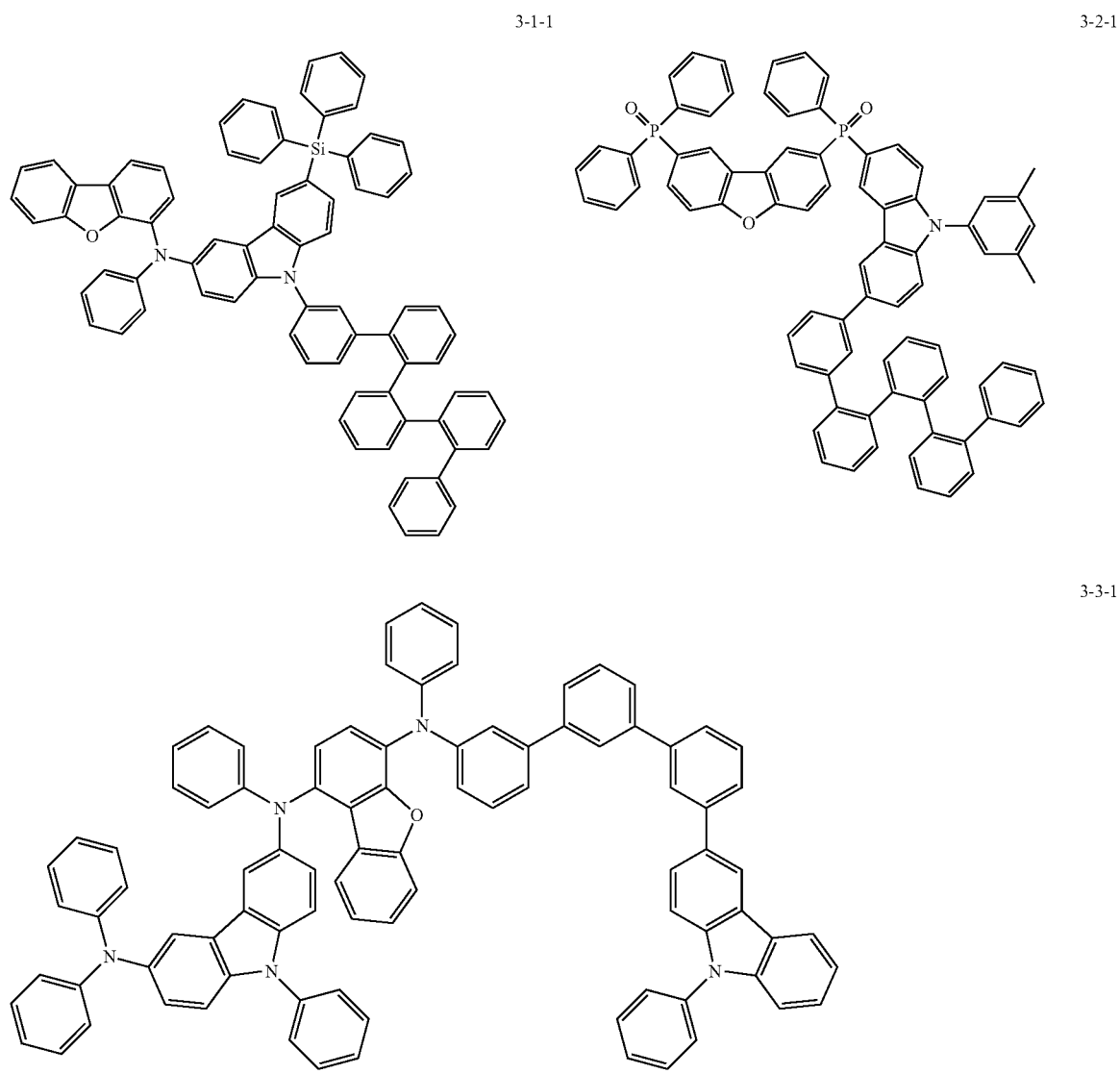

3-4-1
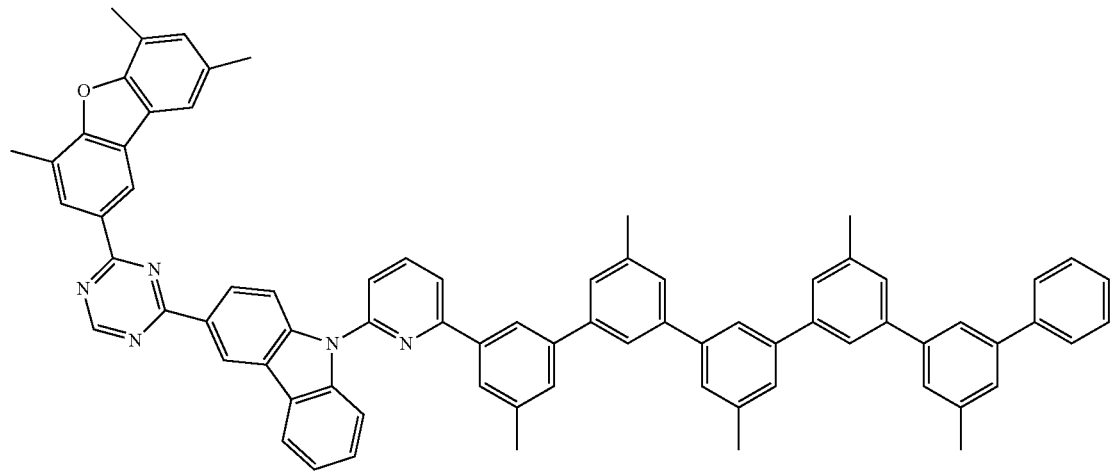
[Formula 125]
3-5-1                    3-6-1
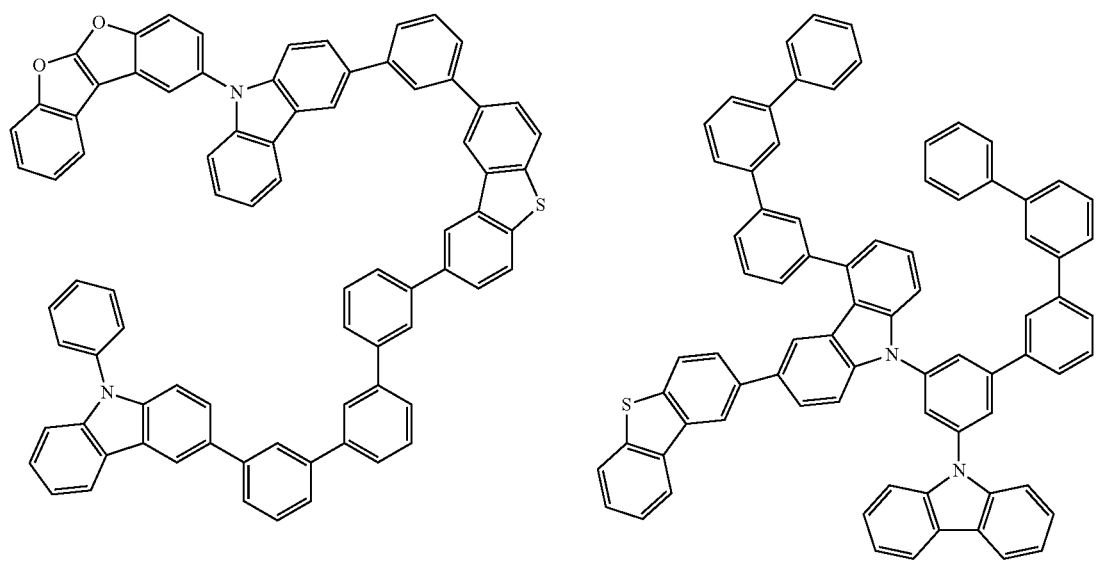

3-7-1
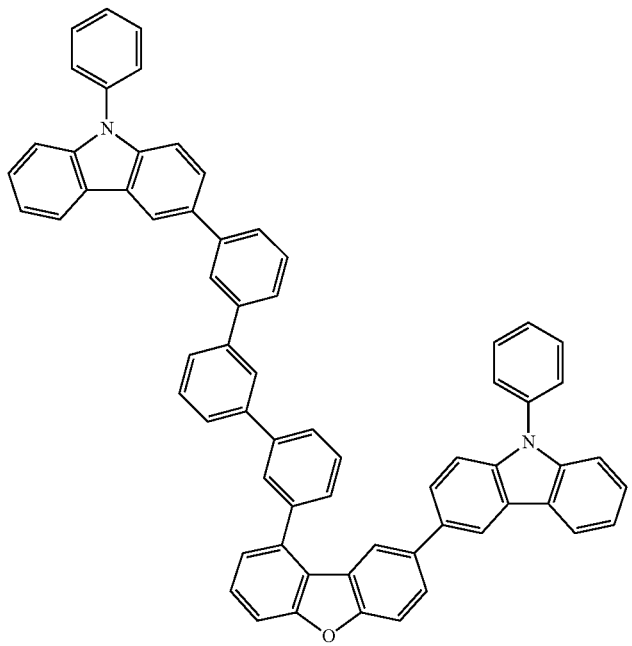
3-7-3
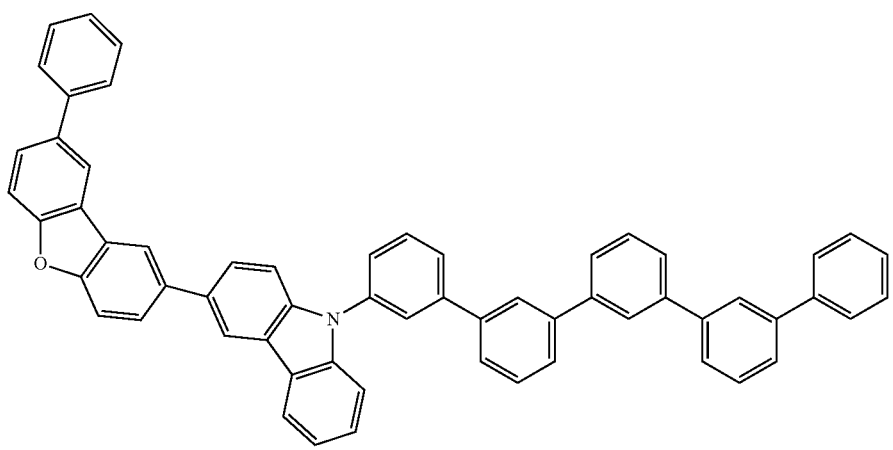
[Formula 126]
3-1-2
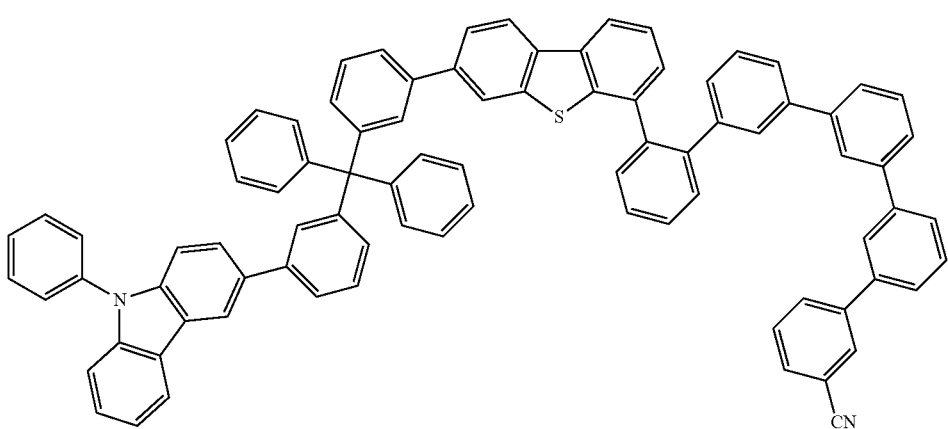

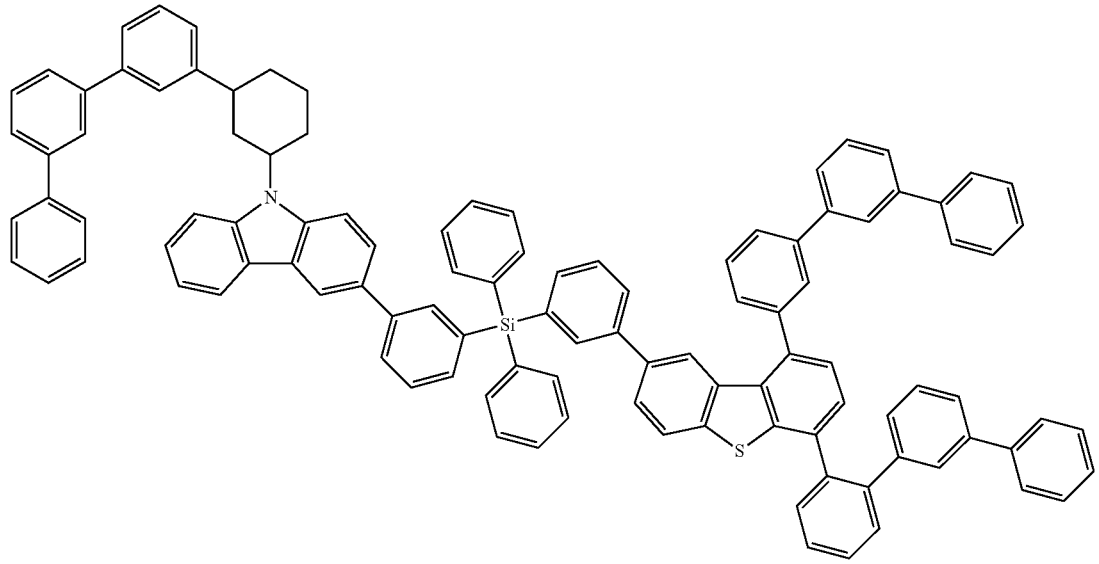
3-2-2
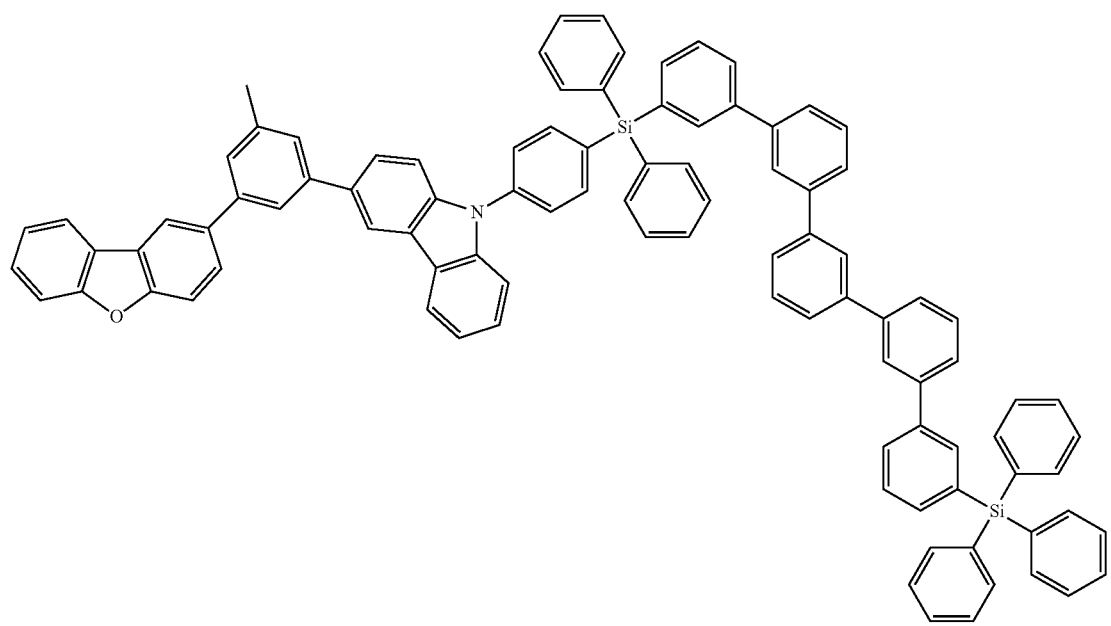
3-3-2

[Formula 127]
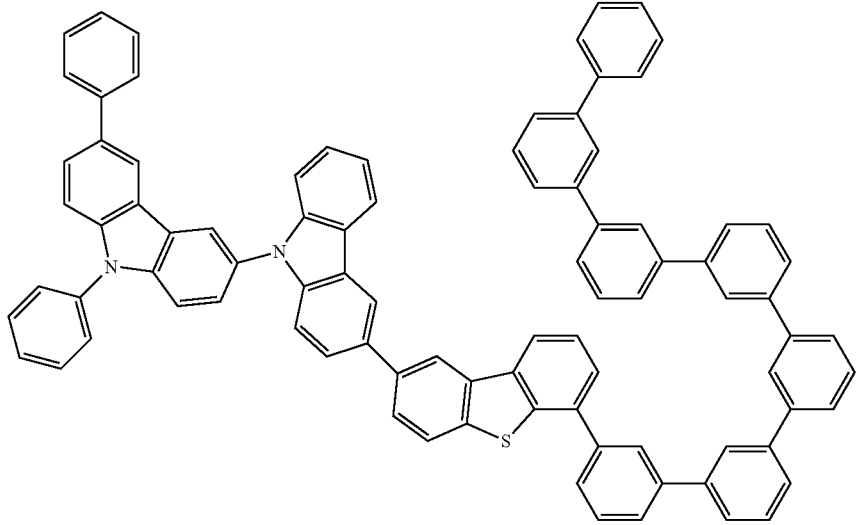
3-4-2
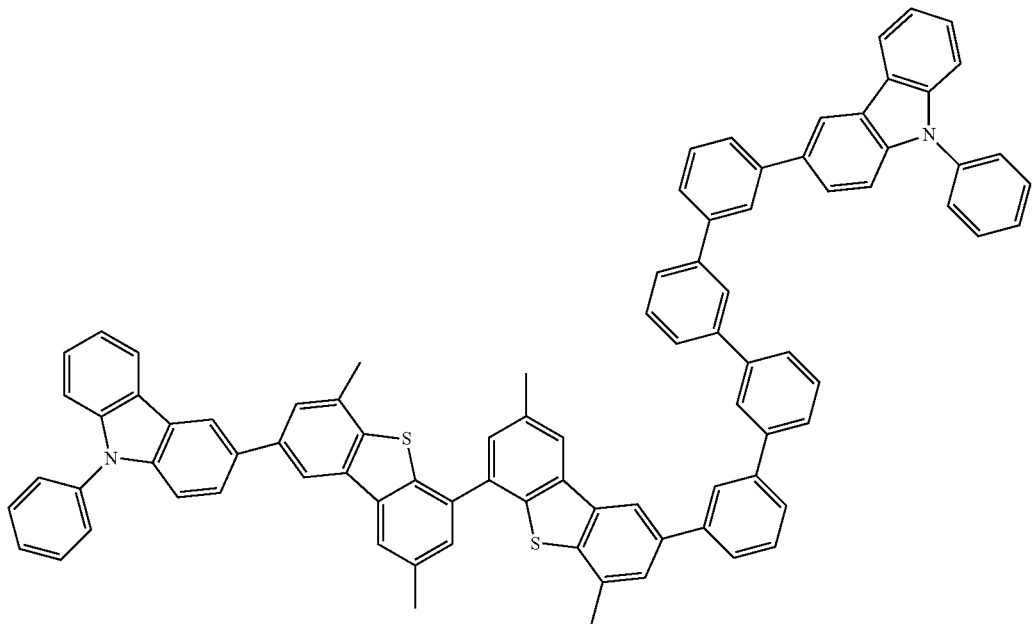
3-5-2
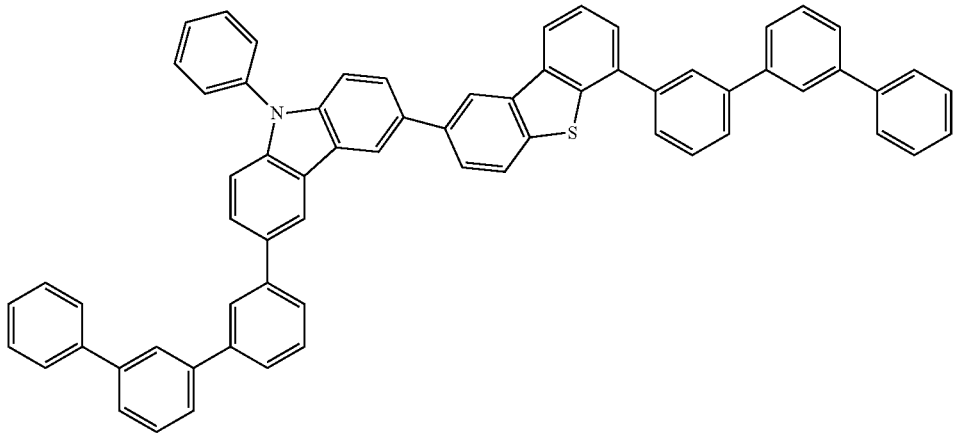
3-6-2

3-7-2
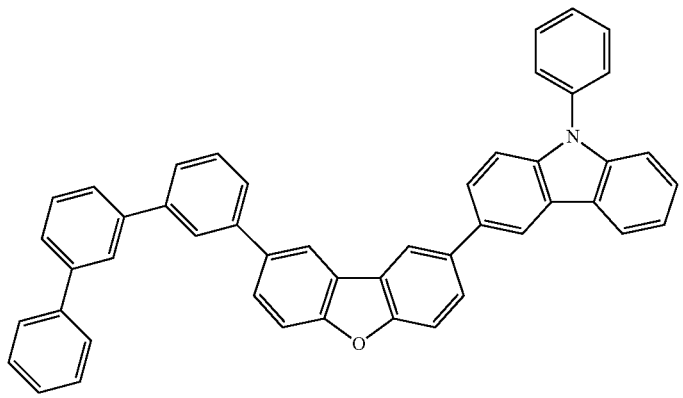
[Formula 128]
4-1-1
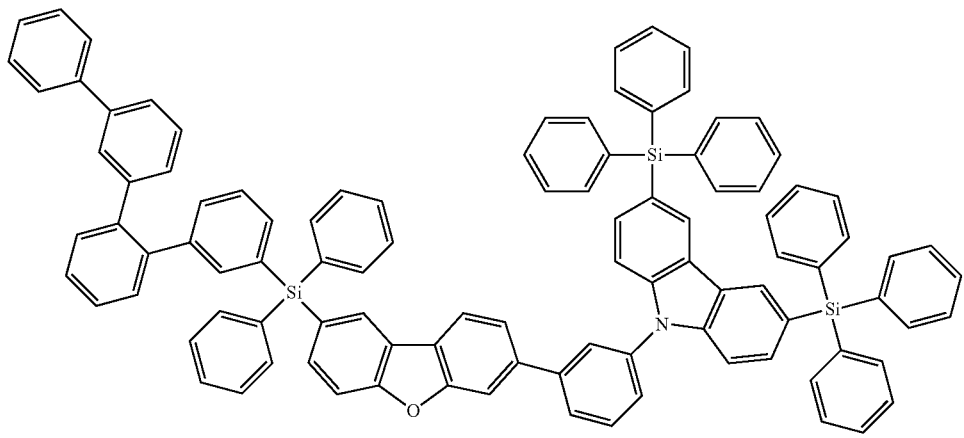
4-2-1
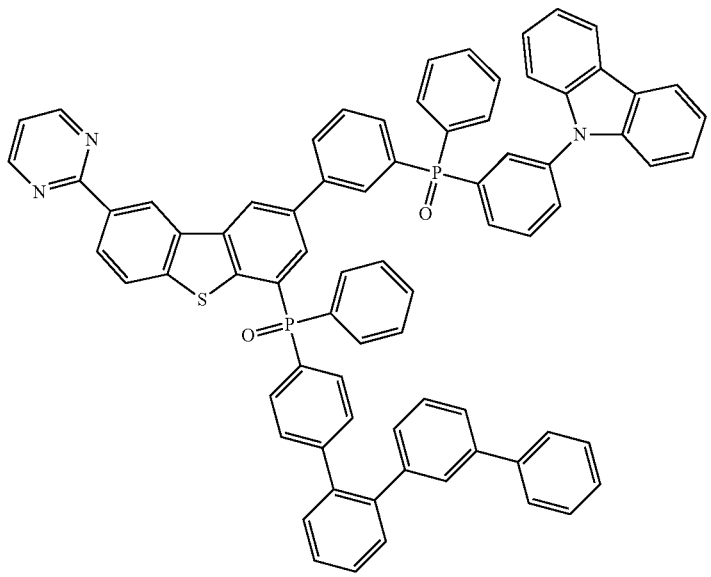

4-3-1
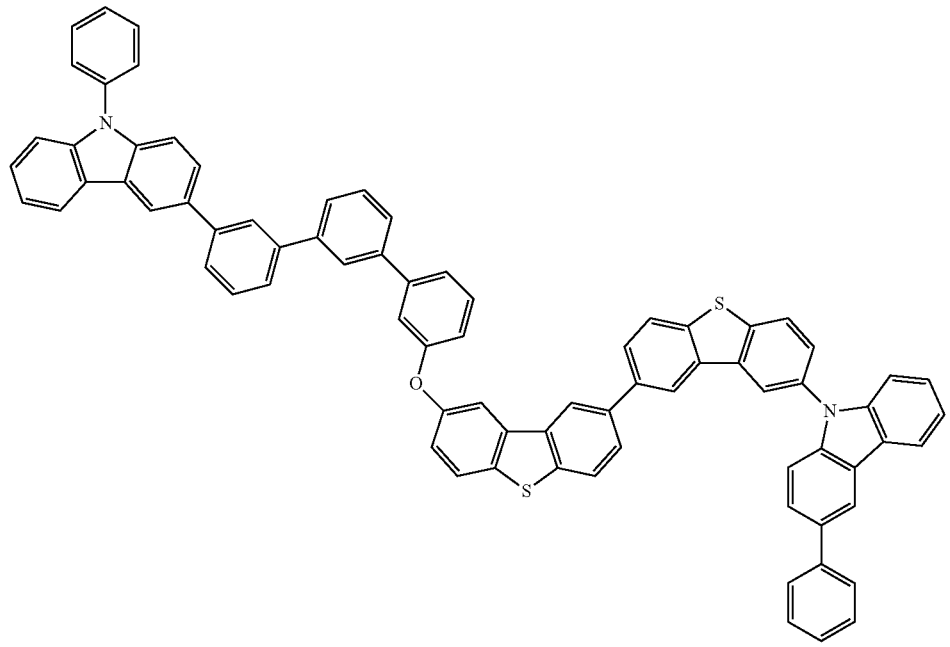
[Formula 129]
4-4-1
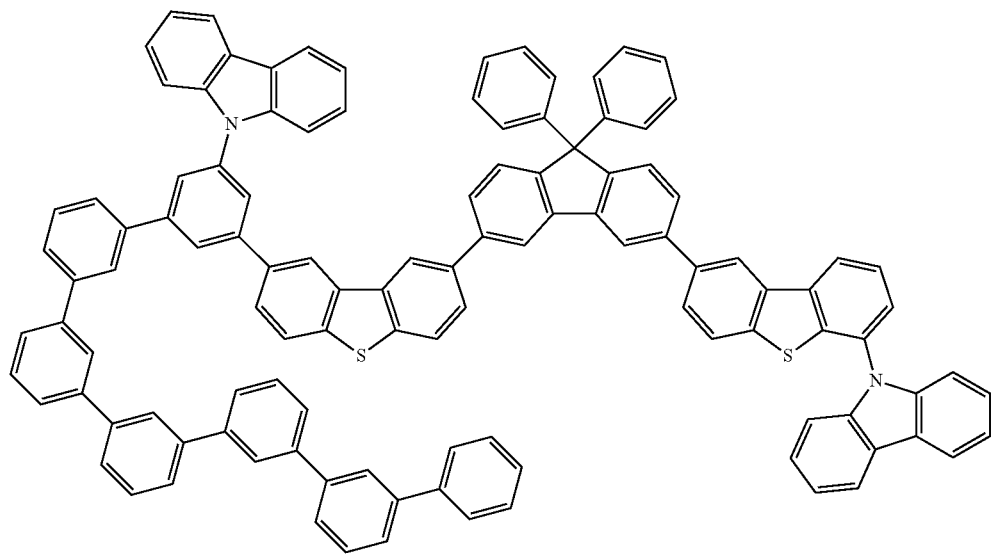

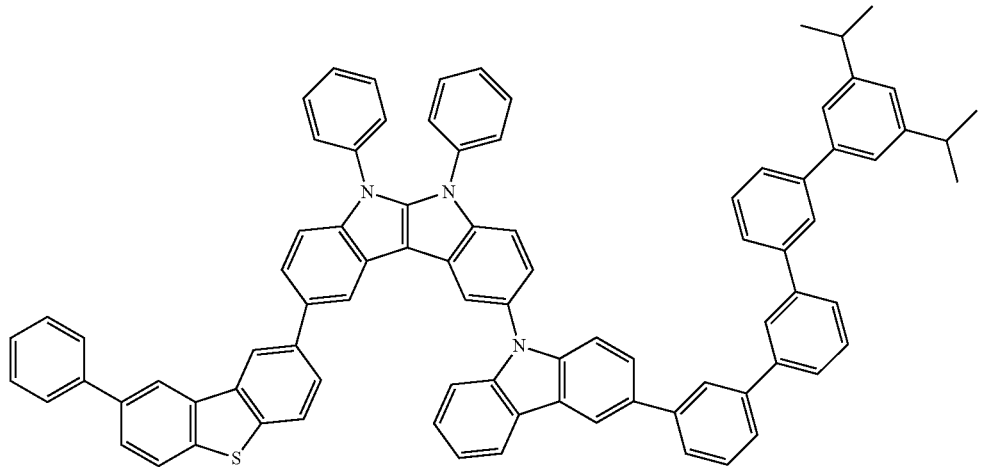
4-5-1
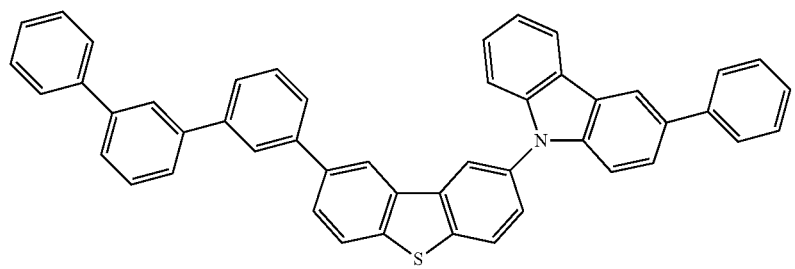
4-6-1
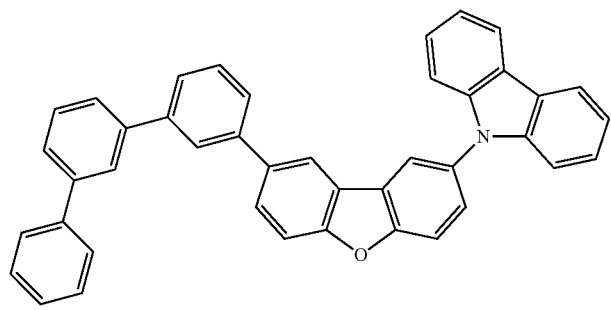
4-7-1

[Formula 130]
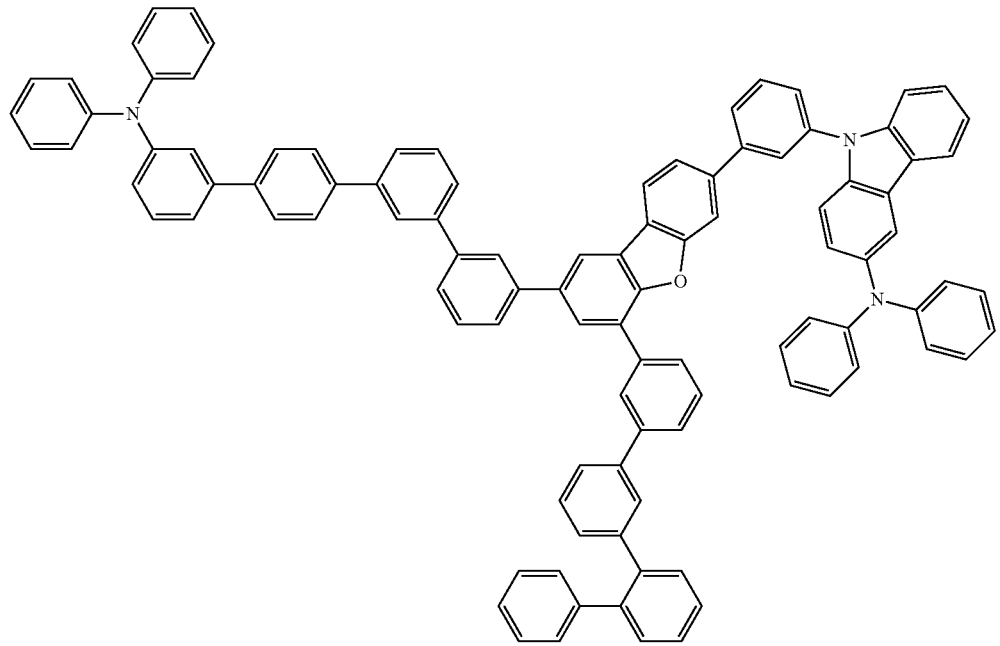
4-1-2
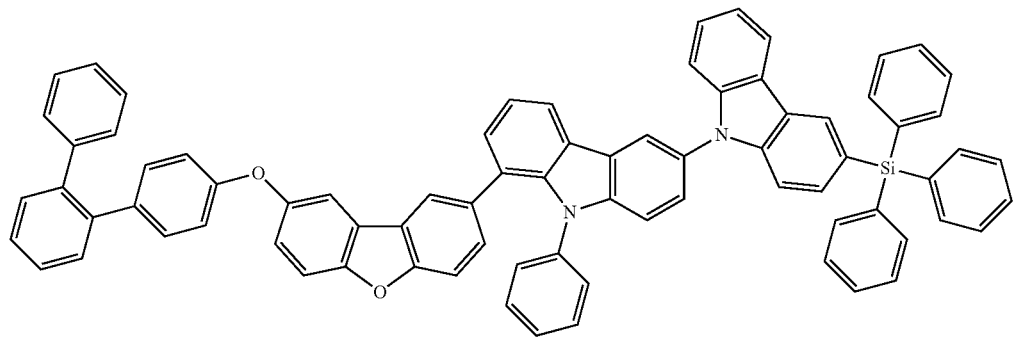
4-2-2
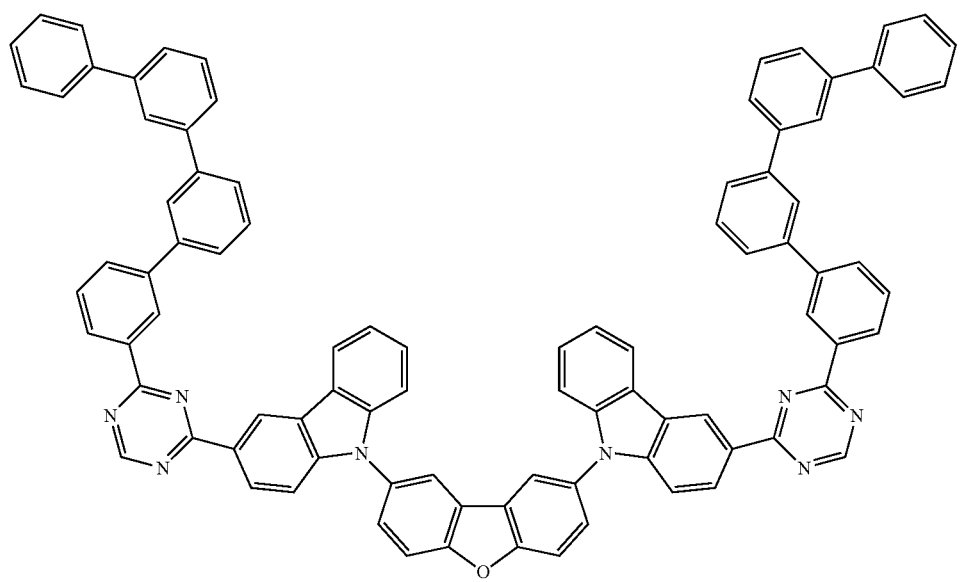
4-3-2

[Formula 131]
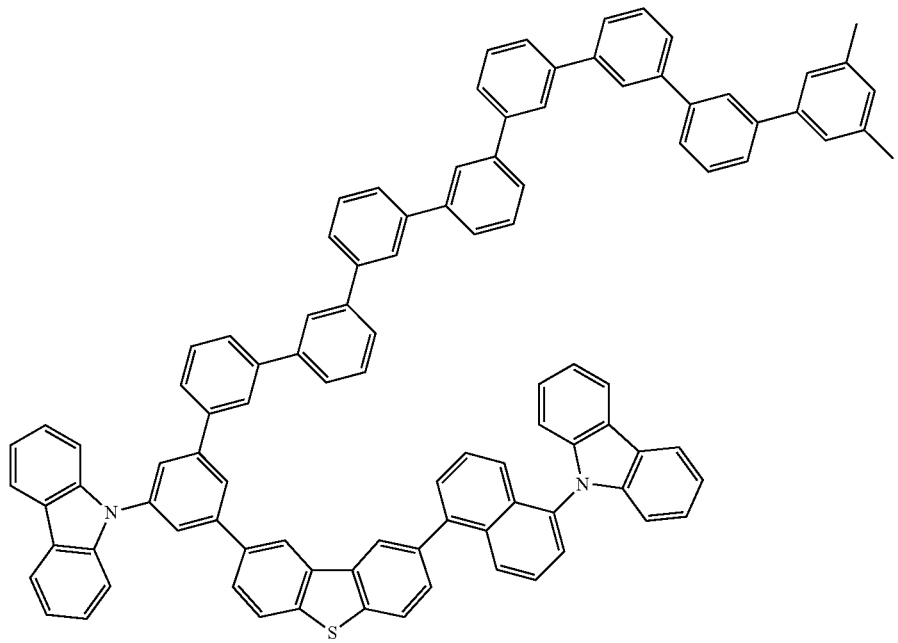
4-4-2
4-5-2
4-6-2

4-7-2
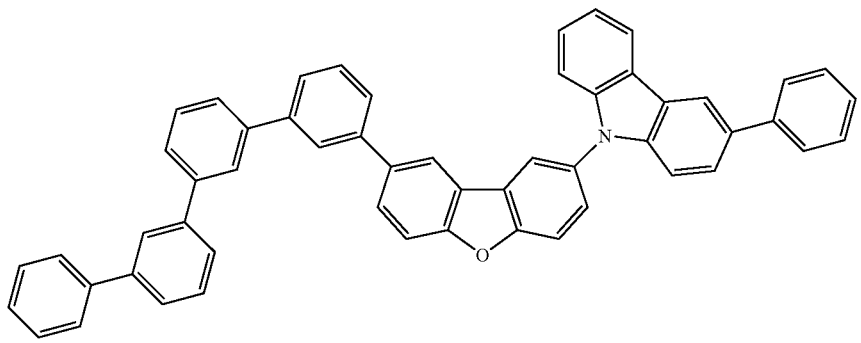
[Formula 132]
6-1-1
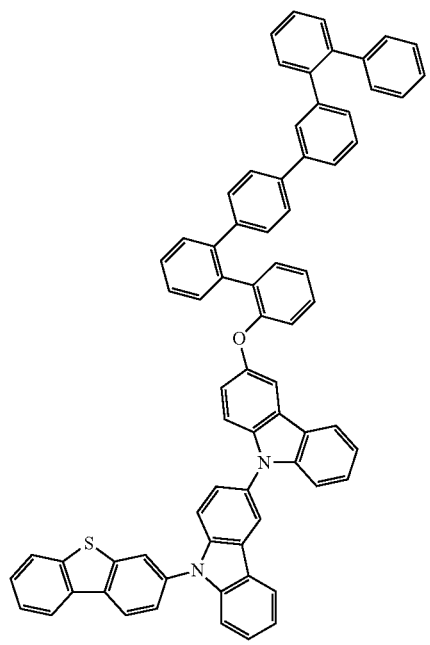
6-1-2
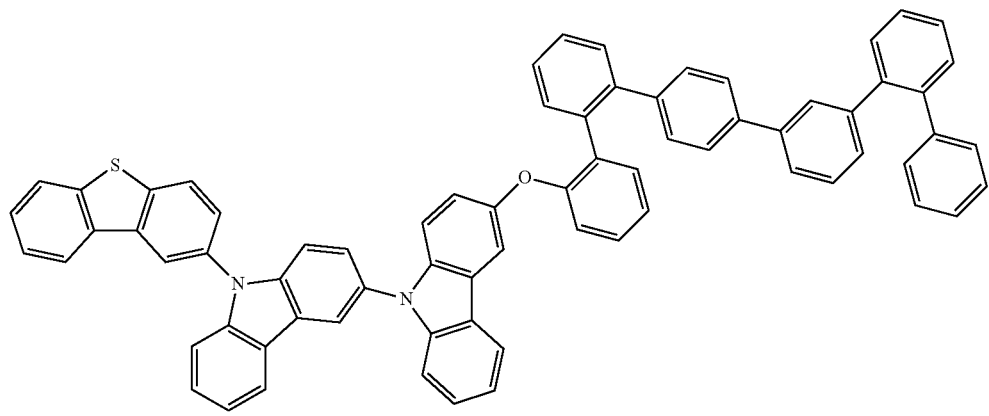

6-1-3
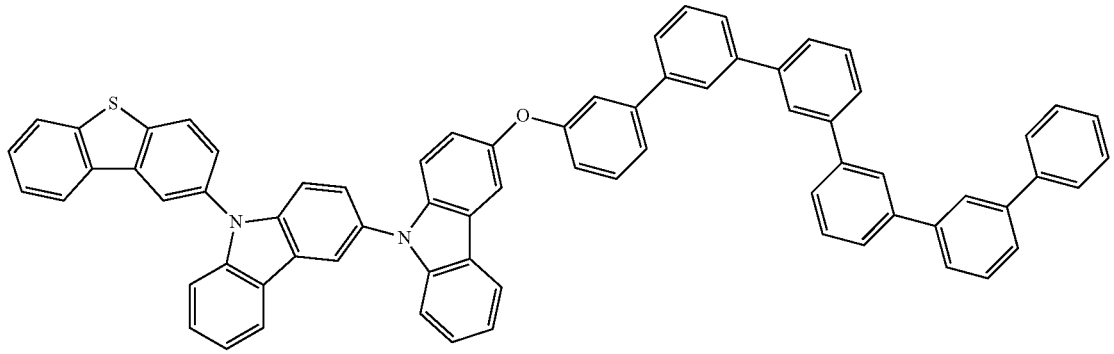
[Formula 133]
6-1-4
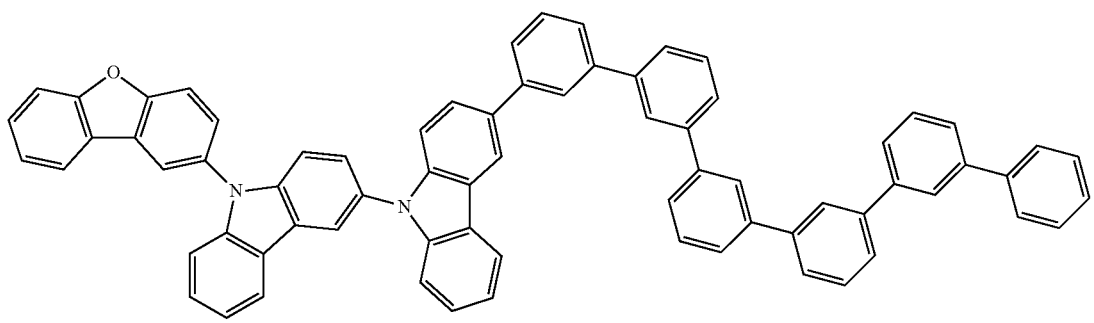
6-1-5
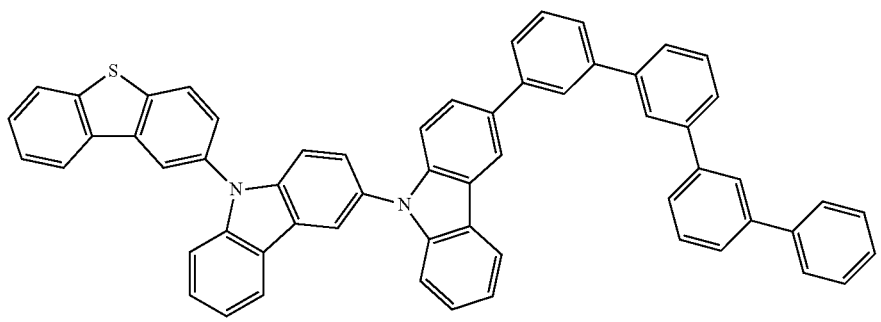
6-1-6
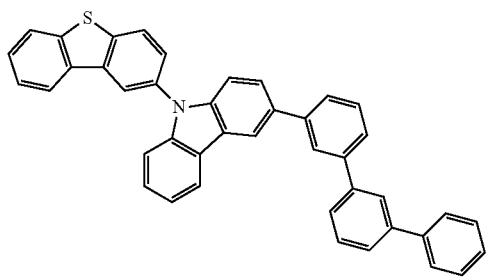
6-1-7
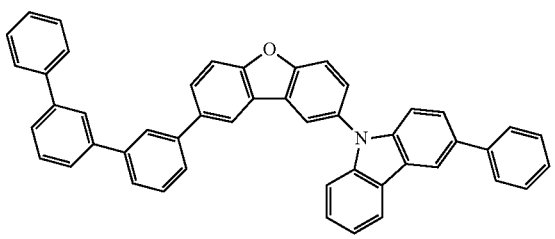

[Formula 134]
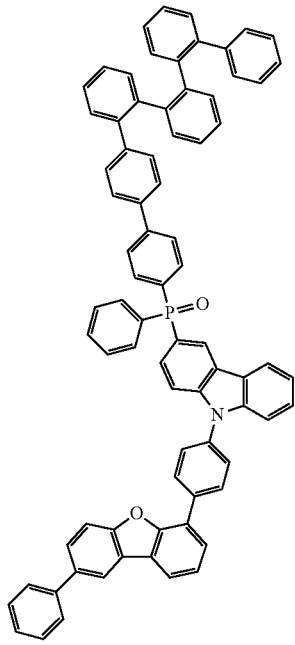
6-2-1
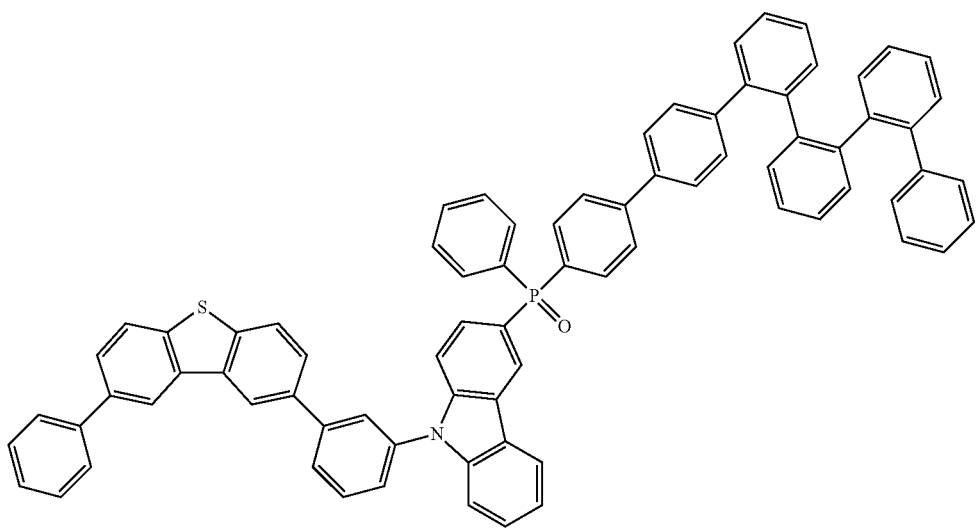
6-2-2
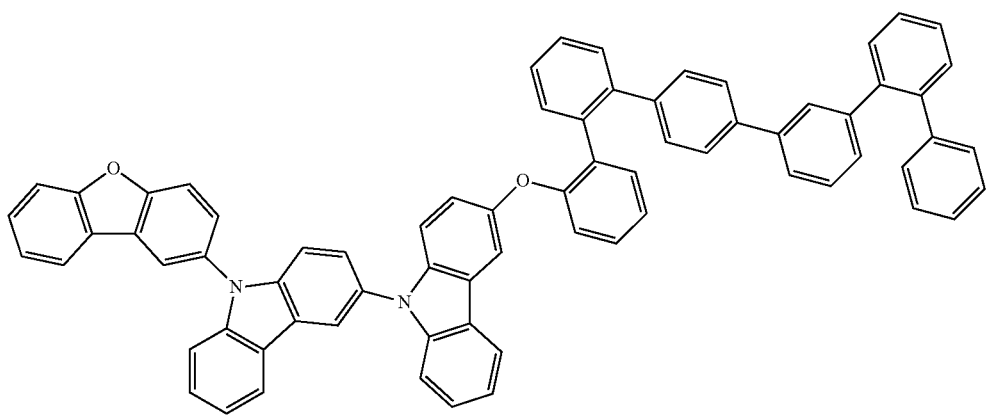
6-2-3

[Formula 135]
6-2-4
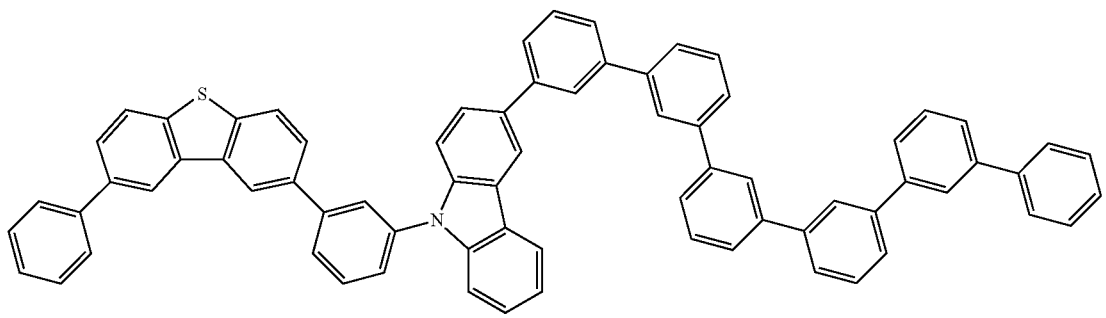
6-2-5
6-2-6
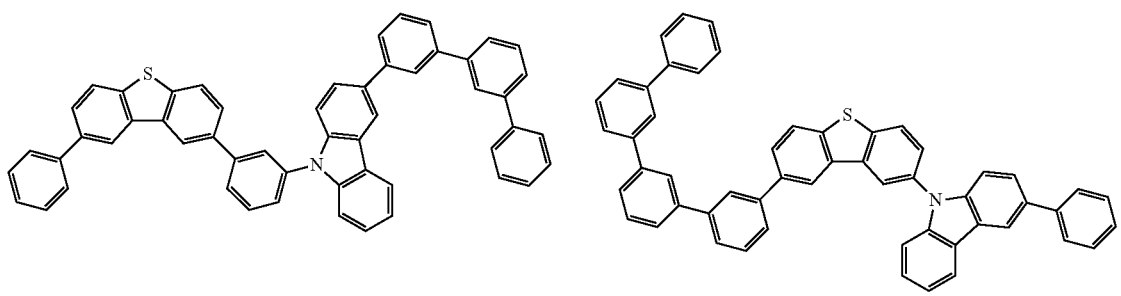
6-2-7
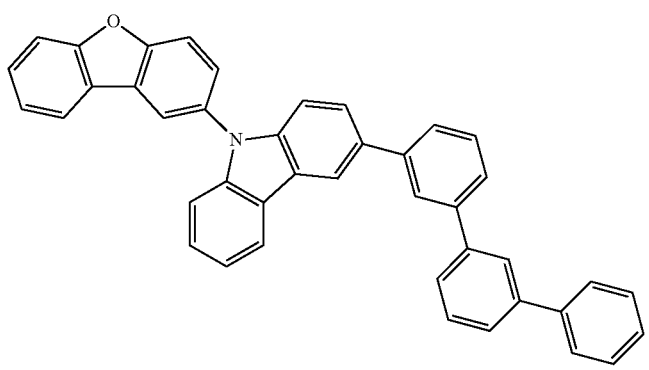
[Formula 136]
6-3-5
6-3-6
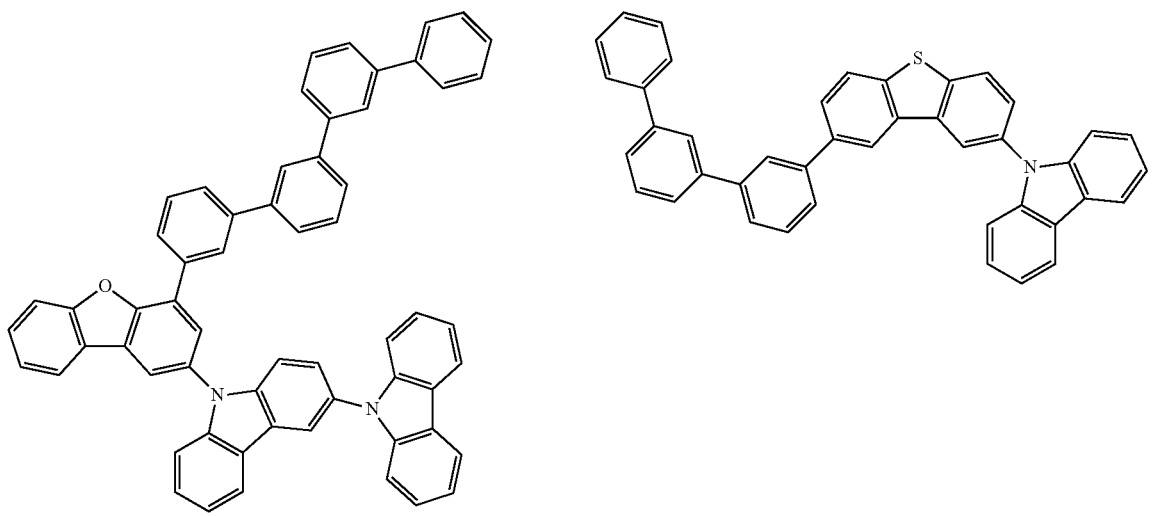

6-3-7
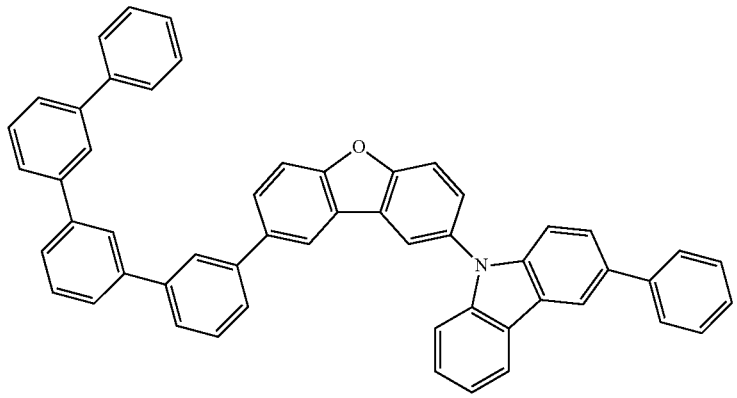
[Formula 137]
6-4-5
6-4-6
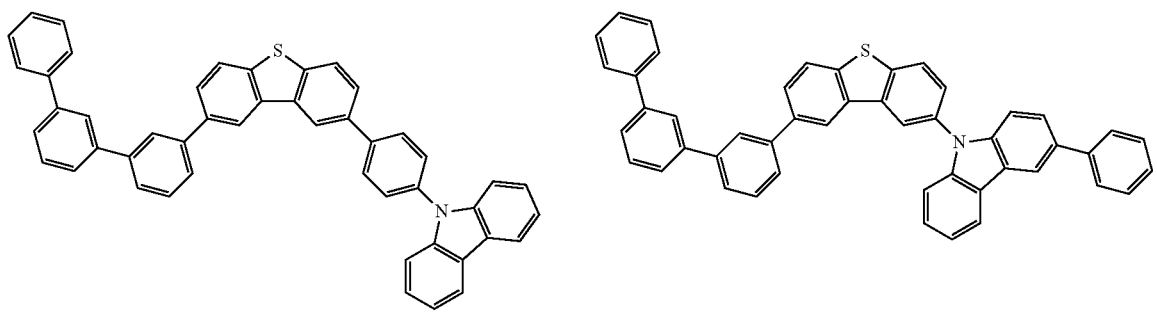
6-4-7
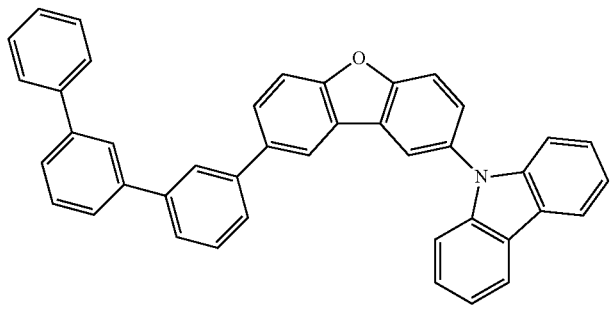
[Formula 138]
7-1-1
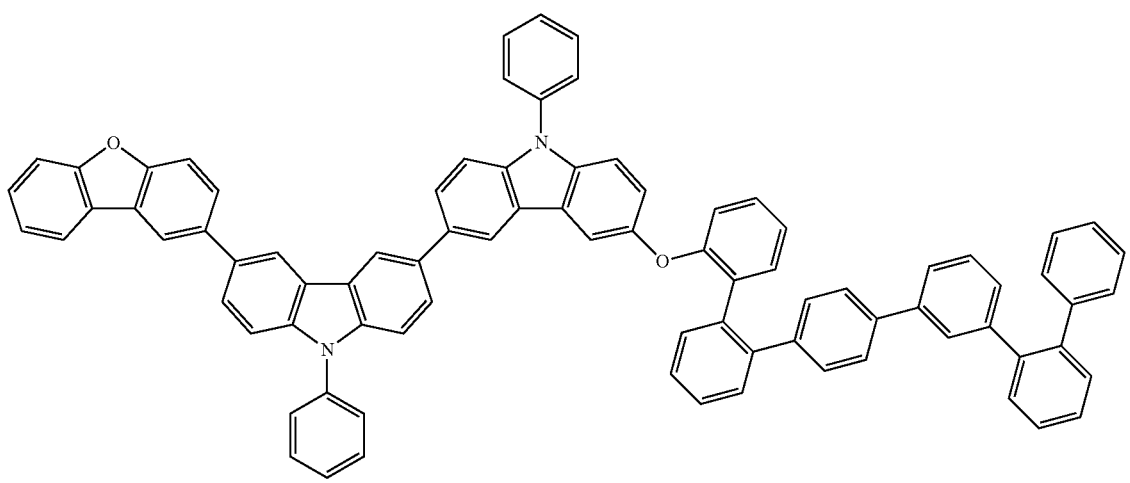

7-1-2
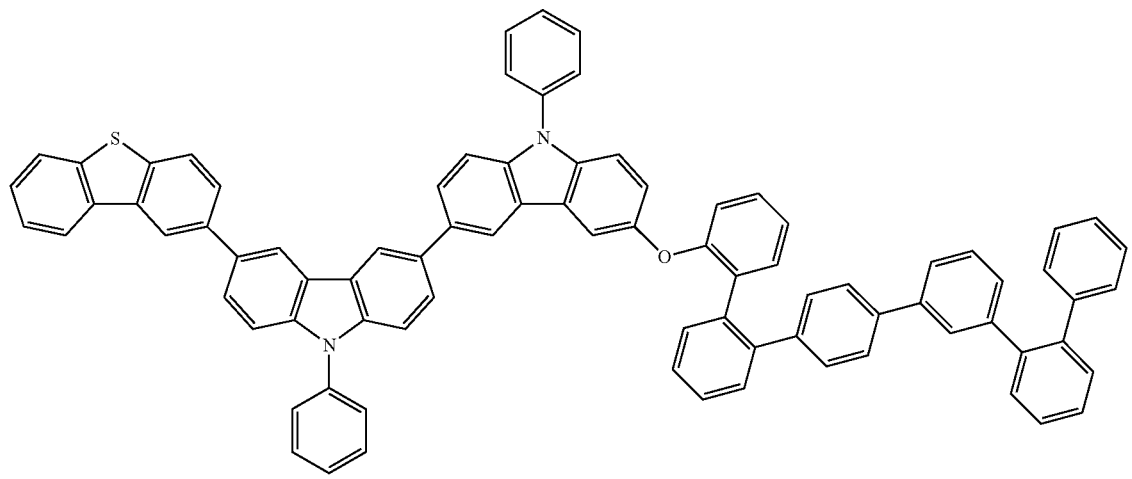
7-1-3
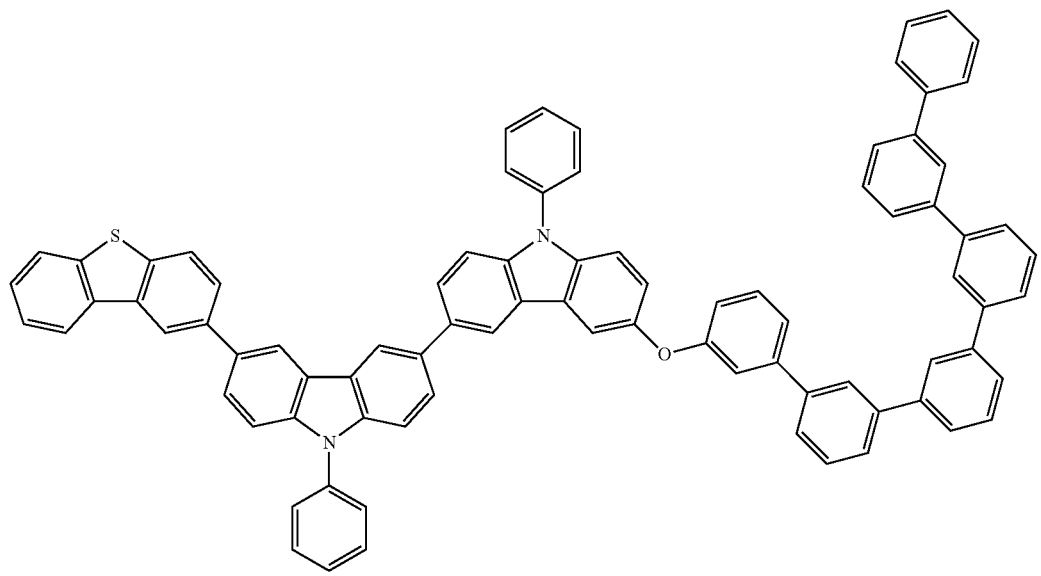
[Formula 139]
7-1-4
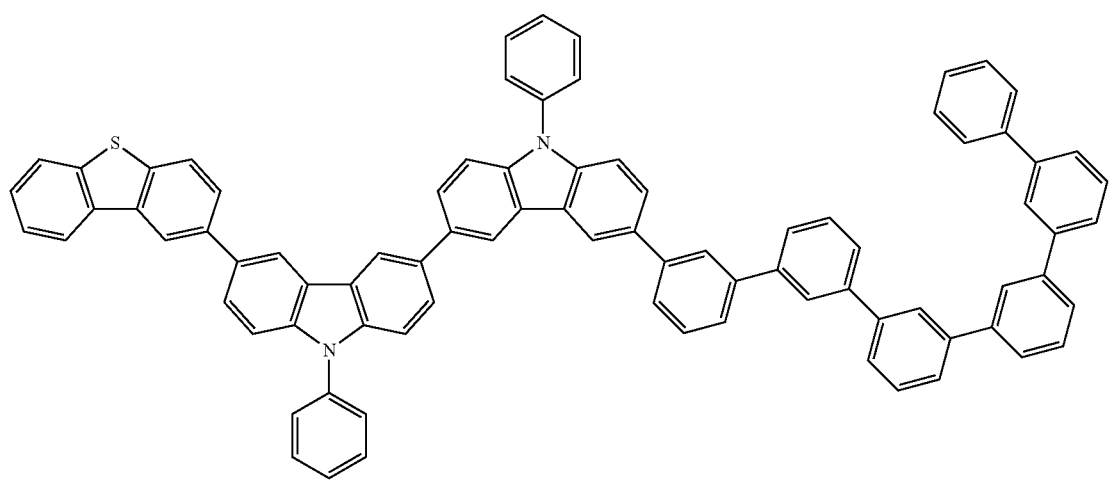

7-1-5
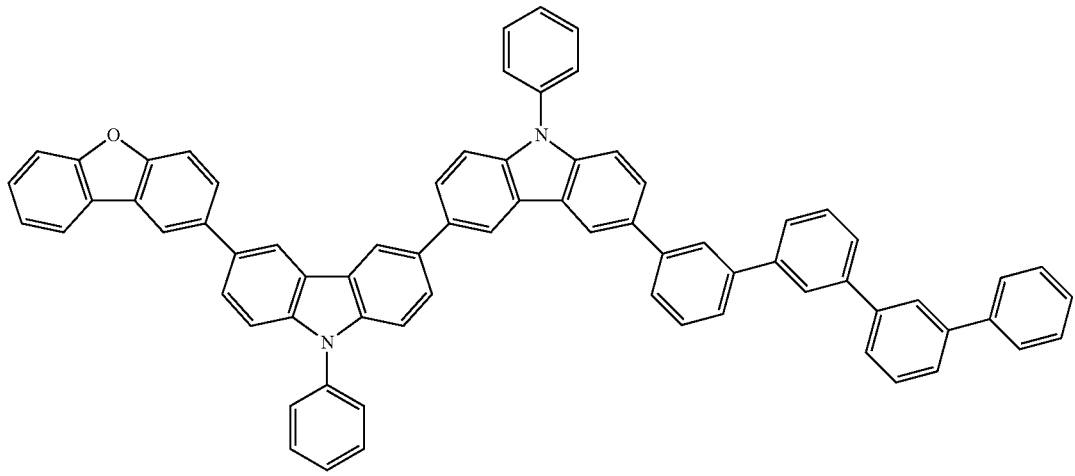
7-1-6
7-1-7
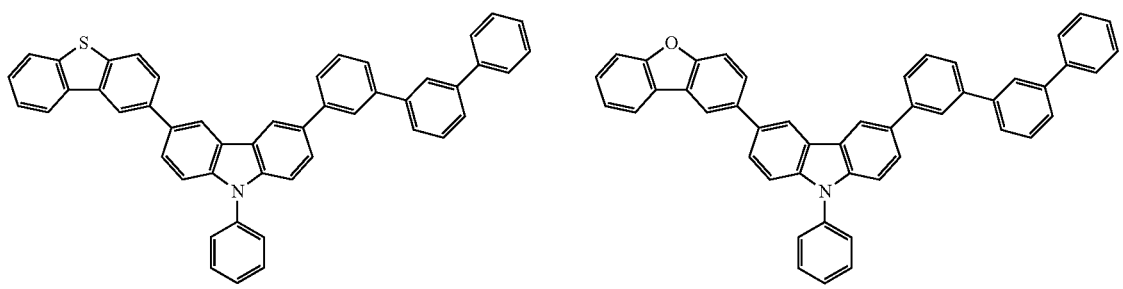
[Formula 140]
7-2-1
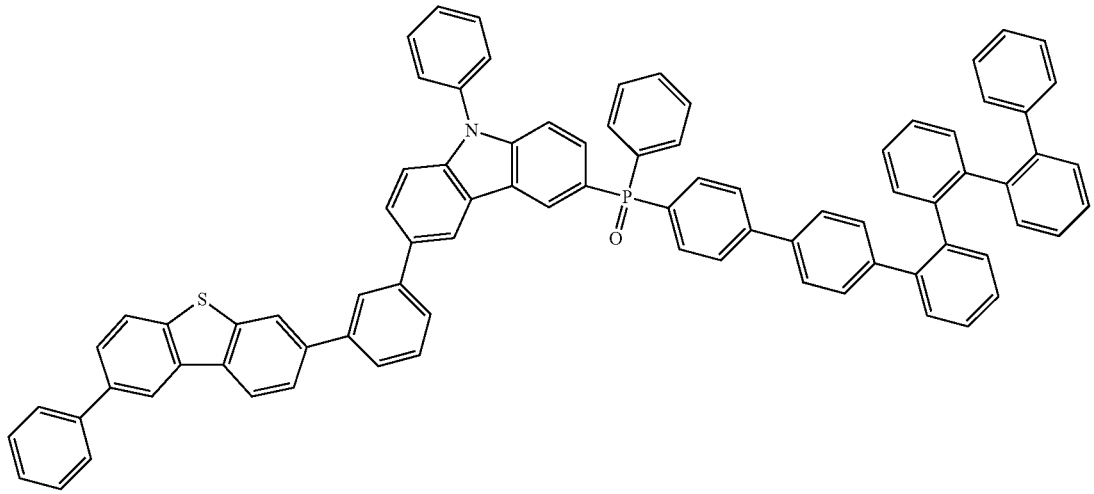

7-2-2
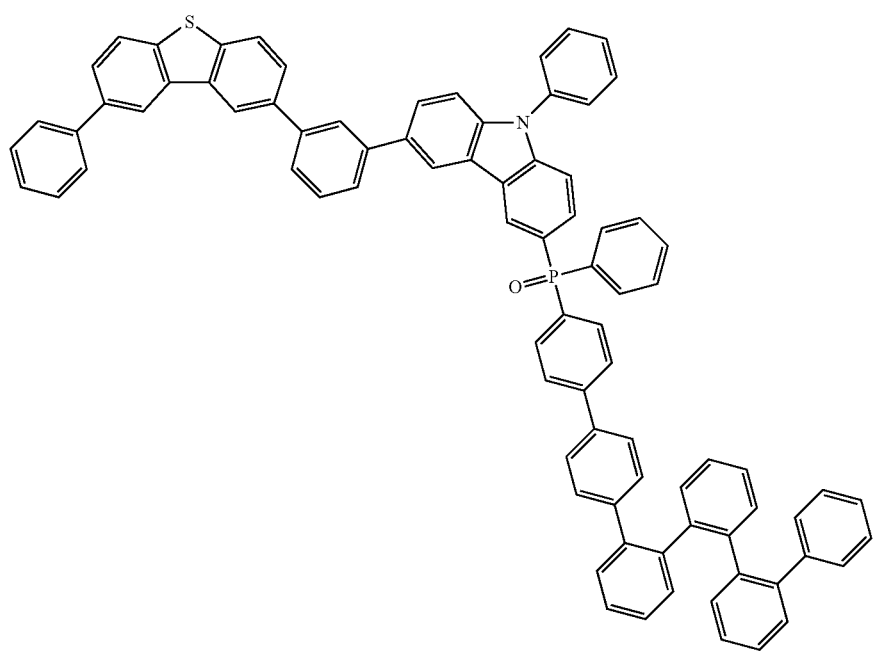
7-2-3
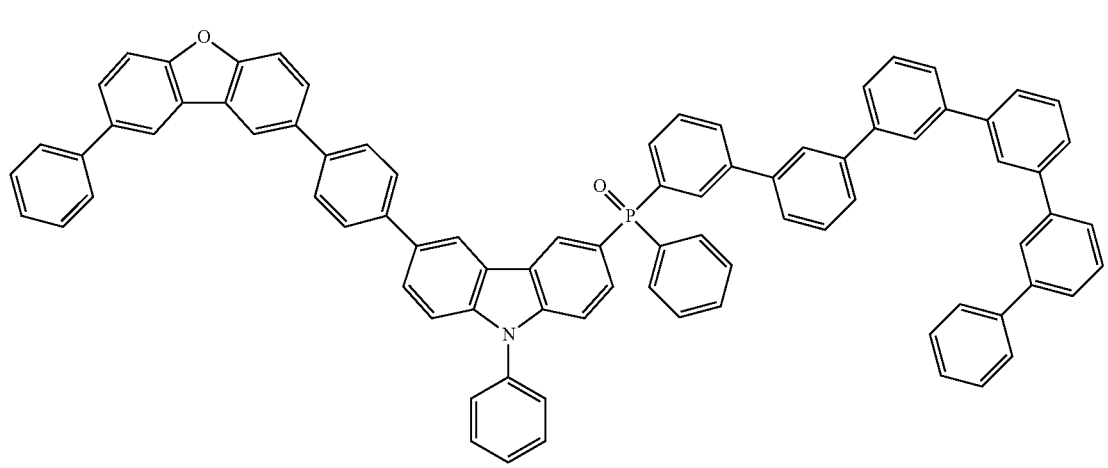
[Formula 141]
7-2-4
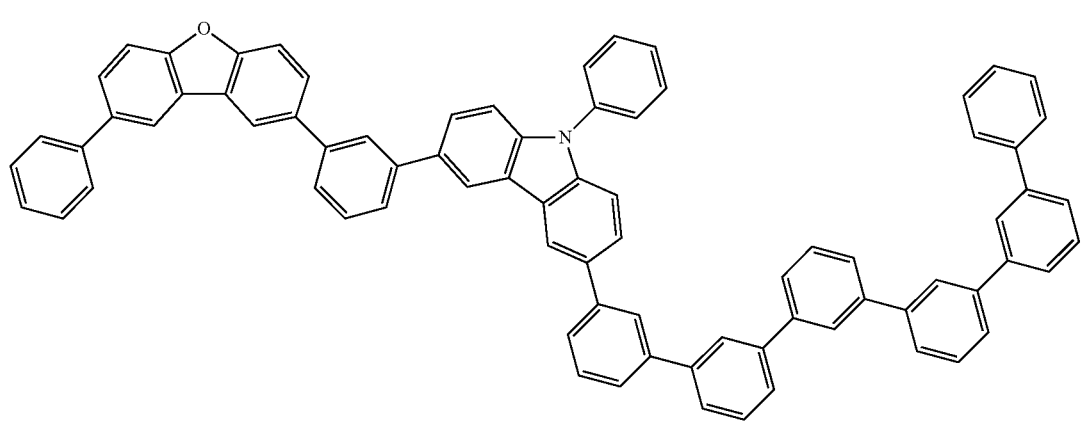

7-2-5
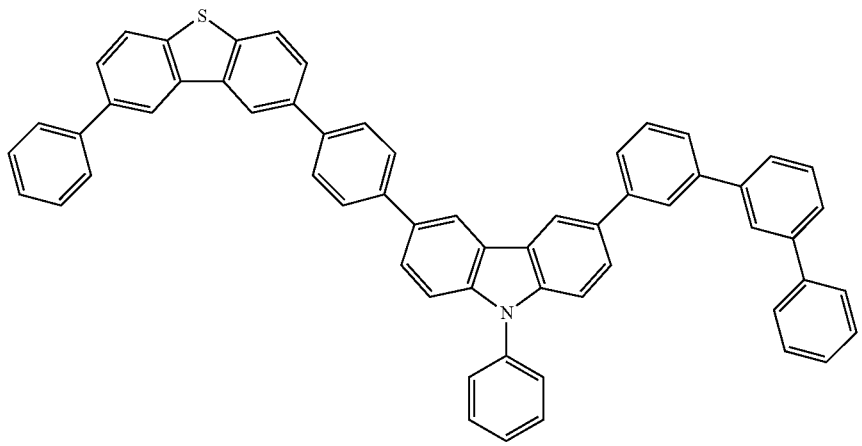
7-2-6
7-2-7
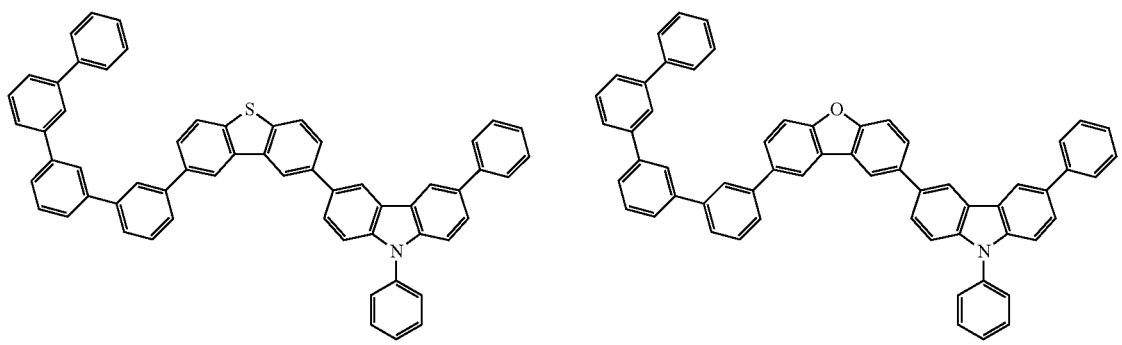
[Formula 142]
7-3-5
7-3-6
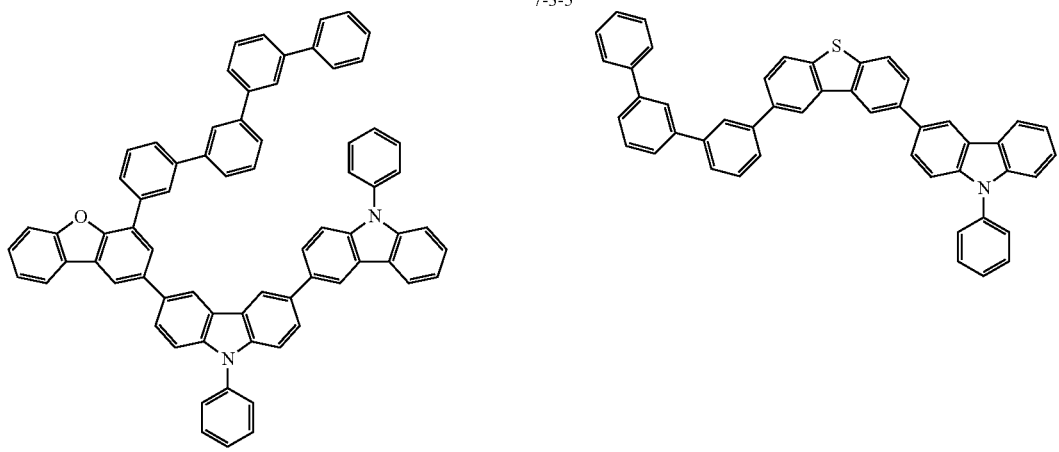

7-3-7
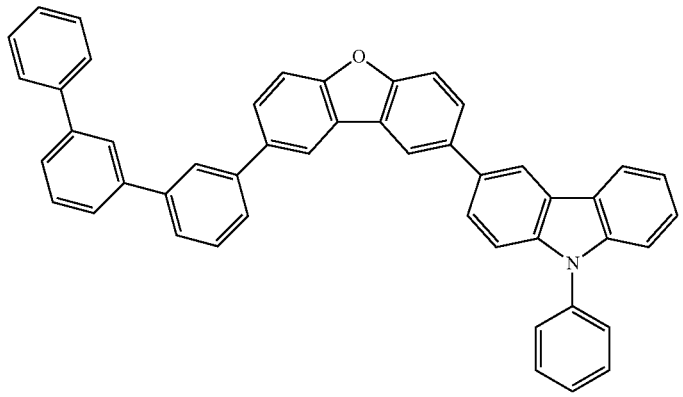
[Formula 143]
7-4-5
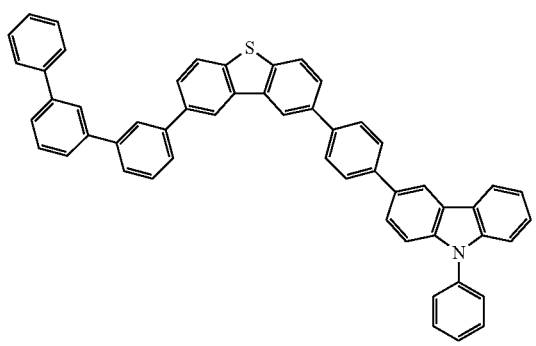
7-4-6
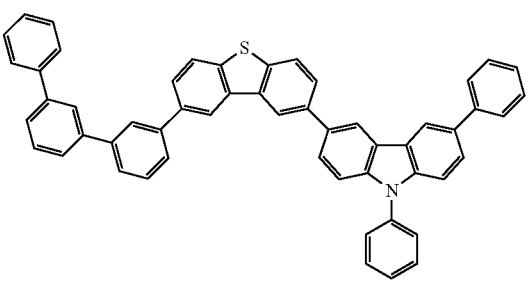
7-4-7
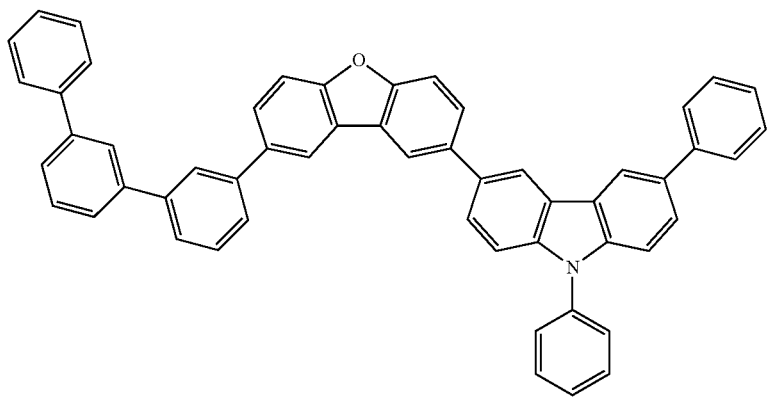
[Formula 144]
comparative-1
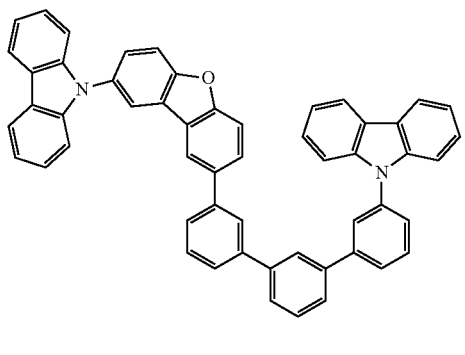
comparative-2
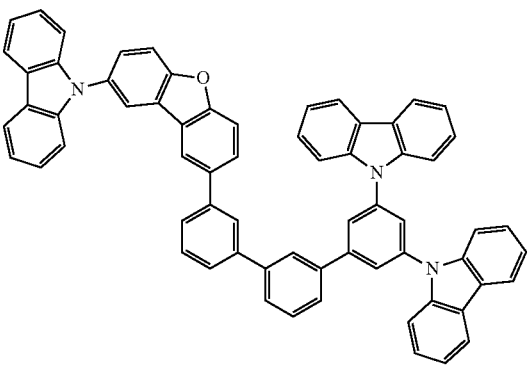

263 264
-continued
comparative-3
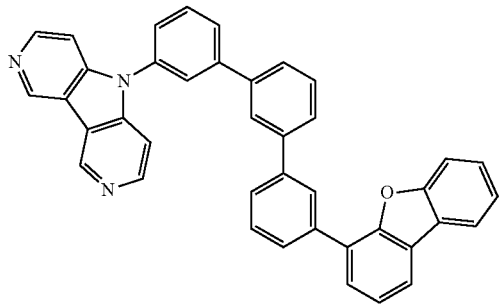
comparative-4
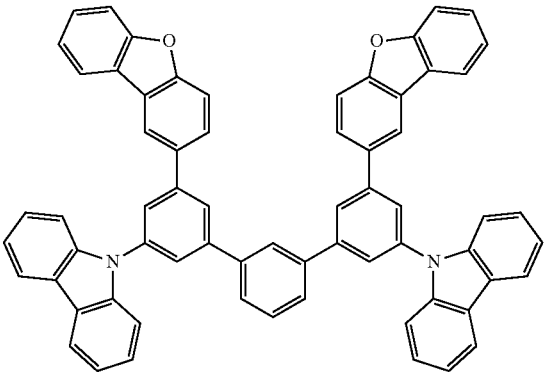
[Formula 145]
comparative-5
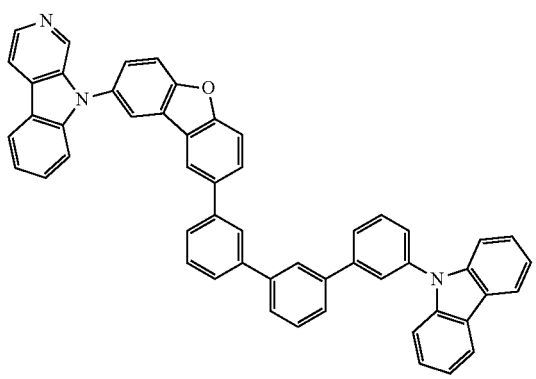
comparative-6
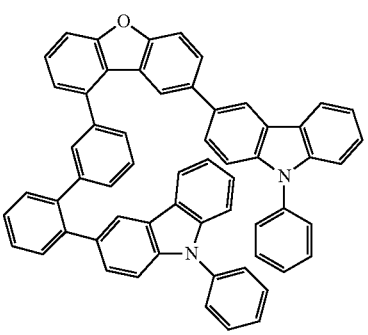
HTM
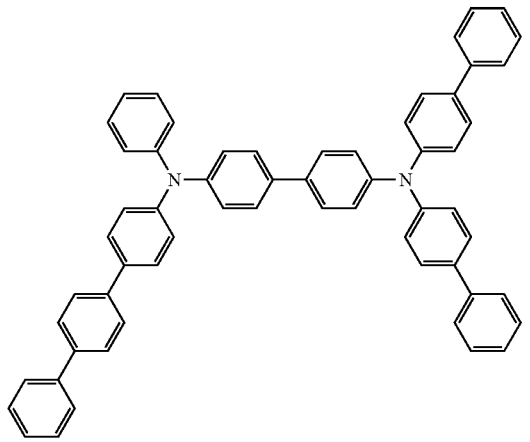
ETM-1
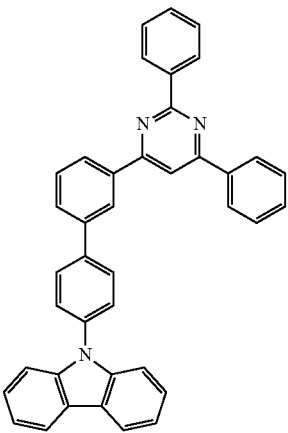
DPM-1
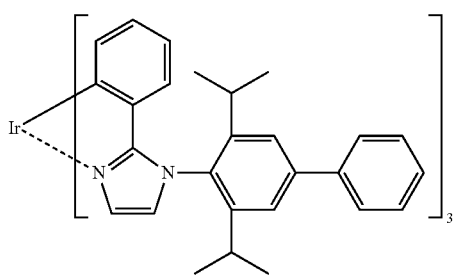
DPM-2
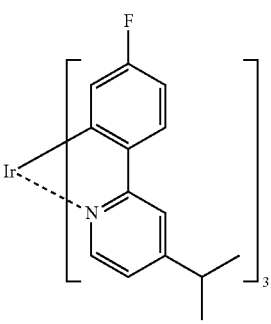

Comparative-1 indicates Compound No. 26 disclosed in U.S. Pat. No. 8,114,530.

Comparative-2 indicates Compound No. 28 disclosed in U.S. Pat. No. 8,114,530.

Comparative-3 indicates Compound No. 81 disclosed in WO2009/008099.

Comparative-4 indicates Compound No. 91 disclosed in WO2009/008099.

Comparative-5 indicates Compound No. 27 disclosed in WO2009/008100.

Comparative-6 indicates Compound 1-325 disclosed in Japanese Patent Application Laid-Open No. 2012-49518.

HTM indicates a compound disclosed in U.S. Pat. No. 8,114,530.

ETM-1 indicates a compound disclosed in U.S. Pat. No. 8,114,530.

DPM-2 indicates Compound K-21 disclosed in U.S. Pat. No. 8,114,530.

Example 1

Preparation of Organic EL Element 1-1

Indium tin oxide (ITO) was applied onto a glass substrate measuring 100 mm×100 mm×1.1 mm (NA45, available from NH Techno Glass Corporation) to form a film having a thickness of 100 nm. The film was patterned to prepare an anode. The transparent support substrate including the ITO transparent electrode was ultrasonically cleaned with isopropyl alcohol, was dried with dry nitrogen gas, and was cleaned with UV ozone for 5 minutes.

The transparent support substrate was fixed to a substrate holder of a commercially available vacuum deposition apparatus. A hole injecting material HT-30 (HT) (200 mg), a hole transporting material HTM (200 mg), a host material Comparative-4 (200 mg), a dopant DPM-2 (200 mg), a first electron transporting material (ETL) ETM-1 (200 mg), and a second electron transporting material ET-7 (200 mg) were placed in respective molybdenum resistive heating boats. These molybdenum resistive heating boats were placed in the vacuum deposition apparatus.

After a vacuum vessel was evacuated to $4\times10^{-4}$ Pa, the heating boat containing the hole injecting material HT-30 was electrically heated to deposit HT-30 on the transparent support substrate at a deposition rate of 0.1 nm/sec. A hole injecting layer having a thickness of 10 nm was prepared.

The heating boat containing the hole transporting material HTM was electrically heated to deposit HTM at a deposition rate of 0.1 nm/sec on the hole injecting layer. A hole transporting layer having a thickness of 30 nm was prepared.

The heating boat containing Comparative-4 and the heating boat containing DPM-2 were electrically heated to codeposit the materials on the hole transporting layer at deposition rates of 0.1 nm/sec and 0.010 nm/sec, respectively. A luminous layer having a thickness of 40 nm was prepared.

The heating boat containing the first electron transporting material ETM-1 was electrically heated to deposit ETM-1 on the luminous layer at a deposition rate of 0.1 nm/sec. A first electron transporting layer having a thickness of 10 nm was prepared.

The heating boat containing the second electron transporting material ET-7 was electrically heated to deposit on the first electron transporting layer at a deposition rate of 0.1 nm/sec. A second electron transporting layer having a thickness of 30 nm was prepared.

Lithium fluoride was then deposited to prepare an electron injecting layer (cathode buffer layer) having a thickness of 0.5 nm, and aluminum was deposited to prepare a cathode having a thickness of 110 nm. Organic EL element 1-1 was prepared.

<<Preparation of Organic EL Elements 1-2 to 1-16>>

Organic EL elements 1-2 to 1-16 were prepared as in Organic EL element 1-1 except that the dopant, the host material, and the first electron transporting material were varied as shown in Table 1.

<<Evaluation of Organic EL Elements 1-1 to 1-16>>

Organic EL elements 1-1 to 1-16 were evaluated. Each organic EL element was disposed on a glass sealing substrate having a thickness of 300 μm. An epoxy photocurable adhesive (Laxtrack LC0629B, available from TOAGOSEI CO., LTD.) was applied around the organic EL element, and a glass case was disposed over the cathode to cover the non-emission surface of the organic EL element. The glass cover was bonded to the glass sealing substrate, and the glass sealing substrate was irradiated with UV light to prepare an illumination device for evaluation illustrated in FIGS. 5 and 6.

These samples were evaluated by the following items. The results are shown in Table 1.

(1) External Extraction Quantum Efficiency

The organic EL element was lit at room temperature (25° C.) and a constant current of 2.5 mA/cm². The luminance (L) [cd/m²] of the emitted light immediately after the lighting was measured, and external extraction quantum efficiency (η) (also simply referred to as efficiency) was calculated.

The luminance was measured with a luminance meter CS-1000 (available form Konica Minolta Sensing, Inc.). The external extraction quantum efficiency of each organic EL element was expressed as a relative value to the external extraction quantum efficiency, 100, of Organic EL element 1-1.

(2) Half-Life

The half-life was evaluated according to the following procedure. Each organic EL element was driven at a constant current that achieved an initial luminance of 1000 cd/m², and the time until the initial luminance reduced to a half thereof (500 cd/m²). The time was defined as the half-life. The half-life of the organic EL element was expressed as a relative value to the half-life, 100, of Organic EL element 1-1.

(3) Driving Voltage

Each organic EL element was driven at room temperature (25° C.) and a constant current of 2.5 mA/cm², and the driving voltage was measured. The voltage was expressed as a relative value to the voltage, 100, of Organic EL element 1-1.

Voltage={(driving voltage of element)/(driving voltage of Organic EL element 1-1)}×100

A smaller value indicates a lower driving voltage.

(4) Increase in Driving Voltage

Each organic EL element was driven at room temperature (25° C.) and a constant current of 2.5 mA/cm², and the driving voltage was measured. The increase in driving voltage was calculated using the following expression. The results of calculation are shown in Table 1.

The increase in driving voltage was expressed as a relative value to that, 100, of Organic EL element 1-1.

Increase in driving voltage (relative value)=(driving voltage at half-life of luminance)−(initial driving voltage)

A smaller value indicates a smaller increase in driving voltage.

(5) Long-Term Stability

Each organic EL element was stored at 60° C. and 70% RH for one month, and the electrical efficiencies before and after the storage were determined. The long-term stability was determined as the ratio of electrical efficiencies before and after the storage from the following expression:

Long-term stability (%)={(electrical efficiency after storage)/(electrical efficiency before storage)}× 100

The electrical efficiency at a front luminance of 1000 cd/m$^2$ was determined from the front luminance and the luminance angle dependency of the organic EL element, which were measured with a spectroradiometric luminance meter CS-1000 (available from Konica Minolta Sensing, Inc.).

(6) Conclusion

Table 1 evidently shows that the organic EL elements prepared with the materials for organic EL elements according to the present invention represented in Formula (1) have higher luminescence efficiencies, prolonged emission lifetimes, lower driving voltages, and smaller increases in driving voltage compared to the organic EL elements in Comparative Examples. Table 1 also shows that the organic EL elements prepared with the materials for organic EL elements according to the present invention represented in Formula (1) have higher long-term stability. Table 1 further shows that addition of the materials for organic EL elements represented in Formula (1) to both the luminous layer and the first electron transporting layer significantly enhances the performance of the organic EL elements.

Example 2

Preparation of Organic EL Elements 2-1 to 2-19

Organic EL elements 2-1 to 2-19 were prepared as in Organic EL element 1-1 except that the hole transporting

TABLE 1

| ELEMENT NUMBER | HOST MATERIAL | DOPANT | FIRST ELECTRON TRANSPORTING MATERIAL | EXTERNAL EXTRACTION QUANTUM EFFICIENCY | HALF-LIFE |
| --- | --- | --- | --- | --- | --- |
| 1-1 | GOMPARATIVE-4 | DPM-2 | ETM-1 | 100 | 100 |
| 1-2 | COMPARATIVE-5 | DPM-2 | ETM-1 | 101 | 105 |
| 1-3 | COMPARATIVE-6 | DPM-2 | ETM-1 | 100 | 105 |
| 1-4 | 3-1-1 | DPM-2 | ETM-1 | 103 | 115 |
| 1-5 | 3-2-1 | DPM-2 | ETM-1 | 104 | 130 |
| 1-6 | 3-3-1 | DPM-2 | ETM-1 | 110 | 165 |
| 1-7 | 3-4-1 | DPM-2 | ETM-1 | 111 | 200 |
| 1-8 | 3-5-1 | DPM-2 | ETM-1 | 116 | 230 |
| 1-9 | 3-6-1 | DPM-2 | ETM-1 | 118 | 260 |
| 1-20 | 3-7-3 | DPM-3 | ETM-1 | 121 | 300 |
| 1-10 | 3-7-1 | DPM-2 | ETM-1 | 121 | 290 |
| 1-17 | 3-7-1 | DP-50 | ETM-1 | 123 | 300 |
| 1-18 | 3-7-1 | DP-41 | ETM-1 | 122 | 320 |
| 1-11 | COMPARATIVE-5 | DPM-2 | 3-6-1 | 104 | 115 |
| 1-12 | COMPARATIVE-5 | DPM-2 | 3-7-1 | 105 | 130 |
| 1-19 | COMPARATIVE-5 | DP-50 | 3-6-1 | 105 | 120 |
| 1-13 | 3-7-1 | DPM-2 | 3-6-1 | 121 | 340 |
| 1-14 | 3-7-1 | DPM-2 | 3-7-1 | 121 | 350 |
| 1-15 | 3-6-1 | DP-50 | 3-6-1 | 117 | 290 |
| 1-16 | 3-7-1 | DP-41 | 3-7-1 | 123 | 360 |

| ELEMENT NUMBER | DRIVING VOLTAGE | INCREASE IN DRIVING VOLTAGE | LONG-TERM STABILITY | NOTE |
| --- | --- | --- | --- | --- |
| 1-1 | 100 | 100 | 60 | COMPARATIVE EXAMPLE |
| 1-2 | 99 | 99 | 62 | COMPARATIVE EXAMPLE |
| 1-3 | 97 | 97 | 61 | COMPARATIVE EXAMPLE |
| 1-4 | 95 | 96 | 65 | INVENTIVE EXAMPLE |
| 1-5 | 93 | 94 | 65 | INVENTIVE EXAMPLE |
| 1-6 | 87 | 92 | 70 | INVENTIVE EXAMPLE |
| 1-7 | 89 | 88 | 71 | INVENTIVE EXAMPLE |
| 1-8 | 85 | 85 | 75 | INVENTIVE EXAMPLE |
| 1-9 | 85 | 84 | 75 | INVENTIVE EXAMPLE |
| 1-20 | 83 | 84 | 78 | INVENTIVE EXAMPLE |
| 1-10 | 84 | 82 | 77 | INVENTIVE EXAMPLE |
| 1-17 | 82 | 79 | 80 | INVENTIVE EXAMPLE |
| 1-18 | 80 | 80 | 78 | INVENTIVE EXAMPLE |
| 1-11 | 95 | 96 | 65 | INVENTIVE EXAMPLE |
| 1-12 | 93 | 94 | 66 | INVENTIVE EXAMPLE |
| 1-19 | 92 | 94 | 67 | INVENTIVE EXAMPLE |
| 1-13 | 80 | 81 | 78 | INVENTIVE EXAMPLE |
| 1-14 | 79 | 79 | 81 | INVENTIVE EXAMPLE |
| 1-15 | 81 | 79 | 76 | INVENTIVE EXAMPLE |
| 1-16 | 77 | 78 | 76 | INVENTIVE EXAMPLE | material HT-2 was used, and the host material, the dopant, and the first electron transporting material were varied as shown in Table 2.

<<Evaluation of Organic EL Elements 2-1 to 2-19>>

Organic EL elements 2-1 to 2-19 were evaluated. Each organic EL element was sealed as in Organic EL elements 1-1 to 1-16 in Example 1 to prepare an illumination device for evaluation illustrated in FIGS. 5 and 6.

Each sample was evaluated as in Example 1 for the external extraction quantum efficiency, the half-life, the driving voltage, the increase in driving voltage, and the long-term stability. The results are shown in Table 2. In Table 2, the results of the external extraction quantum efficiency, the half-life, the driving voltage, and the increase in driving voltage were expressed as relative values to the respective values, 100, of Organic EL element 2-1.

elements according to the present invention represented in Formula (1) have higher long-term stability. Table 2 further shows that addition of the materials for organic EL elements represented in Formula (1) to both the luminous layer and the first electron transporting layer significantly enhances the performance of the organic EL elements.

Example 3

Preparation of Organic EL Element 3-1

Indium oxide tin (ITO) was applied onto a glass substrate with dimensions of 100 mm×100 mm×1.1 mm (NA-45, available from AvanStrate Inc.) to form a film having a thickness of 100 nm. The film was patterned to prepare an anode. The transparent support substrate including the ITO

TABLE 2

| ELEMENT NUMBER | HOST MATERIAL | DOPANT | FIRST ELECTRON TRANSPORTING MATERIAL | EXTERNAL EXTRACTION QUANTUM EFFICIENCY | HALF-LIFE |
|---|---|---|---|---|---|
| 2-1 | COMPARATIVE-1 | DPM-1 | ETM-1 | 100 | 100 |
| 2-2 | COMPARATIVE-2 | DPM-1 | ETM-1 | 102 | 97 |
| 2-3 | COMPARATIVE-3 | DPM-1 | ETM-1 | 95 | 90 |
| 2-4 | 4-1-1 | DPM-1 | ETM-1 | 104 | 120 |
| 2-5 | 4-2-1 | DPM-1 | ETM-1 | 105 | 140 |
| 2-6 | 4-3-1 | DPM-1 | ETM-1 | 109 | 190 |
| 2-7 | 4-4-1 | DPM-1 | ETM-1 | 112 | 230 |
| 2-8 | 4-5-1 | DPM-1 | ETM-1 | 115 | 250 |
| 2-9 | 4-6-1 | DPM-1 | ETM-1 | 120 | 280 |
| 2-10 | 4-7-1 | DPM-1 | ETM-1 | 123 | 310 |
| 2-17 | 4-7-1 | DP-33 | ETM-1 | 118 | 280 |
| 2-18 | 4-7-1 | DP-31 | ETM-1 | 121 | 330 |
| 2-11 | COMPARATIVE-2 | DPM-1 | 4-6-1 | 104 | 118 |
| 2-12 | COMPARATIVE-2 | DPM-1 | 4-7-1 | 107 | 135 |
| 2-13 | 4-7-1 | DPM-1 | 4-6-1 | 124 | 325 |
| 2-14 | 4-7-1 | DPM-1 | 4-7-1 | 123 | 330 |
| 2-15 | 4-6-1 | DP-31 | 4-6-1 | 121 | 310 |
| 2-16 | 4-7-1 | DP-33 | 4-7-1 | 120 | 330 |
| 2-19 | COMPARATIVE-2 | DP-31 | 4-6-1 | 102 | 110 |

| ELEMENT NUMBER | DRIVING VOLTAGE | INCREASE IN DRIVING VOLTAGE | LONG-TERM STABILITY | NOTE |
|---|---|---|---|---|
| 2-1 | 100 | 100 | 56 | COMPARATIVE EXAMPLE |
| 2-2 | 98 | 99 | 59 | COMPARATIVE EXAMPLE |
| 2-3 | 96 | 96 | 53 | COMPARATIVE EXAMPLE |
| 2-4 | 94 | 94 | 62 | INVENTIVE EXAMPLE |
| 2-5 | 93 | 94 | 63 | INVENTIVE EXAMPLE |
| 2-6 | 88 | 90 | 67 | INVENTIVE EXAMPLE |
| 2-7 | 86 | 86 | 69 | INVENTIVE EXAMPLE |
| 2-8 | 84 | 84 | 71 | INVENTIVE EXAMPLE |
| 2-9 | 83 | 80 | 72 | INVENTIVE EXAMPLE |
| 2-10 | 81 | 79 | 75 | INVENTIVE EXAMPLE |
| 2-17 | 82 | 78 | 76 | INVENTIVE EXAMPLE |
| 2-18 | 80 | 80 | 74 | INVENTIVE EXAMPLE |
| 2-11 | 93 | 93 | 65 | INVENTIVE EXAMPLE |
| 2-12 | 90 | 93 | 66 | INVENTIVE EXAMPLE |
| 2-13 | 80 | 78 | 78 | INVENTIVE EXAMPLE |
| 2-14 | 79 | 77 | 80 | INVENTIVE EXAMPLE |
| 2-15 | 81 | 79 | 76 | INVENTIVE EXAMPLE |
| 2-16 | 79 | 76 | 82 | INVENTIVE EXAMPLE |
| 2-19 | 90 | 79 | 63 | INVENTIVE EXAMPLE |

Table 2 evidently shows that the organic EL elements prepared with the materials for organic EL elements according to the present invention represented in Formula (1) have higher luminescence efficiencies, prolonged emission lifetimes, lower driving voltages, and smaller increases in driving voltage compared to the organic EL elements in Comparative Examples. Table 2 also shows that the organic EL elements prepared with the materials for organic EL transparent electrode was ultrasonically cleaned with isopropyl alcohol, was dried with dry nitrogen gas, and was cleaned with UV ozone for 5 minutes.

A diluted solution of 70% poly(3,4-ethylenedioxythiophene)-polystyrene sulfonate (PEDOT/PSS, available from Bayer AG, Baytron P Al4083) in pure water was prepared, and was applied onto the transparent support substrate by spin coating to form a thin film. The substrate was dried at 200° C. for one hour to form a first hole transporting layer having a thickness of 30 nm.

The substrate was placed under a nitrogen atmosphere. A solution of poly(N,N'-bis(4-butyl phenyl)-N,N'-bis(phenyl)) benzidine (ADS-254, available from American Dye Source, Inc.) (50 mg) in toluene (10 ml) was applied onto the first hole transporting layer by spin coating at 2500 rpm for 30 seconds to form a thin film. The substrate was vacuum dried at 60° C. for one hour to form a second hole transporting layer.

A solution of Comparative-6 (100 mg) as a host material and DP-43 (10 mg) as a dopant in butyl acetate (10 ml) was applied onto the second hole transporting layer by spin coating at 2000 rpm for 30 seconds to form a thin film. The substrate was vacuum dried at 60° C. for one hour to prepare a luminous layer having a thickness of about 35 nm.

The substrate was fixed to a substrate holder of a vacuum deposition apparatus. A first electron transporting material ET-42 (200 mg) was placed in a molybdenum resistive heating boat, and a second electron transporting material ET-7 (200 mg) was placed in another molybdenum resistive heating boat. These heating boats were placed in the vacuum deposition apparatus.

After a vacuum vessel was evacuated to $4\times10^{-4}$ Pa, the heating boat containing the first electron transporting material ET-42 was electrically heated to deposit ET-42 onto the luminous layer at a deposition rate of 0.1 nm/sec. A first electron transporting layer having a thickness of 10 nm was prepared.

The heating boat containing the second electron transporting material ET-7 was then electrically heated to deposit ET-7 onto the first electron transporting layer at a deposition rate of 0.1 nm/sec. A second electron transporting layer having a thickness of 30 nm was prepared.

Lithium fluoride was then deposited to prepare an electron injecting layer (cathode buffer layer) having a thickness of 0.5 nm, and aluminum was deposited to prepare a cathode having a thickness of 110 nm. Organic EL element 3-1 was prepared.

<<Preparation of Organic EL Elements 3-2 to 3-19>>

Organic EL elements 3-2 to 3-19 were prepared as in Organic EL element 3-1 except that the dopant, the host material, and the first electron transporting material were varied as shown in Table 3.

<<Evaluation of Organic EL Elements 3-1 to 3-19>>

Organic EL elements 3-1 to 3-19 were evaluated. Each organic EL element was sealed as in Organic EL elements 1-1 to 1-16 in Example 1 to prepare an illumination device for evaluation illustrated in FIGS. 5 and 6.

These samples were evaluated as in Example 1 for the external extraction quantum efficiency, the half-life, the driving voltage, the increase in driving voltage, and the long-term stability. The results are shown in Table 3. In Table 3, the values of the external extraction quantum efficiency, the half-life, the driving voltage, and the increase in driving voltage were expressed as relative values to the respective values, 100, of Organic EL element 3-1.

TABLE 3

| ELEMENT NUMBER | HOST MATERIAL | DOPANT | FIRST ELECTRON TRANSPORTING MATERIAL | EXTERNAL EXTRACTION QUANTUM EFFICIENCY | HALF-LIFE |
|---|---|---|---|---|---|
| 3-1 | COMPARATIVE-6 | DP-43 | ET-42 | 100 | 100 |
| 3-2 | COMPARATIVE-1 | DP-43 | ET-42 | 100 | 90 |
| 3-3 | COMPARATIVE-3 | DP-43 | ET-42 | 100 | 95 |
| 3-4 | 3-1-2 | DP-43 | ET-42 | 102 | 135 |
| 3-5 | 3-2-2 | DP-43 | ET-42 | 102 | 125 |
| 3-6 | 3-3-2 | DP-43 | ET-42 | 105 | 180 |
| 3-7 | 3-4-2 | DP-43 | ET-42 | 105 | 190 |
| 3-8 | 3-5-2 | DP-43 | ET-42 | 108 | 255 |
| 3-9 | 3-6-2 | DP-43 | ET-42 | 108 | 255 |
| 3-10 | 3-7-2 | DP-43 | ET-42 | 109 | 255 |
| 3-17 | 3-7-2 | DP-47 | ET-42 | 107 | 235 |
| 3-18 | 3-7-2 | DP-28 | ET-42 | 113 | 305 |
| 3-11 | COMPARATIVE-6 | DP-43 | 3-6-2 | 104 | 190 |
| 3-12 | COMPARATIVE-6 | DP-43 | 3-7-2 | 106 | 185 |
| 3-13 | 3-6-2 | DP-43 | 3-7-2 | 112 | 270 |
| 3-14 | 3-7-2 | DP-43 | 3-7-2 | 113 | 275 |
| 3-15 | 3-6-2 | DP-43 | 3-6-2 | 110 | 265 |
| 3-16 | 3-7-2 | DP-28 | 3-7-2 | 117 | 320 |
| 3-19 | COMPARATIVE-6 | DP-28 | 3-7-2 | 109 | 210 |

| ELEMENT NUMBER | DRIVING VOLTAGE | INCREASE IN DRIVING VOLTAGE | LONG-TERM STABILITY | NOTE |
|---|---|---|---|---|
| 3-1 | 100 | 100 | 55 | COMPARATIVE EXAMPLE |
| 3-2 | 101 | 102 | 53 | COMPARATIVE EXAMPLE |
| 3-3 | 101 | 97 | 53 | COMPARATIVE EXAMPLE |
| 3-4 | 97 | 92 | 58 | INVENTIVE EXAMPLE |
| 3-5 | 97 | 89 | 58 | INVENTIVE EXAMPLE |
| 3-6 | 94 | 82 | 67 | INVENTIVE EXAMPLE |
| 3-7 | 94 | 81 | 69 | INVENTIVE EXAMPLE |
| 3-8 | 90 | 72 | 76 | INVENTIVE EXAMPLE |
| 3-9 | 89 | 72 | 77 | INVENTIVE EXAMPLE |
| 3-10 | 89 | 71 | 75 | INVENTIVE EXAMPLE |
| 3-17 | 91 | 72 | 78 | INVENTIVE EXAMPLE |
| 3-18 | 90 | 71 | 76 | INVENTIVE EXAMPLE |
| 3-11 | 95 | 81 | 68 | INVENTIVE EXAMPLE |
| 3-12 | 94 | 80 | 68 | INVENTIVE EXAMPLE |

TABLE 3-continued

| | | | | |
|---|---|---|---|---|
| 3-13 | 86 | 67 | 82 | INVENTIVE EXAMPLE |
| 3-14 | 85 | 66 | 80 | INVENTIVE EXAMPLE |
| 3-15 | 87 | 69 | 80 | INVENTIVE EXAMPLE |
| 3-16 | 84 | 65 | 82 | INVENTIVE EXAMPLE |
| 3-19 | 95 | 80 | 69 | INVENTIVE EXAMPLE |

Table 3 evidently shows that the organic EL elements prepared with the materials for organic EL elements according to the present invention represented in Formula (1) have higher luminescence efficiency, prolonged emission lifetimes, lower driving voltages, and smaller increases in driving voltage compared to the organic EL elements in Comparative Examples. Table 3 also shows that the organic EL elements prepared with the materials for organic EL elements according to the present invention represented in Formula (1) have higher long-term stability. Table 3 further shows that the materials for organic EL elements represented in Formula (1) are also suitable for preparation of the organic EL elements by wet processes.

Example 4

Preparation of Organic EL Elements 4-1 to 4-16

Organic EL elements 4-1 to 4-16 were prepared as in Organic EL element 3-1 except that the host material, the dopant, and the first electron transporting material were varied as shown in Table 4.

<<Evaluation of Organic EL Elements 4-1 to 4-16>>

Organic EL elements 4-1 to 4-16 were evaluated. Organic EL elements were sealed as in Organic EL elements 1-1 to 1-16 in Example 1 to prepare illumination devices for evaluation illustrated in FIGS. 5 and 6.

These samples were evaluated as in Example 1 for the external extraction quantum efficiency, the half-life, the driving voltage, the increase in driving voltage, and the long-term stability. The results are shown in Table 4. In Table 4, the values of the external extraction quantum efficiency, the half-life, the driving voltage, and the increase in driving voltage were expressed as relative values to the respective values, 100, of Organic EL element 4-1.

TABLE 4

| ELEMENT NUMBER | HOST MATERIAL | DOPANT | FIRST ELECTRON TRANSPORTING MATERIAL | EXTERNAL EXTRACTION QUANTUM EFFICIENCY | HALF-LIFE |
|---|---|---|---|---|---|
| 4-1 | COMPARATIVE-5 | DPM-2 | ET-42 | 100 | 100 |
| 4-2 | COMPARATIVE-4 | DPM-2 | ET-42 | 101 | 105 |
| 4-3 | COMPARATIVE-2 | DPM-2 | ET-42 | 103 | 110 |
| 4-4 | 4-1-2 | DPM-2 | ET-42 | 104 | 140 |
| 4-5 | 4-2-2 | DPM-2 | ET-42 | 105 | 130 |
| 4-6 | 4-3-2 | DPM-2 | ET-42 | 105 | 210 |
| 4-7 | 4-4-2 | DPM-2 | ET-42 | 106 | 235 |
| 4-8 | 4-5-2 | DPM-2 | ET-42 | 107 | 275 |
| 4-9 | 4-6-2 | DPM-2 | ET-42 | 108 | 270 |
| 4-10 | 4-7-2 | DPM-2 | ET-42 | 109 | 280 |
| 4-17 | 4-7-2 | DP-24 | ET-42 | 114 | 310 |
| 4-18 | 4-7-2 | DP-21 | ET-42 | 116 | 335 |
| 4-11 | COMPARATIVE-4 | DPM-2 | 4-6-2 | 102 | 150 |
| 4-12 | COMPARATIVE-4 | DPM-2 | 4-7-2 | 104 | 160 |
| 4-19 | COMPARATIVE-4 | DP-24 | 4-7-2 | 107 | 175 |
| 4-13 | 4-6-2 | DPM-2 | 4-6-2 | 111 | 305 |
| 4-15 | 4-7-2 | DPM-2 | 4-6-2 | 112 | 315 |
| 4-14 | 4-7-2 | DPM-2 | 4-7-2 | 114 | 335 |
| 4-16 | 4-7-2 | DP-24 | 4-7-2 | 117 | 360 |

| ELEMENT NUMBER | DRIVING VOLTAGE | INCREASE IN DRIVING VOLTAGE | LONG-TERM STABILITY | NOTE |
|---|---|---|---|---|
| 4-1 | 100 | 100 | 58 | COMPARATIVE EXAMPLE |
| 4-2 | 105 | 101 | 60 | COMPARATIVE EXAMPLE |
| 4-3 | 102 | 98 | 62 | COMPARATIVE EXAMPLE |
| 4-4 | 97 | 94 | 66 | INVENTIVE EXAMPLE |
| 4-5 | 95 | 93 | 67 | INVENTIVE EXAMPLE |
| 4-6 | 93 | 90 | 71 | INVENTIVE EXAMPLE |
| 4-7 | 92 | 89 | 72 | INVENTIVE EXAMPLE |
| 4-8 | 90 | 86 | 77 | INVENTIVE EXAMPLE |
| 4-9 | 90 | 86 | 79 | INVENTIVE EXAMPLE |
| 4-10 | 89 | 85 | 80 | INVENTIVE EXAMPLE |
| 4-17 | 86 | 81 | 82 | INVENTIVE EXAMPLE |
| 4-18 | 88 | 83 | 83 | INVENTIVE EXAMPLE |
| 4-11 | 95 | 88 | 70 | INVENTIVE EXAMPLE |
| 4-12 | 93 | 85 | 71 | INVENTIVE EXAMPLE |
| 4-19 | 91 | 83 | 73 | INVENTIVE EXAMPLE |

TABLE 4-continued

| 4-13 | 88 | 83 | 82 | INVENTIVE EXAMPLE |
| 4-15 | 88 | 82 | 84 | INVENTIVE EXAMPLE |
| 4-14 | 87 | 80 | 85 | INVENTIVE EXAMPLE |
| 4-16 | 85 | 79 | 87 | INVENTIVE EXAMPLE |

Table 4 evidently shows that the organic EL elements prepared with the materials for organic EL elements according to the present invention represented in Formula (1) have higher luminescence efficiencies, prolonged emission lifetimes, lower driving voltages, and smaller increases in driving voltage compared to the organic EL elements in Comparative Examples. Table 4 also shows that the organic EL elements prepared with the materials for organic EL elements according to the present invention represented in Formula (1) have higher long-term stability. Table 4 further shows that the materials for organic EL elements represented in Formula (1) are also suitable for preparation of the organic EL elements by wet processes.

Example 5

Preparation of Organic EL Full-Color Display Device

FIG. 7 illustrates a schematic configuration of an organic EL full-color display device.

An ITO transparent electrode layer having a thickness of 100 nm was disposed on a glass substrate 201 (NA45, available from NH Techno Glass Corporation), and was patterned at a pitch of 100 μm (see FIG. 7A) to prepare ITO transparent electrodes 202 as anodes. Partitions 203 composed of non-photosensitive polyimide (width: 20 μm, thickness: 2.0 μm) were deposited by photolithography between the ITO transparent electrodes 202 on the glass substrate 201 (see FIG. 7B).

The following hole injecting layer composition was injected into spaces defined by the ITO electrodes 202 and the partitions 203 with an inkjet head (MJ800C, available from Seiko Epson Corp.). The composition was irradiated with ultraviolet light for 200 seconds, and was dried at 60° C. for 10 minutes to prepare a hole injecting layer 204 having a thickness of 40 nm (see FIG. 7C).

Figure 7A:
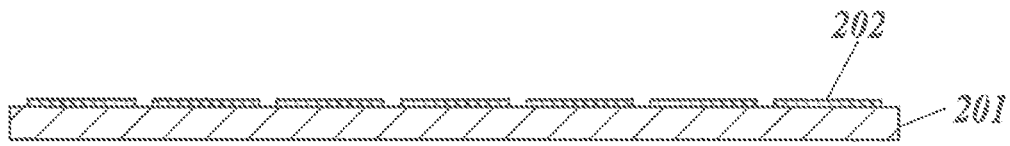
FIG. 7A is a schematic configurational view illustrating an organic EL full-color display device.
Figure 7B:
FIG. 7B is a schematic configurational view illustrating an organic EL full-color display device.
Figure 7C:
FIG. 7C is a schematic configurational view illustrating an organic EL full-color display device.
Figure 7D:
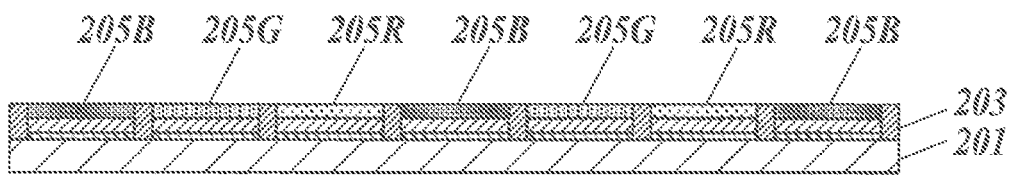
FIG. 7D is a schematic configurational view illustrating an organic EL full-color display device.
Figure 7E:
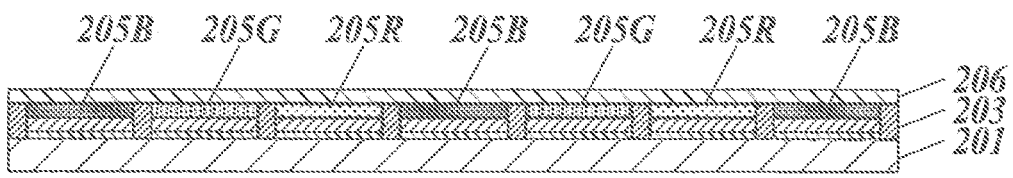
FIG. 7E is a schematic configurational view illustrating an organic EL full-color display device.

The following compositions for blue, green, and red luminous layers were individually ejected onto the hole injecting layer 204 through an inkjet head as described above, and were dried at 60° C. for 10 minutes to prepare luminous layers 205B, 205G, 205R of the respective colors (see FIG. 7D).
(Composition for Hole Injecting Layer)
  HT-44: 20 parts by mass
  Cyclohexylbenzene: 50 parts by mass
  Isopropylbiphenyl: 50 parts by mass
(Composition for Blue Luminous Layer)
  Host material 4-7-2: 0.7 parts by mass
  DP-55: 0.04 parts by mass
  Cyclohexylbenzene: 50 parts by mass
  Isopropylbiphenyl: 50 parts by mass
(Composition for Green Luminous Layer)
  Host material 4-7-2: 0.7 parts by mass
  D-1: 0.04 parts by mass
  Cyclohexylbenzene: 50 parts by mass
  Isopropylbiphenyl: 50 parts by mass
(Composition for Red Luminous Layer)
  Host material 4-7-2: 0.7 parts by mass
  D-10: 0.04 parts by mass
  Cyclohexylbenzene: 50 parts by mass
  Isopropylbiphenyl: 50 parts by mass In the next step, an electron transporting material was deposited over the luminous layers 205B, 205G, and 205R to prepare an electron transporting layer having a thickness of 20 nm (not shown). Lithium fluoride was deposited to prepare an electron injecting layer having a thickness of 0.6 nm (not shown), and Al was deposited to prepare a cathode 206 having a thickness of 130 nm. An organic EL element was thereby prepared (see FIG. 7E).

The organic EL element emitted light beams of blue, green, and red when voltage was applied between the electrodes. It was verified that the organic EL element can be used as a full-color display device.

As described above, the present invention can provide an organic electroluminescent element, an illumination device, and a display device which have high luminescence efficiency, low driving voltage, a prolonged service life, a small increase in driving voltage, and high long-term stability.

An organic EL element having such advantageous effects can be prepared by a wet process.

Example 6

Preparation of Organic EL Elements 6-1 to 6-35

Organic EL elements 6-1 to 6-35 were prepared as in Organic EL element 1-1 except that a hole transporting material HT-2 was used, and the host material, the dopant, and the first electron transporting material were varied as shown in Table 5.

<<Evaluation of Organic EL Elements 6-1 to 6-35>>

Organic EL elements 6-1 to 6-35 were evaluated. Organic EL elements were sealed as in Organic EL elements 1-1 to 1-16 in Example 1 to prepare illumination devices for evaluation illustrated in FIGS. 5 and 6.

These samples were evaluated as in Example 1 for the external extraction quantum efficiency, the half-life, the driving voltage, the increase in driving voltage, and the long-term stability. The results are shown in Table 5. In Table 5, the results of the external extraction quantum efficiency, the half-life, the driving voltage, and the increase in driving voltage were expressed as relative values to the respective values, 100, of Organic EL element 6-1.

TABLE 5

| ELEMENT NUMBER | HOST MATERIAL | DOPANT | FIRST ELECTRON TRANSPORTING MATERIAL | *1 | HALF-LIFE | *2 | INCREASE IN DRIVING VOLTAGE | LONG-TERM STABILITY | NOTE |
|---|---|---|---|---|---|---|---|---|---|
| 6-1 | COMPARATIVE-5 | DP-21 | ET-41 | 100 | 100 | 100 | 100 | 50 | *3 |
| 6-2 | COMPARATIVE-4 | DP-21 | ET-41 | 102 | 95 | 100 | 98 | 51 | *3 |
| 6-3 | COMPARATIVE-2 | DP-21 | ET-41 | 101 | 100 | 98 | 100 | 51 | *3 |
| 6-4 | 6-1-1 | DP-21 | ET-41 | 103 | 165 | 96 | 95 | 55 | *4 |
| 6-5 | 6-2-1 | DP-21 | ET-41 | 104 | 170 | 95 | 97 | 55 | *4 |
| 6-6 | 6-1-2 | DP-21 | ET-41 | 103 | 155 | 95 | 98 | 54 | *4 |
| 6-7 | 6-2-2 | DP-21 | ET-41 | 104 | 175 | 97 | 95 | 56 | *4 |
| 6-8 | 6-1-3 | DP-21 | ET-41 | 105 | 215 | 92 | 90 | 60 | *4 |
| 6-9 | 6-2-3 | DP-21 | ET-41 | 107 | 225 | 91 | 90 | 58 | *4 |
| 6-10 | 6-1-4 | DP-21 | ET-41 | 106 | 230 | 92 | 91 | 62 | *4 |
| 6-11 | 6-2-4 | DP-21 | ET-41 | 105 | 210 | 93 | 89 | 63 | *4 |
| 6-12 | 6-1-5 | DP-21 | ET-41 | 108 | 265 | 88 | 85 | 65 | *4 |
| 6-13 | 6-2-5 | DP-21 | ET-41 | 109 | 280 | 88 | 87 | 64 | *4 |
| 6-14 | 6-3-5 | DP-21 | ET-41 | 110 | 270 | 89 | 84 | 67 | *4 |
| 6-15 | 6-4-5 | DP-21 | ET-41 | 108 | 255 | 87 | 86 | 68 | *4 |
| 6-16 | 6-1-6 | DP-21 | ET-41 | 111 | 295 | 84 | 80 | 70 | *4 |
| 6-17 | 6-2-6 | DP-21 | ET-41 | 109 | 300 | 85 | 81 | 69 | *4 |
| 6-18 | 6-3-6 | DP-21 | ET-41 | 110 | 285 | 84 | 82 | 68 | *4 |
| 6-19 | 6-4-6 | DP-21 | ET-41 | 112 | 310 | 83 | 79 | 71 | *4 |
| 6-20 | 6-1-7 | DP-21 | ET-41 | 114 | 315 | 80 | 75 | 75 | *4 |
| 6-21 | 6-2-7 | DP-21 | ET-41 | 115 | 320 | 81 | 70 | 74 | *4 |
| 6-22 | 6-3-7 | DP-21 | ET-41 | 115 | 325 | 80 | 71 | 76 | *4 |
| 6-23 | 6-4-7 | DP-21 | ET-41 | 114 | 320 | 82 | 72 | 78 | *4 |
| 6-24 | COMPARATIVE-4 | DP-21 | 6-1-7 | 105 | 215 | 90 | 85 | 74 | *4 |
| 6-25 | COMPARATIVE-4 | DP-21 | 6-2-7 | 106 | 205 | 91 | 84 | 71 | *4 |
| 6-26 | COMPARATIVE-4 | DP-21 | 6-3-7 | 107 | 220 | 89 | 84 | 75 | *4 |
| 6-27 | COMPARATIVE-4 | DP-21 | 6-4-7 | 106 | 230 | 88 | 83 | 77 | *4 |
| 6-28 | 6-1-6 | DP-21 | 6-1-6 | 114 | 315 | 80 | 75 | 75 | *4 |
| 6-29 | 6-2-6 | DP-21 | 6-2-6 | 115 | 325 | 81 | 74 | 79 | *4 |
| 6-30 | 6-3-6 | DP-21 | 6-3-6 | 116 | 325 | 82 | 71 | 77 | *4 |
| 6-31 | 6-4-6 | DP-21 | 6-4-6 | 115 | 335 | 80 | 72 | 75 | *4 |
| 6-32 | 6-1-7 | DP-21 | 6-1-7 | 118 | 360 | 81 | 65 | 80 | *4 |
| 6-33 | 6-2-7 | DP-21 | 6-2-7 | 119 | 375 | 80 | 68 | 82 | *4 |
| 6-34 | 6-3-7 | DP-21 | 6-3-7 | 118 | 370 | 79 | 69 | 81 | *4 |
| 6-35 | 6-4-7 | DP-21 | 6-4-7 | 120 | 380 | 79 | 65 | 84 | *4 |

*1: EXTERNAL EXTRACTION QUANTUM EFFICIENCY
*2: DRIVING VOLTAGE
*3: COMPARATIVE EXAMPLE
*4: INVENTIVE EXAMPLE

Table 5 evidently shows that the organic EL elements prepared with the materials for organic EL elements according to the present invention represented in Formula (1) have higher luminescence efficiencies, prolonged emission lifetimes, lower driving voltages, and smaller increases in driving voltage compared to the organic EL elements in Comparative Examples. Table 5 also shows that the organic EL elements prepared with the materials for organic EL elements according to the present invention represented in Formula (1) have higher long-term stability. Table 5 further shows that addition of the materials for organic EL elements represented in Formula (1) to both the luminous layer and the first electron transporting layer significantly enhances the performance of the organic EL element.

Example 7

Preparation of Organic EL Elements 7-1 to 7-35

Organic EL elements 7-1 to 7-35 were prepared as in Organic EL element 1-1 except that a hole transporting material HT-2 was used, and the host material, the dopant, and the first electron transporting material were varied as shown in Table 6.

<<Evaluation of Organic EL Elements 7-1 to 7-35>>

Organic EL elements 7-1 to 7-35 were evaluated. Organic EL elements were sealed as in Organic EL element 1-1 to 1-16 in Example 1 to prepare illumination devices for evaluation illustrated in FIGS. 5 and 6.

These samples were evaluated as in Example 1 for the external extraction quantum efficiency, the half-life, the driving voltage, the increase in driving voltage, and the long-term stability. The results are shown in Table 6. In Table 6, the results of the external extraction quantum efficiency, the half-life, the driving voltage, and the increase in driving voltage were expressed as relative values to the respective values, 100, of Organic EL element 7-1.

TABLE 6

| ELEMENT NUMBER | HOST MATERIAL | DOPANT | FIRST ELECTRON TRANSPORTING MATERIAL | *1 | HALF-LIFE | *2 | INCREASE IN DRIVING VOLTAGE | LONG-TERM STABILITY | NOTE |
|---|---|---|---|---|---|---|---|---|---|
| 7-1 | COMPARATIVE-6 | D-46 | ET-41 | 100 | 100 | 100 | 100 | 51 | *3 |
| 7-2 | COMPARATIVE-1 | D-46 | ET-41 | 103 | 110 | 103 | 101 | 52 | *3 |

TABLE 6-continued

| ELEMENT NUMBER | HOST MATERIAL | DOPANT | FIRST ELECTRON TRANSPORTING MATERIAL | *1 | HALF-LIFE | *2 | INCREASE IN DRIVING VOLTAGE | LONG-TERM STABILITY | NOTE |
|---|---|---|---|---|---|---|---|---|---|
| 7-3 | COMPARATIVE-3 | D-46 | ET-41 | 100 | 120 | 103 | 102 | 51 | *3 |
| 7-4 | 7-1-1 | D-46 | ET-41 | 102 | 160 | 95 | 96 | 56 | *4 |
| 7-5 | 7-2-1 | D-46 | ET-41 | 105 | 155 | 95 | 96 | 54 | *4 |
| 7-6 | 7-1-2 | D-46 | ET-41 | 102 | 140 | 96 | 97 | 63 | *4 |
| 7-7 | 7-2-2 | D-46 | ET-41 | 103 | 160 | 96 | 96 | 57 | *4 |
| 7-8 | 7-1-3 | D-46 | ET-41 | 106 | 200 | 91 | 91 | 61 | *4 |
| 7-9 | 7-2-3 | D-46 | ET-41 | 108 | 220 | 92 | 89 | 57 | *4 |
| 7-10 | 7-1-4 | D-46 | ET-41 | 107 | 225 | 93 | 90 | 61 | *4 |
| 7-11 | 7-2-4 | D-46 | ET-41 | 104 | 195 | 92 | 90 | 64 | *4 |
| 7-12 | 7-1-5 | D-46 | ET-41 | 107 | 250 | 87 | 86 | 66 | *4 |
| 7-13 | 7-2-5 | D-46 | ET-41 | 110 | 265 | 87 | 88 | 65 | *4 |
| 7-14 | 7-3-5 | D-46 | ET-41 | 111 | 265 | 90 | 83 | 66 | *4 |
| 7-15 | 7-4-5 | D-46 | ET-41 | 107 | 250 | 88 | 85 | 67 | *4 |
| 7-16 | 7-1-6 | D-46 | ET-41 | 110 | 280 | 83 | 81 | 71 | *4 |
| 7-17 | 7-2-6 | D-46 | ET-41 | 108 | 285 | 84 | 82 | 70 | *4 |
| 7-18 | 7-3-6 | D-46 | ET-41 | 111 | 270 | 83 | 83 | 69 | *4 |
| 7-19 | 7-4-6 | D-46 | ET-41 | 113 | 305 | 84 | 78 | 70 | *4 |
| 7-20 | 7-1-7 | D-46 | ET-41 | 113 | 310 | 81 | 74 | 74 | *4 |
| 7-21 | 7-2-7 | D-46 | ET-41 | 114 | 305 | 80 | 71 | 75 | *4 |
| 7-22 | 7-3-7 | D-46 | ET-41 | 114 | 310 | 79 | 72 | 77 | *4 |
| 7-23 | 7-4-7 | D-46 | ET-41 | 115 | 305 | 81 | 73 | 79 | *4 |
| 7-24 | COMPARATIVE-6 | D-46 | 7-1-7 | 106 | 210 | 91 | 84 | 73 | *4 |
| 7-25 | COMPARATIVE-6 | D-46 | 7-2-7 | 107 | 200 | 92 | 83 | 70 | *4 |
| 7-26 | COMPARATIVE-6 | D-46 | 7-3-7 | 106 | 205 | 88 | 85 | 76 | *4 |
| 7-27 | COMPARATIVE-6 | D-46 | 7-4-7 | 105 | 215 | 87 | 84 | 78 | *4 |
| 7-28 | 7-1-6 | D-46 | 7-1-6 | 113 | 300 | 79 | 76 | 76 | *4 |
| 7-29 | 7-2-6 | D-46 | 7-2-6 | 116 | 320 | 82 | 73 | 78 | *4 |
| 7-30 | 7-3-6 | D-46 | 7-3-6 | 117 | 320 | 83 | 70 | 76 | *4 |
| 7-31 | 7-4-6 | D-46 | 7-4-6 | 116 | 320 | 79 | 73 | 76 | *4 |
| 7-32 | 7-1-7 | D-46 | 7-1-7 | 117 | 345 | 80 | 66 | 81 | *4 |
| 7-33 | 7-2-7 | D-46 | 7-2-7 | 118 | 370 | 81 | 67 | 81 | *4 |
| 7-34 | 7-3-7 | D-46 | 7-3-7 | 119 | 365 | 80 | 66 | 80 | *4 |
| 7-35 | 7-4-7 | D-46 | 7-4-7 | 121 | 375 | 78 | 68 | 85 | *4 |

*1: EXTERNAL EXTRACTION QUANTUM EFFICIENCY
*2: DRIVING VOLTAGE
*3: COMPARATIVE EXAMPLE
*4: INVENTIVE EXAMPLE

Table 6 evidently shows that the organic EL elements prepared with the materials for organic EL elements according to the present invention represented in Formula (1) have higher luminescence efficiencies, prolonged emission lifetimes, lower driving voltages, and smaller increases in driving voltage compared to the organic EL elements in Comparative Examples. Table 6 also shows that the organic EL elements prepared with the materials for organic EL elements according to the present invention represented in Formula (1) have higher long-term stability. Table 6 further shows that addition of the materials for organic EL elements represented in Formula (1) to both the luminous layer and the first electron transporting layer significantly enhances the performance of the organic EL element.

Example 8

Preparation of Organic EL Elements 8-1 to 8-31

Organic EL elements 8-1 to 8-31 were prepared as in Organic EL element 4-1 except that the host material, the dopant, and the first electron transporting material were varied as shown in Table 7.

<<Evaluation of Organic EL Elements 8-1 to 8-31>>

Organic EL elements 8-1 to 8-31 were evaluated. Organic EL elements were sealed as in Organic EL element 1-1 to 1-16 in Example 1 to prepare illumination devices for evaluation illustrated in FIGS. 5 and 6.

These samples were evaluated as in Example 1 for the external extraction quantum efficiency, the half-life, the driving voltage, the increase in driving voltage, and the long-term stability. The results are shown in Table 7. In Table 7, the results of the external extraction quantum efficiency, the half-life, the driving voltage, and the increase in driving voltage were expressed as relative values to the respective values, 100, of Organic EL element 8-1.

TABLE 7

| ELEMENT NUMBER | HOST MATERIAL | DOPANT | FIRST ELECTRON TRANSPORTING MATERIAL | *1 | HALF-LIFE | *2 | INCREASE IN DRIVING VOLTAGE | LONG-TERM STABILITY | NOTE |
|---|---|---|---|---|---|---|---|---|---|
| 8-1 | COMPARATIVE-5 | DP-21 | ET-41 | 100 | 100 | 100 | 100 | 50 | *3 |
| 8-2 | COMPARATIVE-4 | DP-21 | ET-41 | 101 | 94 | 99 | 99 | 52 | *3 |
| 8-3 | COMPARATIVE-2 | DP-21 | ET-41 | 102 | 101 | 96 | 101 | 52 | *3 |

TABLE 7-continued

| ELEMENT NUMBER | HOST MATERIAL | DOPANT | FIRST ELECTRON TRANSPORTING MATERIAL | *1 | HALF-LIFE | *2 | INCREASE IN DRIVING VOLTAGE | LONG-TERM STABILITY | NOTE |
|---|---|---|---|---|---|---|---|---|---|
| 8-4 | 6-1-6 | DP-21 | ET-41 | 111 | 295 | 84 | 80 | 70 | *4 |
| 8-5 | 6-2-6 | DP-21 | ET-41 | 109 | 300 | 86 | 82 | 69 | *4 |
| 8-6 | 6-3-6 | DP-21 | ET-41 | 110 | 285 | 84 | 82 | 69 | *4 |
| 8-7 | 6-4-6 | DP-21 | ET-41 | 112 | 315 | 82 | 80 | 71 | *4 |
| 8-8 | 7-1-6 | DP-21 | ET-41 | 113 | 295 | 84 | 80 | 71 | *4 |
| 8-9 | 7-2-6 | DP-21 | ET-41 | 111 | 305 | 86 | 81 | 69 | *4 |
| 8-10 | 7-3-6 | DP-21 | ET-41 | 110 | 290 | 84 | 83 | 69 | *4 |
| 8-11 | 7-4-6 | DP-21 | ET-41 | 113 | 315 | 84 | 79 | 71 | *4 |
| 8-12 | 6-1-7 | DP-21 | ET-41 | 114 | 320 | 80 | 75 | 75 | *4 |
| 8-13 | 6-2-7 | DP-21 | ET-41 | 115 | 330 | 81 | 74 | 80 | *4 |
| 8-14 | 6-3-7 | DP-21 | ET-41 | 116 | 325 | 82 | 71 | 77 | *4 |
| 8-15 | 6-4-7 | DP-21 | ET-41 | 115 | 340 | 80 | 77 | 77 | *4 |
| 8-16 | 7-1-7 | DP-21 | ET-41 | 113 | 325 | 81 | 75 | 75 | *4 |
| 8-17 | 7-2-7 | DP-21 | ET-41 | 115 | 325 | 81 | 75 | 77 | *4 |
| 8-18 | 7-3-7 | DP-21 | ET-41 | 117 | 335 | 82 | 71 | 78 | *4 |
| 8-19 | 7-4-7 | DP-21 | ET-41 | 115 | 335 | 79 | 74 | 73 | *4 |
| 8-20 | COMPARATIVE-4 | DP-21 | 6-1-7 | 104 | 200 | 89 | 84 | 77 | *4 |
| 8-21 | COMPARATIVE-4 | DP-21 | 6-2-7 | 104 | 210 | 90 | 86 | 75 | *4 |
| 8-22 | COMPARATIVE-4 | DP-21 | 6-3-7 | 105 | 225 | 90 | 86 | 76 | *4 |
| 8-23 | COMPARATIVE-4 | DP-21 | 6-4-7 | 107 | 215 | 87 | 82 | 73 | *4 |
| 8-24 | 6-1-7 | DP-21 | 6-1-7 | 118 | 345 | 76 | 66 | 82 | *4 |
| 8-25 | 6-2-7 | DP-21 | 6-2-7 | 118 | 355 | 77 | 64 | 80 | *4 |
| 8-26 | 6-3-7 | DP-21 | 6-3-7 | 117 | 350 | 77 | 65 | 82 | *4 |
| 8-27 | 6-4-7 | DP-21 | 6-4-7 | 121 | 375 | 74 | 61 | 81 | *4 |
| 8-28 | 7-1-7 | DP-21 | 7-1-7 | 116 | 345 | 79 | 64 | 81 | *4 |
| 8-29 | 7-2-7 | DP-21 | 7-2-7 | 120 | 350 | 78 | 67 | 84 | *4 |
| 8-30 | 7-3-7 | DP-21 | 7-3-7 | 116 | 360 | 74 | 66 | 82 | *4 |
| 8-31 | 7-4-7 | DP-21 | 7-4-7 | 119 | 365 | 75 | 64 | 80 | *4 |

*1: EXTERNAL EXTRACTION QUANTUM EFFICIENCY
*2: DRIVING VOLTAGE
*3: COMPARATIVE EXAMPLE
*4: INVENTIVE EXAMPLE

Table 7 evidently shows that the organic EL elements prepared with the materials for organic EL elements according to the present invention represented in Formula (1) have higher luminescence efficiencies, prolonged emission lifetimes, lower driving voltages, and smaller increases in driving voltage compared to the organic EL elements in Comparative Examples. Table 7 also shows that the organic EL elements prepared with the materials for organic EL elements according to the present invention represented in Formula (1) have higher long-term stability. Table 7 further shows that addition of the materials for organic EL elements represented in Formula (1) to both the luminous layer and the first electron transporting layer significantly enhances the performance of the organic EL element.

INDUSTRIAL APPLICABILITY

The present invention provides a material for an organic electroluminescent element having high luminescence efficiency, low driving voltage, a prolonged service life, a small increase in driving voltage, and high long-term stability, and an organic electroluminescent element, illumination device, and a display device which contain the material.

The present invention also provides a material for an organic electroluminescent element suitable for preparation of organic electroluminescent elements by wet processes, and an organic electroluminescent element, an illumination device, and a display device which contain the material.

REFERENCE NUMERAL LIST

1 Display
3 Pixel
5 Scanning line
6 Data line
7 Power supply line
10 Organic EL element
11 Switching transistor
12 Driving transistor
13 Capacitor
101 Organic EL element
102 Glass cover
105 Cathode
106 Organic EL layer
107 Glass substrate with transparent electrode
108 Nitrogen gas
109 Water getter
201 Glass substrate
202 ITO transparent electrode
203 Partition
204 Hole injecting layer
205B, 205G, 205R Luminous layer
206 Cathode
A Display unit
B Control unit

The invention claimed is:

1. A material for an organic electroluminescent element, comprising a compound represented by Formula (4):

Formula (4)

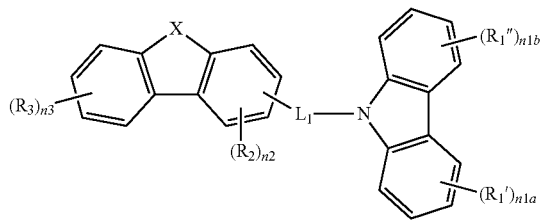

where $R_2$, $R_3$, $R_1'$, and $R_1''$ each independently represent a deuterium atom, a halogen atom, a cyano group, an alkyl group, an alkenyl group, an alkynyl group, an alkoxy group, a carbonyl group, an amino group, a silyl group, a hydroxy group, a thiol group, a phosphine oxide group, an aromatic hydrocarbon ring group, an aromatic heterocyclic group, a non-aromatic hydrocarbon ring group, or a non-aromatic heterocyclic group, and may further have an optional substituent; at least one of $R_2$, $R_3$, $R_1'$, and $R_1''$ is a group represented by Formula (2); if pluralities of $R_2$'s, $R_3$'s, $R_1''$'s, and $R_1'''$'s are present, these $R_2$'s, $R_3$'s, $R_1''$'s, and $R_1'''$'s may be the same or different or may be bonded to each other to form a ring; n2 represents an integer of 0 to 3; n3, n1a, and n1b each independently represent an integer of 0 to 4; n2+n3+n1a+n1b is 1 or more; X represents an oxygen atom or a sulfur atom; L1 represents a single bond or a divalent linking group Formula (2)

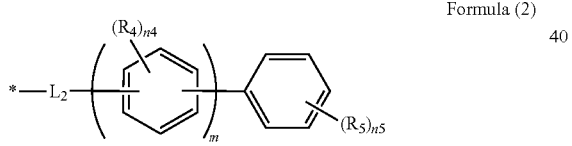

where * represents a binding site to the structure represented by Formula (4); $L_2$ represents a single bond; $R_4$ represents a substituent; $R_5$ represents a deuterium atom, a halogen atom, a cyano group, an alkyl group, an alkenyl group, an alkynyl group, an alkoxy group, a carbonyl group, a silyl group, a phosphine oxide group, an aromatic hydrocarbon ring group, an aromatic heterocyclic group bonded to a phenyl group via a carbon atom of the aromatic heterocyclic group, a non-aromatic hydrocarbon ring group, or a non-aromatic heterocyclic group; $R_5$ may further have optional substituents; if pluralities of $R_5$'s are present, these substituents may be the same or different, provided that $R_5$'s are not bonded to each other to form a ring; n4 represents an integer of 0; n5 represents an integer of 0 to 5; m represents an integer of 2 to 10.

2. The material for an organic electroluminescent element according to claim 1,
wherein the compound represented by Formula (4) is a compound represented by Formula (7):

Formula (7)

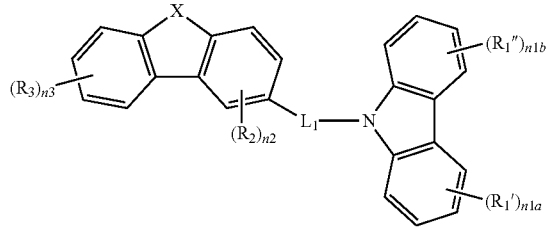

where $R_2$, $R_3$, $R_1'$, $R_1''$, n2, n3, n1a, n1b, X, and $L_1$ are the same as $R_2$, $R_3$, $R_1'$, $R_1''$, n2, n3, n1a, n1b, X, and $L_1$ defined in Formula (4).

3. The material for an organic electroluminescent element according to claim 1,
wherein the group represented by Formula (2) is a group represented by Formula (5):

Formula (5)

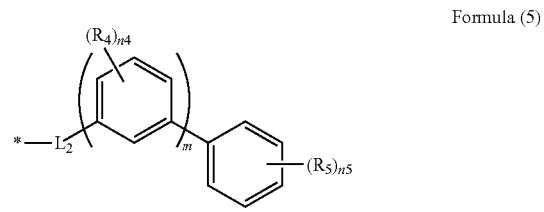

where * represents a binding site to a structure represented by Formula (4); $L_2$ represents a single bond; $R_4$ represents a substituent; $R_5$ represents a deuterium atom, a halogen atom, a cyano group, an alkyl group, an alkenyl group, an alkynyl group, an alkoxy group, a carbonyl group, a silyl group, a phosphine oxide group, an aromatic hydrocarbon ring group, a non-aromatic hydrocarbon ring group, or a non-aromatic heterocyclic group; $R_5$ may further have optional substituents, and the optional substituents may be bonded to each other to form a ring; if pluralities of $R_5$'s are present, these $R_5$'s may be the same or different provided that the $R_5$'s are not bonded to each other to form a ring; n4 represents an integer of 0; n5 represents an integer of 0 to 5; m represents an integer of 2 to 10.

4. The material for an organic electroluminescent element according to claim 1,
wherein m in Formula (2) represents an integer of 2 to 5.

5. The material for an organic electroluminescent element according to claim 1,
wherein $L_1$ in Formula (4) represents a single bond.

6. The material for an organic electroluminescent element according to claim 1,
wherein X in Formula (4) represents an oxygen atom.

7. An organic electroluminescent element, comprising:
an anode,
a cathode, and
an organic layer composed of at least one organic layer including a luminous layer, the organic layer being disposed between the anode and the cathode,
wherein the at least one organic layer contains the material for an organic electroluminescent element according to claim 1.

8. The organic electroluminescent element according to claim 7, wherein the at least one organic layer further contains a phosphorescent compound represented by Formula (DP):

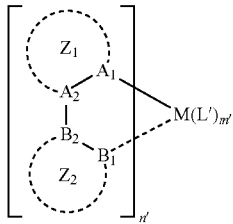

Formula (DP)

where M represents Ir, Pt, Rh, Ru, Ag, Cu, or Os; $A_1$, $A_2$, $B_1$, and $B_2$ each independently represent a carbon atom or a nitrogen atom; ring $Z_1$ represents a 6-membered aromatic hydrocarbon ring or 5- or 6-membered aromatic heterocyclic ring including $A_1$ and $A_2$; ring $Z_2$ represents a 5- or 6-membered aromatic heterocyclic ring including $B_1$ and $B_2$; ring $Z_1$ and ring $Z_2$ may have optional substituents, and the optional substituents may be bonded to form a fused ring structure; substituents of ligands may be bonded to each other to link the ligands; L' represents a monoanionic bidentate ligand coordinated with M; m' represents an integer of 0 to 2; n' represents an integer of 1 to 3; m'+n' is 2 or 3; if m' and n' both are 1 or more, ligands represented by ring $Z_1$ and ring $Z_2$ may be the same as or different from L'.

9. The organic electroluminescent element according to claim 7, wherein a color of light emitted is white.

10. An illumination device, comprising the organic electroluminescent element according to claim 7.

11. A display device, comprising the organic electroluminescent element according to claim 7.

* * * * *